United States Patent
Anderson et al.

(10) Patent No.: US 11,376,337 B2
(45) Date of Patent: Jul. 5, 2022

(54) EXPRESSION OF NEUROPEPTIDES

(71) Applicant: California Institute of Technology, Pasadena, CA (US)

(72) Inventors: David J Anderson, Altadena, CA (US); Moriel Zelikowsky, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 477 days.

(21) Appl. No.: 16/178,461

(22) Filed: Nov. 1, 2018

(65) Prior Publication Data

US 2019/0125900 A1 May 2, 2019

Related U.S. Application Data

(60) Provisional application No. 62/580,846, filed on Nov. 2, 2017.

(51) Int. Cl.

| A61K 31/5513 | (2006.01) |
|---|---|
| C12N 15/86 | (2006.01) |
| A61K 48/00 | (2006.01) |
| C07K 14/47 | (2006.01) |
| C07K 14/705 | (2006.01) |
| A61N 5/06 | (2006.01) |

(52) U.S. Cl.
CPC ...... *A61K 48/0083* (2013.01); *A61K 31/5513* (2013.01); *C07K 14/47* (2013.01); *C07K 14/70571* (2013.01); *C12N 15/86* (2013.01); *A01K 2207/35* (2013.01); *A01K 2227/105* (2013.01); *A01K 2267/0393* (2013.01); *A61N 5/062* (2013.01); *A61N 2005/0663* (2013.01); *C12N 2750/14143* (2013.01); *C12N 2800/30* (2013.01)

(58) Field of Classification Search
None
See application file for complete search history.

(56) References Cited

U.S. PATENT DOCUMENTS

| 9,540,657 | B2 | 1/2017 | Yu et al. |
|---|---|---|---|
| 9,585,971 | B2 | 3/2017 | Deverman et al. |
| 2005/0163777 | A1 | 7/2005 | Rosen et al. |
| 2005/0256112 | A1 | 11/2005 | Brodney et al. |
| 2007/0142431 | A1 | 6/2007 | Chan et al. |
| 2010/0168215 | A1 | 7/2010 | During et al. |
| 2011/0313372 | A1 | 12/2011 | Eifler et al. |
| 2013/0123277 | A1 | 5/2013 | Jain et al. |
| 2014/0125678 | A1 | 5/2014 | Wang et al. |
| 2014/0155575 | A1 | 6/2014 | Bai et al. |
| 2014/0178305 | A1* | 6/2014 | Anderson .......... A61K 49/0008 514/17.7 |
| 2017/0166926 | A1 | 6/2017 | Deverman et al. |
| 2017/0198308 | A1* | 7/2017 | Qi ..................... C12N 9/22 |
| 2017/0296528 | A1 | 10/2017 | Ressler et al. |
| 2019/0125738 | A1 | 5/2019 | Anderson et al. |
| 2019/0125900 | A1 | 5/2019 | Anderson et al. |

FOREIGN PATENT DOCUMENTS

| WO | WO 2005/094801 A1 | 10/2005 |
|---|---|---|
| WO | WO 2017/049252 A1 | 3/2017 |
| WO | WO 2017/153995 A1 | 9/2017 |
| WO | WO 2017/165747 A1 | 9/2017 |

OTHER PUBLICATIONS

Andero et al (Neuron 83: 444-454, 2014).*
Nation et al (J Neurophysiol 115:3123-3129, 2016).*
Dissen et al (Reprod Domest Anim 52: 354-358 (1-9), Apr. 2017).*
Neurokinin B—Wikipedia, pp. 1-6, downloaded from <https://en.wikipedia.org/wiki/Neurokinin_B> on Feb. 15, 2020.*
Shen et al (Hum Gen Ther 11: 1509-1519, 2000).*
Roth BL (Neuron 89: 683-694 (1-25), Feb. 2016).*
Foti et al (Gene Ther 16: 1314-1319 (1-13), 2009).*
Kügler et al. (Gene Therapy 10: 337-347, 2003).*
Rorato et al (Endo Soc Meeting abstract SAT 246, Apr. 2, 2016).*
Rinker et al (Alcoholism: Clin Exptl Res 39: Supp p. 235A, Abstract 898, Jun. 2015).*
Anthony, Todd et al., "Control of Stress-Induced Persistent Anxiety by an Extra-Amygdala Septohypothalamic Circuit", Cell, Jan. 30, 2014 Elsevier Inc., vol. 156, pp. 522-536.
Beajounan, Jean-Claude et al., "A 25-year adventure in the field of Tachykinins", Peptides 25, 2004 Elsevier Inc., pp. 339-357.
Blanchard, Caroline et al., "Defensive Responses to Predictor Threat in the Rat and Mouse", Current Protocols in Neuroscience, 2005 John Wiley & Sons, Inc., Unit 8.19, Supplement 30, pp. 1-20.
Blanchard, Caroline, "The Mouse Defense Test Battery: pharmacological and behavioral assays for anxiety and panic", European Journal of Pharmacology, 2003 Elvesier, Inc, vol. 463, Issue No. 1-3, pp. 97-116.
Cai, Haijang et al., "Central amygdala PKC neurons mediate the influence of multiple anorexigenic signals.", Nature Neuroscience, Sep. 2014, vol. 17, No. 9, pp. 1240-1248.
Chou, Kee-Lee et al., "The Association Between Social Isolation and *DSM-IV* Mood, Anxiety, and Substance Use Disorders: Wave 2 of the National Epidemiologic Survey on Alcohol and Related Conditions", J Clin Psychiatry, Nov. 2011, vol. 72 (11), pp. 1468-1476.
Culman, Juraj et al, "Central tachykinins: mediators of defence reaction and stress reactions." Can. J. Physiol Pharmacol., 1995, vol. 73, pp. 885-891.
Cushman, Jesse, et al., "The Role of the δ Gaba (A) Receptor in Ovarian Cycle-Linked Changes in Hippocampus-Dependent Learning and Memory", Neurochem Research, 2014, vol. 39, pp. 1140-1146.
Deneen, Benjamin, et al., "The Transcription Factor NFIA Controls the Onset of Gliogenesis in the Developing Spinal Cord", Neuron 52, Dec. 21, 2006, vol. 52, pp. 953-968.

(Continued)

*Primary Examiner* — Daniel E Kolker
*Assistant Examiner* — Aditi Dutt
(74) *Attorney, Agent, or Firm* — Knobbe, Martens, Olson & Bear, LLP

(57) ABSTRACT

Methods of expressing a neuropeptide in a neuron of a subject are described. Methods of altering a behavior in a subject in need thereof are described. Kits are described. Vectors are described.

15 Claims, 84 Drawing Sheets

Specification includes a Sequence Listing.

(56) References Cited

OTHER PUBLICATIONS

Deverman, Benjamin, et al., "Cre-dependent selection yields AAV variants for widespread gene transfer to the adult brain", Nature Biotechnology, Feb. 2016, vol. 34, No. 2, pp. 204-209.
Friedler, Brett, et al. One is the deadliest number: the detrimental effects of social isolation on cerebrovascular diseases and cognition, Acta Neuropathol, 2015, vol. 129, pp. 493-509.
Griebel, Guy et al., "Neuropeptide receptor ligands as drugs for psychiatric diseases: the end of the beginning?", Natures Reviews | Drug Discovery, Jun. 2012, vol. 11, pp. 462-478.
Haubensak, Wulf et al., "Genetic dissection of an amygdala microcircuit that gates conditioned fear", Nature, Nov. 11, 2010, vol. 468, pp. 270-276.
Hong, Weizhe et al., "Antagonistic Control of Social versus Repetitive Self-Grooming Behaviors by Separable Amygdala Neuronal Subsets", Cell 158, Sep. 11, 2014, pp. 1348-1361.
Hong, Weizhe et al., "Automated measurement of mouse social behaviors using depth sensing, video tracking, and machine learning", PNAS, Sep. 9, 2015, pp. E5351-E5360.
Hsiao, Elaine et al., "Microbiota Modulate Behavioral and Physiological Abnormalities Associates with Neurodevelopmental Disorders", Cell 155, Dec. 19, 2013, pp. 1451-1463.
Huang, Huang, et al., "Isolation Housing Exacerbates Alzheimer's Disease Like Pathophysiology in Aged APP/PS1 Mice", International Journal of Neuropsychopharmacology, 2015, pp. 1-10.
Kim, Jeansok J., et al., "N-Methyl-D-Aspartate Receptor Antagonist APV Blocks Acquisition but Not Expression of Fear Conditioning", Behavioral Neuroscience, 1991, vol. 105, No. 1, pp. 126-133.
Koch, M, "The Neurobiology of Startle", Progress in Neurobiolgy, 1999, vol. 59, pp. 107-128.
Kunwar, Prabhat, et al., "Ventromedial hypothalamic neurons control a defensive emotion state", eLife Sciences, 2015, vol. 4, No. e06633, pp. 1-30.
Lee, Hyosang et al., "Scalable control of mounting and attack by Esr1$^+$ neurons in the ventromedial hypothalmus", Nature, May 29, 2014, vol. 509, pp. 627-632.
Lein, Ed et al., "Genome-wide atlas of gene expression in the adult mouse brain", Nature, Jan. 11, 2007, vol. 445, pp. 168-176.
Lin, John Y., "A user's guide to channelrhodopsin variants: features, limitations and future developments", The Experimental Physiology, The Author Journal compilation, 2010, vol. 96.1, pp. 19-25.
Madisen, Linda et al., "A robust and high-throughput Cre reporting and characterization system for the whole mouse brain", Nature Neuroscrience, Jan. 2010, vol. 13, No. 1, pp. 133-140.
Maggio, J.E, "Tachykinins", Ann. Rev Neurosci, 1988, vol. 11, pp. 13-28.

Mongeau, Raymond et al., "Neural Correlates of Competing Fear Behaviors Evoked by an Innately Aversive Stimulus", The Journal of Neuroscience, May 1, 2003, vol. 29, No. 9, pp. 3855-3868.
Naito, Yuki., et al., "SiDirect 2.0: updated software for designing functional siRNA with reduced seed-dependent off-target effect", BMC Brioinformatics, 2009, vol. 10, No. 392, pp. 1-8.
Shi, Limin, et al., Maternal Influenza Infection Causes Marked Behavioral and Pharmacological Changes in the Offspring, The Journal of Neuroscience, Jan. 1, 2003, vol. 23, No. 1, pp. 297-302.
Thompson, Carol L, et al., "Genomic Anatomy of the Hippocampus", Neuron 60, Dec. 26, 2008, pp. 1010-1021.
Williams, J. Bradley, et al., "A Model of Gene-Environment Interaction Reveals Altered Mammary Gland Gene Expression and Increased Tumor Growth Following Social Isolation", Amercian Association Cancer Research Journal, Oct. 2009, vol. 2, No. 10, pp. 850-861.
Yilmaz, Melis, et al., "Rapid Innate Defensive Responses of Mice to Looming Visual Stimuli", Current Biology, Oct. 21, 2013, vol. 23, No. 20, pp. 2011-2015.
Zelikowsky, Moriel, et al., "Neuronal Ensembles in Amygdala, Hippocampus, and Prefrontal Cortex Track Differential Components of Contextual Fear", The Journal of Neuroscience, Jun. 18, 2014, vol. 34, No. 25, pp. 8462-8466.
International Search Report and Written Opinion dated Jan. 22, 2019 in Application No. PCT/US2018/058808.
International Search Report and Written Opinion dated Jan. 29, 2019 in Application No. PCT/US18/58809.
Office Action dated Jun. 14, 2019 in U.S. Appl. No. 16/178,460.
Office Action dated Jan. 28, 2020 in U.S. Appl. No. 16/178,460.
Sambrook et al. (Molecular Cloning: A Laboratory Manual. Cold Spring Harbor Laboratory Press, N.Y. (1989).
File History of U.S. Appl. No. 16/178,460.
Office Action received in U.S. Appl. No. 16/178,460 dated Feb. 5, 2021 in 20 pages.
Office Action received in U.S. Appl. No. 16/178,460 dated Jun. 11, 2021 in 4 pages.
Office Action received in U.S. Appl. No. 16/178,460 dated Sep. 8, 2020 in 18 pages.
Extended European Search Report in European Application No. 18873410.7 dated Aug. 5, 2021 in 9 pages.
Salome et al., Selective blockade of NK2 or NK3 receptors produces anxiolytic- and antidepressant-like effects in gerbils, Pharmacology Biochemistry and Behavior, Elsevier, vol. 83, No. 4, Apr. 2006, pp. 533-539.
Mar et al., Genetic marking and characterization of Tac2-expressing neurons in the central and peripheral nervous system, Molecular Brain, Jan. 24, 2012, 5:3.

* cited by examiner

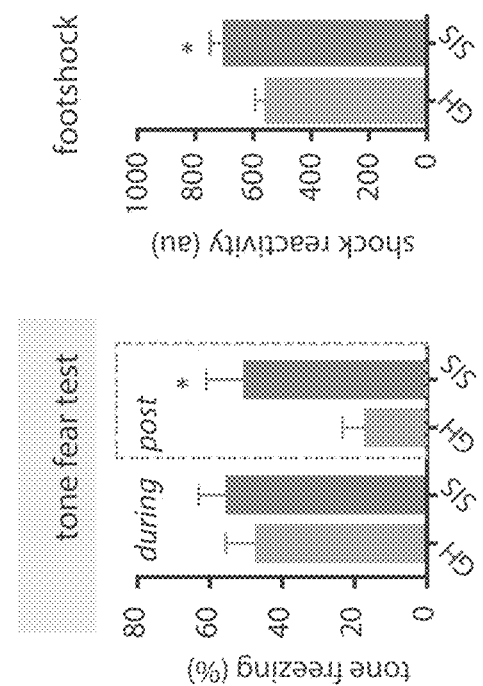
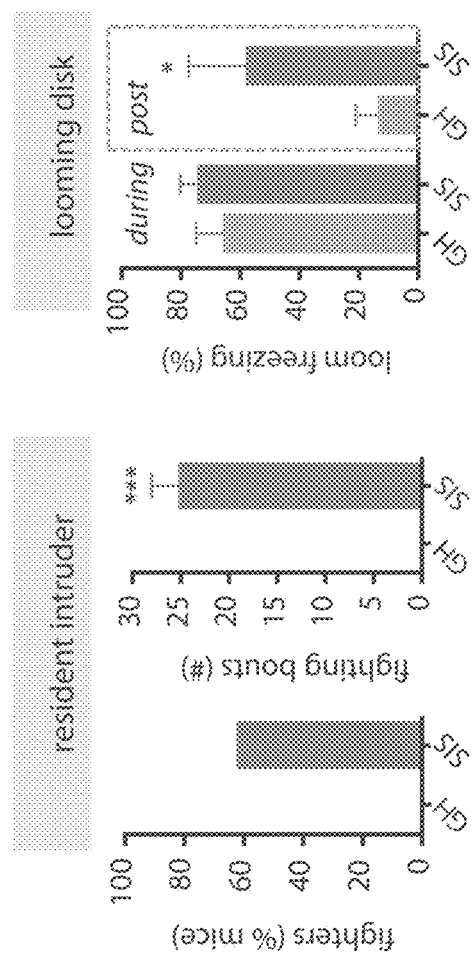
FIG. 1F  FIG. 1G  FIG. 1H  FIG. 1I  FIG. 1J

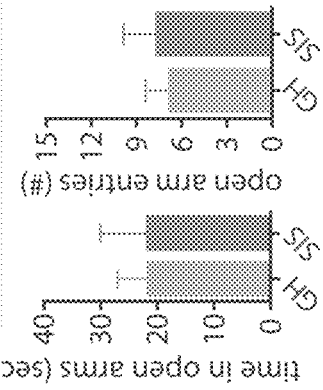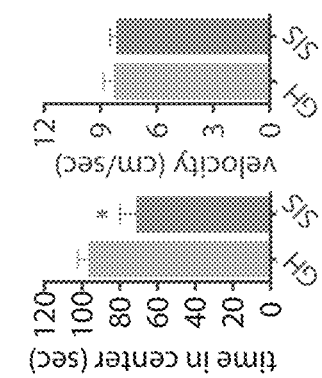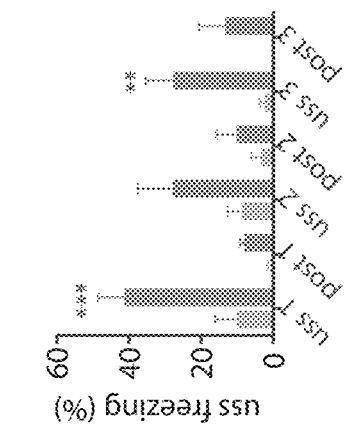
FIG. 1K  FIG. 1L  FIG. 1M  FIG. 1N  FIG. 1O  FIG. 1P  FIG. 1Q

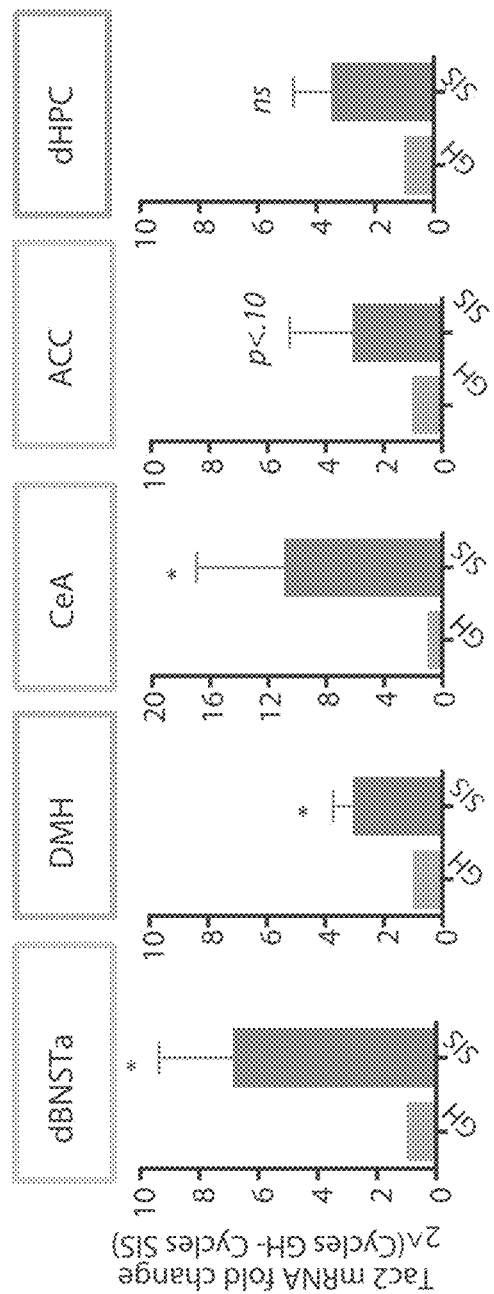
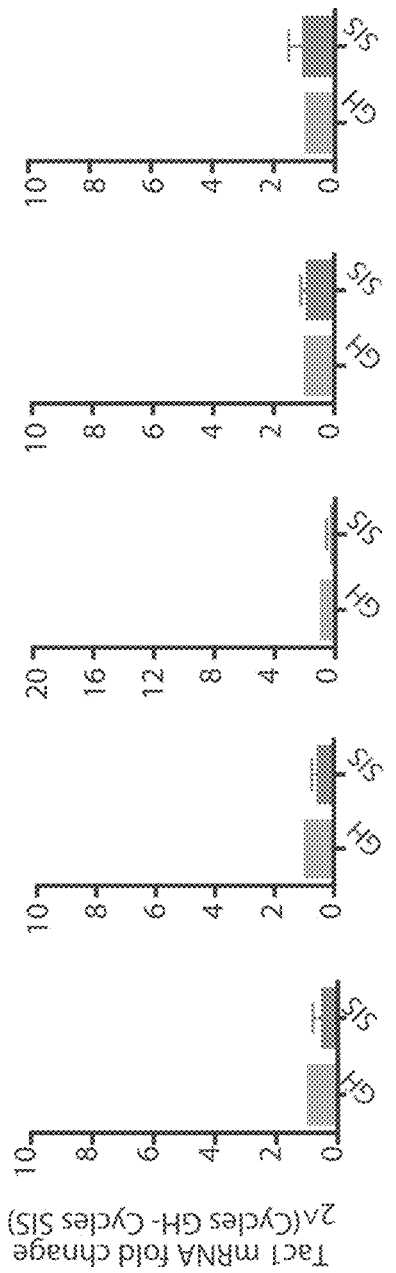

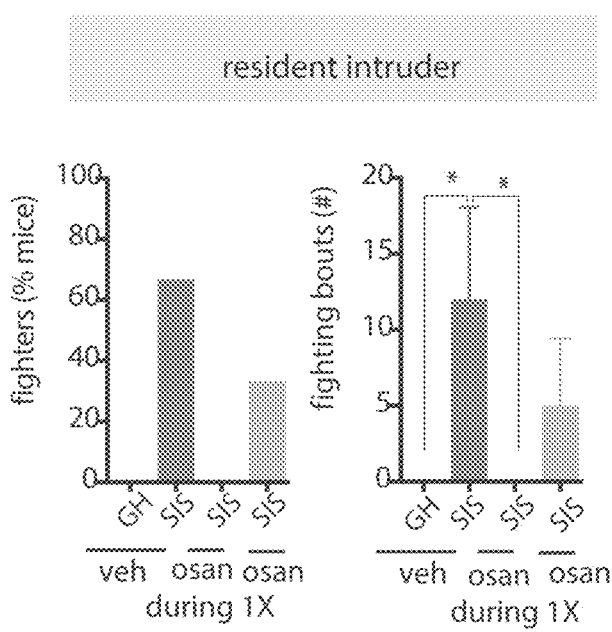
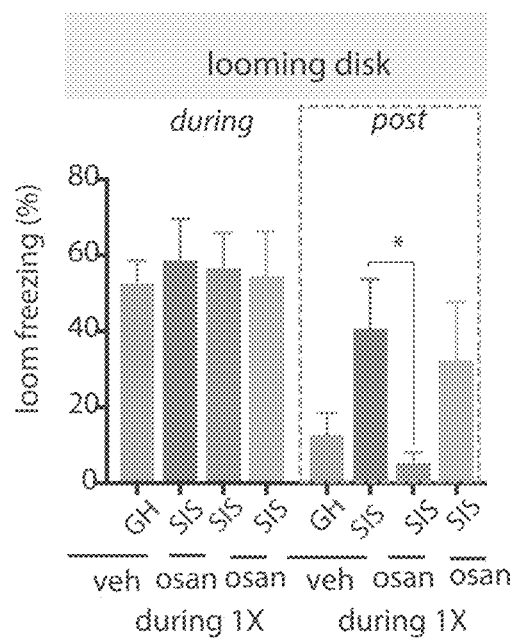
FIG. 3H  FIG. 3I  FIG. 3J

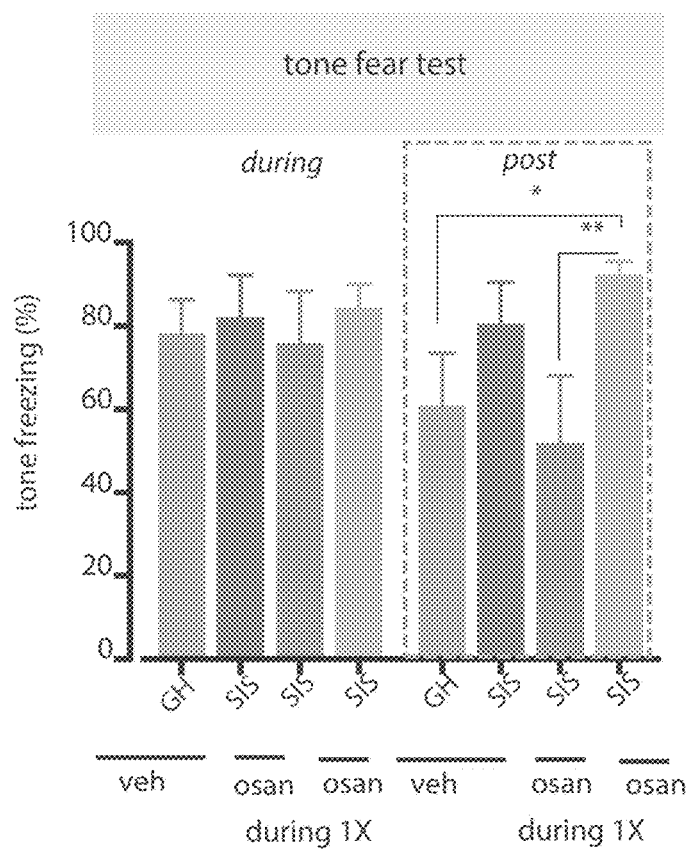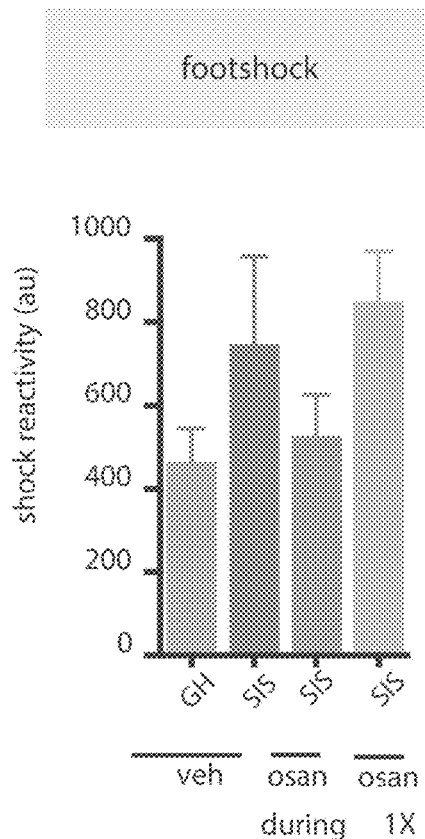
FIG. 3K
FIG. 3L

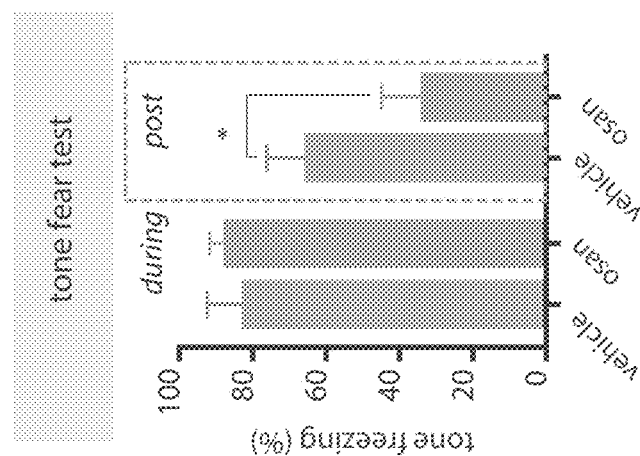
FIG. 4F
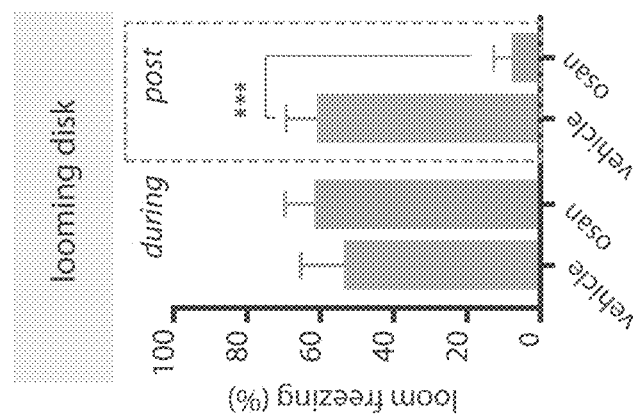
FIG. 4E
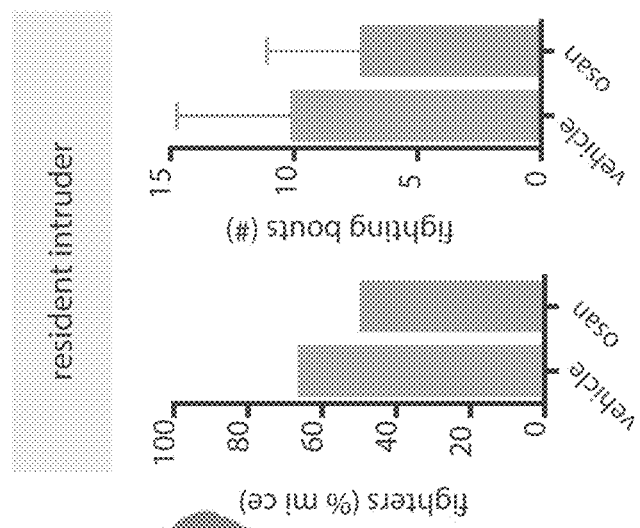
FIG. 4D
FIG. 4C
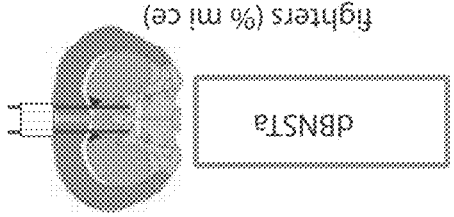
FIG. 4B

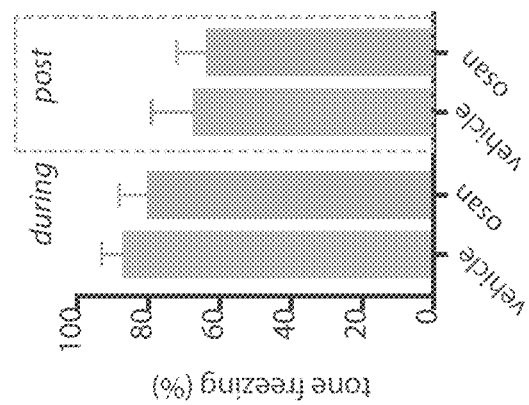
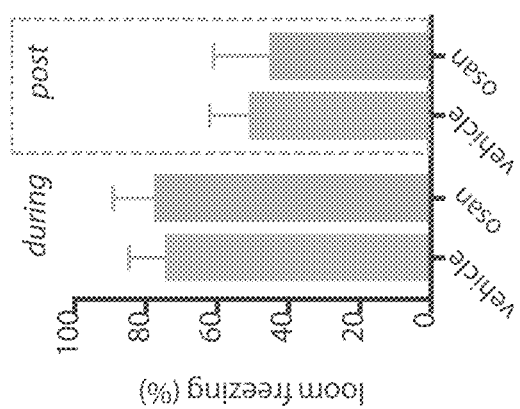
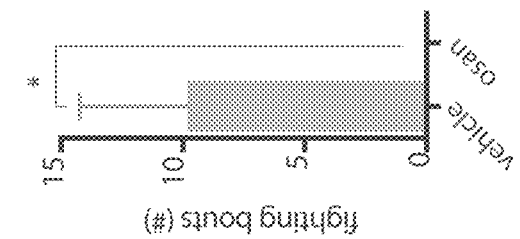
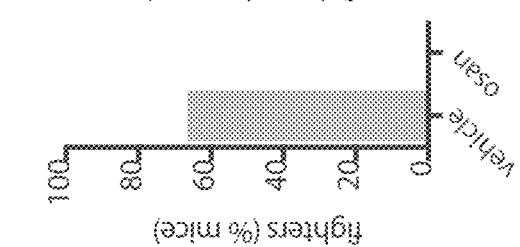
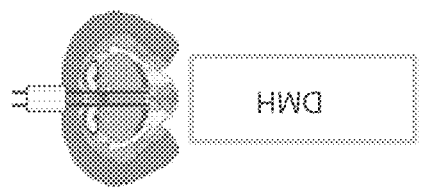

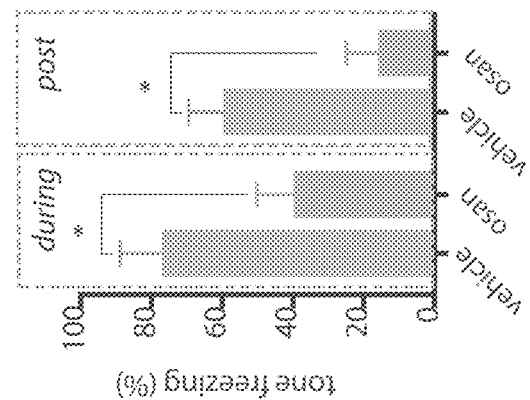
FIG. 4P
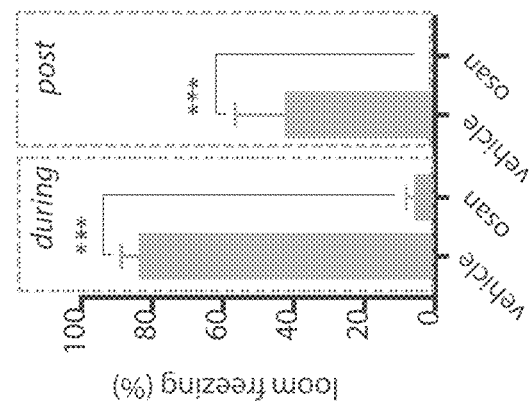
FIG. 4O
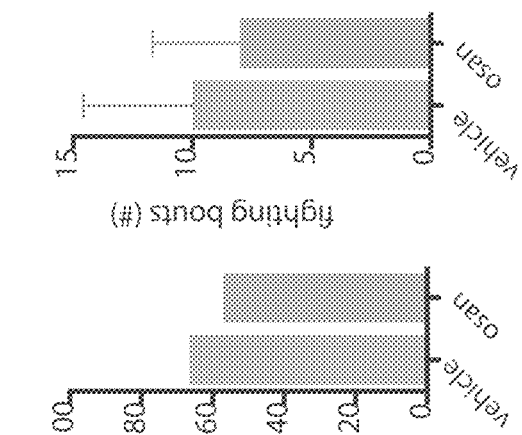
FIG. 4N
FIG. 4M
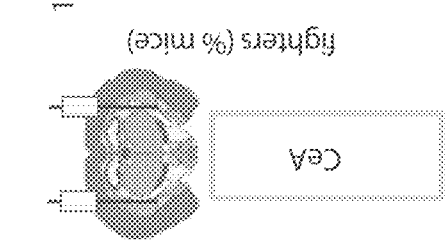
FIG. 4L

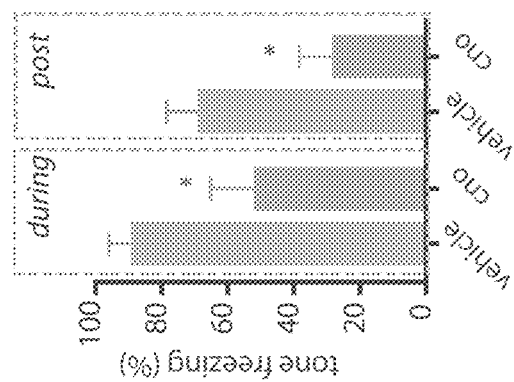
FIG. 5P
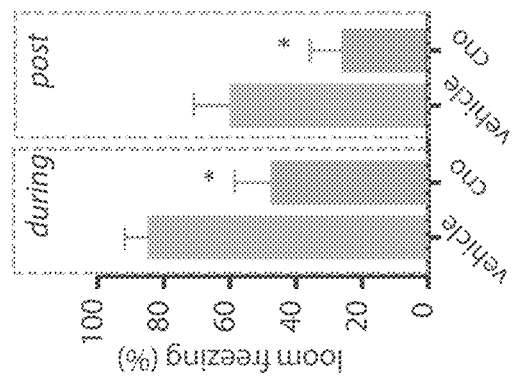
FIG. 5O
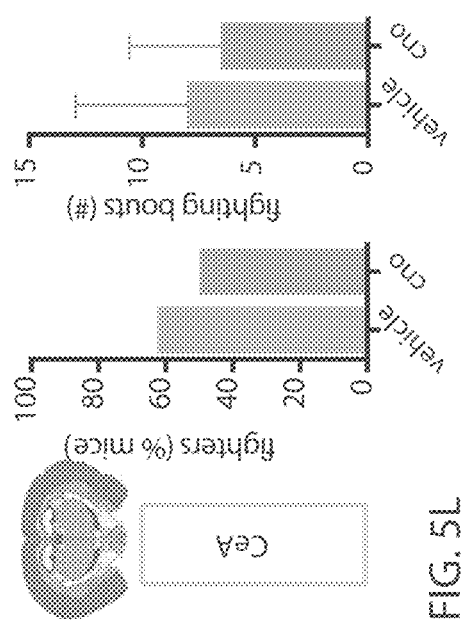
FIG. 5L
FIG. 5M
FIG. 5N

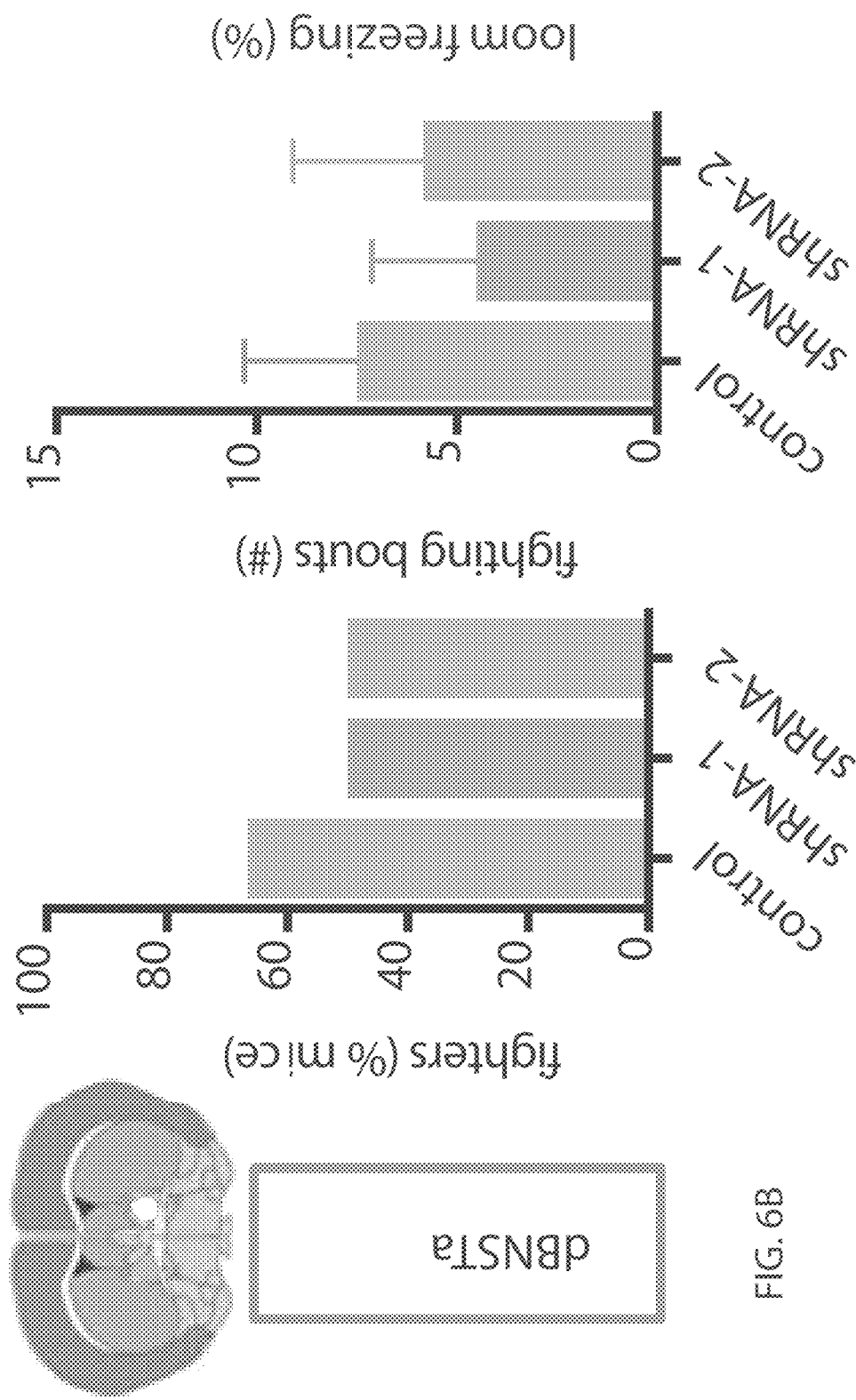

FIG. 6Q looming disk baseline fear at test tone fear test

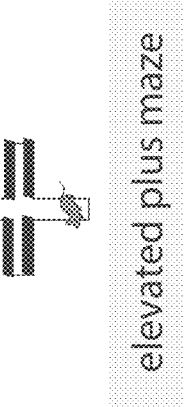
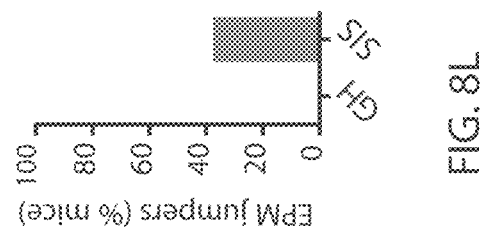
FIG. 8K
FIG. 8L
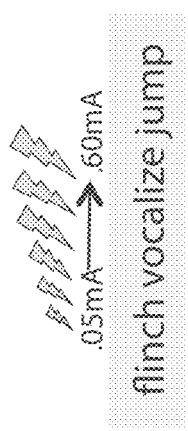
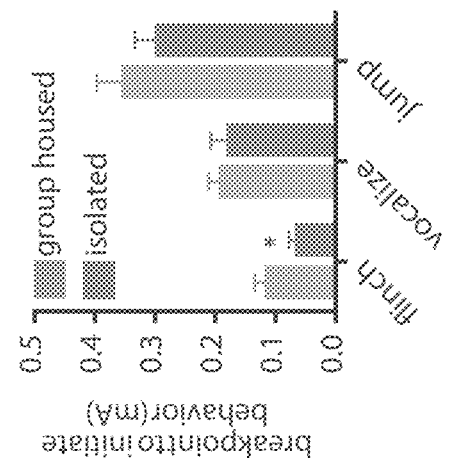
FIG. 8I
FIG. 8J
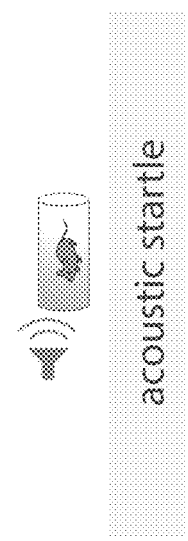
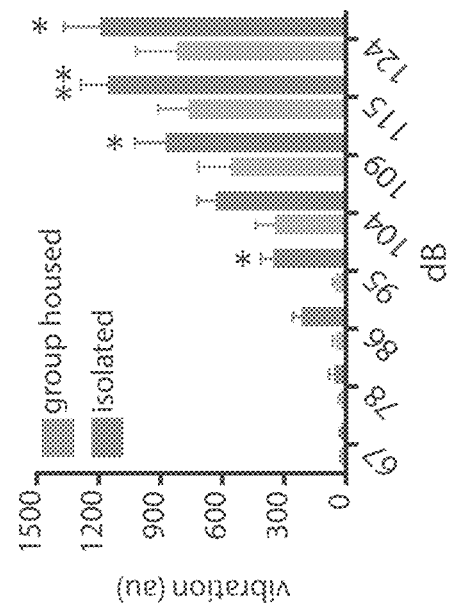
FIG. 8G
FIG. 8H

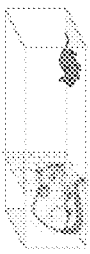
FIG. 8M
FIG. 8Q
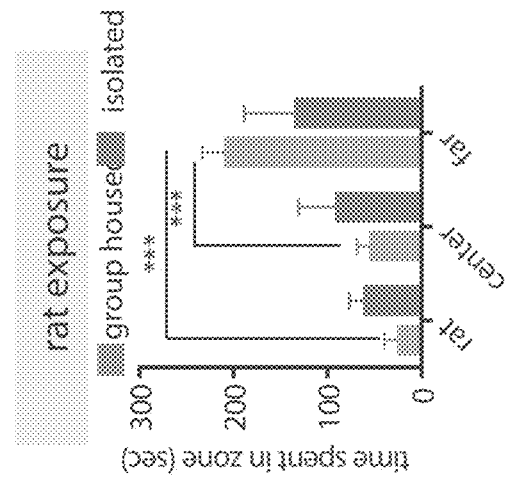
FIG. 8R
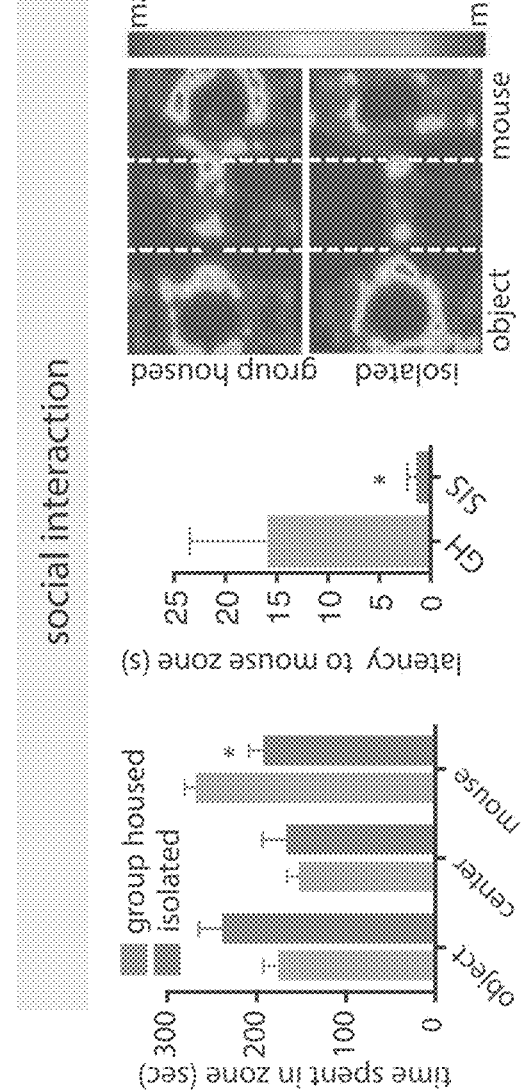
FIG. 8P
FIG. 8O
FIG. 8N

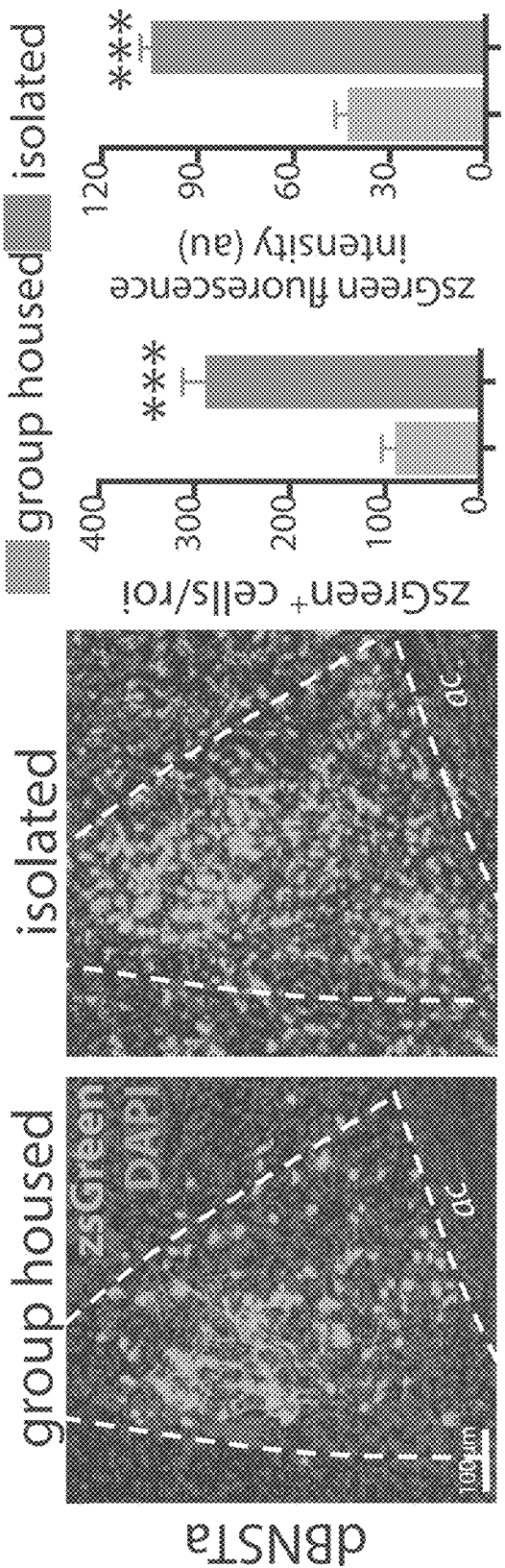

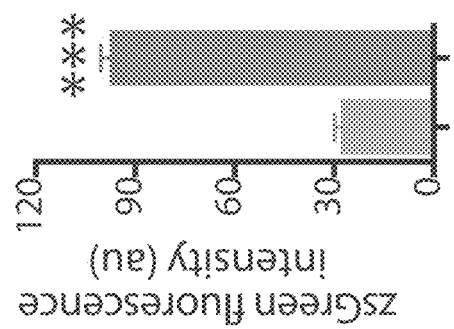
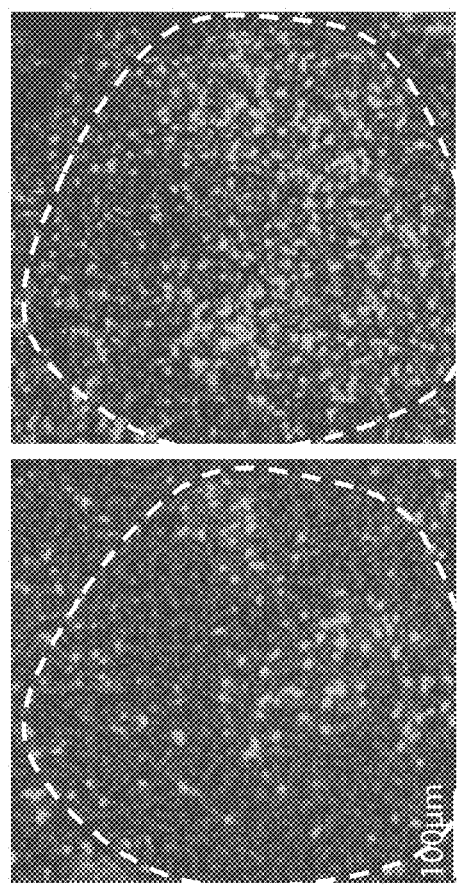
FIG. 9E FIG. 9F FIG. 9G FIG. 9H

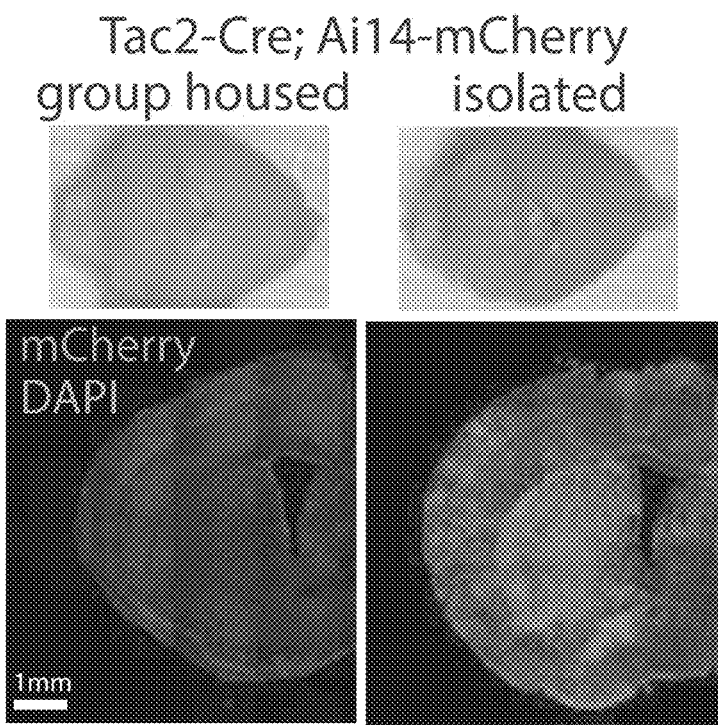
FIG. 9EE
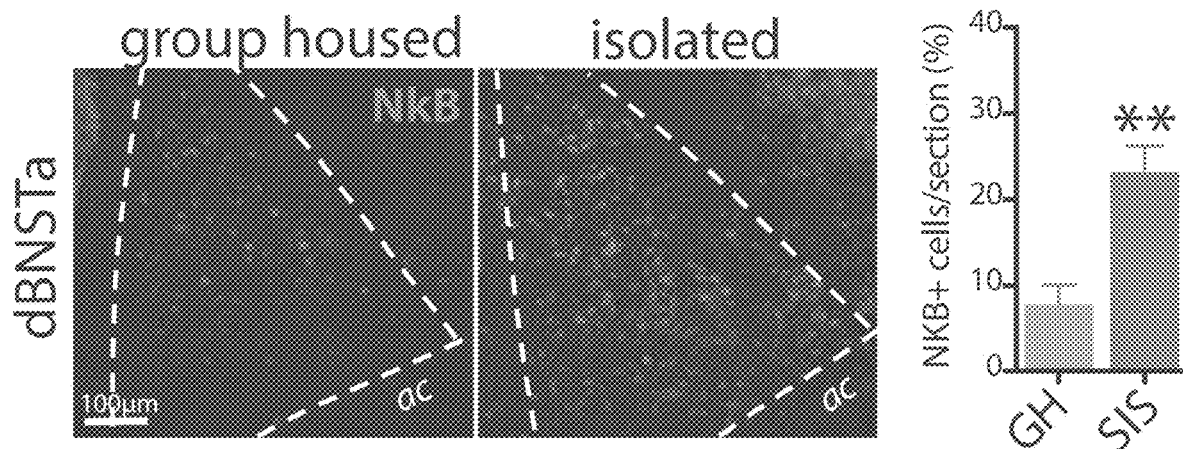
FIG. 9FF
FIG. 9GG social interaction

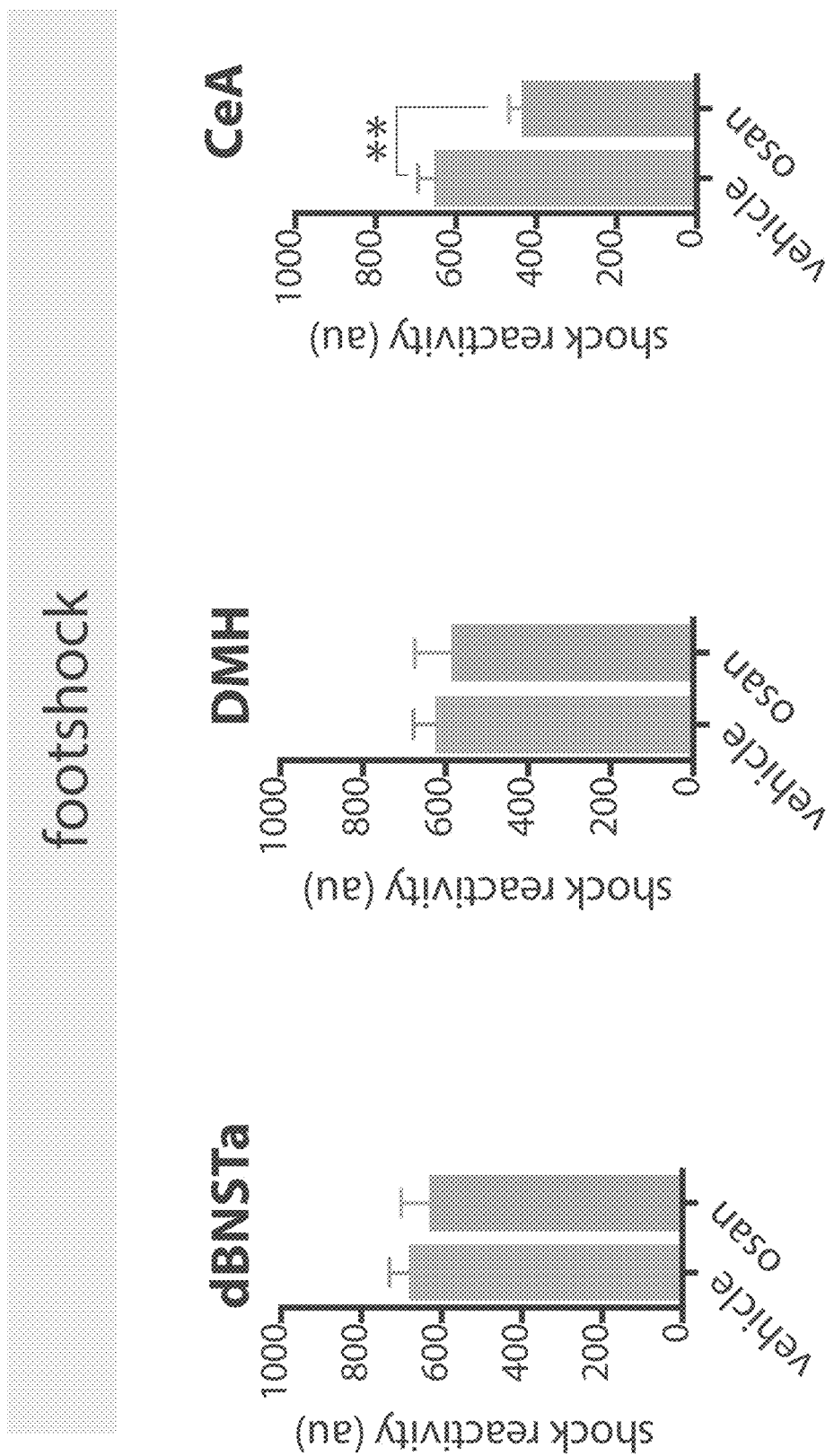

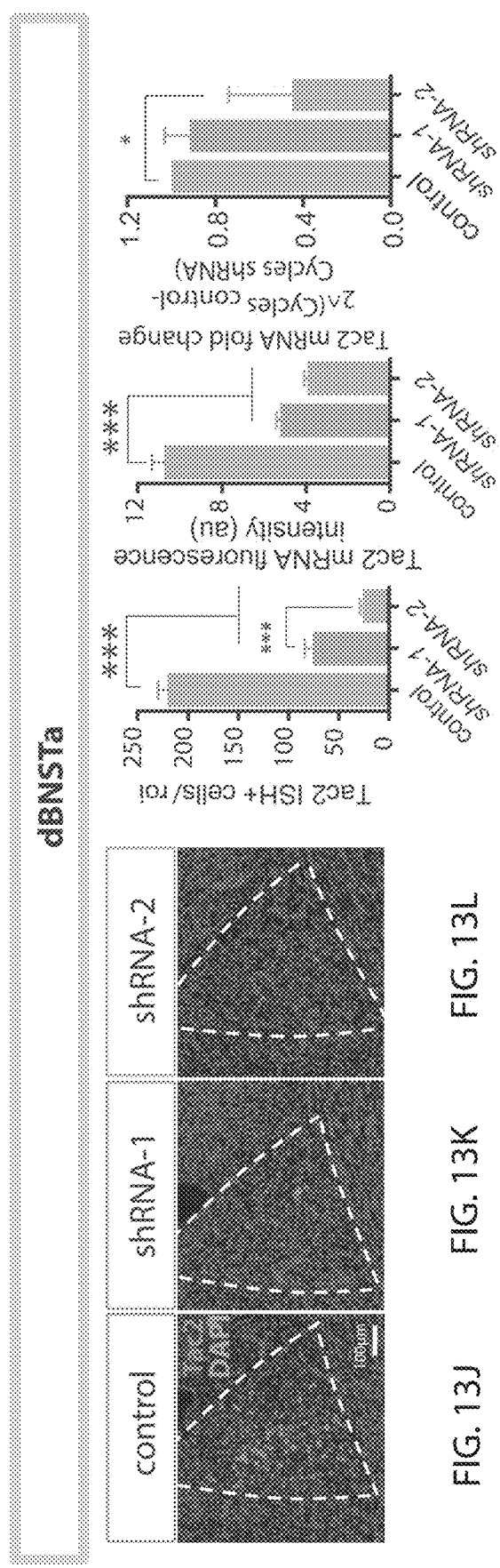

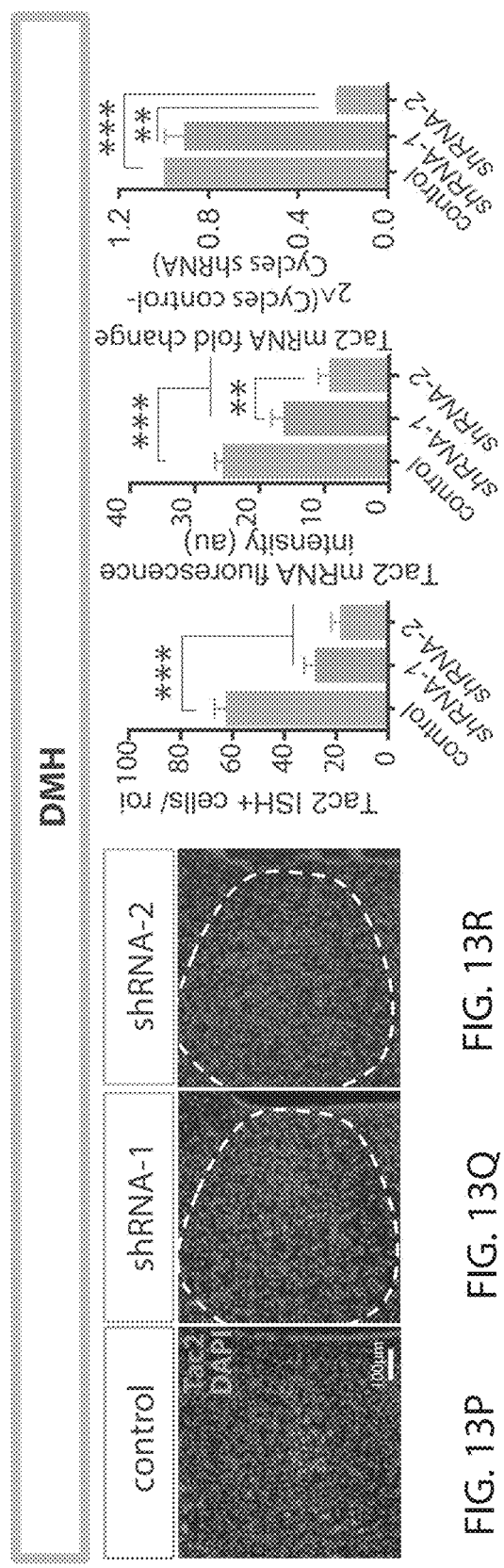

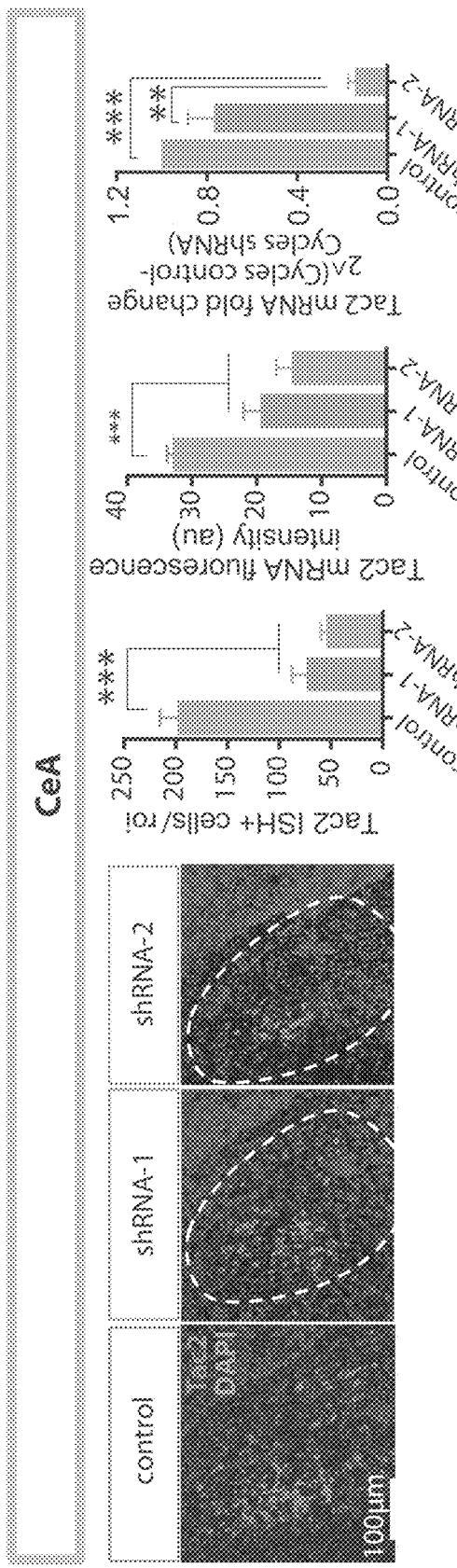

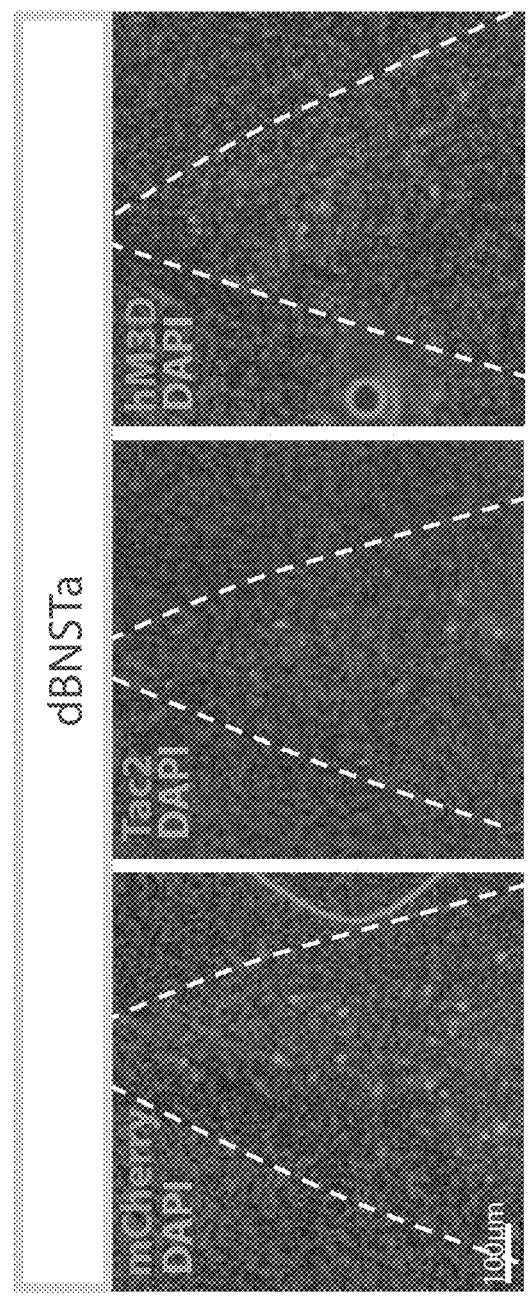
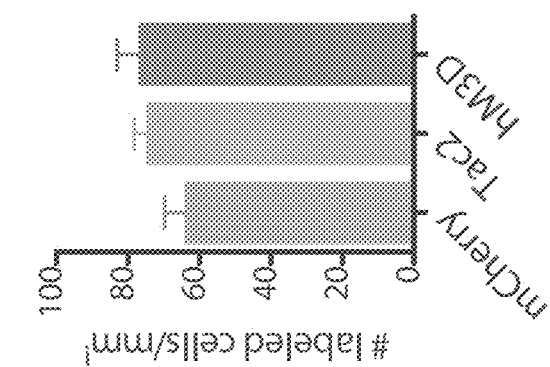
FIG. 14A  FIG. 14B  FIG. 14C  FIG. 14D

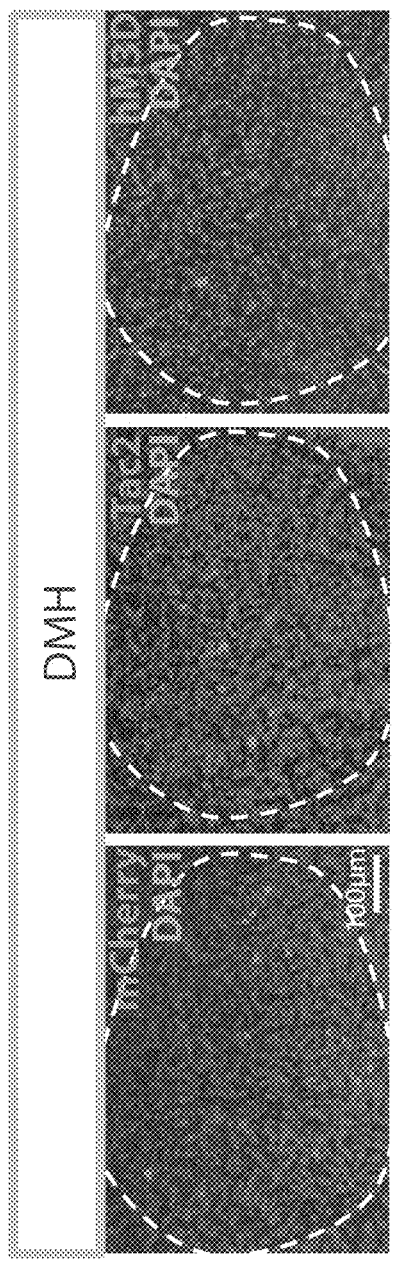
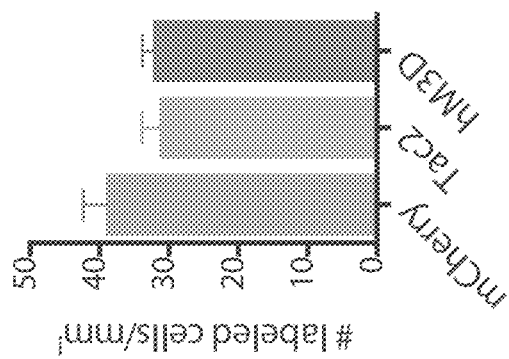
FIG. 14E  FIG. 14F  FIG. 14G  FIG. 14H

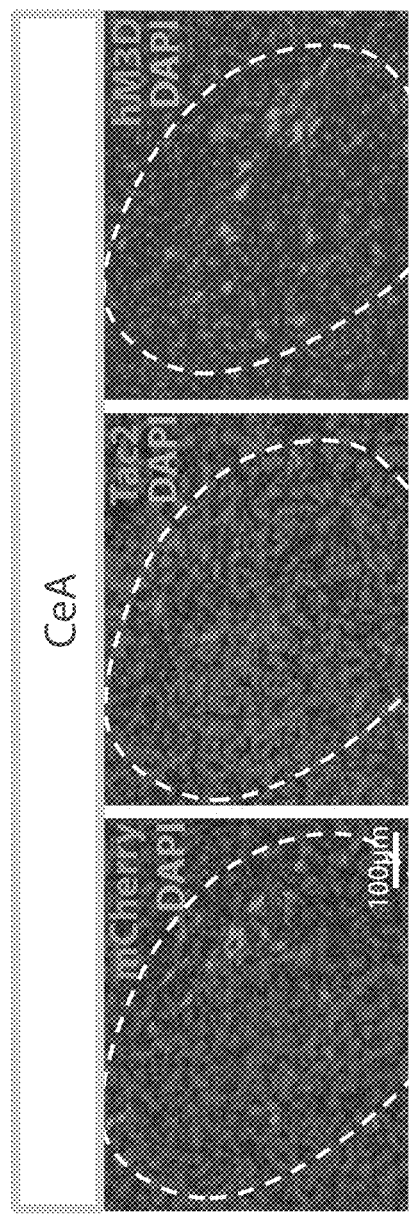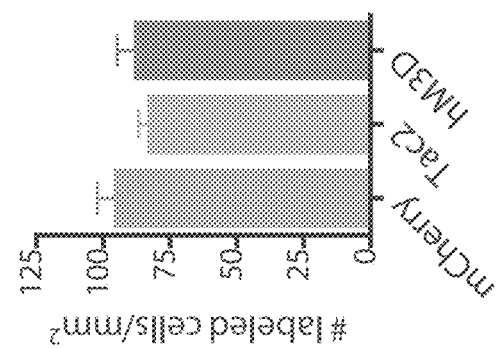
FIG. 14I   FIG. 14J   FIG. 14K   FIG. 14L

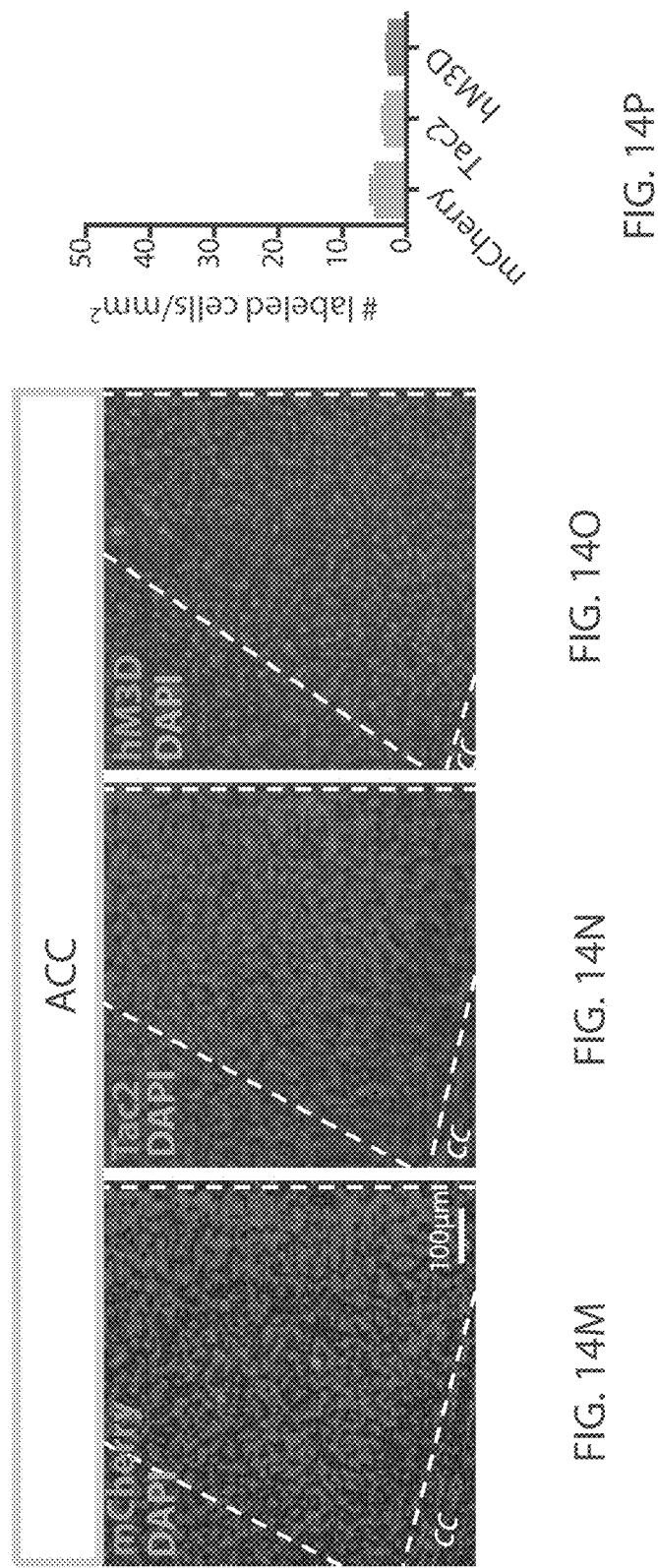

SEQUENCE LISTING

```
<160> NUMBER OF SEQ ID NOS: 33

<210> SEQ ID NO 1
<211> LENGTH: 129
<212> TYPE: PRT
<213> ORGANISM: Homo sapiens

<400> SEQUENCE: 1

Met Lys Ile Leu Val Ala Leu Ala Val Phe Phe Leu Val Ser Thr Gln
1               5                   10                  15

Leu Phe Ala Glu Glu Ile Gly Ala Asn Asp Asp Leu Asn Tyr Trp Ser
                20                  25                  30

Asp Trp Tyr Asp Ser Asp Gln Ile Lys Glu Glu Leu Pro Glu Pro Phe
            35                  40                  45

Glu His Leu Leu Gln Arg Ile Ala Arg Arg Pro Lys Pro Gln Gln Phe
        50                  55                  60

Phe Gly Leu Met Gly Lys Arg Asp Ala Asp Ser Ser Ile Glu Lys Gln
65                  70                  75                  80

Val Ala Leu Leu Lys Ala Leu Tyr Gly His Gly Gln Ile Ser His Lys
                85                  90                  95

Arg His Lys Thr Asp Ser Phe Val Gly Leu Met Gly Lys Arg Ala Leu
                100                 105                 110

Asn Ser Val Ala Tyr Glu Arg Ser Ala Met Gln Asn Tyr Glu Arg Arg
            115                 120                 125

Arg

<210> SEQ ID NO 2
<211> LENGTH: 121
<212> TYPE: PRT
<213> ORGANISM: Homo sapiens

<400> SEQUENCE: 2

Met Arg Ile Met Leu Leu Phe Thr Ala Ile Leu Ala Phe Ser Leu Ala
1               5                   10                  15
```

-continued

Gln Ser Phe Gly Ala Val Cys Lys Glu Pro Gln Glu Glu Val Val Pro
            20                  25                  30

Gly Gly Gly Arg Ser Lys Arg Asp Pro Asp Leu Tyr Gln Leu Leu Gln
        35                  40                  45

Arg Leu Phe Lys Ser His Ser Ser Leu Glu Gly Leu Leu Lys Ala Leu
    50                  55                  60

Ser Gln Ala Ser Thr Asp Pro Lys Glu Ser Thr Ser Pro Glu Lys Arg
65                  70                  75                  80

Asp Met His Asp Phe Phe Val Gly Leu Met Gly Lys Arg Ser Val Gln
                85                  90                  95

Pro Asp Ser Pro Thr Asp Val Asn Gln Glu Asn Val Pro Ser Phe Gly
            100                 105                 110

Ile Leu Lys Tyr Pro Pro Arg Ala Asp
        115                 120

<210> SEQ ID NO 3
<211> LENGTH: 7
<212> TYPE: PRT
<213> ORGANISM: Artificial Sequence
<220> FEATURE:
<223> OTHER INFORMATION: targeting peptide

<400> SEQUENCE: 3

Thr Leu Ala Val Pro Phe Lys
1               5

<210> SEQ ID NO 4
<211> LENGTH: 7
<212> TYPE: PRT
<213> ORGANISM: Artificial Sequence
<220> FEATURE:
<223> OTHER INFORMATION: targeting peptide

<400> SEQUENCE: 4

Ser Val Ser Lys Pro Phe Leu
1               5

<210> SEQ ID NO 5
<211> LENGTH: 7
<212> TYPE: PRT
<213> ORGANISM: Artificial Sequence
<220> FEATURE:
<223> OTHER INFORMATION: targeting peptide

<400> SEQUENCE: 5

Phe Thr Leu Thr Thr Pro Lys
1               5

<210> SEQ ID NO 6
<211> LENGTH: 7
<212> TYPE: PRT
<213> ORGANISM: Artificial Sequence
<220> FEATURE:
<223> OTHER INFORMATION: targeting peptide

<400> SEQUENCE: 6

Tyr Thr Leu Ser Gln Gly Trp
1               5

<210> SEQ ID NO 7
<211> LENGTH: 7
<212> TYPE: PRT
<213> ORGANISM: Artificial Sequence
<220> FEATURE:

```
<223> OTHER INFORMATION: targeting peptide

<400> SEQUENCE: 7

Gln Ala Val Arg Thr Ser Leu
1               5

<210> SEQ ID NO 8
<211> LENGTH: 7
<212> TYPE: PRT
<213> ORGANISM: Artificial Sequence
<220> FEATURE:
<223> OTHER INFORMATION: targeting peptide

<400> SEQUENCE: 8

Leu Ala Lys Glu Arg Leu Ser
1               5

<210> SEQ ID NO 9
<211> LENGTH: 62
<212> TYPE: DNA
<213> ORGANISM: Artificial Sequence
<220> FEATURE:
<223> OTHER INFORMATION: shRNA1 first strand

<400> SEQUENCE: 9
ccgacgtggt tgaagagaac accgcttcct gtcacggtgt tctcttcaac cacgtctttt    60
tt                                                                   62

<210> SEQ ID NO 10
<211> LENGTH: 62
<212> TYPE: DNA
<213> ORGANISM: Artificial Sequence
<220> FEATURE:
<223> OTHER INFORMATION: shRNA1 second strand

<400> SEQUENCE: 10
aaaaaagacg tggttgaaga gaacaccgtg acaggaagcg gtgttctctt caaccacgtc    60
gg                                                                   62

<210> SEQ ID NO 11
<211> LENGTH: 62
<212> TYPE: DNA
<213> ORGANISM: Artificial Sequence
<220> FEATURE:
<223> OTHER INFORMATION: shRNA2 first strand

<400> SEQUENCE: 11
ccgcctcaac cccatagcaa ttagcttcct gtcactaatt gctatggggt tgaggctttt    60
tt                                                                   62

<210> SEQ ID NO 12
<211> LENGTH: 62
<212> TYPE: DNA
<213> ORGANISM: Artificial Sequence
<220> FEATURE:
<223> OTHER INFORMATION: shRNA2 second strand

<400> SEQUENCE: 12
aaaaaagcct caaccccata gcaattagtg acaggaagct aattgctatg gggttgaggc    60
gg                                                                   62

<210> SEQ ID NO 13
<211> LENGTH: 40
```

```
<212> TYPE: DNA
<213> ORGANISM: Artificial Sequence
<220> FEATURE:
<223> OTHER INFORMATION: shRNA1 Forward

<400> SEQUENCE: 13
aaccacgtct tttttaattc tagttattaa tagtaatcaa                    40

<210> SEQ ID NO 14
<211> LENGTH: 33
<212> TYPE: DNA
<213> ORGANISM: Artificial Sequence
<220> FEATURE:
<223> OTHER INFORMATION: shRNA1 Reverse

<400> SEQUENCE: 14
cttcaaccac gtcggctggg aaagagtggt ctc                           33

<210> SEQ ID NO 15
<211> LENGTH: 40
<212> TYPE: DNA
<213> ORGANISM: Artificial Sequence
<220> FEATURE:
<223> OTHER INFORMATION: shRNA2 Forward

<400> SEQUENCE: 15
ggttgaggct tttttaattc tagttattaa tagtaatcaa                    40

<210> SEQ ID NO 16
<211> LENGTH: 33
<212> TYPE: DNA
<213> ORGANISM: Artificial Sequence
<220> FEATURE:
<223> OTHER INFORMATION: shRNA2 Reverse

<400> SEQUENCE: 16
atggggttga ggcggctggg aaagagtggt ctc                           33

<210> SEQ ID NO 17
<211> LENGTH: 18
<212> TYPE: DNA
<213> ORGANISM: Artificial Sequence
<220> FEATURE:
<223> OTHER INFORMATION: mCherry Forward

<400> SEQUENCE: 17
ctcctcgccc ttgctcac                                            18

<210> SEQ ID NO 18
<211> LENGTH: 24
<212> TYPE: DNA
<213> ORGANISM: Artificial Sequence
<220> FEATURE:
<223> OTHER INFORMATION: mCherry Reverse

<400> SEQUENCE: 18
ggcgcgccat aacttcgtat aatg                                     24

<210> SEQ ID NO 19
<211> LENGTH: 48
<212> TYPE: DNA
<213> ORGANISM: Artificial Sequence
<220> FEATURE:
<223> OTHER INFORMATION: pAAV-GFP Forward

<400> SEQUENCE: 19
```
cctggaccta tggtgagcaa gggcgaggag ctgttcaccg gggtggtg          48

<210> SEQ ID NO 20
<211> LENGTH: 55
<212> TYPE: DNA
<213> ORGANISM: Artificial Sequence
<220> FEATURE:
<223> OTHER INFORMATION: pAAV-GFP Reverse

<400> SEQUENCE: 20
agcatacatt atacgaagtt atggcgcgcc ctacttgagc tcgagatctg agtac    55

<210> SEQ ID NO 21
<211> LENGTH: 1274
<212> TYPE: DNA
<213> ORGANISM: Artificial Sequence
<220> FEATURE:
<223> OTHER INFORMATION: Tac2-P2A-mCherry

<400> SEQUENCE: 21
gctagcgcca ccatgaggag cgccatgctg tttgcggctg tcctcgccct cagcttggct    60
tggaccttcg gggctgtgtg tgaggagcca caggggcagg gagggaggct cagtaaggac   120
tctgatctct atcagctgcc tccgtccctg cttcggagac tctacgacag ccgccctgtc   180
tctctggaag gattgctgaa agtgctgagc aaggcttgcg tgggaccaaa ggagacatca   240
cttccacaga aacgtgacat gcacgacttc tttgtggaca ttatgggcaa gaggaacagc   300
caaccagaca ctcccaccga cgtggttgaa gagaacaccc ccagctttgg catcctcaaa   360
ggaagcggag ctactaactt cagcctgctg aagcaggctg agacgtggga ggagaaccct   420
ggacctatgg tgagcaaggg cgaggaggat aacatggcca tcatcaagga gttcatgcgc   480
ttcaaggtgc acatggaggg ctccgtgaac ggccacgagt tcgagatcga gggcgagggc   540
gagggccgcc cctacgaggg cacccagacc gccaagctga aggtgaccaa gggtggcccc   600
ctgcccttcg cctgggacat cctgtcccct cagttcatgt acggctccaa ggcctacgtg   660
aagcaccccg ccgacatccc cgactacttg aagctgtcct tccccgaggg cttcaagtgg   720
gagcgcgtga tgaacttcga ggacggcggc gtggtgaccg tgaccaggac tcctccctgc   780
aggacggcga gttcatctac aaggtgaagc tgcgcggcac caacttcccc tccgacggcc   840
ccgtaatgca gaagaagacc atgggctggg aggcctcctc cgagcggatg tacccccagg   900
acggcgccct gaagggcgag atcaagcaga ggctgaagct gaaggacggc ggccactacg   960
acgctgaggt caagaccacc tacaaggcca gaagcccgt gcagctgccc ggcgcctaca  1020
acgtcaacat caagttggac atcacctccc acaacgagga ctacaccatc gtggaacagt  1080
acgaacgcgc cgagggccgc cactccaccg gcggcatgga cgagctgtac aagtaaggcg  1140
cgccataact tcgtataatg tatgctatac gaagttatta gaggtttca tattgctaat  1200 agcagctaca atccagctac cattctgcat aacttcgtat aaagtatcct atacgaagtt  1260
attccggagt cgac                                                   1274

<210> SEQ ID NO 22
<211> LENGTH: 18
<212> TYPE: DNA
<213> ORGANISM: Artificial Sequence
<220> FEATURE:
<223> OTHER INFORMATION: Digoxigenin-labeled Tac2 Forward

<400> SEQUENCE: 22
agccagctcc ctgatcct                                                18

<210> SEQ ID NO 23
<211> LENGTH: 18
<212> TYPE: DNA
<213> ORGANISM: Artificial Sequence
<220> FEATURE:
<223> OTHER INFORMATION: Digoxigenin-labeled Tac2 Reverse

<400> SEQUENCE: 23
ttgctatggg gttgaggc                                          18

<210> SEQ ID NO 24
<211> LENGTH: 20
<212> TYPE: DNA
<213> ORGANISM: Artificial Sequence
<220> FEATURE:
<223> OTHER INFORMATION: Tac1 Forward

<400> SEQUENCE: 24
gatgaaggag ctgtccaagc                                        20

<210> SEQ ID NO 25
<211> LENGTH: 20
<212> TYPE: DNA
<213> ORGANISM: Artificial Sequence
<220> FEATURE:
<223> OTHER INFORMATION: Tac1 Reverse

<400> SEQUENCE: 25
tcacgaaaca ggaaacatgc                                        20

<210> SEQ ID NO 26
<211> LENGTH: 19
<212> TYPE: DNA
<213> ORGANISM: Artificial Sequence
<220> FEATURE:
<223> OTHER INFORMATION: Tac2 Forward

<400> SEQUENCE: 26
gccatgctgt ttgcggctg                                         19

<210> SEQ ID NO 27
<211> LENGTH: 20
<212> TYPE: DNA
<213> ORGANISM: Artificial Sequence
<220> FEATURE:
<223> OTHER INFORMATION: Tac2 Reverse

<400> SEQUENCE: 27
ccttgctcag cactttcagc                                        20

<210> SEQ ID NO 28
<211> LENGTH: 19
<212> TYPE: DNA
<213> ORGANISM: Artificial Sequence
<220> FEATURE:
<223> OTHER INFORMATION: GAPDH Forward

<400> SEQUENCE: 28
tgaagcaggc atctgaggg                                         19

<210> SEQ ID NO 29
<211> LENGTH: 20
<212> TYPE: DNA
<213> ORGANISM: Artificial Sequence
<220> FEATURE:

<223> OTHER INFORMATION: GAPDH Reverse

<400> SEQUENCE: 29
cgaaggtgga agagtgggag                                                                                   20

<210> SEQ ID NO 30
<211> LENGTH: 20
<212> TYPE: DNA
<213> ORGANISM: Artificial Sequence
<220> FEATURE:
<223> OTHER INFORMATION: 18s Forward

<400> SEQUENCE: 30
gcaattattc cccatgaacg                                                                                   20

<210> SEQ ID NO 31
<211> LENGTH: 20
<212> TYPE: DNA
<213> ORGANISM: Artificial Sequence
<220> FEATURE:
<223> OTHER INFORMATION: 18s Reverse

<400> SEQUENCE: 31
gggacttaat caacgcaagc                                                                                   20

<210> SEQ ID NO 32
<211> LENGTH: 8514
<212> TYPE: DNA
<213> ORGANISM: Homo sapiens

<400> SEQUENCE: 32
cacgcaagcg aaaggagagg aggcggctaa ttaaatattg agcagaaagt cgcgtgggga        60
gaatgtcacg tgggtctgga ggctcaagga ggctgggata aataccgcaa ggcactgagc       120
aggcgaaaga gcgcgctcgg acctccttcc cggcggcagc taccgagagt gcggagcgac       180
cagcgtgcgc tcggaggaac cagagaaact cagcaccccg cgggactgtc cgtcgcagta       240
agtgcccgcg cggtgctggc cgcggctgcc cgggtcaccc cgccccgcat ctgtccgagg       300
tggccgcgct gggggcgccg ctgcggcgag ggacagtggg gagactggct cccaaaacgc       360
caacgcccct ctttgtcttc cacctgcaga gtttcctggt ttgaaggtgt gggttggtgg       420
gttagggggc tggggagtt gggattcagg agaagaggg ttggagaatc tttgggacgc        480
gattctctcg cctaaccggt acaggtgaga cttcagtcct tatgtttttg atcttggttc       540
atccgttgtg gggcagaaaa ttctgttgct ttaactcttg gataaccacc ctaatagat        600 acattatttc tctctttggt gtcttctcct cctacccctt cccagaaatc caacatgaaa       660
atcctcgtgg ccttggcagt ctttttttctt gtctccactc agctgtttgc agaagaaata       720
ggagccaatg atgatctgaa ttactggtcc gactggtacg acagcgacca gatcaaggtg       780
aggccccttc ccaggacggc ccgcacccct cttcctgggc tcgggagctg tcaccttccc       840
acgcaacagc accctagtta acgtggcacg caccgccacc acgaaagag gcagcggttg        900 cgtgcgagag gatggaaagg ggcactattt cccgggttcc ccacgggatt ttgtgcccac       960
gattcaagtt tcttcccgag ggctgcaccg tccggcccag gaactccctg cagtagggat      1020
gccctcccgg atgagcccga gatcctcaca aggcgggaaa tctcgtaaga tttcatcccc      1080
caggacctgg gatttcgggg gctccggtcc agctgcactg ccctagcgtc tgggcacggg      1140
cagaggaggg cgcctgggtc gcgggcagca gcggcacac gcgcgagctg caggggattt      1200
ggagggccgg aggctggagg gaagttaatt tcctgccttc acgtttgttt tgcggacctg      1260

```
aggatgtagc ttgaagtctc cctttagaaa ctcgtaggct acaggcgctg gggagcgcgc    1320
ctcggaaaaa cggtgaaagt cgtctgtaaa gcgttgtcac ccttccccac cggagcccca    1380
gccccagatc ccacacacct gtgtgcattt agggcggtga ggactctaca aagccggcac    1440
cgagacaaga caaagtcagg tggcggcgca gcagatgagg gaaggtcccc gggctgggag    1500
gaaagagcgg aaagcgctcg aagcttgaag acgccgagcc agctgctaac tcgccctggc    1560
aggcttgcgg ggggcgggac gcgagttcgg cggggagggg cgcagagagg cagcgcctcg    1620
ggagggaccc cgctcagccc gagcgtgggg aaggccgcct ccccacgcct cggggccgga    1680
gtacagcggg gggaagggct cggggttgctg ggtgcctcgc tctggttgcc ttacacgccc    1740
tttgtccgtg cttttgtctc ccaggaggaa ctgccggagc cctttgagca tcttctgcag    1800
agaatcgccc ggagacccaa gcctcagcag ttctttggat taatgggcaa acggatgct     1860 ggtgagatag gcgaccgtcc ctaggtgtct tgggcagccc gccctgtctg ctcactcctt    1920
cctggagtac cccagggtct ctcgctctga atagagattt ccactccaag agggtgtaa     1980 ttccccaggc gcgacattgg cccacaccgc actaaggcac gcacgggccc gcgggggag     2040 ggaaagatct ggttcgcatg cctcactgta ttcgagtgaa gcgctccctt gactaaagat    2100
ccaaactgac aaagggaagg cacgggcctc caggggtagt actgcggatg atccaagtgc    2160
atgtggaaga ggattttata gcattccctg aggtgagagt acatttgtct tgggatagaa    2220
atatcgtttc cttgaattca tcgcacggtc agtggaacat gtagttaatg acaattcgtc    2280
tcttgtcaga ttcctcaatt gaaaaacaag tggccctgtt aaaggctctt tatggtaaac    2340
attcctataa atctttatt tactattgtg aaagcacatg taggaaagtg aaataaaatc     2400
ttttatgggc tgaaatacaa gatctgggtc atgcctgttt aataaagaga tggatttgcg    2460
cactctctct cggtttctct ctctctctgt cactctctct gtctctctct ctctgtcact    2520
ctctctcagt ctctctctct ctctttctct ctctctctca gtgggtggcc agccttgaag    2580
gtgggatgtg ttacagtctt atagttaata agaggcctca gaagtctcat agtcctaggt    2640
ttgaatccca tagaaggcac ttaataaaaa ttccatttgt ttgtttaaat atttagtttt    2700
tatgattaat aatttgttta gcatttatgg ttctgcttta ttcctcagga taatatatag    2760
atagaaaatg ttacatattt tgagaatcaa attattttat aaaagatata atgtagcatc    2820
tttaaaaaca aatctatatg tgtttgctaa ttttatcttt cttctaggac atggccagat    2880
ctctcacaaa agtaagttca aaattatttt gacatttatc aaatttaaat gtaaaattat    2940
attgaatttc actttatta tcttaccta ttttctgtca tgactctagg gcttaatatg      3000
tttaatgaag acaatataag aatggggag attcatatta catccagaat atggttgttt     3060
agacatattg tacttagcaa agagatgcat tatattaaaa aagaaaaaaa tgtctttaa     3120 gtcccttcaa ttgttagttt tagagaagaa tttcaatcct aggattagaa atctaccata    3180
catatttctt cccagccacc cacccctaa gcttactttc actgtaaaca aacaaacaaa     3240
caaacacgaa accccacaa gcattatag gcatctccta actcattta gtatgcttgg      3300 tccaataatg atgtcattta ttagggtcat ccagcagcca attaaatgga atgagtgagt    3360
gaacatgagt agagaatcca tactaaaaat gaagacggta gagatgcagt ttttttaatcc   3420 cctaattgaa tgggaaaact cgatcagtaa aacatttctt agggcagcaa agatggcaaa    3480
attgtggtat gtgaaggtca ttaaatttgt ttctcagtta atggaaccgg agttgacaag    3540
aagtggaaag ggtctatctt catcgtattg tccactcacc tattgtaccc tgtcatggat    3600
```

```
ttggttcatt gggtggcaga gcaggccaca ttaacgtagc agctctattc tcaactatta    3660
aaataaaaac caagagaaat tctctcacta gcattaaaat agtaaccttt ccaaagagtt    3720
catctttgaa aaataaatag tattcatatt tactttctaa ggatttgact ttgaagagaa    3780
ttatatataa aaattctatg taataaaaaa tgtactctgt tcatgtgaaa actaataaac    3840
ttttctgaaa ggagtatctt ttaatatcca ataaaataaa aacagtgacc ttttagaaga    3900
ttataatcat caaggaaagg aatctggttt aattaaggtc tacttgctga gaagtacaac    3960
ttattaataa cacaaggaat tatgcttgga tatttcactc tcacacaaat gtgaaattga    4020
cttcctaaaa aatcaaacct agctcaaata acaatatttt atataaaata ttttagaccc    4080
ttacataaca gataaaatat atgaatagag agtgcttgct aatattaaat atagaattaa    4140
gaaaagtggt ttcattgtat tgttttagtg taatttataa aacttttaag gaatctttat    4200
ttcttcagtc tcaccaaaac ttgaagtaga tagatatttta ttatacagac atatattcag    4260
aagcttgctt tgttctggtt ataatagttt gttcctcaa agatatacat attaaaatac    4320
ccctaaatgt atttttccag gacataaaac agattccttt gttggactaa tgggcaaaag    4380
agctttaaat tctggtatgt atgaaattat gactgaaaat agacagtatc tcaaatctat    4440
ttctattttt tctaagacat agttttaaaa tattaaaaag gagtggtaga tataaaaatg    4500
agtattatgg tggaaaaatt taattgttgt acttgtaacc acaaatggat ttatagctgg    4560
ttaagctaat actaccacag tatctgtcta tttctctcca atcaccattc ttaccagtgt    4620 ctgcccatt taatcattac caacctgaat ctttgggtta gtgctatatt ctttcctata    4680
gatctgttaa ataagccgtg tttaacctta ctgaactaag ggggagtggg gagtgcaggg    4740
aagaatgagg gtgatttca cttgttatca agtaatttg aaagttttac aagacattac    4800
atttggcgat cttccaatac aaaaataaat tcacaaaaca aattctttat gcaaattaat    4860 cacttttat gaagttgtag aaattcaaaa tctaaacatc ctgatggatg ttggagagga    4920
caaaagtgat acggtttatt ccagtacttt caaaaaggaa cacaattaaa tatccttgag    4980
tgttataaat tggttctggc tataaactcc ttagagagaa aggatgccac aattctcatt    5040
ttaattctga acaactttt cgtatgatat aaaggctgca ggtttccttc tcttcaattt    5100
ccatcttctt tgtaaatacc acgtacatat atctgaaaac cattattagt taactcattc    5160
atcacactga tttcaatgta aataacccct agatcatttt aatagaagct cacttttgt    5220 taagaccttta tagctcttac ctctagggct tcttggaaaa gctattcaaa ttctattttg    5280
ccttcagtga aaatagaatt aaaatactaa atacgttatt aattataaag taatcagcag    5340
ctgtcttacc catttagaat atttccagtt tctagacaat ctataagatg tgctggctta    5400
atccttaatt atctggatcc taggaaaaat aattatccta gtgttttta atggagatt    5460 ttttctttat tgtgaaatgt aagacttggg tacattaaat aaaaccactt tctgtggggc    5520
aaaaatcaaa acgcgcaata gaaaaaaaaa gttaacacaa tctgggctac ggcagaagcc    5580
agagaatata ttcatataat tgaaaagttc taagtgtttc ataattgacc ttttgataca    5640
aaatttccaa taaatctgga atttgaagtt cttggtgaag tccacaggac ttcctagtgt    5700
tcttattggg tccccacttt ctatttagac actaccttg catcttctca ccagtcattt    5760
tgggctgccg aagtgtaaaa gtgtaagaaa ttatcaatgt gccttaatga aaaacttgta    5820
attgttttat taatatgtat tatcttccca cttttggaaa tgaaatataa atttaaacca    5880
caatggcttt tatttgtacc aatacatact agtcctcact taattgtagt tttcttgata    5940
atcatattag tcatcaactt tccatttcca gaattgatat aggtttcaga acatgcttaa    6000
```

```
ctttacaaat gtagatattg tacaagttag aacagattaa atacaattaa atgtacttaa   6060
aataataaca taattttaag tagtgataaa aatcactgta gtgaatcagg atcaatttat   6120
aactaaatct tgttcctcc attttagtta aggaaatata aataggtgaa atgtggaaaa    6180
aaatgtgata tgatccacag tcaatcaggg atcttttat gtacctcatt gaggcaaggt    6240
tatcatagcc ttaatctata gccctctgat ctttacccac tcatggtcag ggaccccttt   6300
gacaatctga taaatctaga tagatgccct ttcccagaga aaccctcatc agctcataca   6360
ctcaaaaatt tatatcaggc ttcagagggt tcaaagacca ggtaagaaac tctgcttcca   6420
tgtaagagga cattatgttc cagctaaatc actgtctgtc tttagttggt ttacattagc   6480
tttcatctaa tttctctgag gaatagagtc atgttaccta aagcttgtca gagactgaac   6540
tgggccatt catcctgttc ctaatataat caaaccagaa tgagaaataa actgtttcct    6600
tccctcacgc ctgtccagtg ttggctcaga ctgttctgcc tcacaagtgc atacttaatt   6660
gatgtaaaat atgcagctta tgttaaccg cacttaaagg atagctgggt gtttaagacc    6720
agtattaaaa gagggaagtg ataatactgg tgcctttacc tgtcttctct gtcagcaaat   6780
cttctcactg aggaaactgt ttagagtagc acttattatt cctacagatc cttcacagat   6840
cttctactc tttctgttta cattcagtat tttatacagg ccatactgaa tttcaaaaag    6900
catagtagtt ccactatacc atacgtctaa gtctataagg tattcgttaa ggatgaaaaa   6960
tatcccaaaa tacttttatt gcaacagtct gattttacc cctttgtggt tacagatccc    7020
tttgaaatta tatataataa atataatata atataatata caattttggc attttttgt    7080
ccagataatc aatgtattta aattacttgc tagctatatg ttaaatacct ttggaagcaa   7140
taattaatgc ttcacaggcc attaaggtgc tagtgaaaag ttaaacagta tggtatttag   7200
atggctcaac tgacttacct atggtaaatg ggctgttttt agtcttgagg gcagtccatc   7260
actgggaggt atccacaagg taggaagaga cccctacaca attagatgcc ccttgaacaa   7320
agatcagcaa acttttcctg aaaagaaaca gattataaat attttaggct tgtgagcca   7380
tgtaatctct gttgcaacta cccaaatctg ttattttagg ccaaagcagc catagacaat   7440
atgtaaatga atgagtgtgt ctgtattcct ataaacctct ttacaagaac aaatggtatt   7500
ctagatttgg cccatggtct ctgctagaat aaaagtccca catttggttt ttatcctact   7560
agtattcctg gttattttag gcattgtcct ttctagaatt cactatgggt atctgccact   7620
gcttgagaaa gctgctgaga atcaacactg caatatattg tggaaatatg ctttgggggc   7680
accaagtata tgatgaatga tgaatgaaac cgagttctgt ggttagatca tttccaatca   7740
gaatagagac tgaggcagga ttggaagatg tgcagataac attcttagaa atacttctgt   7800
agagggaaaa tgtcattatg agtttaaaat aaattactat atgccctgaa ctttagttgt   7860
gtaactccct cagtgaattc acttaaaaaa cactttatct cttctttgtt ttcagtggct   7920
tatgaaagga gtgcaatgca gaattatgaa agaagacgtt aataaactac ctaacattat   7980
ttattcagct tcatttgtgt caatgggcaa tgacaggtaa attaagacat gcactatgag   8040
gaataattat ttatttaata acaattgttt ggggttgaaa attcaaaaag tgtttatttt   8100
tcatattgtg ccaatatgta ttgtaaacat gtgttttaat tccaatatga tgactccctt   8160
aaaatagaaa taagtggtta tttctcaaca aagcacagtg ttaaatgaaa ttgtaaaacc   8220
tgtcaatgat acagtcccta agaaaaaaaa atcattgctt tgaagcagtt gtgtcagcta   8280
ctgcggaaaa ggaaggaaac tcctgacagt cttgtgcttt tcctatttgt tttcatggtg   8340
```

```
aaaatgtact gagattttgg tattacactg tatttgtatc tctgaagcat gtttcatgtt    8400
ttgtgactat atagagatgt ttttaaaagt ttcaatgtga ttctaatgtc ttcatttcat    8460
tgtatgatgt gttgtgatag ctaacatttt aaataaaaga aaaaatatct tgaa          8514

<210> SEQ ID NO 33
<211> LENGTH: 6564
<212> TYPE: DNA
<213> ORGANISM: Homo sapiens

<400> SEQUENCE: 33
ctttatcagg gagctgggac tgagtgactg cagccttcct agatcccctc cactcggttt      60
ctctctttgc aggagcaccg gcagcaccag tgtgtgaggg gagcaggcag cggtcctagc     120
cagttccttg atcctgccag accacccagc ccccggcaca gagctgctcc acaggtaggc     180
aagtgggaga atgctggatg gaccagagct ggcaccaggg gacaggagcc agcgtcagga     240
gggaataaag cagatggcag cctctgatag gggagcaggg gactgggaag gtgagcacaa     300
agcacctgta gggccgagag ctggttggtg tttggagcct gtggctacag actcattctt     360
tcataccaga aagttttgc ctaagtcttg ggattatcta gtactggaaa atagcatcca      420
ggatccctcc tccagctgac tgaggaaaca gaccagtcca tgtcctacaa atctatcatc     480
tttcttggga gctagagtcc tcctggcacc actatagcat tgcacatctc ctggggagat     540
atctgatggg gtagcaggga aactaagccc aagggctgta ccccttctc agaaatactt      600 tccaccctct ctccagacca gggcttggac agtggagttg ggggctgggg aagcagggtc     660
aagccaagct gctggtaatg aatgtctctt gtgtcttcac ccatgctgta tcttcctctt     720
ctctccttta cctgagtcct gtccctttgc tctcccaggc accatgagga tcatgctgct     780
attcacagcc atcctggcct tcagcctagc tcagagcttt ggggctgtct gtaaggagcc     840
acaggaggag gtggttcctg gcggggccg cagcaaggta agtctcccct ggcagagtac      900
tggggacatc acgggaactt gggactctgc ctgtctggac agctgtagtg aggaaactgg     960
ggtggggggg ttgtccgtca gagggcattt tgcctccctt tggatttctt tgtttctctg    1020
gtcctttcat gttcccactg tctccaggtg tgtttgtgtc tctgtatctc tgcatgtctt    1080
tgacaccttg tacataaaag gtgccctaca aatatgttgt ttggtgggtt gattgatggg    1140
agacttggtg attggatggt actgtgaggg gtgagctagg gtggtctaag gctctctata    1200
gtctacctca ggtcccttg caagggacag atctcttcta tttcctggat ggtatgaaac     1260
agtcagaatt tctttcccaa atggttattt gtgtgctatt ttacctatca gttatgtgta    1320 ttgtttttatt ttcaaaatgc aaataaattc ccttatcttt tgctcatcca cccccagtaa   1380
cctcaggtgc ttctaagatc caacccctt ccttcttctc ttttctccct tgcccgcctc     1440
tatcctctgc ttagtcagga taggaaaaca acaacagcaa aaaaaccaga ttgagcctcg    1500
atttccacag ttcctttacg aaaaagaata ggaattgtca gggtagggt acaggggag      1560 gatagggagg aagtcttttc aaggttttga aatgacagca attacatcgg tacaaatgct    1620
tttaagatga ttgcgggtgg gacttattac aaattcaatg tgtgaagttt aactgcctct    1680
tcagctcaaa tctgttcagc atctcattat aggaggtggg cagagtattc aacaatttgg    1740
gaaaagtggc tgcctgaaca ccacatgctg ggccaaggga gttatcacca gggcagcctt    1800
gcaggtggca gcagttgtgc catatccaaa aggccagaac cgttaaaaaa aaaacacccc    1860
aggggagtgc caagtatggg ctggacaccg tttggagcca caaagttcca gcccaggata    1920
gttagagtat ctgagttctt ctgagacaaa cttgtttcaa gaccttggcc aatgagatgt    1980
```

```
ccctctgcc cctcttggtc aatgaatgag agggattgcc atcctacccc ttctccttga   2040
gagtctgtga ggatgaggga aattggggca ggaagagggt agtacatagg tgtgcctagg   2100
caactgggtt ggtatgtgtg ggggtgtgtt ctgtgtaaat gcacttctgt gtgtgcacaa   2160
cagccgaagg atgcctgggt tctgaaagaa gaggcgctgc tgagacttga gatttgagat   2220
gaaaatctcc agccatgatc attgttattg tctctctgca gctgcaatta actggctgtg   2280
tggtgtgtgc ccaccaccct gctgtacgca agttgctaaa aaaaaaaaaa aaatcacagg   2340
gacaatcaag agcccgtgct gggcaacagc tctagaactt gggattcagt tgtggagaga   2400
agaagacgtg ccttctgagc atgttgcctt cctggaattc tagacctagg gccaaaaggg   2460
agagggagag aaaactagag gcggaaagcc atggagaata gagaagagg tggtggaaaa   2520 cagggagaga aacatccatg gacatcgtgc agagtggggg aatcacaggt gcagatgtgt   2580
gcctccaatc tcaccatgca tgtgaatcac ctgggggggct gcttaaaatg cagattctgt   2640
ctcaggaggt ctggggtagg aacaagagtc tgcatttcta acaggctctg tgtagtgctg   2700
gtgttgctgt tggtccacag gtcactcctg gagcacctac ttctcgtcca gtgtgaacca   2760
gaggaaactc tgaaagaaat agggtgtcgg attcaggatg ggctcaggaa gaggctgttt   2820
cttgtgggaa aaggatgagt ggatccgggt gggagcctcc tgcctcaccc ctctttgttt   2880
cttccctaga gggatccaga tctctaccag ctgctccaga gactcttcaa aagccactca   2940
tctctggagg gattgctcaa agccctgagc caggctagca caggtaggag gcggccctag   3000
gggagagggg aatgagggc aggattctga agataagagg cctgggagat cctttcagat   3060
gggagagaga tgggggatag cttagtgaat cggtgagggt tgtgatctga accccgctct   3120
catcactttc caacttcact ccccatttag acatctgttc ttggtttcac agatcctaag   3180
gaatcaacat ctcccgagaa acgtaagtac cctcttctcc ctccctatct cttgccactt   3240
gcccagagct ctgtggggca ttgggcccag gggccatttt gtccagcccc ttctcacctg   3300
gtacaaacaa tatgccagct cccactgctc agccaacctt tcctgaaagg gagaggccat   3360
ccagaactag gaggaagctg tgtgagggg catggtgggc tctccctctg ctggctggtc   3420
cttggaaaac aaggggatct cttcgtggcc ctgaaaattc caaatcaggc acctgctaga   3480
gcagaaaatt cttgaaatgt ggaggaagga aaggtgagca gagagagtgg gtttagggga   3540
ggcacttgct aactgtgagg agtcatgctt tgacaagaaa aaggaacaga gaccagaaac   3600
ccagtctcag aagtgttgac ccatgtctgg ggagatgctt cactttctca tcatcactgc   3660
tgacaatgtt ggccctttc tgcaggtgac atgcatgact tctttgtggg acttatgggc   3720
aagaggagcg tccagccagg taggagtgtg tggaggtaca gtggaagggc ttagggtact   3780
ggcagagtat gacagaagtc acgtgcctca tatttgtcac cagagggaaa gacaggacct   3840
ttcttacctt cagtgagggt tcctcggccc cttcatccca atcagcttgg atccacagga   3900
aagtcttccc tgggaacaga ggagcagaga cctttataag gtagtcctgt tgcagctggg   3960
aggaaggata gggagactct gcttccaccc cagtctccca actctgtctt tgaacactgc   4020
ccgtcatagc cagccctttg ctgttggatc agggtgtagt tcacattcag aaagatccct   4080
cttacttaca ctgttcgctt taccctagac tctcctacgg atgtgaatca agagaacgtc   4140
cccagctttg gcatcctcaa gtatccccg agagcagaat agggtaagga ttgttcatta   4200 gagagggggag agggggactgg ggaggggggct gtgggggttg ccagctgtgc atttcctccc   4260
atgctacagg tattaaagct catagatttg ccctgaaata cactgccaat gcccagcaca   4320
```

```
ctgtcggcca aacacaaaga cacttagagg cacgtgtgtt tgtacacatc ccccgtctttt    4380
catctctttc ctctggatca tggacggcag ctgactattg agcaggagtg agtgttggga    4440
gatgaggaga gagggcttc cccgatgggc aatttctgtt gtttggactt cattcttttg    4500
taatctatgc aaaaagatgg agaaattatt atctgataat tacaaatacc acaaccaatt    4560
cacaggcaag catttgcctc ccaggcaggc tgagcctttc aaatcactca gaatcctggg    4620
ttacggggcc cagaaggtag tcatacacaa ggatgattca ggaagaaatg caaggaactc    4680
tgaaatctaa tggggattag caggaaacca tatctgaatc tctctttagc ataatgaata    4740
agaacaatgg cctgaatgtg aatcctggat ctgccactct atctgtatct ttttggccaa    4800
ggtacatatc ctcctgtgct tcagtttcct catctgaaaa atgaaagtga taatagtatc    4860
tcacagggtt gtggttttga ggattgagta taggtaaagt gttcagaaca gtgccgggtg    4920
cacagtgctg tgtgccaatt ttatgataat tgtcccagtt tgggaggtat gggggatgtc    4980
ctaatgtttc ccctgactgg ctctgtctgg accccaggcc tgagtgggct gacaaattcc    5040
tcacttggta tgcgagtgta agagtccccc agggaagtgt ctagtcaaaa cacgaacctt    5100
ccgccttgac actgtcttcc cacacacagc aagagcagct ccaccaatgg cttctttttc    5160
actagcttcc aaagaattgg ggtggaggga gtgaaaagga gagggagaga gattgggaag    5220
gctcgtaatc atggagagcc tcctgctttt ctctctgtgt ccctgttacc catactcact    5280
ggtctcaagg tggcacgccc aagacccaag gagctggtgc ttgatgatgc tgcctgtgca    5340
tgaattcctg ggaccagaga ctgagtctgg ccccccattt agtgttgggt gagagggcac    5400
aaagagctat aataactgta acttgctgat tacatggtag ttactgtatc attttgctct    5460
cattagatgt ttatttcagt cctgccgacg gccagataat tatacgagca gctatatctg    5520
gatgacatac tctgctccag cgttatgcac tggccataaa gataattaca gtgcaatttt    5580
gctatagtat tttatacaaa tggcaaaaac aagtgcattg tggaaatcta cttttaatgc    5640
ttgtttgtgc atccaggctc tttcagaggg acccataatt gcagctttca taatcttacc    5700
attgagggag cattcccaac ctgttaggtg tcaggcagaa taggacataa ggtttctggg    5760
agctggcatt taaagattag atgagatgga tcaacacaga tcattgtgtc atctgatttc    5820
attcatgtga aactgtaagt aatccctggg cctgtgcttc ctctgggagg tttctgggaa    5880
gaggaggaac tggataaggc aggggagca ttcatagtag ggcaccttgg gcagggctgt    5940
gtgtgtgtct ggctcatggt ggtgctagga tggcatgaac ttggttccta catctttggt    6000
ccacatgggc cccactggcc atgcacacag gtgtgtagag taatgtaaat atggcagctg    6060
ggaaggtgca agtacctgcg gctaggagag ttccatcctc aggcccaaag cctggagggc    6120
aggctgaggg tcaagacttg ttcttttcctc tctcacagac gcctctcccc ttctctcctg    6180
ctgccacagc aggttttcag tgggactttt ttacaggata aagatgtga tttcagtgtt    6240
ttttttttgtt ttgttttgtt tttgtcctc agtactccac ttccggactc ctggactgca    6300
ttaggaagac ctcttcctc gtcccaatcc ccaggtgcgc acgctcctgt taccctttct    6360
cttccctgtt cttgtaacat tcttgtgctt tgactccttc tccatctttt ctacctgacc    6420
ctggtgtgga aactgcatag tgaatatccc caaccccaat gggcattgac tgtagaatac    6480
cctagagttc ctgtagtgtc ctacattaaa aatataatgt ctctctctat tcctcaacaa    6540
taaaggattt ttgcatatga atga                                           6564
```

EXPRESSION OF NEUROPEPTIDES

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. The present application claims the benefit of U.S. Provisional Application No. 62/580,846, filed Nov. 2, 2017, which is hereby incorporated by reference in its entirety.

STATEMENT REGARDING FEDERALLY SPONSORED R&D

This invention was made with government support under Grant No(s). MH085082 & MH108734 awarded by the National Institutes of Health. The government has certain rights in the invention.

REFERENCE TO SEQUENCE LISTING, TABLE, OR COMPUTER PROGRAM LISTING

The present application is being filed along with a Sequence Listing in electronic format. The Sequence Listing is provided as a file CALTE133ASEQUENCE.txt, created and last modified on Oct. 31, 2018, which is 29,717 bytes in size. The information in the electronic format of the Sequence Listing is incorporated herein by reference in its entirety.

BACKGROUND

Neuropeptides (NPs) are a class of neuromodulators that play an important role in the control of emotion, mood and affect, as well as in motivational states such as hunger and sexual arousal or in sensory states such as pain. Neuropeptides are released from specific subsets of neuropeptidergic neurons (NPNs), and exert their effects on target cells that comprise specific subsets of neuropeptide receptor-expressing neurons (NPRNs). In general, neuropeptides are released and act in a more cell type-specific manner than classical neurotransmitters, such as glutamate, acetylcholine and dopamine.

Field

Some embodiments relate to compositions and methods for expressing neuropeptides in a subject.

SUMMARY

In some embodiments, a method of expressing a neuropeptide in a neuron of a subject is described. The method can comprise administering a first nucleic acid to the neuron in the subject, the first nucleic acid encoding the neuropeptide, in which a first promoter is operably linked to the first nucleic acid. The neuropeptide can be expressed in the neuron. The method can comprise administering a second nucleic acid to the neuron in the subject, the second nucleic acid encoding an conditional receptor configured to alter the polarity of the neuron upon application of an agonist or stimulus, wherein the first promoter or a second promoter is operably linked to the second nucleic acid, whereby the conditional receptor is expressed in the neuron. The method can comprise applying the agonist or stimulus to the neuron of the subject, causing the conditional receptor induces a change in polarity in the neuron that expresses the neuropeptide. In some embodiments, the altered polarity in the neuron activates the neuron. In some embodiments, the altered polarity induces an action potential by the neuron. In some embodiments, the neuron is a neuropeptidergic neuron. In some embodiments, the neuropeptide comprises a neurokinin. In some embodiments, the neuropeptide is selected from the group consisting of neurokinin A, neurokinin B, neuropeptide K, neuropeptide gamma, and substance P. In some embodiments, the first nucleic acid further encodes a signal peptide In some embodiments, the first nucleic acid and the second nucleic acid are administered to the neuron in the subject in a single vector. In some embodiments, the single vector is an AAV. In some embodiments, the single vector comprises the first nucleic acid under the control of the first promoter, and the second nucleic acid under the control of the first promoter or second promoter. In some embodiments, the first nucleic acid is administered to the neuron in the subject in a first vector, and wherein the second nucleic acid is administered to the neuron in the subject in a second vector. In some embodiments, one or both of the first vector and second vector is an AAV. In some embodiments, the conditional receptor comprises a hM3DREADD and the agonist comprises clozapine-N-oxide, or wherein the conditional receptor comprises an optogenetic channel such as channel rhodopsin and the agonist comprises electromagnetic radiation.

In some embodiments, a method of altering a behavior in a subject in need thereof is described. The method can comprise administering a first nucleic acid to the subject, in which the first nucleic acid encodes a neuropeptide. The method can comprise administering a second nucleic acid the subject, in which the second nucleic acid encodes a conditional receptor. The first nucleic acid and the second nucleic acid can be administered in a vector system that provides the first nucleic acid and the second nucleic acid to a target neuron of the subject, in which the target neuron expresses the neuropeptide and the conditional receptor. The method can comprise applying an agonist or stimulus to the neuron of the subject, causing the conditional receptor induces a change in polarity in the neuron that expresses the neuropeptide, thus altering a behavior of the subject. In some embodiments, the altered behavior comprises a symptom of social isolation stress, aggression, or depression. In some embodiments, the altered polarity in the neuron activates the neuron. In some embodiments, the altered polarity induces an action potential by the neuron. In some embodiments, the neuron is a neuropeptidergic neuron. In some embodiments, the neuropeptide comprises a neurokinin. In some embodiments, the neurokinin is selected from the group consisting of neurokinin A, neurokinin B, neuropeptide K, neuropeptide gamma, and substance P. In some embodiments, the first nucleic acid further encodes a signal peptide. In some embodiments, the first nucleic acid and the second nucleic acid are administered to the neuron in the subject in a single vector. In some embodiments, the single vector is an AAV. In some embodiments, the single vector comprising the first nucleic acid under the control of the first promoter, and the second nucleic acid under the control of the first promoter or second promoter. In some embodiments, the first nucleic acid is administered to the neuron in the subject in a first vector, and wherein the second nucleic acid is administered to the neuron in the subject in a second vector. In some embodiments, one or both of the first vector and second vector is an AAV. In some embodiments, the conditional receptor comprises a hM3DREADD and the agonist comprises clozapine-N-oxide, or wherein the conditional receptor comprises an optogenetic channel such as channel rhodopsin and the agonist comprises electromagnetic radiation.

In some embodiments, a kit is described. The kit can comprise a first nucleic acid encoding a neuropeptide. The kit can comprise a second nucleic acid encoding a conditional receptor configured to alter neuron polarity upon binding of an agonist or application of a stimulus to the conditional receptor. Either (a) a single vector comprises the first nucleic acid and the second nucleic acid, or (b) a first vector comprises the first nucleic acid and a second vector comprises the second nucleic acid. In some embodiments, (a) the kit comprises the single vector, further comprising a single promoter that is operably linked to the first nucleic acid and second nucleic acid, the single promoter configured to drive expression specifically in neuropeptidergic neurons. In some embodiments, (b) the kit comprises the first vector and the second vector, the first vector further comprising a first promoter that is operably linked to the first nucleic acid, the first promoter configured to drive expression specifically in a neuropeptidergic neuron, and the second vector comprising a second promoter that is operably linked to the second nucleic acid, the second promoter configured to drive expression specifically in a neuropeptidergic neuron. In some embodiments, the single vector comprises an AAV, and/or the first vector and second vector each comprise an AAV. In some embodiments, the kit further comprises the agonist or the stimulus. In some embodiments, the neuropeptide comprises a neurokinin. In some embodiments, the neurokinin is selected from the group consisting of neurokinin A, neurokinin B, and substance P. In some embodiments, the first nucleic acid further encodes a signal peptide. In some embodiments, the first and second promoter are each a neuropeptide promoter or a neuropeptide receptor promoter; or wherein the single promoter is a neuropeptide promoter or a neuropeptide receptor promoter In some embodiments, a vector is described. The vector can comprise a first nucleic acid encoding a neuropeptide. The vector can comprise a second nucleic acid encoding an conditional receptor configured to alter neuron polarity upon binding of an agonist or application of a stimulus to the conditional receptor. In some embodiments, the vector further comprises a single promoter that is operably linked to the first nucleic acid and second nucleic acid, the single promoter configured to drive expression specifically in neuropeptidergic neurons. In some embodiments, the vector further comprises a first promoter that is operably linked to the first nucleic acid, the first promoter configured to drive expression specifically in a neuropeptidergic neuron. The vector can further comprise a second promoter that is operably linked to the second nucleic acid, the second promoter configured to drive expression specifically in a neuropeptidergic neuron. In some embodiments, the vector comprises, consists essentially of, or consists of an adeno-associated virus (AAV).

BRIEF DESCRIPTION OF THE DRAWINGS

FIGS. 1A-R show that prolonged social isolation stress (SIS) alters behavior in accordance with some embodiments. FIGS. 1A-D show alternative models for peptidergic control of an internal state influencing multiple behaviors controlled by different brain regions (dark gray circles, behavior A, behavior B, etc.). Control may be achieved by multiple (FIG. 1A) or a single (FIGS. 1B-D) neuropeptides (pQ, pX, etc.) acting directly on multiple regions (FIG. 1A, FIGS. 1C-D) expressing receptors (RX, RY, etc.) for the peptides, or on a single peptide-responsive "hub" region (FIG. 1B). In FIG. 1D the same peptide (pX) is expressed in different regions (small light gray circles, top) that control different behaviors in different peptide-responsive regions (large dark gray circles, bottom). FIGS. 1E-Q show a comparison between wild-type (WT) group housed (GH) control mice and isolated (SIS) mice (n=8 mice/condition) in the assays indicated (FIG. 1E, FIG. 1K, FIG. 1M, schematics). FIGS. 1F-G show aggression measured by the resident-intruder test. FIGS. 1H-I show freezing responses during ("during") or immediately after ("post") presentations of an overhead looming disk (FIG. 1H) or conditioned tone (FIG. 1I). FIG. 1J shows reactivity to footshock following tone tests. FIG. 1L shows frequency of freezing to a 17-20 kHz ultrasonic sound stimulus (USS). FIGS. 1N-Q show anxiety assays. FIGS. 1N-O show results obtained from open field tests (OFT), FIGS. 1P-Q show results obtained from elevated plus maze (EPM) tests. FIG. 1R shows a summary of results. Dark gray up-pointing arrows indicate isolation-induced increases in behavior, light gray down-pointing arrows indicate isolation-reduced behavioral responding. "n.c.", no change.

In FIGS. 1A-R through FIGS. 7A-I, data are represented as mean±SEM. *$p<0.05$, $p<0.01$, *$p<0.001$. Pairwise contrasts were tested and corrections for multiple comparisons were applied for post-hoc comparisons; bars without asterisks did not reach significance ($p>0.05$). ANOVA's, F values, t values, as well as additional statistical information for this and subsequent figures can be found in Table 2. See also related FIGS. 8A-R.

FIG. 2A is an illustration summarizing tachykinin ligand-receptor specificities. In FIG. 2F, the intensity of zsGreen expression was greater in isolated as compared to group housed mice. In FIG. 2G, the intensity of zsGreen expression was comparably low for both group house and isolated mice.

FIGS. 3A-M show that systemic Nk3R antagonism attenuates the effects of SIS in accordance with some embodiments. FIG. 3A depicts the experimental protocol. Following isolation, SIS or GH mice were injected (i.p.) with osanetant or vehicle and tested for the indicated behaviors (n=6 mice/condition.). FIGS. 3B-F show that osanetant blocked SIS-induced aggression (FIGS. 3B-C), post-loom freezing (FIG. 3D), post-tone freezing (FIG. 3E), and increased shock reactivity (FIG. 3F). FIG. 3G shows an experiment to test whether osanetant delivered daily during SIS can protect against its behavioral effects. "osan 1X" indicates an additional control group given a single dose of osanetant 24 hours before testing to control for carry-over of the drug (n=6/condition). FIGS. 3H-L show the effect of osanetant administered during SIS on (FIGS. 3H-I) aggression, (FIG. 3J) post-loom freezing, (FIG. 3K) post-tone freezing. FIG. 3L shows shock reactivity; a trend to protection (SIS-veh vs. osan during) was observed but did not reach the significance threshold (p>0.05). FIG. 3M shows a summary of results. "osan pre-test" indicates osanetant was given 20 min prior to each assay (FIGS. 3B-F) but not during SIS, "osan during SIS" indicates osanetant was given during SIS only (FIGS. 3H-L), and not 20 min before each assay. Faint gray arrows indicate original effects produced by SIS. Black X's indicate SIS-induced effects that were blocked by the manipulation. See also related FIGS. 10A-J.

FIG. 4A shows the experimental protocol. Mice were implanted with bilateral cannulae in dBNSTa, DMH, or CeA, isolated, and given osanetant or vehicle microinfusions (300 nl) 20 min before testing (n=6-7/condition). FIGS. 4B-P show the effect of osanetant infusion into dBNSTa, (FIGS. 4B-F), DMH (FIGS. 4G-K), or CeA (FIGS. 4L-P) on indicated assays. Osanetant (bars labeled "osan") selectively blocked persistent freezing in dBNSTa ("post"; FIGS. 4E-F), aggression in DMH (FIGS. 4H-I), and acute freezing in CeA ("during";

FIGS. 4O-P). FIG. 4Q shows a summary of results. Notations are as in FIG. 3M. n/a, not applicable (secondary to lack of freezing during stimulus). Down-pointing arrows indicate manipulation-induced reduction in a behavior not altered by SIS. See also related FIGS. 11A-K.

FIG. 5A shows a schematic of the experimental protocol. Tac2-Cre mice were bilaterally injected in the indicated regions with a Cre-dependent AAV expressing hM4DREADD-mCherry, isolated, and injected (i.p.) with CNO or vehicle prior to testing (n=7-8 mice/condition). FIGS. 5B-P show the effect of vehicle or CNO on mice expressing Tac2-hM4DREADD in dBNSTa (FIGS. 5B-F), DMH (FIGS. 5G-K), or CeA (FIGS. 5L-P) on indicated assays. CNO blocked persistent freezing in dBNSTa ("post"; FIGS. 5O-P). FIG. 5Q shows a summary of results. Notations as in FIG. 4Q. CNO had no effect in mCherry-expressing mice (FIG. 12G). See related FIGS. 12A-G.

FIG. 6A shows the experimental protocol. 3 weeks prior to testing, WT mice were injected with an AAV expressing shRNA-zsGreen for specific knockdown of Tac2 (shRNA-1 or shRNA-2), or with an shRNA virus targeting the luciferase gene (control) (n=6-7/mice condition), and maintained in isolation until testing. FIGS. 6E, F). FIG. 6Q shows a summary of results. The effects of shRNA-1 (left column) and shRNA-2 (right column) are presented for each region. See related FIGS. 13A-AA.

FIGS. 7A-I show that activation of $Tac2^+$ neurons plus Tac2 overexpression mimics the effect of SIS in GH mice in accordance with some embodiments, FIG. 7A shows the experimental protocol. GH Tac2-Cre mice were intravenously injected with Cre-dependent AAV-PHP.B viruses expressing the chemogenetic activator hM3DREADD, a Tac2 cDNA, both, or mCherry (controls). Mice remained group housed (4 weeks) with CNO-spiked drinking water provided during the final 2 weeks (for hM3DREADD activation). Mice received an injection of CNO (i.p.) 20 min prior to each assay (n=6 mice/condition). FIGS. 7B-F show the effect of each manipulation on the indicated assays. All animals were treated with CNO and received the same total amount of virus. Only mice receiving both the hM3DREADD and Tac2 cDNA viruses showed a "SIS-like" phenotype (darkest bars), including increased aggression (FIGS. 7B-C), post loom freezing (FIG. 7D), and post-tone freezing (FIG. 7E). FIG. 7F shows reactivity to the footshock. FIG. 7G shows a summary of results. Arrows indicate effects of perturbations to generate SIS-like effects. FIG. 7H is a schematic illustrating how Tac2 and its receptor (Nk3R) control SIS-induced behavior. Without being limited by theory, either the same or different cells may express the peptide and the receptor within each region. FIG. 7I is an illustration summarizing LOF and GOF effects on behavior (Upper). Without being limited by theory, model graphs (Lower) show different thresholds for acute vs. persistent freezing, and different dose-dependencies of freezing on Tac2 levels in dBNSTa vs. CeA (bottom graph), could explain the differential effects of shRNA-1 (weaker) and -2 (stronger; upper graphs) in the two regions (see FIG. 6Q). Without being limited by theory, the model also illustrates how an increase in Tac2 levels caused by SIS (line labeled "CeA") could convert acute (CeA-dependent) to persistent (dBNSTa-dependent) freezing. Dot labelled "GH," baseline levels of Tac2 in GH mice are higher in CeA than in dBNSTa, based on FISH data (FIG. 2W, FIG. 2Y). See related FIGS. 14A-T.

FIGS. 8A-H show that prolonged SIS alters subsequent social and asocial behavior in accordance with some embodiments. FIGS. 8A-F show SIS or GH mice (n=8 mice/condition) tested in various behavioral assays (see also FIG. 1E). Tail rattles during the overhead looming disk assay were elevated in isolated mice (see FIG. 1H for looming data). FIGS. 8C-D show baseline freezing to the tone fear test context averaged across the three minutes of context exposure prior to the initial tone (related tone test data presented in FIG. 1I). No significant generalized freezing to the test context in either group was observed. FIGS. 8E-F show breakdown of tone fear freezing to each tone (30 s, "during") and each trace interval (20 s, "post"). Freezing in SIS mice persisted into each trace interval (see FIG. 1I for averaged values). FIGS. 8G-L show testing of SIS or GH mice (n=8 mice/condition) in the acoustic startle assay (FIGS. 8G-H) and the flinch-vocalization-jump assay (FIGS. 8I-J) to measure reactivity to noxious stimuli presented at varying intensities. Startle responses to a white noise auditory stimulus were enhanced in SIS animals, even at sound decibel (dB) intensities that were sub-threshold for eliciting startle (FIGS. 8G-H). SIS mice showed flinch responses to footshocks of a lower magnitude (milliamp, mA) compared to GH mice (FIGS. 8I-J). FIGS. 8K-L show the percent of mice that jumped off of the EPM within 5 seconds of initial placement in the center of the maze. EPM open vs. closed-arm time data presented in FIGS. 1P-Q. In FIGS. 8M-P, SIS or GH WT mice (n=8 mice/condition) were tested in the social interaction assay. SIS mice spent significantly less time in the zone containing a novel naïve mouse in a pencil cup (left graph), but showed a shorter latency to initially enter the zone containing the mouse (right graph). Representative heatmaps (right panels) reflecting time spent in each location of the interaction apparatus (color scale of maximum time and minimum time shown on the right) for a GH (top) or SIS (bottom) mouse. For group housed mice, maximum time was observed for locations containing a novel naïve mouse (top right panel, circular markings on the right). For isolated mice, maximum time was observed for locations containing an object (lower left panel, circular markings in bottom third). For isolated mice presented with a novel naïve mouse, minimum time was predominant (lower right panel). Group housed mice presented with an object showed interaction ranging from minimum to intermediate (top left panel). In FIGS. 8Q-R, mice that had been tested in the USS assay (FIG. 1K) were tested in a rat exposure assay. GH mice spent significantly more time in the zone farthest away from the rat compared to the other zones. This preference for the "far" zone was absent in SIS mice.

In FIGS. 8A-R to FIGS. 14A-T, *p<0.05, p<0.01, *p<0.001. Bars without asterisks did not reach significance (p>0.05). ANOVA's, F's, and t values as well as additional statistical information for this and subsequent figures can be found in Table S1. Data are represented as mean±SEM.

In FIGS. 9A-P, Tac2-Cre mice were crossed to Ai6-zsGreen reporter mice (see FIG. 2D, FIG. 2F). Representative coronal sections through dBNSTa, CeA, and ACC (top to bottom) illustrating Tac2-dependent zsGreen expression in GH (left panels) vs. SIS mice (right panels) are shown in FIG. 9A, FIG. 9B, FIG. 9E, FIG. 9F, FIG. 9I, FIG. 9J, FIG. 9M, and FIG. 9N. Quantification of zsGreen+ cell counts (FIGS. 9C, 9G, 9K, and 9O, left) and average fluorescence (FIGS. 9D, 9J, 9L and 9P, right) are presented for each respective region in FIG. 9C (zsGreen+ cell counts for regions in FIGS. 9A-B), FIG. 9D (average fluorescence for regions in FIGS. 9A-B), FIG. 9G (for zsGreen+ cell counts for regions in FIGS. 9E-F), FIG. 9H (average fluorescence for regions in FIGS. 9R-F), FIG. 9K (zsGreen+ cell counts for regions in FIGS. 9I-J), FIG. 9L (average fluorescence for regions in FIGS. 9I-J), FIG. 9O (zsGreen+ cell counts for regions in FIGS. 9M-N), and FIG. 9P (average fluorescence for regions in FIGS. 9H-N). Counts/fluorescence were restricted to each region as outlined (white dashed line). SIS produced significant increases in zsGreen expression across regions. For all panels shown in FIG. 9A, FIG. 9B, FIG. 9E, FIG. 9F, FIG. 9I, FIG. 9J, FIG. 9M, and FIG. 9N, the intensity of fluorescent staining was representative of the quantitations shown in FIG. 9C, FIG. 9D, FIG. 9G, FIG. 9H, FIG. 9K, FIG. 9L, FIG. 9O, and FIG. 9P. For example, greater fluorescent intensity was seen in isolated mice as compared to group housed mice for dBNSTa, DMH, CeA, and ACC, with fluorescent intensity lowest in ACC of group housed mice. FIGS. 9AA-DD show zsGreen+ cells in the dBNSTa co-labeled with the neuronal marker NeuN, the glial marker nuclear factor I-A (NFIA) and the oligodendrocyte marker proteolipid protein (PLP) (top to bottom). Coronal sections and percentage of zsGreen+ cells that are double labeled with each respective marker in GH (left) as compared to SIS mice (right) (n=2-4 mice/condition; 3-4 sections/mouse). Up-regulation of Tac2/zsGreen occurred preferentially in neuronal cells. For all panels shown in FIG. 9AA, fluorescent staining of double labeled cells was representative of the quantitations shown in FIGS. 9BB-DD. In FIG. 9EE. Tac2-Cre mice were crossed to Ai14-mCherry reporter mice and GH or isolated to confirm that the SIS-induced increase in zsGreen expression was not an artifact due to the reporter mouse (n=4 mice/condition). Representative coronal sections illustrating increased Tac2-mCherry. Robust mCherry staining was seen in isolated mice. By contrast, mCherry staining was weak to undetectable in group housed mice. FIGS. 9FF-GG show neurokinin B (NkB)-like immunoreactivity in dBNSTa following 2 weeks of SIS compared to group housing (n=4 mice/condition), Representative confocal image (FIG. 9FF, left) and quantification (FIG. 9GG, right) show elevated signal in SIS mice. BLA, basolateral amygdala. AC, anterior commissure. For the panels shown in FIG. 9FF, the intensity of fluorescent staining was representative of quantitations shown in FIG. 9GG. It is noted that greater fluorescent intensity was seen in isolated mice as compared to group housed mice.

FIG. 10A shows the general behavioral protocol for results shown in FIGS. 10B-G. FIGS. 10B-C show the number of tail rattles produced during the looming disk assay (see FIG. 3D for looming data). SIS-induced tail rattles were attenuated by osanetant. FIGS. 10D-E show the effects of acutely administered, systemic osanetant on social interaction (n=6 mice/condition). Osanetant attenuated SIS-induced reduction in time spent in the social zone. FIGS. 10F-G show the effects of osanetant on the acoustic startle assay (n=8 mice/condition). Osanetant attenuated SIS-induced increased startle responses. FIG. 10H shows the experimental protocol to test whether osanetant also blocked aggression produced by 2 weeks of sexual experience (2 weeks of continuous cohabitation with a female, no isolation; results shown in FIGS. 10I-J), in contrast to the effect of osanetant to attenuate SIS-induced aggression, it had no effect to attenuate sexual experience-induced aggression (FIGS. 10I-J).

FIGS. 11A-K show that local Nk3R antagonism in dBNSTa, DMH and CeA blocks dissociable effects of SIS on behavior in some embodiments. FIGS. 11A-C show representative sagittal sections illustrating Nk3R expression in the indicated regions (Mouse Brain Atlas, Allen Institute for Brain Science; Exp. 80342167; accessible on the world wide web at mouse.brain-map.org/experiment/show/80342167). FIG. 11D shows that the latency to orient to the looming stimulus was reduced in SIS mice that had osanetant microinfused into DMH (related to FIG. 4J). FIGS. 11E-G show reactivity to the footshock in SIS mice with osanetant microinfused into the indicated region. Only CeA osanetant blocked SIS-enhanced shock reactivity. Data are related to FIGS. 4F, 4K, and 4P. FIGS. 11H-K show the effect of osanetant microinfusions into the ACC or striatum on freezing behavior in the looming assay. No significant effects were observed.

FIGS. 12A-C show representative coronal sections of Cre-dependent hM4DREADD-mCherry viral expression in indicated regions of Tac2-Cre mice. mCherry fluorescent staining was greatest in dBNSTa, followed by CeA that showed a cluster of strong staining in the center and more isolated staining in the periphery of the indicated region. Less mCherry staining was seen in DMH as compared to dBNSTa and CeA, with isolated rather than clustered staining appearing throughout. FIGS. 12D-F show that hM4DREADD-driven chemogenetic silencing of Tac2+ neurons in CeA (FIG. 12F), but not dBNST (FIG. 12D) or DMH (FIG. 12E), attenuated SIS-enhanced shock reactivity. Data are related to FIG. 5F, FIG. 5K, and FIG. 5P. FIG. 12G shows results obtained in tone fear tests for SIS mice injected with AAV2-EF1a-DIO-hM4D-mCherry or AAV2-EF1a-DIO-mCherry control virus in the dBNSTa (n=6-7 mice per condition). CNO administered to hM4DREADD mice attenuated post-tone persistent freezing (see also FIG. 5F), while CNO administered to control mCherry virus-expressing mice produced no significant effects in comparison to vehicle-treated animals.

FIGS. 13A-AA show that local Tac2 knockdown attenuates the effects of SIS in some embodiments. FIGS. 13A-C show shRNAi-mediated knockdown of Tac2 in CeA (FIG. 13C), but not dBNST (FIG. 13A) or DMH (FIG. 13B), attenuated SIS-enhanced shock reactivity. Data are related to FIG. 6E, FIG. 6K, and FIG. 6P. FIGS. 13J-AA show the efficacy of Tac2 shRNAs. Following behavior testing, brain sections and tissue taken from shRNA mice were processed for Tac2 mRNA using FISH or qRT-PCR to confirm knockdown of Tac2. Representative coronal images, Tac2 mRNA cell counts and intensity, and fold changes in Tac2 mRNA were performed for all animals. Significant decreases in Tac2 mRNA were observed in dBNSTa (FIGS. 13J-O), DMH (FIGS. 13P-U), and CeA (FIGS. 13V-AA) (n=6-7 mice per condition; 4-11 sections/mouse). Note that shRNA-2 produces a stronger knockdown than shRNA-1 in many cases. Dashed white outlines indicate regions within which quantifications were made. The quantitations made in FIG. 13D refer to the regions depicted in FIG. 13E. The quantitations made in FIG. 13F refer to the regions depicted in FIG. 13G. The quantitations made in FIG. 13H refer to the regions depicted in 13I. The quantizations made in FIGS. 13M-O (dBNSTa) refer to the regions depicted in FIGS. 13J-L. The quantitations made in FIGS. 13S-U (DMH) refer to the regions depicted in FIGS. 13P-R. The quantitations made in FIGS. 13Y-AA (CeA) refer to the regions depicted in FIGS. 13V-X.

Figures 13A, 13B, 13C:
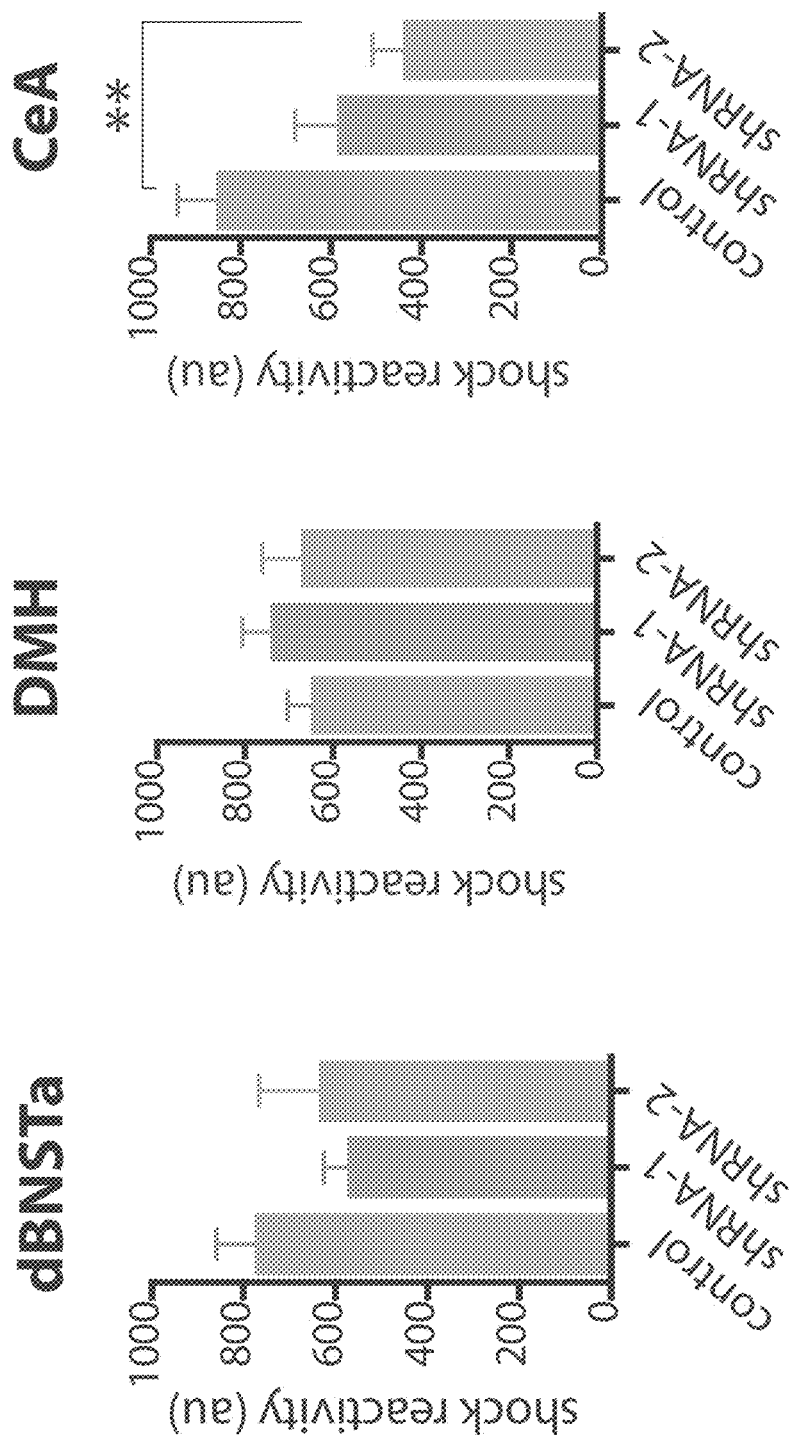
Figure 13D:
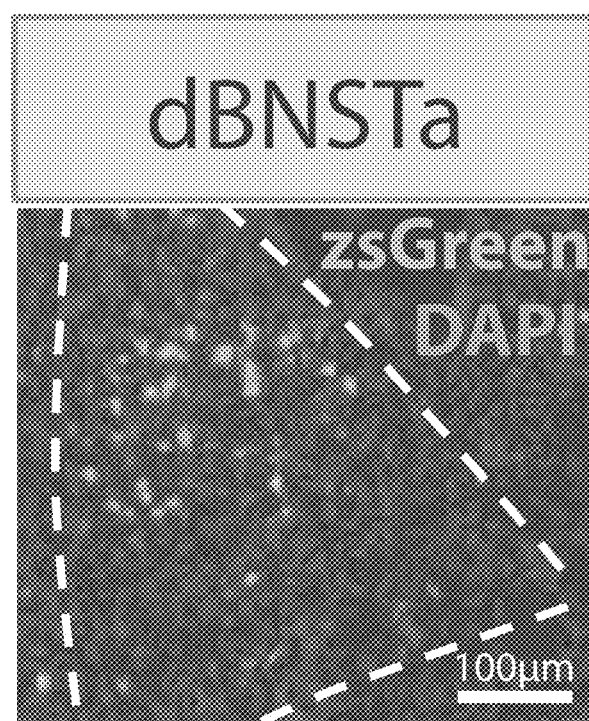
FIG. 13D, FIG. 13F, and FIG. 13H show representative coronal sections of shRNA-2-zsGreen viral expression in indicated regions of WT mice. zsGreen viral expression was seen in dBNSTa, DMH, and CeA as indicated by the presence of fluorescence in each section representative of quantitations shown in FIG. 13E (dBNSTa; corresponding to the region in FIG. 13D), FIG. 13G (DMH; corresponding to the region in FIG. 13E), FIG. 13I (CeA; corresponding to the region in FIG. 13I). Lack of any significant difference in the number of zsGreen+ cells between Tac2 shRNA virus-injected vs control (luciferase shRNA) virus-injected mice suggests that cell death is not the cause of the Tac2 shRNA phenotypes (FIG. 13E, FIG. 13G, FIG. 13I).
Figure 13E:
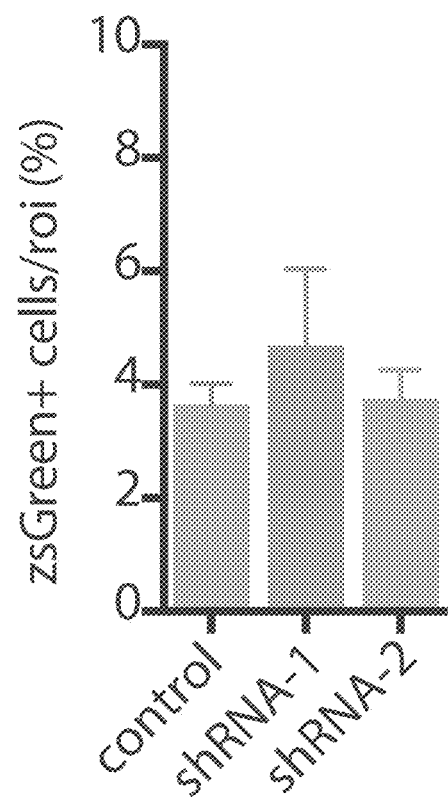
Figure 13F:
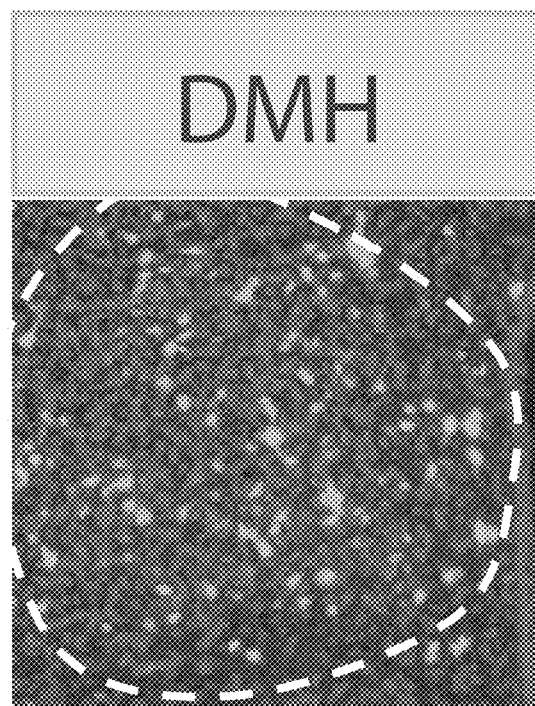
Figure 13G:
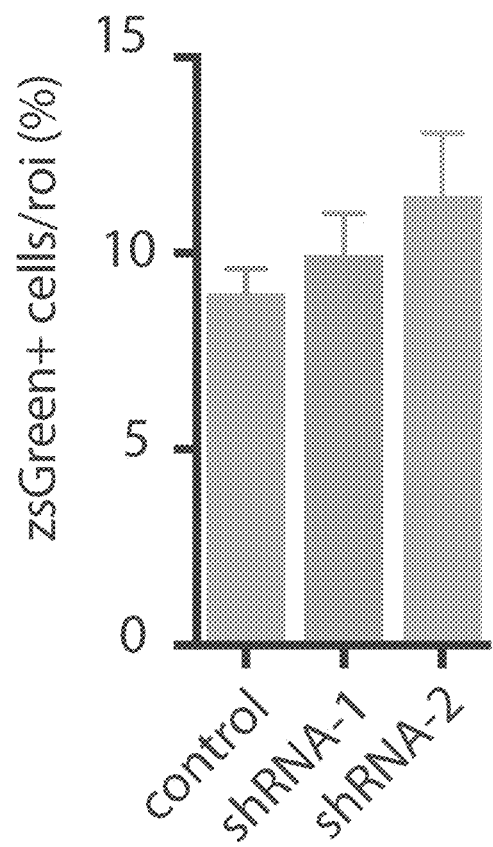
Figure 13H:
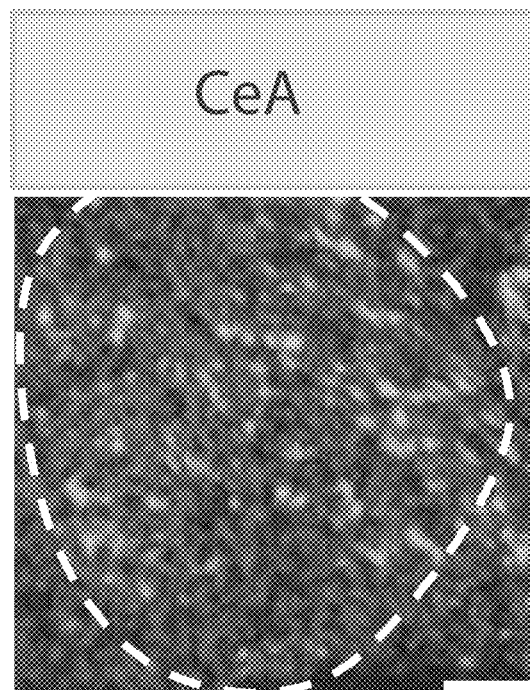
Figure 13I:
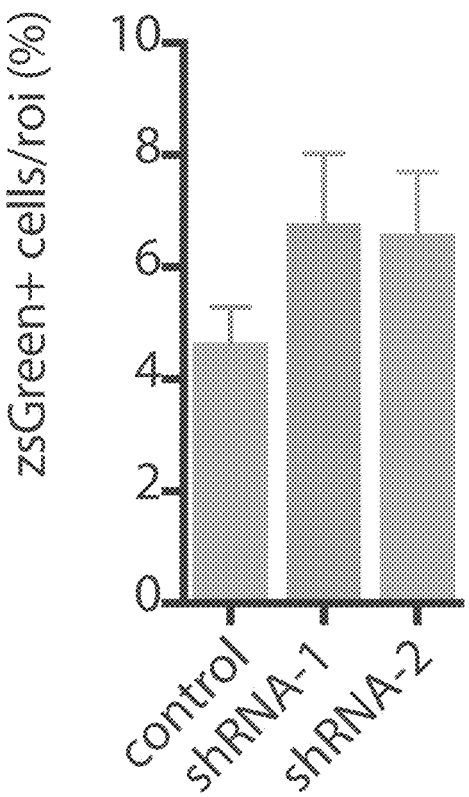

For control sections shown in FIG. 13J and FIG. 13P, fluorescence indicating Tac2 mRNA was seen. This Tac2-identifying fluorescence was reduced in the presence of shRNA-1 or shRNA-2, with few fluorescent cells remaining visible for dBNSta FIGS. 13K-L) and DMH (FIGS. 13Q-R). In CeA sections, fluorescence identifying Tac2 mRNA appeared reduced in the presence of shRNA.-1 and shRNA-2 relative to control (FIG. 13V-X).

Figures 14Q, 14R, 14S:
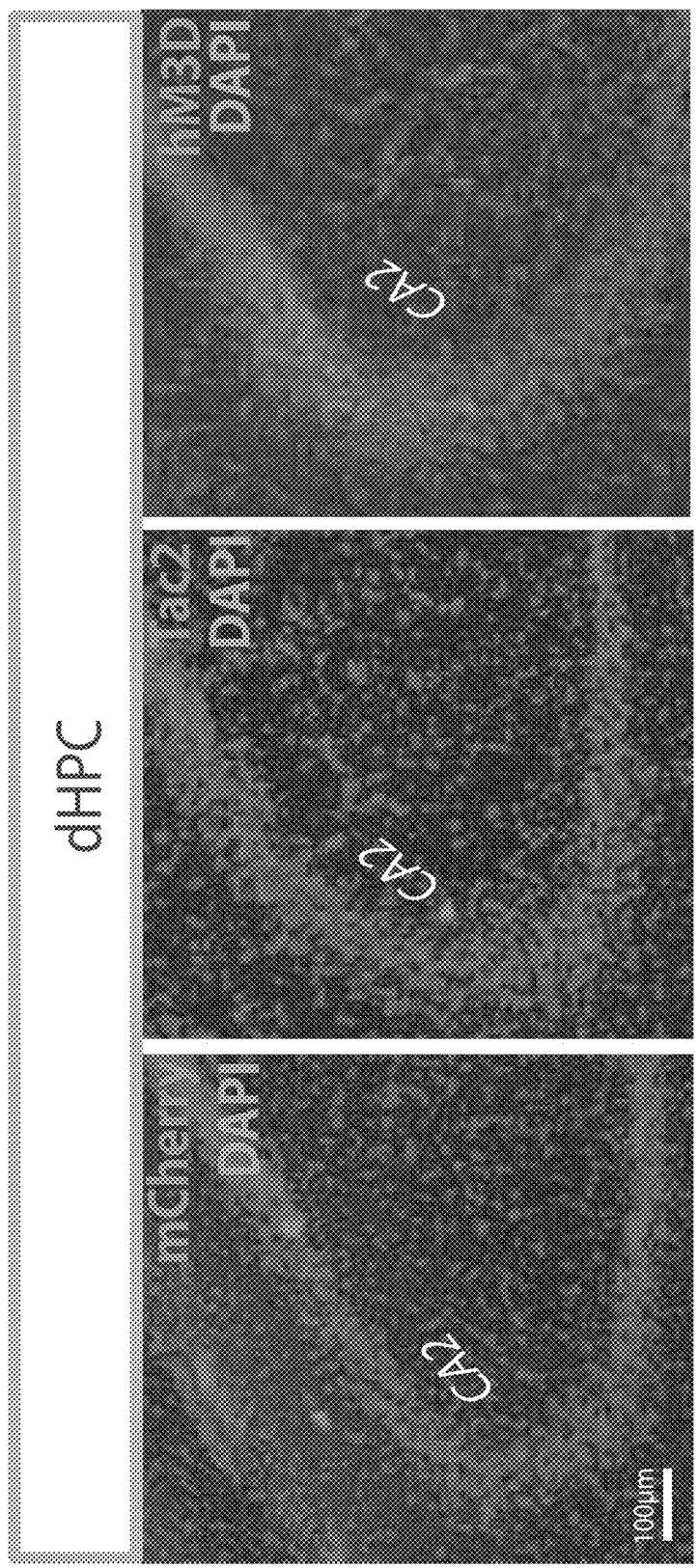
Figure 14T:
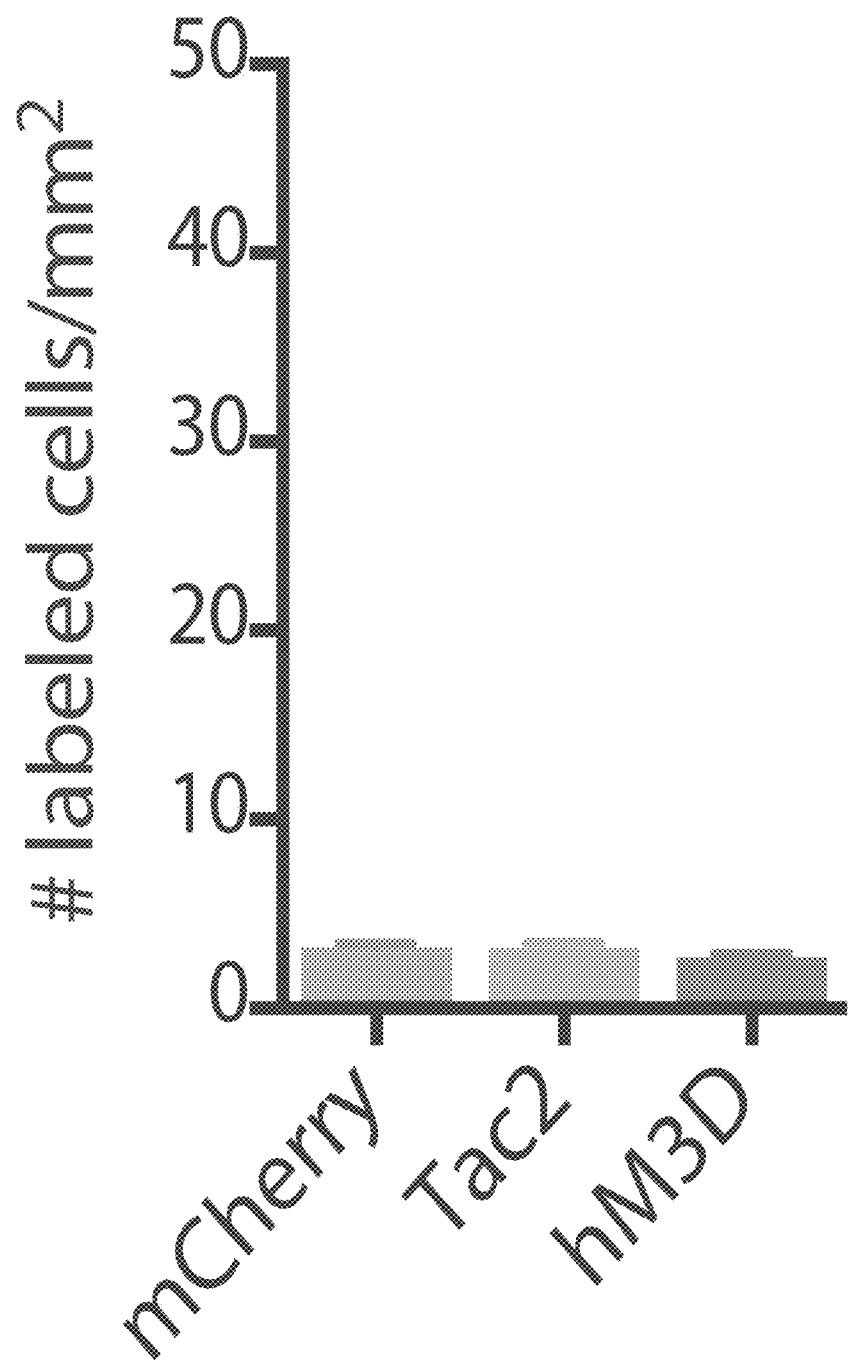

FIGS. 14A-T show Cre-dependent CNS expression from intravenous administration of AAV-PHP.B encoding GOF effectors in some embodiments. FIGS. 14A-C, FIGS. 14E-G, FIGS. 14I-K, FIGS. 14M-O, and FIGS. 14Q-S show representative coronal sections to illustrate expression of the control virus mCherry (left panels), Tac2 cDNA-mCherry virus (center panels), or hM3DREADD-mCherry virus (right panels) in the indicated regions of GH mice injected intravenously with the viruses. Quantification of the number of cells expressing each virus per $mm^2$ is presented for each region as follows: FIG. 14D (for regions shown in FIGS. 14A-C), FIG. 14H (for regions shown in FIGS. 14E-G), FIG. 14L (for regions shown in FIGS. 14I-L, FIG. 14P (for regions shown in FIGS. 14M-O), and FIG. 14T (for regions shown in FIGS. 14Q-S). Numbers of mCherry+ cells are low in ACC and dHPC because Tac2-Cre expression is low in these regions in GH mice. "cc", corpus callosum. In sections of dBNSTa (FIGS. 14A-C), DMH (FIGS. 14E-G), and CeA (FIGS. 14I-K), comparable mCherry staining was seen for control virus mCherry (FIGS. 14A, E and I), Tac2 cDNA-mCherry virus (FIGS. 14B, F, and J), or hM3DREADD-mCherry virus (FIGS. 14C, G, and K) as indicated by the presence of fluorescence. Fluorescence for mCherry (FIGS. 14M and 14Q), Tac2 (FIGS. 14N and 14R) and hM3DREADD-mCherry (FIGS. 14O and 14S) was low to absent in ACC (FIGS. 14M-O) and dHPC sections (FIGS. 14Q-S).

Figure 15A:
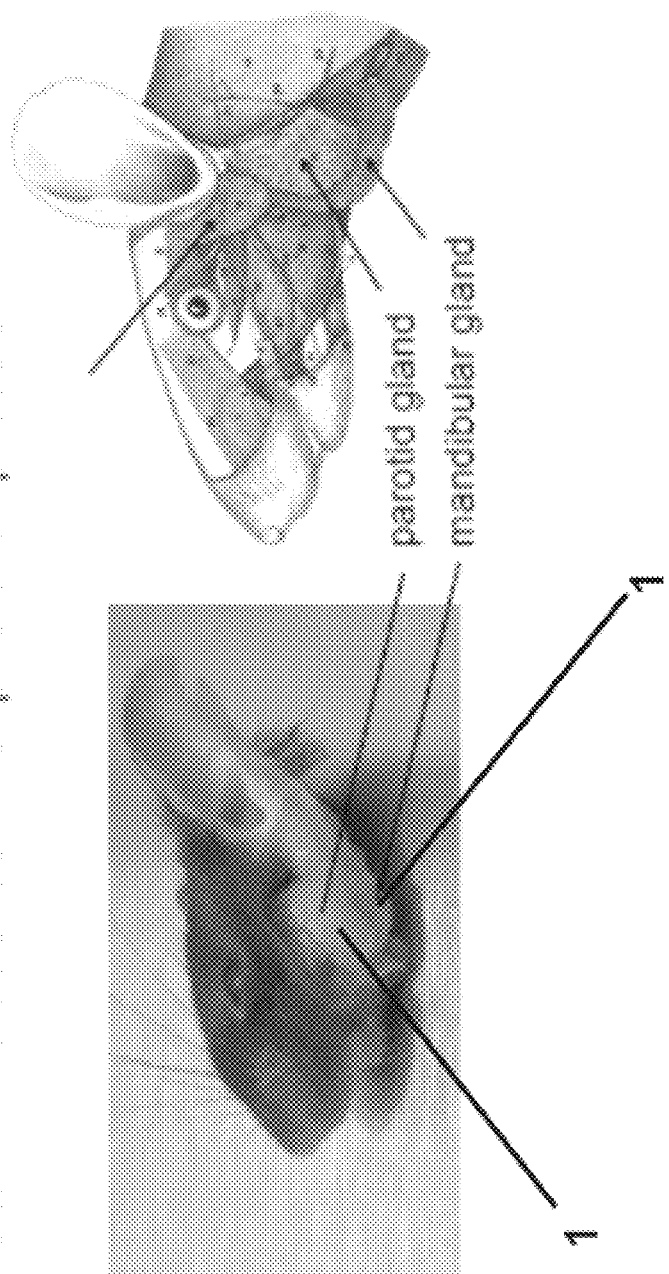
Figure 15B:
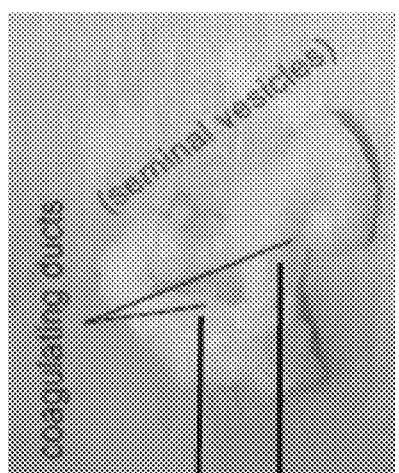
Figure 15C:
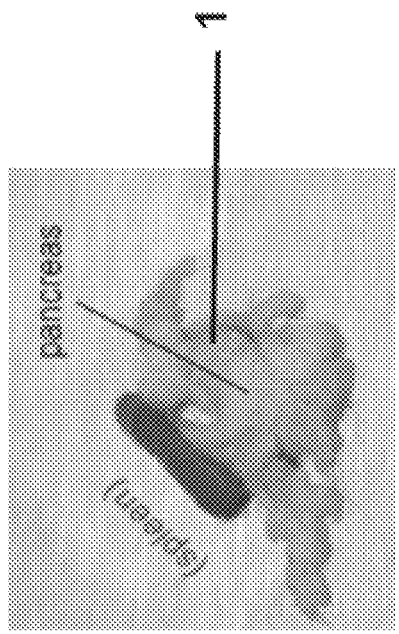
Figure 15D:
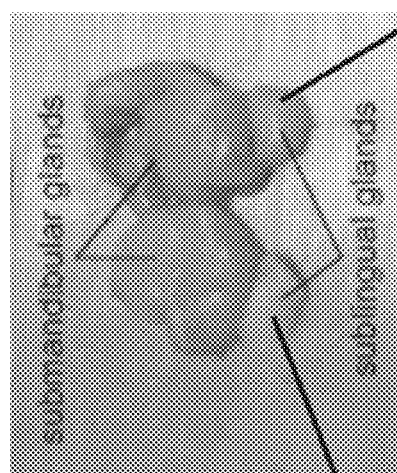
Figure 15E:
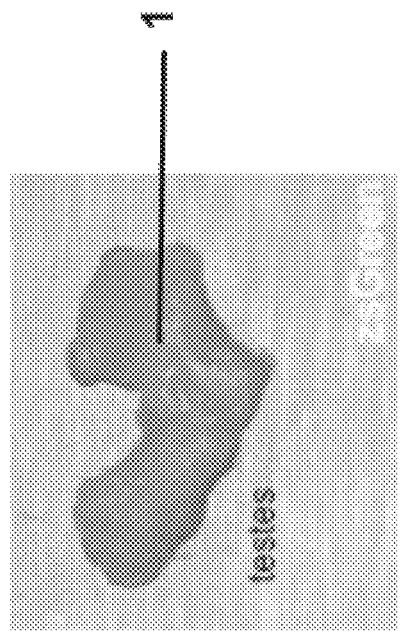

FIGS. 15A-E are a series of images Tac2-IRES2-Cre Ai6-zsGreen mouse organs in some embodiments. zsGreen staining 1 is shown. For reference, FIG. 15A depicts a schematic diagram of the parotid gland and the mandibular gland, as well as an image of zsGreen staining 1 in the Tac2-IRES2-Cre Ai6-zsGreen mouse, indicating that the parotid gland and the mandibular gland had zsGreen staining. Tac2 staining was also observed in the coagulating ducts (FIG. 15B), pancreas (FIG. 15C), sublingual glands (FIG. 15D) and testes (FIG. 15E).

DETAILED DESCRIPTION

Neuropeptides (NPs) are a class of neuromodulators that play an important role in the control of emotion, mood and affect, as well as in motivational states such as hunger and sexual arousal or in sensory states such as pain. Typically, neuropeptides act on receptors on neurons in the central nervous system. However, as neuropeptides typically have molecular weights that are too high for readily crossing the blood-brain barrier, neuropeptides conventionally have not amenable to direct administration to a subject. That is, neuropeptides directly administered through routes such as intravenous administration would not be expected to readily cross the blood-brain barrier. In some embodiments herein, gene expression systems, vectors, and methods for expressing neuropeptides in the central nervous system are described. It has been observed herein that expressing neuropeptides alone is generally insufficient to produce a behavioral state that mimics the endogenous neuropeptide (See Example 8). On the other hand, simultaneously activating a neuron and expressing the neuropeptide in the neuron can induce changes in behavior (See Example 8). Furthermore, neuropeptides are typically released under specific behavioral or internal state conditions, which are not easily mimicked by drug administration. Thus, without being limited by theory, it is contemplated that small molecule neuropeptide receptor agonists and antagonists (rather than the neuropeptides themselves) may not produce a behavior state that mimics endogenous neuropeptides. On the other hand, in accordance with methods and kits of some embodiments herein, combining two manipulations, (1) expressing the neuropeptide in neurons and (2) activating the neurons that express the neuropeptide, together promote the release of the neuropeptide by the neurons, and can mimic the effects of an endogenous neuropeptide.

Neuropeptides and Neurokinins

Neuropeptides such as neurokinins are a class of class of peptide neuromodulators. Examples of neurokinins include neurokinin A, neurokinin B, neuropeptide K, neuropeptide gamma, and substance P. In humans, there are three canonical classes of neurokinin receptor, neurokinin 1 receptor (NK1R), neurokinin 2 receptor (NK2R), and neurokinin 3 receptor (NK3R). The endogenous ligands of neurokinin receptors are neurokinins, a class of peptides encoded by the tachykinins genes.

The human TAC1 gene (annotated as GenBank Accession No: CR541730.1) encodes several tachykinins as via alternate splicing and/or post-translational processing, including, neurokinin A, neuropeptide K, and substance P. As murine experiments are also described herein, it is noted that murine Tac 1 is an ortholog of human TAC1. As such, wherever murine Tac 1 is mentioned herein, human TAC1 (and tachykinins encoded by TAC1) are expressly contemplated. TAC1 encodes protachykinin-1, which can be cleaved into several different neurokinins. An example human TAC1-encoded protachykinin-1 neuropeptide sequence (which can be cleaved into Substance P, Neurokinin A, or Neuropeptide K) is (SEQ ID NO: 1 MKILVALAVFFLVSTQLFAEEI-GANDDLNYWSDWYDSDQIKEELPEPFEHLLQRIAR RPKPQQFFGLMGKRDADSSIEKQVALLKALYGHGQ-ISHKRHKTDSFVGLMGKRALN SVAYERSAMQNY-ERRR). Upon cleavage of protachykinin-1, Substance P can comprise, consist essentially of, or consist of residues 58-68 of SEQ ID NO: 1. Upon cleavage of protachykinin-1, Neuropeptide K can comprise, consist essentially of, or consist of residues 72-107 of SEQ ID NO: 1. Upon cleavage of protachykinin-1, Neurokinin A can comprise, consist essentially of, or consist of residues 98-107 of SEQ ID NO: 1. It is noted that residues 1-19 of SEQ ID NO: 1 represent a signal peptide.

The human TAC3 gene (annotated as annotated as GenBank Accession No: CR457193.1) encodes neurokinin B. As murine experiments are also described herein, it is noted that murine Tac2 is an ortholog of human TAC3. As such, wherever murine Tac2 is mentioned herein, human TAC3 (and tachykinins encoded by TAC3) are expressly contemplated. An example human TAC3-encoded neurokinin B neuropeptide sequence is (SEQ ID NO: 2; MRIMLLF-TAILAFSLAQSFGAVCKEPQEEVVPGGGRSKRDPD-LYQL LQRLFKSHSSLEGLLKALSQASTDPKESTS-PEKRDMHDFFVGLMGKRSVQPDSPTDV NQENVPSFULKYPPRAD). It is noted that residues 1-16 of SEQ ID NO: 2 represent a signal peptide.

Under physiological conditions, NK1R has a greater affinity for substance P than other tachykinins. Under physiological conditions, NK2R has a greater affinity for neurokinin A than other tachykinins. Under physiological conditions, NK3R has a greater affinity for neurokinin B than other tachykinins.

When a "neurokinin" is mentioned herein, it will be appreciated that a neurokinin is encoded by a tachykinin gene, and typically binds to a neurokinin receptor. For conciseness, the term "neurokinin" may be used herein to refer to a neurokinin peptide, and it will also be understood that references to neurokinin genes and nucleic acids refers to those genes or nucleic acids that encode neurokinins, including a corresponding tachykinin gene, as appropriate for the context. For example, a "neurokinin nucleic acid" will be understood to refer to a nucleic acid that encodes a neurokinin. For conciseness, the term "tachykinin" may be used herein to refer to a tachykinin gene, or a tachykinin gene product (such as a peptide), and it will be understood that the corresponding neurokinin (or neurokinins) and their corresponding receptor are contemplated as is appropriate for the context. For example, if human neurokinin B is mentioned, it will be understood to be encoded by the TAC3 gene, and refer to a higher affinity ligand of NK3R. For example, if murine tac2 or human TAC3 is mentioned, it will be understood to encode neurokinin B, which is the higher affinity ligand for NK3R. Similarly, a "neuropeptide nucleic acid" will be understood to refer to a nucleic acid that encodes a neuropeptide."

Conditional receptors

As used herein, "conditional receptor" has its customary and ordinary meaning as would be understood by one of ordinary skill in the art in view of this disclosure. It refers to a receptor that can be expressed in a cell, and modulates activity of the cell when a condition is present, for example binding of an agonist, or stimulation with electromagnetic radiation. For example, the conditional receptor can comprise an ion channel, and can conditionally permit or prevent the passage of ions through the ion channel. For example, the conditional receptor can comprise a G protein coupled receptor, and can conditionally induce signaling in the cell that expresses the receptor. In some embodiments, the conditional receptor comprises, consists essentially of, or consists of a chemogenic receptor or an optogenetic receptor. Examples of chemogenic receptors are reviewed in Roth (2016), "DREADDs for Neuroscientists" Neuron. 89: 683-694, which is incorporated by reference in its entirety herein. Examples of optogenetic receptors are reviewed in Lin (2011) "A User's Guide to Channelrhodopsin Variants: Features, Limitations and Future Developments" Exp. Physiol. 96: 19-25, which is incorporated by reference in its entirety herein. It will be understood that a "conditional receptor nucleic acid" refers to a nucleic acid that encodes a conditional receptor.

In some embodiments, the conditional receptor comprises a chemogenic receptor such as a Designer Receptor Exclusively Activated by Designer Drugs (DREADD). The DREADD may encode a receptor such as a G protein coupled receptor configured to depolarize or activate a neuron. An example DREADD is hM3DREADD, which comprises a modified human M3 muscarinic receptor, and is activated by the agonist clozapine-N-oxide (CNO). The CNO can be administered to a subject, for example systemically or directly to the CNS, and can thus bind to hM3DREADD. Binding of CNO to hM3DREADD induces Gq G-protein coupled signaling, which induces the release of intracellular calcium in neurons, enhancing neuron activation.

In some embodiments, the conditional receptor comprises an optogenetic receptor such as a channel rhodopsin (e.g., ChR2 or VChR1). Channel rhodopsin comprises an ion channel, the opening of which is stimulated by electromagnetic radiation of a suitable wavelength. For example, ChR2 is stimulated by light in the blue spectrum (e.g., about 450 nm to about 470 nm) and VChR1 is stimulated by light in the green spectrum (e.g., about 550 nm to about 570 nm). Accordingly, in methods, uses, and kits of some embodiments, the conditional receptor comprises an optogenetic receptor, and is stimulated by electromagnetic radiation, thus inducing opening of an ion channel, and a change in polarity of the neuron that expresses the conditional receptor.

Vectors

In some embodiments, vectors are described. The vectors can be used in kits, and to express nucleic acids (such as those encoding neuropeptides and conditional receptors) in cells such as neurons as described herein.

As used herein, the terms "nucleic acid" and "polynucleotide" are interchangeable and refer to nucleic acid, which may be composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sultone linkages, and combinations of such linkages. The terms "nucleic acid" and "polynucleotide" also specifically include nucleic acids composed of bases other than the five biologically occurring bases (adenine, guanine, thymine, cytosine and uracil).

In method and kits of some embodiments, the vector comprises, consists essentially of, or consists of an adeno-associated vector (AAV). Adeno-associated virus (AAV) is a replication-deficient parvovirus, the single-stranded DNA genome of which is typically about 4.7 kb in length including 145 nucleotide inverted terminal repeat (ITRs). The ITRs play a role in integration of the AAV DNA into the host cell genome. When AAV infects a host cell, the viral genome integrates into the host's chromosome resulting in latent infection of the cell. In a natural system, a helper virus (for example, adenovirus or herpesvirus) provides genes that allow for production of AAV virus in the infected cell. In the case of adenovirus, genes E1A, E1B, E2A, E4 and VA provide helper functions. Upon infection with a helper virus, the AAV provirus is rescued and amplified, and both AAV and adenovirus are produced. In the instances of recombinant AAV vectors having no Rep and/or Cap genes, the AAV can be non-integrating. AAVs can provide long-term transgene expression, they are not known to be associated with any human disease, they elicit a relatively weak immune response, and are capable of transducing a variety of cell types.

An AAV vector in accordance with methods and kits of some embodiments herein can encode one or more gene products of interest, such as a neuropeptide and/or conditional receptor, and can contain a promoter that is operably linked to the gene product(s) of interest. As such, upon insertion of the AAV vector into a mammalian cell such as a neuron, the gene product(s) of interest can be expressed.

In methods and kits of some embodiments, an AAV is capable of delivering nucleic acids to a target environment, for example, a neuron, a population of neurons, a tissue (such as a central nervous system (CNS) tissue), an organ (such as the brain), or a combination thereof, in a subject transducted with the AAV. The AAV may further comprise one or more inserted nucleic acids, which may be inserted into an insertion site, for example a multiple cloning site. The inserted nucleic acid may encode a neuropeptide and/or a conditional receptor as described herein. The AAV may further comprise a promoter operably linked to the inserted nucleic acid (or multiple cloning site). In some embodiments, an AAV comprises, from 5' to 3', a 5' ITR, a promoter, inserted nucleic acid (such as a neurokinin nucleic acid and/or conditional receptor nucleic acid), and a 3' ITR. In some embodiments, the AAV comprises a posttranscriptional regulatory element downstream of the restriction site and upstream of the 3' AAV ITR. In some embodiments, the AAV comprises a regulatory element, for example, a promoter, enhancer, splicing signal, polyadenylation signal, terminator, protein degradation signal, internal ribosome-entry element (IRES), 2A sequences, and the like, that provide for and/or regulate expression of a coding sequence and/or production of an encoded polypeptide in a host cell.

The AAV in methods and kits of some embodiments can target and deliver nucleic acids to the nervous system, for example, central nervous system (CNS) and/or peripheral nervous system (PNS) of a subject. For example, the capsid sequence of an AAV can be engineered to target an AAV to a neuron, and thus deliver a nucleic acid encoding a neuropeptide and/or inducible receptor to the neuron. Examples of directed evolution methods for engineering AAV's targeted to cells (such as neurons) are described in detail in U.S. Pat. No. 9,585,971. In some embodiments, an AAV comprises a targeting peptide that can preferentially tranduce in neurons of the CNS or PNS. For example, the capsid of the AAV may comprise a targeting peptide which can target the AAV to the CNS or PNS. Examples of AAV, and AAV targeting peptides in particular that target the CNS are taught in US Pub. No. 2017/0166926, which is incorporated by reference in its entirety herein. Examples of AAVs (and targeting peptides) that efficiently transduce the CNS are shown in US Pub. No. 2017/0166926 at Table 3, for example AAV-PHP.B, AAV-PHP.B2, AAV-PHP.B. In some embodiments, the AAV comprises a targeting peptide selected from the group consisting of TLAVPFK (SEQ ID NO: 3), SVSKPFL (SEQ ID NO: 4), FTLTTPK (SEQ ID NO: 5), YTLSQGW (SEQ ID NO: 6), QAVRTSL (SEQ ID NO: 7), and LAKERLS (SEQ ID NO: 8). The targeting peptide can be configured to target the AAV to a neuron.

A suitable AAV can be produced using suitable genetic engineering techniques well known in the art, including, without limitation, the standard techniques of restriction endonuclease digestion, ligation, transformation, plasmid purification, and DNA sequencing, for example as described in Sambrook et al. (Molecular Cloning: A Laboratory Manual. Cold Spring Harbor Laboratory Press, N.Y. (1989)), which is incorporated by reference in its entirety herein.

Other types of vectors may also be suitable for methods, uses, and kits of some embodiments, for example retroviral vectors such as lentiviral vectors (which can integrate into the genome of a host cell), and/or vectors such as adenoviral vectors (which typically do not integrate into the genome of a host cell).

In some embodiments a vector is described. The vector can comprise a first nucleic acid encoding a neuropeptide. The vector can comprise a second nucleic acid encoding a conditional receptor configured to alter neuron polarity upon binding of an agonist or application of a stimulus to the conditional receptor. In some embodiments, a single promoter is operably linked to the first nucleic acid and second nucleic acid. In some embodiments, a single promoter is operably linked to the first nucleic acid and second nucleic acid, and the single promoter is configured to drive expression of both nucleic acids specifically in neuropeptidergic neurons. In some embodiments, a first promoter is operably linked to the first nucleic acid and a second promoter is operably linked to the second nucleic acid. The first and second promoter can be configured to drive expression specifically in a neuropeptidergic neuron, for example a neuropeptide promoter as described herein, such as a tachykinin promoter. The first and second promoter can be the same or different. In some embodiments, the vector comprises, consists essentially of, or consists of an adeno-associated virus (AAV). In some embodiments, two vectors are provided, in which the first vector comprises a first promoter operably linked to the first nucleic acid, and the second vector comprises a second promoter operably linked to the second nucleic acid. The first and second vector can be the same as each other or can be different from each other, for example having different regulatory elements such as different promoters.

Promoters

A number of suitable promoters may be used to express neuropeptides and/or conditional receptors in neurons. The promoter may be disposed 5' of an inserted nucleic acid (or insertion site) in a vector as described herein, for example an AAV. In some embodiments, the promoter is a neuropeptide promoter, for example, a tachykinin promoter. Example tachykinin promoters include the promoter of TAC1 (Genbank GeneID 6863; the nucleotide sequence of the TAC1 gene is provided as SEQ ID NO: 32 and the promoter of TAC3 (Genbank GeneID 6866; the nucleotide sequence of the TAC3 gene is provided as SEQ ID NO: 33.

As used herein, the term "operably linked" has its ordinary and customary meaning as would be understood by one of ordinary skill in the art in view of this disclosure. It refers to the connection between regulatory elements (such as promoters and/or enhancers) and a gene or its coding region. Typically, gene expression is placed under the control of one or more regulatory elements, for example, without limitation, constitutive or inducible promoters, tissue-specific regulatory elements, and enhancers. A gene or coding region said to be "operably linked to" or "operatively linked to" or "operably associated with" the regulatory elements, refers to the gene or coding region being controlled or influenced by the regulatory element. For instance, a promoter is operably linked to a coding sequence if the promoter effects transcription or expression of the coding sequence.

In method and kits of some embodiments, promoters, or promoter/enhancer sequences that yield constitutive or promiscuous expression in many cell types may be used. Examples of such promoters, or promoter/enhancer pairs include, but are not limited to the cytomegalovirus (CMV) immediate early promoter/enhancer sequences, the Rous sarcoma virus (RSV) promoter/enhancer sequences and the other viral promoters/enhancers active in a variety of mammalian cell types; promoter/enhancer sequences from ubiquitously or promiscuously expressed mammalian genes including, but not limited to, beta actin, ubiquitin or EF1alpha; and/or synthetic elements that are not present in nature.

In methods and kits of some embodiments, a single promoter is operably linked to two or more gene product coding sequences. Accordingly, the single promoter can drive the expression of the two or more gene products. For example, a single promoter can be operably linked to a neuropeptide and a conditional receptor as described herein. The coding sequences of the neuropeptide and conditional receptor can be separated by an element that permits the two gene products to be produced as separate polypeptides. For example the coding sequences of the neuropeptide and conditional receptor can be separated by an IRES, a 2A sequence, or a protease target site such as a furin consensus sequence (e.g., Arg-X-X-Arg, preferably Arg-X-Lys/Arg-Arg). Examples of 2A sequences are taught, for example, in U.S. Pat. No. 9,540,657 at Table 1.

In methods and kits of some embodiments, two separate promoters are each operably linked to a different gene product coding sequences (such as a neuropeptide and a conditional receptor). For example, in some embodiments, a first promoter is operably linked to a first nucleic acid comprising, consisting essentially of, or consisting of a neuropeptide coding sequence, and a second promoter is operably linked to a second nucleic acid comprising, consisting essentially of, or consisting of a conditional receptor coding sequence.

As used herein, the term "enhancer" has its customary and ordinary meaning as understood by one of ordinary skill in the art in view of this disclosure. It refers to a type of regulatory element that can modulate the efficiency of transcription. In some embodiments, an enhancer modulates transcription regardless of the distance or orientation of the enhancer relative to the start site of transcription. In some embodiments, an enhancer modulates transcription regardless of the orientation of the enhancer relative to the start site of transcription.

Administration and Dosing

The nucleic acids (and vectors comprising nucleic acids such as AAVs) can be administered to neurons of subjects by a number of suitable routes. In methods and kits of some embodiments, a therapeutically effective amount of the nucleic acid (or vectors comprising the nucleic acids such as AAVs) is administered to the subject by via one or more route standard in the art. Non-limiting examples of the route include intramuscular, intravaginal, intravenous, intraperitoneal, subcutaneous, epicutaneous, intradermal, rectal, intraocular, pulmonary, intracranial, intraosseous, oral, buccal, systematic, or nasal, or a combination of two or more of the listed items. In some embodiments, the nucleic acids (or vectors comprising the nucleic acids such as AAVs) are administered to the subject by systematic transduction. In some embodiments, the nucleic acids (or vectors comprising the nucleic acids such as AAVs) are administered to the subject by intramuscular injection. In some embodiments, the nucleic acids (or vectors comprising the nucleic acids such as AAVs) are administered to the subject by intravaginal injection. In some embodiments, the nucleic acids (or vectors comprising the nucleic acids such as AAVs) are administered to the subject by the parenteral route (e.g., by intravenous, intramuscular or subcutaneous injection), by surface scarification or by inoculation into a body cavity of the subject. Route(s) of administration and serotype(s) of vectors comprising nucleic acids (such as AAVs) can be readily determined by one skilled in the art taking into account the infection and/or disease state being treated and the target cells/tissue(s) that are to express the protein of interest. In some embodiments, it can be advantageous to administer the nucleic acids (or vectors comprising the nucleic acids such as AAVs) via intravenous administration. In methods, vectors, and/or kits of some embodiments, the subject is a human. In methods, vectors, and/or kits of some embodiments, the subject is a non-human primate.

In some embodiments, the nucleic acids (or vectors comprising the nucleic acids such as AAVs) are delivered to the nervous system (e.g., CNS, PNS, or PNS and CNS) of a subject, for example via injection, to a subject at a dose of between $1 \times 10^{10}$ genome copies (GC) of the nucleic acids (or vector such as AAV) per kg of the subject and $2 \times 10^{14}$ GC per kg, for example between $5 \times 10^{11}$ GC/kg and $5 \times 10^{12}$ GC/kg. In some embodiments, the dose of the nucleic acids (or vector such as AAV) administered to the subject is no more than $2 \times 10^{14}$ GC per kg. In some embodiments, the dose of the nucleic acids (or vector such as AAV) administered to the subject is no more than $5 \times 10^{12}$ GC per kg. In some embodiments, the dose of the nucleic acids (or vector such as AAV) administered to the subject is no more than $5 \times 10^{11}$ GC per kg.

Actual administration of the nucleic acids (or vector such as AAV) to the subject can be accomplished by using any physical method that will transport the nucleic acids (or vector such as AAV) into the target tissue of the subject. For example, the nucleic acids (or vector such as AAV) can be administered intravenously. As disclosed herein, capsid proteins of AAV's can be modified so that the AAV is targeted to a particular target environment of interest such as central nervous system, and to enhance tropism to the target environment of interest (e.g, CNS tropism). In some embodiments, an AAV delivers a nucleic acid to the heart, peripheral nerves, or a combination thereof. Pharmaceutical compositions can be prepared, for example, as injectable formulations.

The nucleic acids (or vector such as AAV) to be used can be utilized in liquid or freeze-dried form (in combination with one or more suitable preservatives and/or protective agents to protect the virus during the freeze-drying process). For gene therapy (e.g., of neurological disorders which may be ameliorated by a specific gene product) a therapeutically effective dose of the recombinant virus expressing the therapeutic protein is administered to a host in need of such treatment. The use of the recombinant virus disclosed herein in the manufacture of a medicament for inducing immunity in, or providing gene therapy to, a host is within the scope of the present application.

In instances where human dosages for nucleic acids (or vector such as AAV) have been established for at least some condition, those same dosages, or dosages that are between about 0.1% and 500%, more preferably between about 25% and 250% of the established human dosage can be used. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

A therapeutically effective amount of the nucleic acids (or vector such as AAV) can be administered to a subject at various points of time in accordance with methods and kits of some embodiments. For example, in methods and kits of some embodiments, the nucleic acids (or vector such as AAV) can be administered to the subject prior to, during, or after the subject has developed a disease or disorder. In methods and kits of some embodiments, the nucleic acids (or vector such as AAV) can also be administered to the subject prior to, during, or after the occurrence of a neurological disease or disorder (examples of neurological diseases or disorders include degenerative diseases of the nervous system such as Huntington's disease (HD), Alzheimer's disease, Parkinson's disease, Amyotrophic lateral sclerosis, spinal muscular atrophy, types I and II, Friedreich's Ataxia, Spinocerebellar ataxia, or behavioral disorders, such as social isolation stress, depression, anxiety, schizophrenia, post traumatic stress disorder, or a combination of two or more of the listed items). In some embodiments, the neurological disease or disorder comprises, consists essentially of depression, anxiety, schizophrenia, post traumatic stress disorder, or a combination of two or more of the listed items. In some embodiments, the neurological disease or disorder comprises, consists essentially of social isolation stress, depression, anxiety, schizophrenia, or a combination of two or more of the listed items. In some embodiments, the neurological disease or disorder comprises, consists essentially of depression, anxiety, schizophrenia, or a combination of two or more of the listed items.

In some embodiments, the neurological disease or disorder comprises, consists essentially of, or consists of a brain disorder that can be ameliorated by increasing the level of a particular neuropeptide. In some embodiments, the nucleic acids (or vector such as AAV) are administered to the subject during remission of the disease or disorder. In methods and kits of some embodiments, the nucleic acids (or vector such as AAV) are administered prior to the onset of the disease or disorder in the subject. In some embodiments, the nucleic acids (or vector such as AAV) are administered to a subject at a risk of developing the disease or disorder.

The dosing frequency of the nucleic acids (or vector such as AAV) administered in accordance with methods and kits of some embodiment can vary. For example, in methods and kits of some embodiments, the nucleic acids (or vector such as AAV) can be administered to the subject about once every week, about once every two weeks, about once every month, about one every six months, about once every year, about once every two years, about once every three years, about once every four years, about once every five years, about once every six years, about once every seven years, about once every eight years, about once every nine years, about once every ten years, or about once every fifteen years. In methods and kits of some embodiments, the nucleic acids (or vector such as AAV) are administered to the subject at most about once every week, at most about once every two weeks, at most about once every month, at most about one every six months, at most about once every year, at most about once every two years, at most about once every three years, at most about once every four years, at most about once every five years, at most about once every six years, at most about once every seven years, at most about once every eight years, at most about once every nine years, at most about once every ten years, or at most about once every fifteen years.

Pharmaceutical Compositions

In methods and kits of some embodiments, the nucleic acids (or vector comprising nucleic acids such as an AAV) are provided in a pharmaceutical composition. The pharmaceutical composition can be formulated for administration to a subject in need thereof. In the methods and kits of some embodiments, the pharmaceutical composition comprises, consists essentially of, or consists of the nucleic acids (encoding a neuropeptide and a conditional receptor as described herein) or vector(s) comprising the nucleic acids (such as AAV) and one or more pharmaceutically acceptable carriers. The pharmaceutical composition can also comprise additional ingredients such as diluents, stabilizers, excipients, and adjuvants. As used herein, "pharmaceutically acceptable" carriers, excipients, diluents, adjuvants, and/or stabilizers have their customary and ordinary meaning as would be understood by one of ordinary skill in the art in view of this disclosure. They refer to the ones nontoxic to the subject being exposed thereto (preferably inert) at the dosages and concentrations employed or that have an acceptable level of toxicity as determined by the skilled practitioners.

The carriers, diluents and adjuvants can include buffers such as phosphate, citrate, or other organic acids; antioxidants such as ascorbic acid; low molecular weight polypeptides (e.g., less than about 10 residues); proteins such as serum albumin, gelatin or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween™, Pluronics™ or polyethylene glycol (PEG). In some embodiments, the physiologically acceptable carrier is an aqueous pH buffered solution.

Titers of the nucleic acids (or AAV comprising nucleic acids) to be administered will vary depending, for example, on the particular AAV, the mode of administration, the treatment goal, the individual, and the cell type(s) being targeted, and can be determined by methods standard in the art.

Social Isolation Stress

As used herein "social isolation stress" and variations of this root term has its customary and ordinary meaning as would be understood by one of ordinary skill in the art in view of this disclosure. It refers to stress that results from an absence of social interaction. The absence of social interaction can be for a matter of days, for example at least about 2 days, such as at least 2, 3, 4, 5, 6, 7 days, or 1, 2, 3, 4, or 5 weeks. It is noted that social isolation stress may occur even if some trivial social interactions take place. Accordingly, while social isolation stress may result from actual physical separation from other individuals, social isolation stress may also result from a lack of meaningful social contacts with other individuals, for example, grieving in isolation (for example, following the loss of a spouse), feelings of isolation as an adolescent, or residing as a patient in a skilled nursing facility. Symptoms of social isolation stress can include, for example, aggression (e.g., higher than a baseline level of aggression), persistent responses to threats, persistent freezing in response to innate and conditioned fear-evoking stimuli, enhanced reactivity to aversive stimuli, and/or reduced social interactions. In some embodiments, social isolation stress comprises, consists essentially of, or consists of aggression and/or persistent responses to threats.

Social isolation stress can exacerbate other disorders. Social isolation stress has been shown to exacerbate cancer (Williams et al. (2009) "A model of gene-environment interaction reveals altered mammary gland gene expression and increased tumor growth following social isolation" Cancer Prev 2: 850-861, which is incorporated by reference in its entirety herein); major depressive disorder, dysthymic disorder, social phobia, and generalized anxiety disorder, alcohol abuse and dependence, drug abuse, and nicotine dependence (Chou et al. (2011) "The association between social isolation and DSM-IV mood, anxiety, and substance use disorders: wave 2 of the National Epidemiologic Survey on Alcohol and Related Conditions" J Clin Psychiatry. 72: 1468-76, which is incorporated by reference in its entirety herein), atherosclerosis and coronary heart disease, ischemic stroke, cognitive impairment, and Alzheimer's disease (Friedler et al. (2015) "One is the Deadliest Number: The Detrimental Effects of Social Isolation on Cerebrovascular Diseases and Cognition" Acta Neuropathol. 129: 493-509, which is incorporated by reference in its entirety herein). Exacerbation of Alzheimer's disease by social isolation stress is also reported by Huang et al. (2015) "Isolation Housing Exacerbates Alzheimer's Disease-Like Pathophysiology in Aged APP/PS1 Mice: International Journal of Neuropsychopharmacology, doi:10.1093/ijnp/pyu1161-10.

Accordingly, in the methods and uses of some embodiments, a subject in need of treatment has social isolation stress or is at risk of social isolation stress, and further has a disorder in which social isolation causes or is known to cause exacerbation of the disorder. In the methods and uses of some embodiments, a subject in need of treatment has social isolation stress or is at risk of social isolation stress, and further has a disorder in which social isolation is known to cause exacerbation of the disorder. In some embodiments, a disorder that can be exacerbated by social isolation stress includes, for example, aggression, cancer, major depressive disorder, dysthymic disorder, social phobia, generalized anxiety disorder, alcohol abuse and dependence, drug abuse, nicotine dependence, atherosclerosis, coronary heart disease, ischemic stroke, cognitive impairment, Alzheimer's disease, agoraphobia, isolated post-traumatic stress disorder (PTSD), bereavement, grieving in isolation, or single member living schizophrenia, or two or more of the listed items. In some embodiments, a disorder that can be exacerbated by social isolation stress includes, for example, aggression, cancer, major depressive disorder, dysthymic disorder, social phobia, generalized anxiety disorder, alcohol abuse and dependence, drug abuse, nicotine dependence, atherosclerosis, coronary heart disease, ischemic stroke, cognitive impairment, or Alzheimer's disease, or two or more of the listed items Method of Expressing a Neuropeptide In some embodiments, a method of expressing a neuropeptide in a neuron of a subject is described. The method can comprise administering a first nucleic acid to the neuron in the subject. The first nucleic acid can encode the neuropeptide. A first promoter can be operably linked to the first nucleic acid. Thus, the neuropeptide can be expressed in the neuron. The method can comprise administering a second nucleic acid to the neuron in the subject. The second nucleic acid can encode a conditional receptor configured to alter the polarity of the neuron upon contact with an agonist or stimulus. The first promoter or a second promoter (that is different from the first promoter) can be operably linked to the second nucleic acid. Thus, the conditional receptor can be expressed in the neuron. The method can further comprise applying the agonist or stimulus to the neuron of the subject, causing the conditional receptor induces a change in polarity in the neuron that expresses the neuropeptide. For example, the conditional receptor can induce a change of polarity via the opening of an ion channel, or via G protein coupled receptor (GPCR) signaling, which can open ion channels, or trigger the intracellular release of ions into the cytosol of the neuron (for example, $Ca^{2+}$ release from the endoplasmic reticulum or mitochondria). In some embodiments, the first and second nucleic acid are comprised by a single vector, such as an AAV as described herein. In some embodiments, the first and second nucleic acid are comprised by separate vectors. In some embodiments, the conditional receptor causes activation of the neuron that expresses the neuropeptide. In some embodiments, a change in a behavioral or mental state of the subject occurs.

It is noted that wherever a method of expressing a neuropeptide comprising administering nucleic acids (such as the first and second nucleic acids, or a vector comprising the same), nucleic acids for medical use are also contemplated. For example, for a method of expressing a neuropeptide in a neuron that comprises administering a first nucleic acid and second nucleic acid (or vector comprising the first and second nucleic acid) to a neuron, the first nucleic acid and second nucleic acid (or vector) for medical use are also expressly contemplated. Accordingly, in some embodiments, a first nucleic acid and a second nucleic acid (or a vector comprising the first nucleic acid and second nucleic acid) as described herein are for medical use. In some embodiments, a first nucleic acid and a second nucleic acid (or a vector comprising the first nucleic acid and second nucleic acid) as described herein are for use in treating, inhibiting, ameliorating, reducing the severity of, delaying the onset of, or preventing a neurological disease or disorder, for example degenerative diseases of the nervous system such as Huntington's disease (HD), Alzheimer's disease, Parkinson's disease, Amyotrophic lateral sclerosis, spinal muscular atrophy, types I and II, Friedreich's Ataxia, Spinocerebellar ataxia, and/or behavioral disorders, such as depression, anxiety, schizophrenia, post traumatic stress disorder (PTSD), or a combination of two or more of the listed items. In some embodiments, the neurological disease or disorder comprises, consists essentially of, or consists of a brain disorder that can be ameliorated by increasing the level of a particular neuropeptide A conditional receptor, upon binding of an agonist or stimulation, can alter the polarity of a neuron. Altered neuron polarity can cause neuron activation or increase the likelihood of neuron activation. In some embodiments, the altered polarity in the neuron activates the neuron. For example, the altered polarity can depolarize the neuron. In some embodiments, the altered polarity increases the likelihood of activity in the neuron. In some embodiments, the altered polarity increased the likelihood of an action potential, or induces an action potential in the neuron.

In some embodiments, the neuron is a neuropeptidergic neuron. As such, in some embodiments, the altered polarity triggers the release of a neuropeptide by the neuron. In some embodiments, the neuropeptidergic neuron is located in the stria terminalis (dBNSTa), central nucleus of the amygdala (CeA), dorsomedial hypothalamus (DMH), the anterior cingulate cortex (ACC), or combination of any of the listed items.

In some embodiments, the neuropeptide comprises a neurokinin. In some embodiments, the neurokinin is selected from the group consisting of neurokinin A, neurokinin B, neuropeptide K, neuropeptide gamma, substance P, or a combination of two or more of the listed items. In some embodiments, the neuropeptide comprises a synthetic or variant neurokinin. For example, in some embodiments, the neurokinin is a variant having at least 80%, 81%, 82%, 83%, 84%, 85%, 86%, 87%, 88%, 89%, 90%, 91%, 92%, 93%, 94%, 95%, 96%, 97%, 98%, 99% identity to at least one of neurokinin A, neurokinin B, neuropeptide K, neuropeptide gamma, or substance P. In some embodiment, the variant neuropeptide comprises, consists essentially of, or consists of a neuropeptide receptor agonist. In some embodiment, nucleic acids encoding two or more different neuropeptides are administered to the subject. For example, in some embodiments, a vector comprises a first nucleic acid encoding a first neurokinin and a third nucleic acid encoding a second neurokinin. The first and third nucleic acids can be under the control of the same or different promoters. The second neurokinin can be the same or different from the first neurokinin. For example, in some embodiments, a first vector comprising a first nucleic acid encoding a first neurokinin and second vector comprising a third nucleic acid encoding a second neurokinin are administered to a subject. The second neurokinin can be the same or different from the first neurokinin. In some embodiments, a vector encodes at least 2, 3, 4, or 5 neurokinins, including ranges between any two of the listed values, such as 2-3, 2-4, 2-5, 3-4, 3-5, or 4-5.

It is noted that signal peptides can facilitate the release of polypeptides by cells. Accordingly, in some embodiments, the first nucleic acid further encodes a signal peptide. Examples of signal peptides can be found, for example, in Table 3 of U.S. Pat. No. 9,540,657, which is incorporated by reference in its entirety herein. Additional examples of neurokinin signal peptides are described herein.

In some embodiments, the first nucleic acid and the second nucleic acid are administered to the neuron of the subject in a single vector, for example an AAV as described herein. In some embodiments the first nucleic acid and the second nucleic acid are under the control of a single promoter (e.g., the first promoter) in the vector. In some embodiments the first nucleic acid and the second nucleic acid are under the control of a separate promoters (e.g., the first nucleic acid is under the control of the first promoter, and the second nucleic acid is under the control of the second promoter) in the vector. The separate promoters can be the same type of promoter (e.g., two copies of a TAC1 promoter), or different types of promoter (e.g., the nucleic acid encoding the neurokinin can be under the control of a ubiquitous promoter, and the nucleic acid encoding the conditional channel can be under the control of a TAC1 promoter). In some embodiments, the single vector comprises the first nucleic acid under the control of the first promoter, and the second nucleic acid under the control of the first promoter or second promoter. In some embodiments, the single vector comprising the first nucleic acid and the second nucleic acid comprises, consists essentially of, or consists of an AAV. In some embodiments, the single promoter is a neuropeptide promoter as described herein, for example a tachykinin promoter such as a TAC1 or TAC3 promoter. In some embodiments, the first and/or the second promoter is a neuropeptide promoter as described herein, for example a tachykinin promoter such as TAC1 or TAC3 promoter. In some embodiments, the first and second promoter are each a neuropeptide promoter as described herein, for example a tachykinin promoter such as TAC1 or TAC3 promoter. In some embodiments, a neuropeptide nucleic acid is under the control of its endogenous promoter.

In some embodiments, the first nucleic acid is administered to the neuron in the subject in a first vector, and the second nucleic acid is administered to the neuron in the subject in a second vector. The first vector and the second vector can be the same types of vectors, or different types of vectors. Additionally, the first nucleic acid and the second nucleic acid can be under the control of the same type of promoter or different types of promoter. In some embodiments, the first nucleic acid is operably linked to a first promoter is administered to the neuron in the subject in a first vector (such as an AAV), and the second nucleic acid is operably linked to another copy of the first promoter is administered to the neuron in the subject in a second vector (such as an AAV). In some embodiments, the first nucleic acid operably linked to a first promoter is administered to the neuron in the subject in a first vector (such as an AAV), and the second nucleic acid operably linked to a second promoter (that is different from the first promoter) is administered to the neuron in the subject in a second vector (such as an AAV). In some embodiments, one or both of the first vector and second vector is an AAV. In some embodiments, the first vector and second vector are administered to the subject concurrently. In some embodiments, the first vector and second vector are administered to the subject in a single composition. In some embodiments, the first vector and second vector are administered to the subject concurrently, but in separate compositions. In some embodiments, the first vector and second vector are administered to the subject at different times (and thus in separate compositions). For example, in some embodiments, the nucleic acid encoding the neurokinin is administered first, and the nucleic acid encoding the conditional receptor is administered second. In some embodiments, the nucleic acid encoding the conditional receptor is administered first, and the nucleic acid encoding the neurokinin is administered second.

In some embodiments, the conditional receptor comprises, consists essentially of, or consists of a hM3DREADD (and the agonist comprises, consists essentially of, or consists of clozapine-N-oxide), or the conditional receptor comprises, consists essentially of, or consists of an optogenetic channel such as channel rhodopsin (and the agonist comprises, consists essentially of, or consists of electromagnetic radiation such as light).

In some embodiments, the subject has a neurological disease or disorder, for example degenerative diseases of the nervous system such as Huntington's disease (HD), Alzheimer's disease, Parkinson's disease, Amyotrophic lateral sclerosis, spinal muscular atrophy, types I and II, Friedreich's Ataxia, Spinocerebellar ataxia, and/or behavioral disorders, such as depression, anxiety, schizophrenia, post traumatic stress disorder, or a combination of two or more of the listed items. In some embodiments, the neurological disease or disorder comprises, consists essentially of, or consists of a brain disorder that can be ameliorated by increasing the level of a particular neuropeptide. In some embodiments, administering the neuropeptide treats, inhibits, ameliorates, reduces the severity of, delays the onset of, or prevents the neurological disease or disorder.

In methods and kits of some embodiments, the nucleic acids (or vector such as AAV) are administered to the subject at most about once every week, at most about once every two weeks, at most about once every month, at most about one every six months, at most about once every year, at most about once every two years, at most about once every three years, at most about once every four years, at most about once every five years, at most about once every six years, at most about once every seven years, at most about once every eight years, at most about once every nine years, at most about once every ten years, or at most about once every fifteen years.

Methods of Altering a Behavior

Some embodiments include a method of altering a behavior in a subject in need thereof. The method can comprise administering a first nucleic acid to the subject, in which the first nucleic acid encodes the neuropeptide. The method can comprise administering a second nucleic acid the subject, in which the second nucleic acid encodes a conditional receptor as described herein. The first nucleic acid and the second nucleic acid can be administered in a vector system that provides the first nucleic acid and the second nucleic acid to a target neuron of the subject (for example, by transducing), in which the target neuron expresses the neuropeptide and the conditional receptor. The method can comprise administering an agonist or stimulus to the subject, in which the agonist or stimulus induces the conditional receptor to alter the polarity of the target neuron. The expression of the neuropeptide in the neuron having the altered polarity can cause a change in the behavior of the subject. In some embodiments, the agonist is administered systemically, for example orally administered. In some embodiments, the stimulus is applied systemically. In some embodiments, the stimulus is applied to a targeted region of the brain, for example, the stria terminalis (dBNSTa), central nucleus of the amygdala (CeA), dorsomedial hypothalamus (DMH), the anterior cingulate cortex (ACC), or a combination of any of the listed items. In some embodiments, the behavior is a social behavior.

In some embodiments, the altered behavior comprises a symptom of social isolation stress, aggression, or depression.

In some embodiments, the altered polarity in the neuron activates the neuron. For example, the altered polarity of the neuron can reduce polarization of the neuron, or depolarize the neuron, and thus can increase the likelihood of an action potential, or can induce an action potential in the neuron.

In some embodiments, the neuron is a neuropeptidergic neuron, for example neuropeptidergic neurons of the CNS. In some embodiments, the neuropeptidergic neurons are located in the stria terminalis (dBNSTa), central nucleus of the amygdala (CeA), dorsomedial hypothalamus (DMH), the anterior cingulate cortex (ACC), or combination of any of the listed items.

In some embodiments, the neuropeptide comprises a neurokinin as described herein. In some embodiments, the neuropeptide is selected from the group consisting of neurokinin A, neurokinin B, neuropeptide K, neuropeptide gamma, and substance P. In some embodiments, the neuropeptide comprises a synthetic or variant neurokinin. For example, in some embodiments, the neurokinin is a variant having at least 80%, 81%, 82%, 83%, 84%, 85%, 86%, 87%, 88%, 89%, 90%, 91%, 92%, 93%, 94%, 95%, 96%, 97%, 98%, 99% identity to at least one of neurokinin A, neurokinin B, neuropeptide K, neuropeptide gamma, or substance P.

In some embodiments, the first nucleic acid further encodes a signal peptide, for example as described herein or as shown, for example, in Table 3 of U.S. Pat. No. 9,540, 657, which is hereby incorporated by reference in its entirety.

In some embodiments, the first nucleic acid and the second nucleic acid are administered to the neuron in the subject in a single vector. In some embodiments, the single vector is an AAV. In some embodiments, the first nucleic acid are under control of a single promoter in the single vector. For example, first nucleic acid and the second nucleic acid can be separated by an IRES, 2A sequence, or protease site. In some embodiments, the first nucleic acid are under control of different prompters in the single vector. The two different promoters can be of the same type, or of different types. As such, in some embodiments, the single vector comprises the first nucleic acid under the control of the first promoter, and the second nucleic acid under the control of the first promoter or second promoter. In some embodiments, the first nucleic acid is 5' of the second nucleic acid. In some embodiments, the second nucleic acid is 5' of the first nucleic acid. In some embodiments, the single promoter is a neuropeptide promoter as described herein, for example a tachykinin promoter such as TAC1 or TAC3 promoter. In some embodiments, the first and/or second promoter is a neuropeptide promoter as described herein, for example a tachykinin promoter such as TAC1 or TAC3 promoter. In some embodiments, the first and second promoter are each a neuropeptide promoter as described herein, for example a tachykinin promoter such as TAC1 or TAC3 promoter. In some embodiments, a neuropeptide nucleic acid is under the control of its endogenous promoter.

In some embodiments, the first and second nucleic acids are administered to the neuron of the subject in two different vectors. For example, the first nucleic acid can be administered to the subject in a first vector, and the second nucleic acid can be administered to the neuron in the subject in a second vector. The first and second vectors can be of the same type or different types. In some embodiments, one or both of the first vector and second vector is an AAV. In some embodiments, the first and second vector are both AAVs. In some embodiments, the first nucleic acid and the second nucleic acid are administered to the neuron of the subject in two different vectors, but each of the first nucleic acid and the second nucleic acid is under the control of the same type of promoter in its respective vector. For example, each of the first and second nucleic acid can be under the control of the same neurokinin promoter. In some embodiments, the first and second promoter are each a neuropeptide promoter as described herein, for example a tachykinin promoter such as TAC1 or TAC3 promoter. In some embodiments, the first and/or second promoter is a neuropeptide promoter as described herein, for example a tachykinin promoter such as TAC1 or TAC3 promoter. In some embodiments, the first and second promoter are each a neuropeptide promoter as described herein, for example a tachykinin promoter such as TAC1 or TAC3 promoter.

In some embodiments, nucleic acids encoding two or more different neuropeptides are administered to the subject. For example, in some embodiments, a vector comprises a first nucleic acid encoding a first neurokinin and a third nucleic acid encoding a second neurokinin. The first and third nucleic acids can be under the control of the same or different promoters. The second neurokinin can be the same or different from the first neurokinin. For example, in some embodiments, a first vector comprising a first nucleic acid encoding a first neurokinin and second vector comprising a third nucleic acid encoding a second neurokinin are administered to a subject. The second neurokinin can be the same or different from the first neurokinin. In some embodiment, nucleic acids encoding at least two, three, four, or five more different neuropeptides (including ranges between any two of the listed values, for example, 2-3, 2-4, 25, 3-4, 3-5, or 4-5) are administered to the subject.

In some embodiments, the conditional receptor comprises a hM3DREADD. Accordingly, the agonist can comprise clozapine-N-oxide (CNO). In some embodiments, the conditional receptor comprises an optogenetic channel such as channel rhodopsin and the agonist comprises electromagnetic radiation.

In methods and kits of some embodiments, the nucleic acids (or vector such as AAV) are administered to the subject at most about once every week, at most about once every two weeks, at most about once every month, at most about one every six months, at most about once every year, at most about once every two years, at most about once every three years, at most about once every four years, at most about once every five years, at most about once every six years, at most about once every seven years, at most about once every eight years, at most about once every nine years, at most about once every ten years, or at most about once every fifteen years.

In some embodiments, the subject suffers from social isolation stress, the neuropeptide comprises neurokinin B, and the conditional receptor comprises an hM4DREADD. The agonist can comprise CNO. The neuropeptide and conditional receptor can be expressed under the control of a Tac1 promoter. In some embodiment, the subject further suffers from or is at risk of a disorder that is exacerbated by social isolation stress. In some embodiments, the subject suffers from social isolation stress, the conditional receptor comprises an hM4DREADD, but the neuropeptide is not expressed. The conditional receptor can be expressed under the control of a Tac1 promoter. In some embodiment, the subject further suffers from or is at risk of a disorder that is exacerbated by social isolation stress. In some embodiments, the subject suffers from aggression, cancer, major depressive disorder, dysthymic disorder, social phobia, generalized anxiety disorder, alcohol abuse and dependence, drug abuse, nicotine dependence, atherosclerosis, coronary heart disease, ischemic stroke, cognitive impairment, Alzheimer's disease, agoraphobia, isolated post-traumatic stress disorder (PTSD), bereavement, grieving in isolation, or single member living schizophrenia, or two or more of the listed items. The subject can further suffer from or be at risk of social isolation stress. In some embodiments, the subject suffers from, cancer, major depressive disorder, dysthymic disorder, social phobia, generalized anxiety disorder, alcohol abuse and dependence, drug abuse, nicotine dependence, atherosclerosis, coronary heart disease, ischemic stroke, cognitive impairment, or Alzheimer's disease, or two or more of the listed items. The subject can further suffer from or be at risk of social isolation stress.

Kits

In some embodiments, kits are described. The kit can comprise a first nucleic acid encoding a neuropeptide. The kit can comprise a second nucleic acid encoding a conditional receptor configured to alter neuron polarity upon binding of an agonist or application of a stimulus to the conditional receptor. Either (a) a single vector can comprise the first nucleic acid and the second nucleic acid, or (b) a first vector can comprise the first nucleic acid and a second vector can comprise the second nucleic acid. In some embodiments, the single vector comprises, consists essentially of, or consists of an AAV. In some embodiments, the first and second vector each comprises, consists essentially of, or consists of an AAV. In some embodiments, the kit comprises a single vector, or a first and second vector as described herein.

In some embodiments, kit comprises, consists essentially of, or consists of a single vector comprising the first and second nucleic acids. In some embodiments, (a) the kit comprises, consists essentially of, or consists of the single vector, and the single vector further comprises a single promoter that is operably linked to the first nucleic acid and second nucleic acid. The single promoter can be configured to drive expression specifically in neuropeptidergic neurons. In some embodiments, the single promoter is a neuropeptide promoter as described herein, for example a tachykinin promoter such as a TAC1 or TAC3 promoter. In some embodiments, (a), the single vector comprises, consists essentially of, or consists of an AAV.

In some embodiments, kit comprises, consists essentially of, or consists of a first vector comprising the first nucleic acid, and a second vector comprising the second nucleic acids. In some embodiments, (b) the kit comprises, consists essentially of, or consists of the first vector and the second vector. The first vector can further comprise a first promoter that is operably linked to the first nucleic acid. The first promoter can be configured to drive expression specifically in a neuropeptidergic neuron. The second vector can comprise a second promoter that is operably linked to the second nucleic acid, the second promoter configured to drive expression specifically in a neuropeptidergic neuron. In some embodiments, the first and second promoter are each a neuropeptide promoter as described herein, for example a tachykinin promoter such as TAC1 or TAC3 promoter. In some embodiments, the first nucleic acid is under the control of the endogenous promoter of the neuropeptide encoded by the first nucleic acid. In some embodiments, (b) the first vector and the second vector each comprise, consist essentially of, or consist of an AAV. In some embodiments, the first and second vector are in a single composition. In some embodiments, the first and second vector are in separate compositions.

In the kit of some embodiments, the first and second promoter are each a neuropeptide promoter or a neuropeptide receptor promoter, or the single promoter is a neuropeptide promoter or a neuropeptide receptor promoter. In the kit of some embodiments, the first and second promoter are each a neuropeptide promoter as described herein, for example a tachykinin promoter such as TAC1 or TAC3 promoter. In the kit of some embodiments, the single promoter is a neuropeptide promoter as described herein, for example a tachykinin promoter such as TAC1 or TAC3 promoter.

In the kit of some embodiments, (a) the single vector comprises an AAV, and/or (b) the first vector and second vector each comprise an AAV.

The kit of some embodiments comprises the agonist or the stimulus. For example, if the conditional receptor comprises hM3DREADD, the kit may further comprise the agonist clozapine-N-oxide (CNO). For example, if the conditional receptor comprises an optogenetic channel such as channel rhodopsin, the kit may further comprise an illumination source configured emit electromagnetic radiation at a wavelength that stimulates the conditional receptor.

In the kit of some embodiments, the neuropeptide comprises, consists essentially of, or consists of a neurokinin. In the kit of some embodiments, the neurokinin is selected from the group consisting of neurokinin A, neurokinin B, neuropeptide K, neuropeptide gamma, and substance P, or a combination of two or more of the listed items. In the kit of some embodiments, the neurokinin comprises, consists essentially of, or consists of a variant of a neurokinin, for example a variant of neurokinin A, neurokinin B, neuropeptide K, neuropeptide gamma, or substance P.

In the kit of some embodiments, the first nucleic acid further encodes a signal peptide. In the kit of some embodiments, the second nucleic acid further encodes a signal peptide. In the kit of some embodiments, the first nucleic acid and second nucleic acid each further encode a signal peptide.

Additional Embodiments

Without being limited by theory, it is contemplated herein that in order to produce a behavioral state that mimics the effects of an endogenous neuropeptide, it may not be sufficient to simply increase the expression of the neuropeptide (either by systemic drug administration or by genetic means), or to increase the activity of neuropeptidergic neurons that release the neuropeptide. Rather, combining two manipulations: that is, genetically increasing the level of expression of the neuropeptide, and activating the neurons that express the peptide, can promote its release. In some embodiments, these manipulations are performed in specific neuropeptidergic neurons cells in the brain.

In some embodiments, a therapeutic approach is described for treating a brain disorder that may be ameliorated by increasing the level of a particular neuropeptide. That is, rather than spending years to develop a drug that mimics the binding of the neuropeptide to its receptor (for cases in which the therapeutic indication requires an agonist of the receptor), the endogenous neurons that express the neuropeptide of interest can be genetically modified to 1) express increased levels of the neuropeptide; and 2) allow their conditional electrical activation (e.g., by pharmacogenetic, optogenetic or other genetically targetable methods for neuronal activation). Genetic modification can be accomplished using any number of genetic techniques (including viral vectors that cross the BBB such as AAVs), together with cell type-specific promoters that restrict expression of neuropeptides to particular classes of neuropeptidergic neurons. One way of controlling of the level of expression and release of the neuropeptides can then be accomplished by administration of inducing drugs that are orally bioavailable, and generic, allowing the system to be turned on or off at will. This method has the additional benefit that the therapeutically activated neuropeptide will be released only at the endogenous sites where it is normally released onto appropriate neuropeptide receptor-expressing neurons, thus reducing unwanted side-effects produced by non-specific, systemic delivery of an neuropeptide drug. The methods and kits can also be used to reduce the release of a neuropeptide, instead of administering an antagonist to the NP receptor, using genetic methods to 1) reduce the expression of the NP and 2) to inhibit the activity of the NPNs.

In addition to the disclosure elsewhere herein, the following options are described:

1. A method of expressing a neuropeptide in a neuron of a subject, the method comprising:
    administering a first nucleic acid to the neuron in the subject, the first nucleic acid encoding the neuropeptide, wherein a first promoter is operably linked to the first nucleic acid, whereby the neuropeptide is expressed in the neuron;
    administering a second nucleic acid to the neuron in the subject, the second nucleic acid encoding an conditional receptor configured to alter the polarity of the neuron upon application of an agonist or stimulus, wherein the first promoter or a second promoter is operably linked to the second nucleic acid, whereby the conditional receptor is expressed in the neuron; and applying the agonist or stimulus to the neuron of the subject, causing the conditional receptor induces a change in polarity in the neuron that expresses the neuropeptide.

2. The method of option 1, wherein the altered polarity in the neuron activates the neuron.

3. The method of any one of options 1-2, wherein the altered polarity induces an action potential by the neuron.

4. The method of any one of options 1-3, wherein the neuron is a neuropeptidergic neuron.

5. The method of any one of options 1-4, wherein the neuropeptide comprises a neurokinin.

6. The method of any one of options 1-5, wherein the neuropeptide is selected from the group consisting of neurokinin A, neurokinin B, neuropeptide K, neuropeptide gamma, and substance P.

7. The method of any one of options 1-6, wherein the first nucleic acid further encodes a signal peptide 8. The method of any one of options 1-7, wherein the first nucleic acid and the second nucleic acid are administered to the neuron in the subject in a single vector.

9. The method of option 8, wherein the single vector is an AAV.

10. The method of any one of options 8-9, wherein the single vector comprises the first nucleic acid under the control of the first promoter, and the second nucleic acid under the control of the first promoter or second promoter.

11. The method of any one of options 1-7, wherein the first nucleic acid is administered to the neuron in the subject in a first vector, and wherein the second nucleic acid is administered to the neuron in the subject in a second vector.

12. The method of option 11, wherein one or both of the first vector and second vector is an AAV.

13. The method of any one of options 1-12, wherein the conditional receptor comprises a hM3DREADD and the agonist comprises clozapine-N-oxide, or wherein the conditional receptor comprises an optogenic channel such as channel rhodopsin and the agonist comprises electromagnetic radiation.

14. A method of altering a behavior in a subject in need thereof, the method comprising:

administering a first nucleic acid to the subject, the nucleic acid encoding a neuropeptide;

administering a second nucleic acid the subject, the second nucleic acid encoding a conditional receptor, wherein the first nucleic acid and the second nucleic acid are administered in a vector system that provides the first nucleic acid and the second nucleic acid to a target neuron of the subject, wherein the target neuron expresses the neuropeptide and the conditional receptor; and applying an agonist or stimulus to the neuron of the subject, causing the conditional receptor induces a change in polarity in the neuron that expresses the neuropeptide, thus altering a behavior of the subject.

15. The method of option 14, wherein the altered behavior comprises a symptom of social isolation stress, aggression, or depression.

16. The method of any one of options 14-15, wherein the altered polarity in the neuron activates the neuron.

17. The method of any one of options 14-16, wherein the altered polarity induces an action potential by the neuron.

18. The method of any one of options 14-17, wherein the neuron is a neuropeptidergic neuron.

19. The method of any one of options 14-18, wherein the neuropeptide comprises a neurokinin.

20. The method of any one of options 14-19, wherein the neurokinin is selected from the group consisting of neurokinin A, neurokinin B, neuropeptide K, neuropeptide gamma, and substance P.

21. The method of any one of options 14-20, wherein the first nucleic acid further encodes a signal peptide 22. The method of any one of options 14-21, wherein the first nucleic acid and the second nucleic acid are administered to the neuron in the subject in a single vector.

23. The method of option 22, wherein the single vector is an AAV.

24. The method of any one of options 22-23, the single vector comprising the first nucleic acid under the control of the first promoter, and the second nucleic acid under the control of the first promoter or second promoter.

25. The method of any one of options 14-24, wherein the first nucleic acid is administered to the neuron in the subject in a first vector, and wherein the second nucleic acid is administered to the neuron in the subject in a second vector.

26. The method of option 25, wherein one or both of the first vector and second vector is an AAV.

26. The method of any one of options 14-26, wherein the conditional receptor comprises a the conditional receptor comprises a hM3DREADD and the agonist comprises clozapine-N-oxide, or wherein the conditional receptor comprises an optogenic channel such as channel rhodopsin and the agonist comprises electromagnetic radiation.

27. A kit comprising:

a first nucleic acid encoding a neuropeptide;

a second nucleic acid encoding an conditional receptor configured to alter neuron polarity upon binding of an agonist or application of a stimulus to the conditional receptor, wherein either (a) a single vector comprises the first nucleic acid and the second nucleic acid, or (b) a first vector comprises the first nucleic acid and a second vector comprises the second nucleic acid.

28. The kit of option 27, wherein (a) the kit comprises the single vector, further comprising a single promoter that is operably linked to the first nucleic acid and second nucleic acid, the single promoter configured to drive expression specifically in neuropeptidergic neurons.

29. The kit of option 27, wherein (b) the kit comprises the first vector and the second vector, the first vector further comprising a first promoter that is operably linked to the first nucleic acid, the first promoter configured to drive expression specifically in a neuropeptidergic neuron, and the second vector comprising a second promoter that is operably linked to the second nucleic acid, the second promoter configured to drive expression specifically in a neuropeptidergic neuron.

31. The kit of any one of options 27-29, wherein (a) the single vector comprises an AAV, and/or (b) the first vector and second vector each comprise an AAV.

30. The kit of any one of options 27-29, further comprising the agonist or the stimulus.

31. The kit of any one of options 27-30, wherein the neuropeptide comprises a neurokinin.

32. The kit of option 31, wherein the neurokinin is selected from the group consisting of neurokinin A, neurokinin B, and substance P.

33. The kit of any one of options 27-32, wherein the first nucleic acid further encodes a signal peptide.

34. The kit of any one of options 27-33, wherein the first and second promoter are each a neuropeptide promoter or a neuropeptide receptor promoter; or wherein the single promoter is a neuropeptide promoter or a neuropeptide receptor promoter 35. A vector comprising:
a first nucleic acid encoding a neuropeptide; and
a second nucleic acid encoding an conditional receptor configured to alter neuron polarity upon binding of an agonist or application of a stimulus to the conditional receptor, 36. The vector of option 35, further comprising a single promoter that is operably linked to the first nucleic acid and second nucleic acid, the single promoter configured to drive expression specifically in neuropeptidergic neurons.

37. The vector of option 35, further comprising:
a first promoter that is operably linked to the first nucleic acid, the first promoter configured to drive expression specifically in a neuropeptidergic neuron, and
a second promoter that is operably linked to the second nucleic acid, the second promoter configured to drive expression specifically in a neuropeptidergic neuron.

38. The vector of any one of options 35-37, wherein the vector comprises an adeno-associated virus (AAV).

MATERIALS AND METHODS FOR EXAMPLES 1-9

Animals

C57BL/6N male mice (experimental), C57BL/6N female mice (for sexual experience), and BALB/c (intruder) WT male mice were obtained from Charles River (at 6-10 weeks of age). For visualization of Tac2 and Tac1 expression, we used previously described Cre-dependent Ai6-zsGreen and Ai14-mCherry fluorescent reporter mice (Madisen et al., 2010; incorporated by reference in its entirety), Tac2-IRES2-Cre (Cai et al., 2014; incorporated by reference in its entirety), and Tac 1-IRES2-Cre knockin mice (obtained from the Allen Institute for Brain Science), which were backcrossed to the C57BL/6N background in the Caltech animal facility. Tac2-Cre mice were used for Cre-dependent LOF/GOF experiments (FIGS. 5A-Q, FIGS. 7A-I). Animals were housed and maintained on a reverse 12-hr light-dark cycle with food and water ad libitum. Behavior was tested during the dark cycle. Care and experimental manipulation of animals were in accordance with the National Institute of Health Guide for Care and Use of Laboratory Animals and approved by the Caltech Institutional Animal Care and Use Committee. As shown in FIGS. 15A-D, in the Tac2-Cre mice Ai6-zsGreen mice, zsGreen staining was observed in the parotid gland and mandibular gland (FIG. 15A), coagulating ducts (FIG. 15B), pancreas (FIG. 15C), sublingual glands (FIG. 15D) and testes (FIG. 15E). Thus, it can be concluded that Tac2 is transcribed outside of the CNS in peripheral tissues such as the parotid gland (FIG. 15A), mandibular gland (FIG. 15A), coagulating ducts (FIG. 15B), pancreas (FIG. 15C), sublingual glands (FIG. 15D) and testes (FIG. 15E).

Social Isolation Stress

WT males (Charles River) were housed in isolation (1 animal per cage), or in groups of 3. Tac2-Cre males (bred in-house) were housed in isolation, or in groups of 2-5. Animals were isolated post-weaning, at 8-16 weeks of age. All cage conditions remained otherwise identical for group-housed mice compared to isolated animals, and mice were housed on the same rack in the same vivarium. Except as otherwise indicated, social isolation was maintained for at least 2 weeks (this period was extended in the case of surgical experiments, i.e. when adequate time for recovery and viral expression levels were required). All mice were between 12-20 weeks of age at the time of behavioral testing.

Viral Constructs

AAV2-EF1a-DIO-hM4D(Gq)-mCherry and AAV2-EF1a-DIO-mCherry were acquired from the University of North Carolina (UNC) viral vector core. The pAAV-Tac2-shRNA1-CMV-zsGreen, pAAV-Tac2-shRNA2-CMV-zsGreen, and pAAV-shRLuc-CMV-zsGreen plasmids were constructed as described below and serotyped with AAV5 coat proteins and packaged in-house (see viral packaging below). The pAAV-hSyn-Tac2-P2A-mCherry and pAAV-hSyn-Tac2-P2A-GFP plasmids were constructed as described below and packaged into AAV-PHP.B (see PHP.B section below). The pAAV-hSyn-DIO-hM3D(Gq)-mCherry and pAAV-hSyn-DIO-mCherry were acquired from Addgene and packaged into AAV-PHP.B (see below).

Construction of Small Hairpin RNA Expressing AAV Vector

Small hairpin RNA (shRNA) for the mouse Tac2 gene (NM_009312.2) were designed using the online designing tool siDirect 2.0 (http://sidirect2.rnai.jp/) (Naito et al., 2009; incorporated by reference in its entirety).

Oligonucleotides encoding Tac2 shRNAs were purchased from IDT. Oligonucleotides used were as follows: shRNA1, 5'-CCGACGTGGTTGAAGAGAACACCGCTTCCTGT-CACGGTGTTCTCTTCAACCACGT C TTTTTT-3' (SEQ ID NO: 9) and 5'-AAAAAAGACGTGGTT-GAAGAGAACACCGTGACAG-GAAGCGGTGTTCTCTTCAAC C ACGTCGG-3' (SEQ ID NO: 10); shRNA2, 5'-CCGCCTCAACCCCAT-AGCAATTAGCTTCCTGTCACTAATTGCTATGGGGTT-GAGG C TTTTTT-3' (SEQ ID NO: 11) and 5'-AAAAAAGCCTCAACCCCATAGCAATT-AGTGACAGGAAGCTAATTGCTATGGGGT TG AGGCGG-3' (SEQ ID NO: 12).

pAAV.H1.shRLuc.CMV.ZsGreen.SV40 (Luc shRNA) plasmid (PL-C-PV1781, Penn Vector Core) was used as shRNA AAV vector backbone and control shRNA construct. The entire Luc shRNA plasmid except the luciferase shRNA sequence was amplified by PCR with the following primers: shRNA1, Forward—AACCACGTCTTTTTTAAT-TCTAGTTATTAATAGTAATCAA (SEQ ID NO: 13); Reverse—CTTCAACCACGTCGGCTGG-GAAAGAGTGGTCTC (SEQ ID NO: 14); shRNA2, Forward—GGTTGAGGCTTTTTTAATTCTAGTTAT-TAATAGTAATCAA (SEQ ID NO: 15); Reverse—ATGGGGTTGAGGCGGCTGGGAAAGAGTGGTCTC (SEQ ID NO: 16). All PCR reactions were performed using PrimeSTAR Max DNA Polymerase (Takara Bio, Kusatsu, Japan). After PCR amplification, template plasmid was digested by DpnI (NEB, Ipswich, Mass.) and PCR amplicons were ligated with annealed shRNA oligos using the GeneArt Seamless Cloning and Assembly Kit (Thermo Fisher Scientific, Waltham, Mass.) following the manufacturer's instructions.

Construction of Tac2-Overexpression AAV Vectors

The Tac2-P2A-mCherry gene fragment was synthesized in the form of IDT gBlocks (see below). pAAV-hSyn-Tac2-P2A-mCherry was generated via ligation to the AccI/NheI site of pAAV-hSyn-DIO-hM3D(Gq)-mCherry plasmid (Addgene #44361) using DNA Ligation Kit Mighty Mix (Takara Bio, Kusatsu, Japan). To generate the pAAV-hSyn-Tac2-P2A-GFP plasmid, the entire pAAV-hSyn-Tac2-P2A-mCherry plasmid except mCherry sequence was amplified by PCR with the following primers: Forward—

CTCCTCGCCCTTGCTCAC (SEQ ID NO: 17); Reverse—GGCGCGCCATAACTTCGTATAATG (SEQ ID NO: 18) and the GFP sequence was amplified from the pAAV-GFP plasmid (AAV-400, Cell Biolabs Inc, San Diego, Calif.) with the following primers: Forward—CCTGGACCTATGGTGAGCAAGGGCGAGGAGCTGTTCACCGGGGTGGTG (SEQ ID NO: 19); Reverse—AGCATACATTATACGAAGTTATGGCGCGCCCTACTTGAGCTCGAGATCTGAGTAC (SEQ ID NO: 20). Both PCR amplicons were treated with DpnI (NEB) and ligated together using the GeneArt Seamless Cloning and Assembly Kit (Thermo Fisher scientific) following the manufacturer's instructions.

The synthesized Tac2-P2A-mCherry gene fragment was as follows:

(SEQ ID NO: 21)
GCTAGCGCCACCATGAGGAGCGCCATGCTGTTTGCGGCTGTCCTCGCCC

TCAGCTTGGCTTGGACCTTCGGGGCTGTGTGTGAGGAGCCACAGGGGCA

GGGAGGGAGGCTCAGTAAGGACTCTGATCTCTATCAGCTGCCTCCGTCC

CTGCTTCGGAGACTCTACGACAGCCGCCCTGTCTCTCTGGAAGGATTGC

TGAAAGTGCTGAGCAAGGCTTGCGTGGGACCAAAGGAGACATCACTTCC

ACAGAAACGTGACATGCACGACTTCTTTGTGGGACTTATGGGCAAGAGG

AACAGCCAACCAGACACTCCCACCGACGTGGTTGAAGAGAACACCCCA

GCTTTGGCATCCTCAAAGGAAGCGGAGCTACTAACTTCAGCCTGCTGAA

GCAGGCTGGAGACGTGGAGGAGAACCCTGGACCTATGGTGAGCAAGGGC

GAGGAGGATAACATGGCCATCATCAAGGAGTTCATGCGCTTCAAGGTGC

ACATGGAGGGCTCCGTGAACGGCCACGAGTTCGAGATCGAGGGCGAGGG

CGAGGGCCGCCCCTACGAGGGCACCCAGACCGCCAAGCTGAAGGTGACC

AAGGGTGGCCCCCTGCCCTTCGCCTGGGACATCCTGTCCCCTCAGTTCA

TGTACGGCTCCAAGGCCTACGTGAAGCACCCCGCCGACATCCCCGACTA

CTTGAAGCTGTCCTTCCCCGAGGGCTTCAAGTGGGAGCGCGTGATGAAC

TTCGAGGACGGCGGCGTGGTGACCGTGACCAGGACTCCTCCCTGCAGGA

CGGCGAGTTCATCTACAAGGTGAAGCTGCGCGGCACCAACTTCCCCTCC

GACGGCCCCGTAATGCAGAAGAAGACCATGGGCTGGGAGGCCTCCTCCG

AGCGGATGTACCCCGAGGACGGCGCCCTGAAGGGCGAGATCAAGCAGAG

GCTGAAGCTGAAGGACGGCGGCCACTACGACGCTGAGGTCAAGACCACC

TACAAGGCCAAGAAGCCCGTGCAGCTGCCCGGCGCCTACAACGTCAACA

TCAAGTTGGACATCACCTCCCACAACGAGGACTACACCATCGTGGAACA

GTACGAACGCCGAGGGCCGCCACTCCACCGGCGGCATGGACGAGCTG

TACAAGTAAGGCGCGCCATAACTTCGTATAATGTATGCTATACGAAGTT

ATTAAGAGGTTTCATATTGCTAATAGCAGCTACAATCCAGCTACCATTC

TGCATAACTTCGTATAAAGTATCCTATACGAAGTTATTCCGGAGTCGAC.

Viral Packaging rAAVs were produced by polyethylenimine (PEI) triple transfection of HEK293T cells. Briefly, 40 µg of equimolar pHelper, pXR5 and pAAV-trans DNA plasmids were mixed with 120 µl of 1 mg/ml Polyethylenimine HCl MAX (Polysciences) in PBS and incubated at RT for 5 minutes. 90% confluent HEK293 cells grown on 15 cm tissue culture plates were transfected with the plasmid/PEI mixture. Cells were collected 72 hours post transfection, freeze-thawed 3 timed and incubated with Benzonase (Millipore) at 5 units/mL for 1 hour. The solution was then centrifuged at 5000×g for 20 minutes. The supernatant was layered on top of a discontinuous gradient of iodixanol and centrifuged at 200,000×g for 2 hours at 18° C. The 40% iodixanol fraction was collected, concentrated, and buffer exchanged with PBS using a Millipore 100 kD centrifugal filter. AAV genomic titers were determined by real-time PCR using primers against the ITR and normalized by dilution with PBS to $1×10^{12}$ genome copies per mL virus.

AAV-PHP.B Production and Intravenous Administration

The AAV-hSyn-DIO-Tac2-P2A-mCherry, AAV-hSyn-DIO-hM3D-mCherry, and AAV-hSyn-DIO-mCherry recombinant AAV genomes were separately packaged into the AAV-PHP.B capsid by triple transfection of HEK293T cells and purified with iodixanol step gradients as previously described (Deverman et al., 2016; incorporated by reference in its entirety). $5×10^{11}$ vector genomes (vg) of each virus were administered intravenously (via the retro-orbital sinus) to Tac2-Cre animals individually or in combination. To equalize the amount of virus given to each mouse, $5×10^{11}$ vg of AAV-PHP.B-hSyn-DIO-mCherry was administered to each animal to bring the amount of virus up to the amount injected in the double Tac2+hM3DREAAD group. Each animal received a total vector dose of $1×10^{12}$ vg.

Surgery and Cannula Implants 8-16 week old mice were anesthetized with isoflurane and mounted in a stereotaxic apparatus (Kopf Instruments). Anesthesia was maintained throughout surgery at 1-1.5% isoflurane. The skull was exposed and small burr holes produced dorsal to each injection site using a stereotaxic mounted drill. Virus was backfilled into pulled fine glass capillaries (~50 µm diameter at tip) and pressure injections of 300 nl were made bilaterally into either the dBNSTa (AP+0.25, ML±0.85, DV−4.1), DMH (AP−1.3, ML±0.35, DV−5.6), or CeA (AP−1.4, ML±2.6, DV−4.73) at a rate of 30 nl per minute using a nanoliter injector (Nanoliter 2000, World Precision Instruments) controlled by an ultra microsyringe pump (Micro4, World Precision Instruments). Capillaries remained in place for 5 minutes following injections to allow for full diffusion of virus and to reduce backflow up the injection tract. Skin above the skull was then drawn together and sealed with GLUture (Zoetis). For bilateral cannula implantations, single or double guide cannulas (custom, Plastics One) aimed 0.5 mm above each region were implanted and held in place with dental cement (Parkell). Compatible dummy cannulas with a 0.5 mm protrusion at the tip were inserted to prevent cannula clogging. Directly following surgery, mice were given a subcutaneous injection of ketoprofen (2 mg/kg) and supplied with drinking water containing 400 mg/L sulphamethoxazole and 200 mg/L ibuprofen and monitored for 7 days. Dummies were replaced every 2-3 days to keep cannula tracts clean. All injections were subsequently verified histologically.

Immunohistochemistry

Immunofluorescence staining proceeded as previously described (Anthony et al., 2014; Cai et al., 2014; Hong et al., 2014; Kunwar et al., 2015; incorporated by reference in their entirety). Briefly, mice were perfused transcardially with 0.9% saline followed by 4% paraformaldehyde (PFA) in 1×PBS. Brains were extracted and post-fixed in 4% PFA overnight at 4° C. followed by 48 hours in 15% sucrose. Brains were embedded in OCT mounting medium, frozen on dry ice, and stored at −80° C. for subsequent sectioning. Sections 40-50 µm thick were cut on a cryostat (Leica Biosystems). Sections were either directly mounted onto Superfrost slides for histological verification of injections/cannula placements or were cut free floating for antibody staining. For antibody staining, brain sections were washed 3× in 1×PBS and blocked in PBS-T (0.3% Triton X-100 in 1×PBS) with 10% normal goat or donkey serum for 1 hr at room temperature (RT). Sections were then incubated in primary antibody diluted in blocking solution at 4° C. for 48-72 hours. Sections were stained for neurokinin B (rabbit anti-proNKB; 1:1000; Ressler lab); the glial marker nuclear factor I-A (rabbit anti-mouse NFIA; 1:1000; Deneen lab) (Deneen et al., 2006; incorporated by reference in its entirety); the oligodendrocyte marker proteolipid protein (chicken anti-PLP; 1:1,000; Millipore) or the nuclear marker NeuN (rabbit anti-NeuN; 1:1000; Millipore). Sections were then washed 3× and incubated in secondary antibodies diluted in blocking buffer (goat anti-rabbit, goat anti-chicken, Alexa Fluor 594, 1:500) overnight at 4° C. Sections were then washed 3×, incubated for 20 minutes at RT in DAPI diluted in 1×PBS (1:2000) for counterstaining, washed again, mounted on Superfrost slides, and coverslipped for imaging on a confocal microscope (Olympus FluoView FV1000).

Fluorescent In Situ Hybridization

Digoxigenin-labeled Tac2 RNA probe was generated following a previously described protocol (http://help.brain-map.org/display/mousebrain/Documentation) (Lein et al., 2007; incorporated by reference in its entirety) with the following primer sets: Forward—AGCCAGCTCCCT-GATCCT (SEQ ID NO: 22); Reverse—TTGC-TATGGGGTTGAGGC (NM_009312.2, 36-608 bp) (SEQ ID NO: 23). Fluorescent in situ hybridization (FISH) was carried out according to the protocol described in (Thompson et al., 2008; incorporated by reference in its entirety) with modifications. Briefly, mice were transcardially perfused with 1×PBS followed by 4% paraformaldehyde/PBS (PFA) in 1×PBS. Brains were fixed in 4% PFA for 3-4 hours at 4° C. and cryoprotected overnight in 15% sucrose at 4° C. Brains were embedded in OCT Compound (Fisher Scientific) and cryosectioned at 30 μm thickness and mounted on Superfrost Plus slides (Fisher Scientific). Sections were fixed in 4% PFA for 30 minutes, acetylated with 0.25% acetic anhydride in 0.1 M triethanolamine for 10 minutes, dehydrated with increasing concentrations of EtOH (50, 70, 95 and 100%), gently treated with proteinase K (6.3 μg/mL in 0.01M Tris-HCl pH 7.4 and 0.001M EDTA) for 10 minutes, and fixed in 4% PFA for 20 minutes. All procedures were performed at room temperature (RT). The hybridization buffer contained 50% deionized formamide, 3× standard saline citrate (SSC), 0.12 M PB (pH 7.4), 10% dextran sulfate, 0.12 mg/ml yeast tRNA, 0.1 mg/mL calf thymus DNA, and 1× Dehardt solution. The sections were prehybridized at 63° C. in hybridization buffer for 30 minutes and then hybridized with the digoxigenin-labeled Tac2 RNA probe (300 ng/ml) in hybridization buffer at 63° C. for 16 hours. After hybridization, the sections were washed with 5 X SSC for 10 minutes, 4× SSC/50% formamide for 20 minutes, 2×SSC/50% formamide for 30 minutes, and 0.1× SSC for 20 minutes twice each at 61° C. The sections were blocked with 4% sheep serum in TNT buffer (Tris-HCl pH7.5, 0.15 M NaCl and 0.00075% Tween 20) for 30 minutes and TNB Blocking buffer (TSA blocking reagent, PerkinElmer, Waltham, Masss.) for 30 minutes at RT. The sections were incubated overnight at RT with anti-digoxigenin-POD antibody (1:600, Roche Diagnostics) in TNB buffer. The sections were washed with TNT buffer and tyramide-biotin signal amplification was performed using the TSA Plus Biotin Kit (PerkinElmer). Signals were visualized after 1 hour incubation with Alexa Fluor 594 Streptavidin (Jackson ImmunoResearch) or Alexa Fluor 488 Streptavidin (Invitrogen) at RT. Sections were counterstained with DAPI (0.5 μg/mL in PBS), washed with 1×PBS, and coverslipped using Fluoro-Gel with Tris Buffer (Electron Microscopy Sciences). Tissue images of entire coronal brain sections were taken using an Olympus VS120-S6-W slide-scanner and cells positive for the probe were counted.

Cell Counting

Following confocal or slide-scanner imaging, quantification of labeled cells was performed using ImageJ and Metamorph. Cells were counted by an observer blind to experimental conditions. Brain images were converted to greyscale (16-bit) in ImageJ and adjusted using automatic thresholding and watershed separation. Cells were either counted automatically using ImageJ's particle analysis algorithm (random sections were counted manually to crosscheck that automated scoring was consistent with manual human scoring); otherwise, cells were counted manually using MetaMorph. Cells that were not entirely contained within a given region of interest (ROI) were excluded from analyses. Relative fluorescent intensities were measured automatically using MetaMorph for a given ROI. Raw cell counts within an ROI were divided by the size of the ROI ($mm^2$) to produce the number of positively labeled cells/$mm^2$.

Quantitative Real-Time Reverse Transcription PCR

Group housed or isolated (30 minutes, 24 hours, 2 weeks) mice were decapitated and brains were quickly removed and placed in RNA Later (Qiagen) at 4° C. Tissue from dBNSTa, DMH, CeA, ACC, and dHPC was microdissected and placed in RNA Later. Tissue was then homogenized and RNA purified using an RNAeasy Plus Mini Kit (Qiagen). 150 ng of total RNA/region/condition was then incubated with 30 of Turbo DNase, 1 μl of Murine RNase Inhibitor in 1× Turbo DNase buffer for 15 minutes at 37° C. to remove any contaminating genomic DNA. Samples were subsequently purified using Dynabeads MyOne Silane beads and eluted in 11 μl. The eluted RNA was used as input into a 20 μl reverse transcriptase reaction (SuperScript III). 1 μl of 100 μM random 9-mers (NNNNNNNNN—IDT corporation) served as primers. The reverse transcriptase reaction was inactivated at 70° C. prior to qPCR analysis on the LightCycler 480 Instrument II. The following primers, ordered from Integrated DNA Technologies, were used: Tac1 (Forward—GATGAAGGAGCTGTCCAAGC (SEQ ID NO: 24); Reverse—TCACGAAACAGGAAACATGC (SEQ ID NO: 25)); Tac2 (Forward—GCCATGCTGTTTGCGGCTG (SEQ ID NO: 26); Reverse—CCTTGCTCAGCACTTTCAGC (SEQ ID NO: 27)); GAPDH (Forward—TGAAGCAGGCATCTGAGGG (SEQ ID NO: 28); Reverse—CGAAGGTGGAAGAGTGGGAG (SEQ ID NO: 29)); and 18s (Forward—GCAATTATTCCC-CATGAACG (SEQ ID NO: 30); Reverse—GGGACT-TAATCAACGCAAGC (SEQ ID NO: 31)). GAPDH and 18s served as housekeeping genes to which Tac1 and Tac2 were normalized. Primers were resuspended in ddH$_2$0 to 100 μM. A 25 μM mix of each primer was used as input for qRT-PCR reactions. Four technical replicates were run for each sample primer pair and the Cp (Crossing Point) value was determined using Lightcycler II Software. The median value of the four technical replicates was used as the representative value for the set. Final mRNA fold increase values were determined by normalizing raw fluorescent values of experimental animals to controls using the following formula: $2^{\wedge(Cycles\ Control-Cycles\ Experimental)}$. Thus, for example, if the control sample required 8 cycles and the experimental sample 3 cycles to reach the Cp, then the fold-increase for experimental/control would be $2^{(8-3)}=2^5=32$-fold.

Resident Intruder Assay

Testing for aggression using the resident intruder assay (Blanchard et al., 2003; incorporated by reference in its entirety) was performed as previously described (Hong et al., 2015; Hong et al., 2014; Lee et al., 2014; incorporated by reference in their entirety). Briefly, experimental mice ("residents") were transported in their homecage to a novel behavior testing room (cagemates in group housed mice were removed from the homecage prior to transport for this and all other behavioral tests), where they acclimated for 5-15 minutes. Homecages were then slotted into a customized behavioral chamber lit with a surround panel of infrared lights and equipped with two synchronized infrared video cameras (Pointgrey) placed at 90-degree angles from each other to allow for simultaneous behavior recording with a front and top view. Synchronized video was acquired using Hunter 4.0 software (custom, Pietro Perona lab, Caltech). Following a two-minute baseline period, an unfamiliar male BALB/c mouse ("intruder") was placed in the homecage of the resident for 10 minutes and mice were allowed to freely interact. Group housed BALB/c males were used as intruders because they are a relatively submissive strain, thereby reducing any intruder-initiated fighting. Behavior videos were hand-annotated by an observer blind to experimental conditions (Behavior Annotator, Piotr's MATLAB toolbox; http://vision.ucsd.edu/~pdollar/toolbox/doc/). Fighting bouts were scored on a frame-by-frame basis and were defined as a frame during which the resident male was engaged in an episode of biting or intense aggressive behavior immediately surrounding a biting episode. Annotation files were then batch analyzed for behavior, including number of fighting bouts, using in-house customized programs in MATLAB (A. Kennedy, Caltech).

Looming Disk Assay

Freezing behavior to presentation of an overhead looming disk proceeded as previously described (Kunwar et al., 2015; Yilmaz and Meister, 2013; incorporated by reference in their entirety). Briefly, mice were transported to a novel behavioral testing room. After 5 minutes of acclimation, mice were placed inside a novel, custom-built open top Plexiglas arena (48×48×30 cm) covered with a flat screen monitor placed directly above and with illumination provided by infrared LEDs (Marubeni). Mice were given a 5 minute baseline period in the arena, after which entry into the center of the arena triggered presentation of a single, 10 second overhead looming disk stimulus (comprised of a single looming disk presentation 0.5 seconds in duration, which was repeated 10 times with an inter-stimulus interval of 0.5 seconds). The stimulus was controlled by custom MATLAB code (M. Meister, Caltech) run on a dedicated computer in an adjacent room. Mice remained in the area for an additional 2 minutes before being transported back. Behavior was recorded using a video recorder attached to a laptop equipped with video capture software (Corel VideoStudio Pro). Acute freezing behavior to the looming disk ("during") as well as in the 30 seconds following the last disk ("post") were scored manually (Behavior Annotator, MATLAB) by an observer blind to environmental conditions.

Tone Fear Conditioning and Shock Reactivity

The protocol for tone trace fear conditioning was performed as previously described (Cushman et al., 2014; incorporated by reference in its entirety) using fear conditioning boxes previously described in detail (Haubensak et al., 2010; Kunwar et al., 2015; incorporated by reference in their entirety). Briefly, mice were transported in squads of four on a white cart to a novel behavioral testing room containing 4 sound-attenuating fear-conditioning chambers (Med Associates). This "training context" was comprised of flat grid flooring (wired to a shock generator and scrambler for footshock delivery, Med Associates), houselights, and the presence of an internal fan for background noise. Chambers were sprayed with 70% Simple Green solution on the underlying chamber pan to generate a unique contextual scent and chambers were cleaned with 70% EtOH between squads. Trace fear conditioning consisted of a 3 minute baseline period followed by 3 tone-shock trials consisting of a 20 second tone conditional stimulus (CS; 75 dB, 2800 Hz), a 20 second trace interval and a 2 second footshock unconditional stimulus (US; 0.7 mA). The inter-trial interval (ITI) between trials was 60 seconds. Mice remained in the chambers an additional 60 seconds before being transported back to the vivarium. The following day, mice were transported in fresh cardboard boxes to a novel behavioral testing room consisting of 4 distinct fear-conditioning boxes to test for tone fear. The "test context" consisted of the houselights and fan turned off, uneven grid flooring, a 1% acetic acid scent and a black plastic insert used to generate a triangular roof. Testing was performed identical to training with the exception that shocks were omitted from test trials to allow for behavior assessment to the tone. A single shock was administered in the last minute of testing to assess activity burst responding to the shock. This allowed assessment of reactivity to the shock under our various manipulations performed during testing without disrupting fear acquisition by performing manipulations during training. All experimental manipulations and data shown herein were performed during the test phase of fear conditioning (training data not shown). Training and testing context were counterbalanced across mice. Freezing behavior during the baseline period as well as during each tone presentation ("during") and trace interval ("post") were assessed as previously described (Zelikowsky et al., 2014; incorporated by reference in its entirety) using automated near-infrared video tracking equipment and computer software (VideoFreeze, Med Associates). Shock reactivity (motion, arbitrary units) was measured during the 2 second shock US as well as the 3 seconds immediately following.

Ultrasonic Sound Stimulus Assay

Behavior was tested as previously described (Mongeau et al., 2003; incorporated by reference in its entirety). Briefly, mice were brought into a novel experimental testing room in their homecages and allowed to acclimate for 5 minutes. Behavior in the homecage to an ultrasonic sound stimulus (USS) was then recorded using a digital video camera connected to a portable laptop equipped with video capture software (Corel VideoStudio Pro). Mice were permitted a 2-minute baseline period of behavior followed by three, 1-minute presentations of the USS (100 ms frequency sweeps between 17 and 20 kHz, 85 dB, alternately ON 2 sec/OFF 2 sec) with a 1-minute inter-trial interval. Following testing, mice were returned to the vivarium. Freezing behavior to each USS and post-USS period (ITI) was manually scored by an observer blind to experimental conditions (Behavior Annotator, MATLAB).

Open Field Test

Open field testing (OFT) was performed as previously described (Anthony et al., 2014; Cai et al., 2014; Kunwar et al., 2015; incorporated by reference in their entirety) to examine anxiety-like behavior (thigmotaxis) in a novel open arena. Briefly, mice were brought into a novel behavior testing room in squads of 4. They were then individually placed in plastic open top arenas (50×50×30 cm) and allowed to freely move for a 10-minute period. Video was captured using an overhead mounted video camera connected to a dedicated computer in an adjacent room equipped with Mediacruise (Canopus) video capture software. Ethovision software was used to generate trajectory maps and analyze time spent in the center of the arena (center 50%) and average velocity.

Elevated Plus Maze

Elevated plus maze (EPM) testing was performed as previously described (Cal et al., 2014; Kunwar et al., 2015; incorporated by reference in their entirety). Briefly, mice were brought into a behavioral testing room and tested for anxiety-like behavior on an elevated plus maze. The EPM was comprised of a platform (74 cm above the floor) with four arms—two opposing open arms (30×5 cm) and two opposing closed arms (30×5×14 cm). Mice were placed in the center of the EPM and their behavior was tracked for 5 minutes using Mediacruise (Canopus) for video capture and Ethovision for trajectory maps, analyses of time spent in each arm, and number of entries. Mice were also scored for whether or not they jumped off of the center of the platform within 5 seconds of being initially placed on the EPM.

Acoustic Startle Response

Startle responding to an acoustic stimulus (Koch, 1999; incorporated by reference in its entirety) was measured using a startle chamber (SR-LAB; San Diego Instruments) as previously described (Shi et al., 2003; incorporated by reference in its entirety). Briefly, mice (in squads of 3) were brought into a novel behavioral testing room in their homecages and allowed to acclimate for 5-10 minutes. Mice were then placed into sound-attenuating startle chambers comprised of a Plexiglas cylinder (5.1 cm diameter) mounted on a platform (20.4×12.7×0.4 cm) with a piezoelectric accelerometer unit attached below to detect startle motion. The chambers contained an overhead loudspeaker and light. Following a 3-minute baseline, mice were presented with a series of 8 noise presentations ramping up from 67-124 dB (67, 78, 86, 95, 104, 109, 115, 124 dB) across a 4 minute period (~30 sec variable inter-trial interval; ITI). The delivery of acoustic stimuli and acquisition of startle motion was controlled by SR-LAB software on a dedicated computer. Prior to each behavioral testing session, sound levels were calibrated with a sound-level meter (Radio Shack), and response sensitivities were calibrated using the SR-LAB Startle Calibration System. Startle chambers were cleaned with 70% EtOH between squads.

Flinch-Vocalize-Jump Assay

Sensitivity to a noxious footshock stimulus was assessed using the flinch-vocalize-jump assay (Kim et al., 1991; incorporated by reference in its entirety). Mice were transported to a behavioral testing room and individually tested in a fear conditioning box (Med Associates) for reactivity to a series of manually delivered shocks ramping up in amplitude. Shocks were administered every 5 seconds beginning from 0.05 mA to 0.6 mA, with each shock increasing by 0.05 mA. The shock intensity level at which a mouse displayed flinching (first perceptible reaction to the shock), vocalization (sound audible to a human observer), and jumping (simultaneous lifting of all 4 paws off the grid) were noted for each mouse.

Social Interaction Assay

Mice were tested for interactive behavior towards a new mouse using the social interaction assay. Behavior testing proceeded as previously described (Hsiao et al., 2013; incorporated by reference in its entirety). Briefly, mice were brought to a behavioral testing room in squads of 4 and individually placed in a long Plexiglass apparatus (50×75 cm) consisting of three chambers—a center chamber and two side chambers each containing an empty pencil cup flipped upside-down. Following a 5-minute baseline period, an unfamiliar male mouse (BALB/c) was placed under one pencil cup, and a novel object (50 mL falcon tube cut in half) was placed under the other (placements counterbalanced across mice). Sociability across a 10-minute time period was assessed. Video was captured using an overhead mounted video camera connected to a dedicated computer in an adjacent room equipped with Mediacruise (Canopus) video capture software. Ethovision software (Noldus) was used to analyze time spent in each chamber and generate an output file containing information on XY coordinates (location). XY coordinates were then used to generate heat maps reflecting the amount of time spent at each location in the social interaction apparatus (Matlab).

Rat Exposure Assay

Behavior was tested as previously described in (Kunwar et al., 2015; incorporated by reference in its entirety). Briefly, mice were tested for behavior towards an intact rat predator (Blanchard et al., 2005; incorporated by reference in its entirety), weighing 300-500 grams. Mice were brought into a novel testing environment in their homecage. Behavior was recorded using a digital video camera attached to a portable laptop running video acquisition software (Corel VideoStudio Pro). Following a 3-minute baseline period, a rat was lowered onto one side of the mouse's homecage in a custom-made mesh enclosure (16×11×15 cm) for a 5-minute time period. To assess where the mouse spent its time, the homecage was divided into three equal zones, with Zone 1 closest to the rat and Zone 3 farthest. Time spent in each zone and freezing behavior (not shown) was calculated using EthovisionXT software (Noldus).

Pharmacology

Mice were administered the Nk3R antagonist osanetant (Axon Medchem, Axon 1533) either systemically or intrabrain region. Osanetant was dissolved in saline with 0.1% Tween 20 (vehicle). For systemic administration mice received an intraperitoneal (i.p.) injection (5 mg/kg) 20 minutes prior to behavioral testing. For microinfusions, guide cannulas were removed from mice and replaced with injector cannulas (Plastics One), which protruded 0.5 mm from the tip of the guide cannula. Injectors were attached to 5 µl Hamilton syringes with PE tubing (Plastics One) and mounted on a microinfusion pump (Harvard Apparatus) for controlled infusion of osanetant (0.3 µl vehicle with 375 ng dose per site injected over 6 minutes). For experiments using systemic administration of clozapine-N-oxide (CNO), CNO (Enzo Life Sciences-Biomol, BML-NS105-0005) was dissolved in saline (9 g/L NaCl) and injected (i.p.) at 5 mg/kg for hM4DREADD silencing or 2 mg/kg for hM3DREADD activation 20 minutes prior to behavioral testing. CNO was also administered chronically in drinking water (0.5 mg CNO/100 ml water).

Quantification and Statistical Analyses

All behavioral data was scored by a trained observer blind to experimental conditions or scored using an automated system (Ethovision, Med Associates). Data were then processed and analyzed using MATLAB, Excel, Prism 6, and G*Power. Statistical analyses were conducted using ANOVAs followed by Bonferroni post hoc tests, Fisher's LSD tests, and unpaired t tests when appropriate. The n value, the mean values ±SEM for each data set, and statistically significant effects are reported in each figure/figure legend. The significance threshold was held at $\alpha=0.05$, two-tailed (not significant, ns, $p>0.05$; *$p<0.05$; $p<0.01$; *$p<0.001$). Full statistical analyses corresponding to each data set, including 95% confidence intervals (CIs) and effect size ($\eta^2$), are presented in Table 2.

TABLE 2

STATISTICAL ANALYSES

Figures 1A, 1B, 1C, 1D:
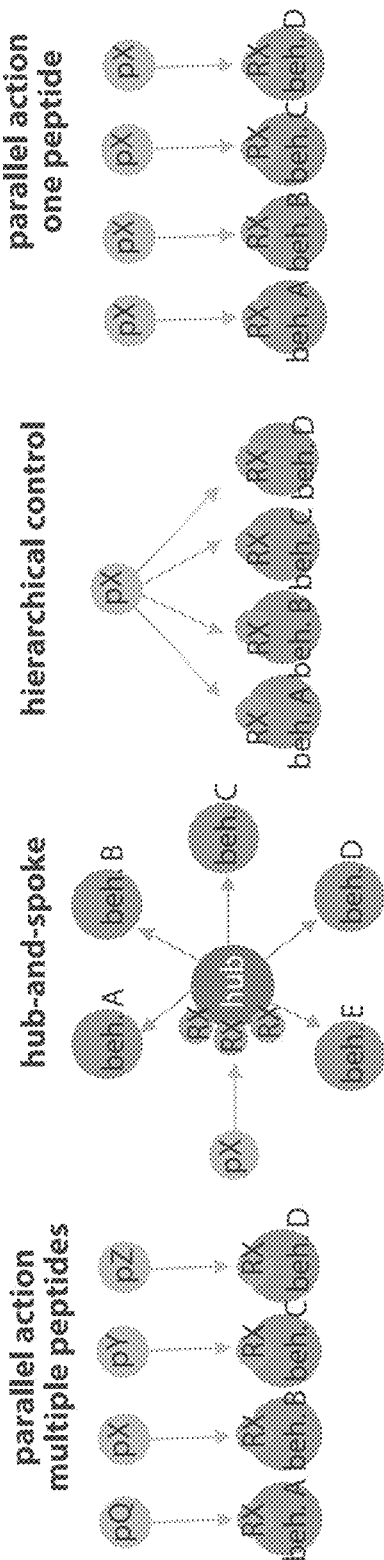
Figure 1E:
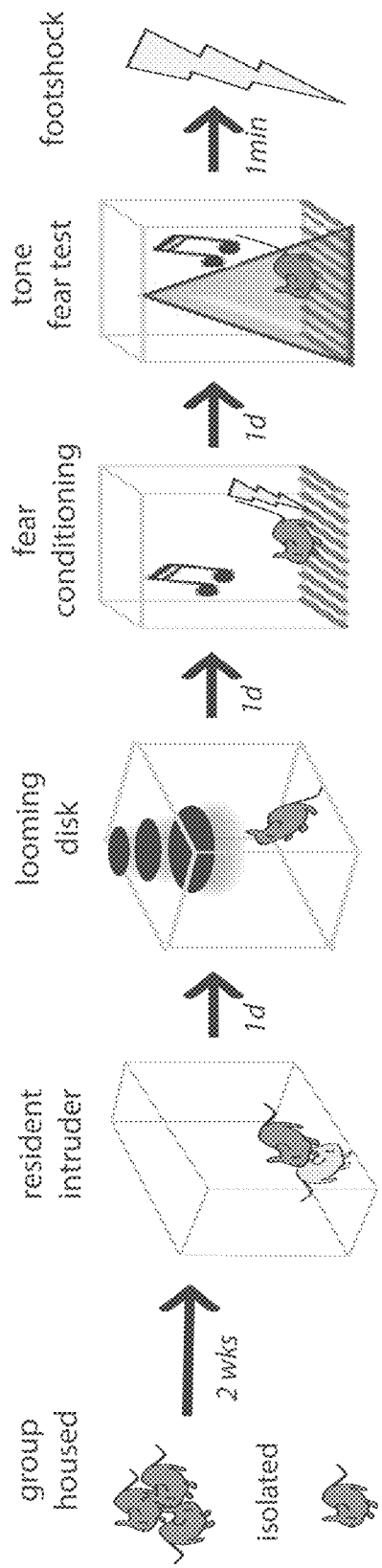
Figure 1R:
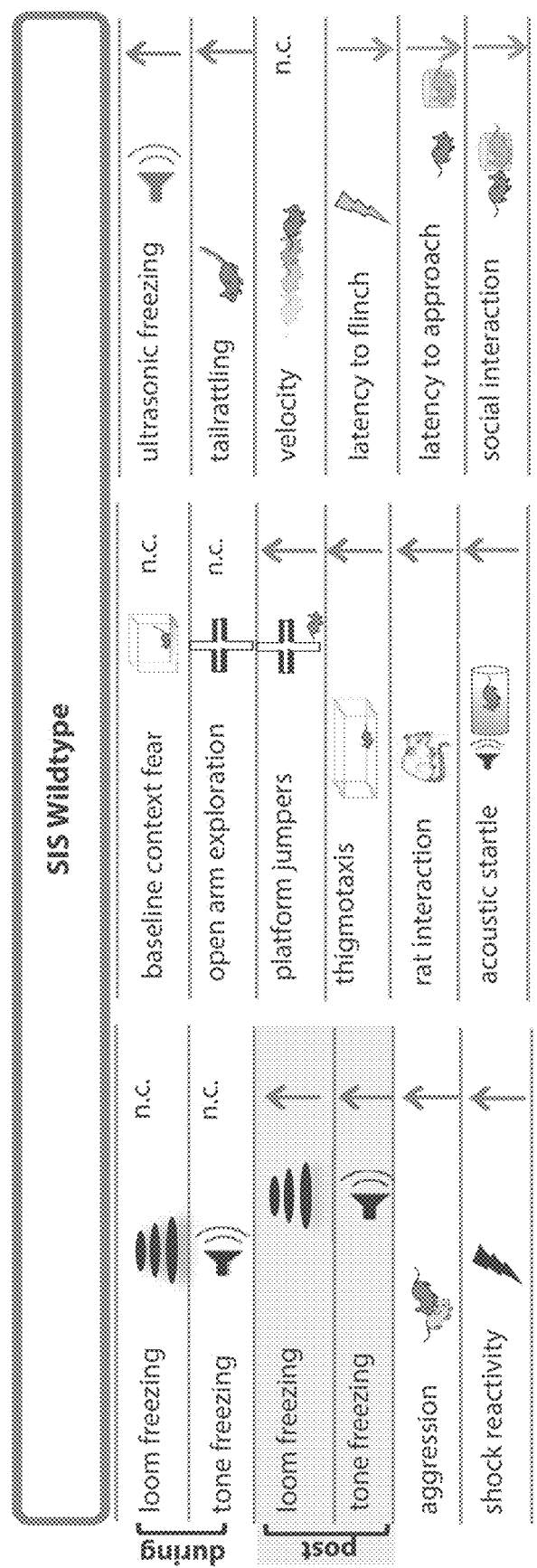

| FIGURE/ASSAY | TEST | F, t VALUE | p VALUE | CI | $\eta^2$ |
|---|---|---|---|---|---|
| FIG. 1 | | | | | |
| F; resident intruder | unpaired t-test | $t_{1,14} = 8.972$ | <0.0001 | 19.21-31.29 | 0.852 |
| G; looming disk | RM ANOVA | time: $F_{1,14} = 11.19$ | =0.005 | | |
| | Bonferroni | post: $t_{1,28} = 2.74$ | <0.05 | -83.28--6.055 | |
| H; fear conditioning | RM ANOVA | time: $F_{1,13} = 11.80$ | =0.004 | | |
| | | stress: $F_{1,13} = 4.042$ | =0.066 | | |
| | | X: $F_{1,13} = 6.239$ | =0.0267 | | |
| | Bonferroni | post: $t_{1,26} = 2.905$ | <0.05 | -61.04--6.147 | |
| I; footshock | unpaired t-test | $t_{1,14} = 2.653$ | =0.019 | 27.84-262.8 | 0.335 |
| K; ultrasonic sound | RM ANOVA | stim: $F_{5,45} = 9.397$ | <0.0001 | | |
| | | stress: $F_{1,9} = 10.72$ | 0.0096 | | |
| | | X: $F_{5,45} = 3.292$ | 0.0128 | | |
| | Bonferroni | USS1: $t_{1,54} = 4.31$ | <0.001 | -50.76--11.32 | |
| | | USS3: $t_{1,54} = 3.506$ | <0.01 | -44.97--5.525 | |
| M; open field | unpaired t-test | $t_{1,14} = 2.362$ | =0.0332 | -48.01--2.311 | 0.285 |
| FIG. 2 | | | | | |
| E; Tac2 qRTPCR | OW ANOVA | See FIG. S2 | | | |
| | Fisher's LSD | dBNST: $t_{1,12} = 2.474$ | =0.029 | -11.01--0.697 | |
| | | DMH: $t_{1,12} = 2.808$ | =0.016 | -3.656--0.461 | |
| | | CEA: $t_{1,12} = 2.271$ | =0.042 | -19.43--0.403 | |
| | | ACC: $t_{1,12} = 1.330$ | =0.2081 | -5.492-1.328 | |
| | | dHPC: $t_{1,2} = 1.921$ | =0.1948 | -3.085-8.06 | |
| L; FISH, dBNSTa | unpaired t-test | cells: $t_{1,18} = 2.197$ | =0.041 | 5.499-245.0 | 0.212 |
| | | inten: $t_{1,19} = 7.562$ | <0.0001 | 21.90-38.67 | 0.751 |
| M; FISH, DMH | unpaired t-test | cells: $t_{1,4} = 7.451$ | =0.002 | 83.99-183.8 | 0.933 |
| | | inten: $t_{1,4} = 9.156$ | =0.001 | 38.51-72.03 | 0.955 |
| N; FISH, CeA | unpaired t-test | cells: $t_{1,17} = 2.127$ | =0.048 | 1.145-285.5 | 0.21 |
| | | inten: $t_{1,15} = 2.503$ | =0.024 | 4.118-51.33 | 0.295 |
| O; FISH, ACC | unpaired t-test | cells: $t_{1,20} = 0.561$ | =0.581 | -17.80-30.89 | 0.015 |
| | | inten: $t_{1,12} = 2.832$ | =0.015 | 1.310-10.05 | 0.401 |
| P; FISH, dHPC | unpaired t-test | cells: $t_{1,25} = 0.983$ | =0.335 | -6.229-17.60 | 0.037 |
| | | inten: $t_{1,44} = 4.68$ | <0.0001 | 3.611-9.073 | 0.332 |
| FIG. 3 | | | | | |
| B; resident intruder | OW ANOVA | $F_{3,20} = 3.213$ | =0.045 | | 0.325 |
| | Fisher's LSD | veh grp vs. veh SIS: $t_{1,20} = 2.449$ | =0.024 | -22.22--1.781 | |
| | | veh SIS vs. osan SIS: $t_{1,20} = 2.245$ | =0.036 | 0.781-21.22 | |
| C; looming disk | RM ANOVA | time: $F_{1,20} = 65.08$ | <0.0001 | | |
| | Fisher's LSD | veh grp vs. veh SIS: $t_{1,40} = 2.661$ | 0.011 | -68.24--9.325 | |
| | | veh SIS vs. osan SIS: $t_{1,40} = 2.198$ | 0.034 | 2.584-61.5 | |
| D; fear conditioning | RM ANOVA | time: $F_{1,20} = 20.34$ | =0.0002 | | |
| | Fisher's LSD | veh grp vs. veh SIS: $t_{1,40} = 2.134$ | =0.039 | -62.8--1.712 | |
| | | veh SIS vs. osan SIS: $t_{1,40} = 3.155$ | =0.003 | 17.14-78.22 | |
| E; footshock | unpaired t-test | veh SIS vs. osan SIS: $t_{1,10} = 3.095$ | =0.011 | -329.6--53.66 | 0.48 |
| G; resident intruder | OW ANOVA | $F_{3,20} = 2.282$ | =0.11 | | 0.255 |
| | Fisher's LSD | veh grp vs. veh SIS: $t_{1,20} = 2.257$ | =0.035 | -23.09--0.91 | |
| | | veh SIS vs. daily osan: $t_{1,20} = 2.257$ | =0.035 | 0.9097-23.09 | |
| H; looming disk | RM ANOVA | time: $F_{1,20} = 43.99$ | <0.0001 | | |
| | Fisher's LSD | veh SIS vs. daily osan: $t_{1,40} = 2.452$ | =0.019 | 6.224-64.58 | |
| I; fear conditioning | RM ANOVA | time: $F_{1,20} = 2.882$ | =0.105 | | |
| | Fisher's LSD | veh grp vs. 24 hr osan: $t_{1,40} = 2.116$ | =0.041 | -36.23-23.75 | |
| | | 24 hr osan vs. daily osan: $t_{1,40} = 2.726$ | =0.010 | -21.5-38.48 | |

TABLE 2-continued

STATISTICAL ANALYSES

| FIGURE/ASSAY | TEST | F, t VALUE | p VALUE | CI | $\eta^2$ |
|---|---|---|---|---|---|
| FIG. 4 | | | | | |
| C; looming disk | RM ANOVA | time: $F_{1,10} = 12.41$ | $=0.006$ | | |
| | | X: $F_{1,10} = 21.33$ | $=0.001$ | | |
| | Bonferroni | $t_{1,20} = 4.33$ | $<0.001$ | 23.36-82.73 | |
| D; fear conditioning | RM ANOVA | time: $F_{1,10} = 11.73$ | $=0.007$ | | |
| | Bonferroni | $t_{1,20} = 2.496$ | $<0.05$ | 0.925-62.43 | |
| E; resident intruder | unpaired t-test | $t_{1,10} = 2.231$ | $=0.049$ | −19.65−−0.012 | 0.332 |
| I; looming disk | RM ANOVA | time: $F_{1,11} = 7.232$ | $=0.021$ | | |
| | | osan: $F_{1,11} = 188.1$ | $<0.0001$ | | |
| | Bonferroni | during: $t_{1,22} = 7.947$ | $<0.0001$ | 54.38-101.6 | |
| | | post: $t_{1,22} = 4.343$ | $<0.001$ | 19.02-66.23 | |
| J; fear conditioning | RM ANOVA | time: $F_{1,11} = 9.612$ | $=0.01$ | | |
| | | osan: $F_{1,11} = 9.711$ | $=0.01$ | | |
| | Bonferroni | during: $t_{1,22} = 2.542$ | $<0.05$ | 1.996-72.09 | |
| | | post: $t_{1,22} = 3.016$ | $<0.05$ | 8.893-78.98 | |
| FIG. 5 | | | | | |
| C; looming disk | RM ANOVA | time: $F_{1,12} = 23.22$ | $=0.0004$ | | |
| | | CNO: $F_{1,12} = 11.65$ | $=0.005$ | | |
| | | X: $F_{1,12} = 5.222$ | $=0.041$ | | |
| | Bonferroni | $t_{1,24} = 4.082$ | $<0.001$ | 19.2-73.51 | |
| D; fear conditioning | RM ANOVA | time: $F_{1,12} = 11.13$ | $=0.006$ | | |
| | | CNO: $F_{1,12} = 10.94$ | $=0.006$ | | |
| | | X: $F_{1,12} = 8.695$ | $=0.012$ | | |
| | Bonferroni | $t_{1,20} = 4.412$ | $<0.001$ | 18.25-61.43 | |
| E; resident intruder | unpaired t-test | $t_{1,14} = 1.865$ | $=0.042$ | −12.63-0.882 | 0.199 |
| I; looming disk | RM ANOVA | time: $F_{1,14} = 28.94$ | $<0.0001$ | | |
| | | CNO: $F_{1,14} = 7.353$ | $=0.017$ | | |
| | Bonferroni | during: $t_{1,28} = 2.689$ | $<0.05$ | 4.427-69.88 | |
| | | post: $t_{1,28} = 2.464$ | $<0.05$ | 1.326-66.78 | |
| J; fear conditioning | RM ANOVA | time: $F_{1,14} = 28.79$ | $<0.0001$ | | |
| | | CNO: $F_{1,14} = 8.405$ | 0.012 | | |
| | Bonferroni | during: $t_{1,28} = 2.643$ | $<0.05$ | 3.854-70.39 | |
| | | post: $t_{1,28} = 2.9$ | $<0.05$ | 7.464-74 | |
| FIG. 6 | | | | | |
| C; looming disk | RM ANOVA | time: $F_{1,15} = 42.94$ | $<0.0001$ | | |
| | | shRNA: $F_{2,15} = 10.69$ | $=0.001$ | | |
| | Bonferroni | during; con vs. shRNA2: $t_{1,30} = 2.889$ | $<0.05$ | 4.473-68.62 | |
| | | post; con vs. shRNA1: $t_{1,30} = 3.367$ | $<0.01$ | 10.51-74.65 | |
| | | post; con vs. shRNA2: $t_{1,30} = 4.495$ | $<0.001$ | 24.78-88.92 | |
| D; fear conditioning | RM ANOVA | time: $F_{1,9} = 15.08$ | $=0.004$ | | |
| | | shRNA: $F_{2,9} = 16.95$ | $=0.001$ | | |
| | | X: $F_{2,9} = 4.878$ | $=0.037$ | | |
| | Bonferroni | during; con vs. shRNA2: $t_{1,18} = 4.481$ | $<0.001$ | 22.12-85.49 | |
| | | during; shRNA1 vs. shRNA2: $t_{1,18} = 3.833$ | $<0.01$ | 14.33-77.7 | |
| | | post; con vs. shRNA1: $t_{1,18} = 3.833$ | $<0.01$ | 14.33-77.7 | |
| | | post; con vs. shRNA2: $t_{1,18} = 5.423$ | $<0.001$ | 33.42-96.79 | |

TABLE 2-continued

STATISTICAL ANALYSES

| FIGURE/ASSAY | TEST | F, t VALUE | p VALUE | CI | $\eta^2$ |
|---|---|---|---|---|---|
| E; resident intruder | unpaired t-test | con vs. shRNA1: $t_{1,10} = 2.049$ | =0.034 | −14.61-0.611 | 0.296 |
|  | unpaired t-test | con vs. shRNA2: $t_{1,10} = 1.883$ | =0.045 | −14.19-1.192 | 0.262 |
| I; looming disk | RM ANOVA | time: $F_{1,14} = 58.3$ | <0.0001 |  |  |
|  |  | shRNA: $F_{2,14} = 12.56$ | =0.001 |  |  |
|  | Bonferroni | during; con vs. shRNA1: $t_{1,28} = 3.18$ | <0.05 | 7.01-63.38 |  |
|  |  | during; con vs. shRNA2: $t_{1,28} = 3.02$ | <0.05 | 5.239-61.61 |  |
|  |  | post; con vs. shRNA1: $t_{1,28} = 3.141$ | <0.05 | 6.58-62.95 |  |
|  |  | post; con vs. shRNA2: $t_{1,28} = 3.345$ | <0.01 | 8.837-65.2 |  |
| J; fear conditioning | RM ANOVA | time: $F_{1,14} = 13.09$ | =0.003 |  |  |
|  |  | shRNA: $F_{2,14} = 10.79$ | =0.002 |  |  |
|  | Bonferroni | during; con vs. shRNA2: $t_{1,28} = 3.58$ | <0.01 | 12.17-72.15 |  |
|  |  | post; con vs. shRNA2: $t_{1,28} = 4.408$ | <0.001 | 21.93-81.91 |  |

FIG. 7

| B; resident intruder | OW ANOVA | $F_{3,20} = 4.149$ | =0.019 |  | 0.384 |
|---|---|---|---|---|---|
|  | Bonferroni | mCherry vs. Tac2 + hM3D: $t_{1,20} = 2.971$ | <0.05 | −22.17--0.166 |  |
|  |  | Tac2 vs. Tac2 + hM3D: $t_{1,20} = 3.016$ | <0.05 | −22.33--0.332 |  |
| C; looming disk | RM ANOVA | time: $F_{1,20} = 37.33$ | <0.0001 |  |  |
|  | Bonferroni | post; mCherry vs. Tac2 + hM3D: $t_{1,40} = 2.517$ | <0.05 | −98.26--0.351 |  |

FIG. 8

| B; tone fear test | RM ANOVA | trial: $F_{5,65} = 4.488$ | =0.001 |  |  |
|---|---|---|---|---|---|
|  |  | stress: $F_{1,13} = 5.037$ | =0.043 |  |  |
|  |  | X: $F_{5,65} = 2.895$ | =0.020 |  |  |
|  | Bonferroni | trace1: $t_{1,78} = 2.376$ | =0.020 | −61.24--5.404 |  |
|  |  | trace2: $t_{1,78} = 2.467$ | =0.016 | −62.51--6.675 |  |
|  |  | trace3: $t_{1,78} = 3.352$ | =0.001 | −74.92--19.09 |  |
| C; looming (1st) | RM ANOVA | time: $F_{1,9} = 18.78$ | =0.002 |  |  |
|  |  | stress: $F_{1,9} = 10.64$ | =0.010 |  |  |
|  | Bonferroni | post: $t_{1,18} = 2.95$ | <0.05 | −65.71--6.128 |  |
| D; tone fear (1st) | RM ANOVA | time: $F_{1,14} = 27.08$ | =0.0001 |  |  |
|  |  | X: $F_{1,14} = 5.44$ | =0.035 |  |  |
|  | Bonferroni | post: $t_{1,28} = 3.04$ | <0.05 | −56.73--7.083 |  |
| E; tail rattles | unpaired t-test | $t_{1,24} = 2.276$ | =0.039 | 0.129-4.371 | 0.27 |
| G; rat exposure | RM ANOVA | zone: $F_{2,16} = 9.563$ | =0.002 |  |  |
|  | Bonferroni | group; rat vs. far: $t_{1,16} = 5.45$ | <0.001 | −274.7--93.91 |  |
|  |  | group; center vs. far: $t_{1,16} = 4.56$ | <0.001 | −244.6--63.82 |  |
| H; flinch voc. jump | unpaired t-test | flinch: $t_{1,14} = 2.688$ | =0.018 | −0.090--0.010 | 0.340 |
| I; acoustic startle | RM ANOVA | trial: $F_{7,98} = 40.43$ | <0.0001 |  |  |
|  |  | stress: $F_{1,14} = 6.905$ | =0.020 |  |  |
|  | Fisher's LSD | 95: $t_{1,112} = 2.019$ | =0.046 | −596.1--5.656 |  |
|  |  | 109: $t_{1,112} = 2.138$ | =0.035 | −613.7--23.28 |  |
|  |  | 115: $t_{1,112} = 2.64$ | =0.001 | −688.6--98.16 |  |
|  |  | 124: $t_{1,112} = 2.482$ | =0.015 | −665--74.53 |  |

TABLE 2-continued

STATISTICAL ANALYSES

| FIGURE/ASSAY | TEST | F, t VALUE | p VALUE | CI | $\eta^2$ |
|---|---|---|---|---|---|
| J; social interaction | RM ANOVA | zone: $F_{2,28} = 4.608$ | =0.019 | | |
| | | X: $F_{2,28} = 2.282$ | =0.024 | | |
| | Bonferroni | mouse zone: $t_{1,42} = 2.743$ | =0.027 | 6.909-144.9 | |
| J; latency | unpaired t-test | $t_{1,8} = 2.376$ | =0.045 | −28.59−−0.430 | 0.414 |
| | | FIG. 9 | | | |
| B; Tac2-Cre; Ai6-zsGreen | unpaired t-test | dBNSTa; cells: $t_{1,17} = 7.22$ | <0.0001 | 141.1-257.6 | 0.754 |
| | | inten: $t_{1,17} = 11.50$ | <0.0001 | 50.20-72.76 | 0.886 |
| | | DMH; cells: $t_{1,30} = 5.934$ | <0.0001 | 58.14-119.2 | 0.54 |
| | | inten: $t_{1,30} = 20.19$ | <0.0001 | 62.73-76.84 | 0.931 |
| | | CeA; cells: $t_{1,21} = 5.161$ | <0.0001 | 77.50-182.1 | 0.559 |
| | | inten: $t_{1,20} = 9.402$ | <0.0001 | 39.89-62.63 | 0.816 |
| | | ACC; cells: $t_{1,17} = 21.49$ | <0.0001 | 641.8-781.5 | 0.965 |
| | | inten: $t_{1,17} = 23.48$ | <0.0001 | 74.87-89.66 | 0.97 |
| F; Tac2 qRTPCR | OW ANOVA | dBNSTa: $F_{3,12} = 2.194$ | =0.142 | | 0.354 |
| | Fisher's LSD | Group vs. 2w: $t_{1,12} = 2.474$ | =0.029 | | |
| | OW ANOVA | DMH: $F_{3,12} = 3.034$ | =0.071 | | 0.431 |
| | Fisher's LSD | Group vs. 2w: $t_{1,12} = 2.808$ | =0.0158 | | |
| | OW ANOVA | CeA: $F_{3,12} = 2.251$ | =0.135 | | 0.36 |
| | Fisher's LSD | Group vs. 2w: $t_{1,12} = 2.271$ | =0.042 | | |
| | OW ANOVA | ACC: $F_{3,12} = 0.706$ | =0.567 | | 0.15 |
| | Fisher's LSD | Group vs. 2w: $t_{1,12} = 1.330$ | =0.208 | | |
| H; Tac2 CeA FISH | TW ANOVA | stress: $F_{1,67} = 9.987$ | =0.002 | | |
| | Fisher's LSD | CeM: $t_{1,67} = 2.018$ | =0.048 | −399.9−−2.191 | |
| | | CeL: $t_{1,67} = 2.103$ | =0.039 | −425.9−−11.12 | |
| I; NkB staining | TW ANOVA | stress: $F_{1,17} = 59.26$ | <0.0001 | | |
| | | region: $F_{2,17} = 8.602$ | =0.0026 | | |
| | Bonferroni | dBNSTa: $t_{1,17} = 4.182$ | <0.01 | −52.09−−11.63 | |
| | | DMH: $t_{1,17} = 4.561$ | <0.001 | −52.16−−13.78 | |
| | | CeA: $t_{1,17} = 4.619$ | <0.001 | −64.00−−17.28 | |
| | | FIG. 10 | | | |
| G; tail rattles | OW ANOVA | $F_{3,20} = 3.247$ | 0.044 | | 0.328 |
| | Bonferroni | veh; group vs SIS: $t_{1,20} = 2.59$ | <0.05 | −6.129−−0.205 | |
| | | SIS: veh vs osan: $t_{1,20} = 2.454$ | <0.05 | 0.038-5.962 | |
| H; social interaction | OW ANOVA | $F_{3,20} = 2.981$ | 0.056 | | 0.309 |
| | Bonferroni | veh; group vs SIS: $t_{1,20} = 2.334$ | 0.030 | 9.423-168 | |
| | | SIS: veh vs osan: $t_{1,20} = 2.688$ | 0.014 | −181.5−−22.91 | |
| I; acoustic startle | RM ANOVA | time: $F_{7,140} = 28.12$ | <0.0001 | | |
| | Bonferroni | 124 dB: veh; SIS vs group: $t_{1,160} = 2.704$ | <0.05 | 47.76-858.6 | |
| | | 124 dB: SIS; veh vs osan: $t_{1,160} = 2.943$ | <0.05 | 87.76-898.6 | |
| M; looming disk | RM ANOVA | time: $F_{1,16} = 28.23$ | <0.0001 | | |
| | | osan: $F_{1,16} = 12.64$ | =0.0026 | | |
| | | X: $F_{1,16} = 24.3$ | =0.0002 | | |
| | Bonferroni | post: $t_{1,32} = 5.767$ | <0.0001 | 33.78-80.3 | |

TABLE 2-continued

| STATISTICAL ANALYSES | | | | | |
|---|---|---|---|---|---|
| FIGURE/ASSAY | TEST | F, t VALUE | p VALUE | CI | $\eta^2$ |
| FIG. 11 | | | | | |
| E; latency to orient | unpaired t-test | $t_{1,10} = 2.33$ | 0.042 | 0.2-8.937 | 0.352 |
| H; footshock CeA | unpaired t-test | $t_{1,11} = 4.201$ | 0.002 | −331--103.4 | 0.616 |
| FIG. 12 | | | | | |
| B; cfos dBNSTa | OW ANOVA | $F_{4,94} = 48.27$ | <0.0001 | | 0.673 |
| | Bonferroni | HC: GH vs SIS: | >0.05 | −7.542-21.94 | |
| | | $t_{1,94} = 1.244$ | | | |
| | | SIS: HC vs LD: | <0.0001 | −63.47--36.36 | |
| | | $t_{1,94} = 9.377$ | | | |
| | | SIS: HC vs FC: | <0.0001 | −76.92--41.54 | |
| | | $t_{1,94} = 8.528$ | | | |
| C; cfos DMH | OW ANOVA | $F_{4,98} = 19.34$ | <0.0001 | | 0.441 |
| | Bonferroni | HC: GH vs SIS: | >0.05 | | |
| | | $t_{1,98} = 2.188$ | | | |
| | | SIS: HC vs RI: | <0.0001 | | |
| | | $t_{1,98} = 6.219$ | | −38.2--16.02 | |
| D; cfos CeA | OW ANOVA | $F_{4,101} = 25.45$ | <0.0001 | | 0.502 |
| | Bonferroni | HC: GH vs SIS: | >0.05 | | |
| | | $t_{1,101} = 1.243$ | | −7.8-22.72 | |
| | | SIS: HC vs LD: | <0.01 | | |
| | | $t_{1,101} = 3.239$ | | −35.21--4.239 | |
| | | SIS: HC vs FC: | <0.0001 | | |
| | | $t_{1,101} = 7.913$ | | −65.79--33.79 | |
| H; footshock CeA | unpaired t-test | $t_{1,14} = 2.68$ | 0.018 | −355.8--39.48 | 0.339 |
| N; tone fear test | RM ANOVA | time: $F_{1,22} = 32.77$ | <0.0001 | | |
| | | group: | =0.0002 | | |
| | | $F_{3,22} = 10.73$ | | | |
| | | X: $F_{3,22} = 3.16$ | =0.045 | | |
| | Bonferroni | CNO; mCherry vs. hM4D: | <0.0001 | 23.10-79.78 | |
| | | $t_{1,44} = 5.014$ | | | |
| | | hM4D; veh vs. CNO: $t_{1,44} = 4.92$ | <0.0001 | 22.97-81.79 | |
| FIG. 13 | | | | | |
| C; footshock CeA | OW ANOVA | $F_{2,14} = 6.064$ | 0.013 | | 0.464 |
| | Bonferroni | con vs shRNA2: | <0.01 | 112.6-710.4 | |
| | | $t_{1,14} = 3.455$ | | | |
| E; Tac2 mRNA dBNSTa: FISH cells | OW ANOVA Bonferroni | $F_{2,27} = 183.8$ | <0.0001 | | 0.932 |
| | | con vs shRNA-1: | <0.0001 | 117.4 to 171.2 | |
| | | $t_{1,27} = 13.69$ | | | |
| | | con vs shRNA-2: | <0.0001 | 167.8 to 221.6 | |
| | | $t_{1,27} = 18.47$ | | | |
| | | shRNA-1 vs shRNA-2: | <0.001 | 23.49 to 77.31 | |
| | | $t_{1,27} = 4.781$ | | | |
| E; Tac2 mRNA dBNSTa:FISH inten | OW ANOVA Bonferroni | $F_{2,168} = 68.24$ | <0.0001 | | 0.448 |
| | | con vs shRNA-1: | <0.0001 | 3.93-7.062 | |
| | | $t_{1,168} = 8.486$ | | | |
| | | con vs shRNA-2: | <0.0001 | 5.284-8.358 | |
| | | $t_{1,168} = 10.73$ | | | |
| E; Tac2 mRNA dBNSTa: qRTPCR | OW ANOVA Fisher's LSD | $F_{2,5} = 4.113$ | =0.088 | | 0.622 |
| | | con vs shRNA-2: | =0.041 | | |
| | | $t_{1,5} = 2.733$ | | | |
| F; Tac2 mRNA DMH: FISH cells | OW ANOVA Bonferroni | $F_{2,51} = 32.65$ | <0.0001 | | 0.562 |
| | | con vs shRNA-1: | <0.0001 | 19.86-48.18 | |
| | | $t_{1,51} = 5.947$ | | | |
| | | con vs shRNA-2: | <0.0001 | 29.40-58.21 | |
| | | $t_{1,51} = 7.529$ | | | |
| F; Tac2 mRNA DMH: FISH inten | OW ANOVA Bonferroni | $F_{2,75} = 27.47$ | <0.0001 | | 0.423 |
| | | con vs shRNA-1: | <0.001 | 4.334-14.51 | |
| | | $t_{1,75} = 4.235$ | | | |
| | | con vs shRNA-2: | <0.0001 | 11.34-21.52 | |
| | | $t_{1,75} = 7.386$ | | | |
| | | shRNA-1 vs shRNA-2: $t_{1,75} = 3.151$ | <0.01 | 2.577-11.44 | |
| F; Tac2 mRNA DMH: qRTPCR | OW ANOVA Bonferroni | $F_{2,5} = 47.44$ | =0.0006 | | 0.95 |
| | | con vs shRNA-2: | <0.001 | 0.476-1.074 | |
| | | $t_{1,5} = 9.172$ | | | |
| | | shRNA-1 vs shRNA-2: | <0.01 | 0.388-0.985 | |
| | | $t_{1,5} = 8.126$ | | | |

TABLE 2-continued

STATISTICAL ANALYSES

| FIGURE/ASSAY | TEST | F, t VALUE | p VALUE | CI | $\eta^2$ |
|---|---|---|---|---|---|
| G; Tac2 mRNA CeA: FISH cells | OW ANOVA Bonferroni | $F_{2,47}$ = 39.04 | <0.0001 | | 0.624 |
| | | con vs shRNA-1: $t_{1,47}$ = 6.827 | <0.0001 | 79.71-170.8 | |
| | | con vs shRNA-2: $t_{1,47}$ = 8.39 | <0.0001 | 101.4-186.6 | |
| G; Tac2 mRNA DMH: FISH inten | OW ANOVA Bonferroni | $F_{2,102}$ = 30.68 | <0.0001 | | 0.376 |
| | | con vs shRNA-1: $t_{1,102}$ = 4.919 | <0.0001 | 7.248-19.72 | |
| | | con vs shRNA-2: $t_{1,102}$ = 7.54 | <0.0001 | 12.77-23.80 | |
| G; Tac2 mRNA DMH: qRTPCR | OW ANOVA Bonferroni | $F_{2,6}$ = 40.01 | =0.0003 | | 0.93 |
| | | con vs shRNA-2: $t_{1,6}$ = 8.646 | <0.001 | 0.532-1.184 | |
| | | shRNA-1 vs shRNA-2: $t_{1,6}$ = 6.311 | <0.01 | 0.300-0.953 | |

Example 1

This example describes the effect of chronic social isolation stress (SIS) on multiple defensive behaviors.

Figure 8A:
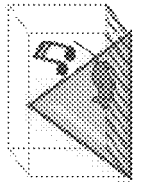
Figure 8C:
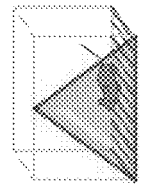
Figure 8E:
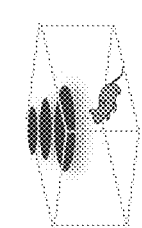
Figure 8B:
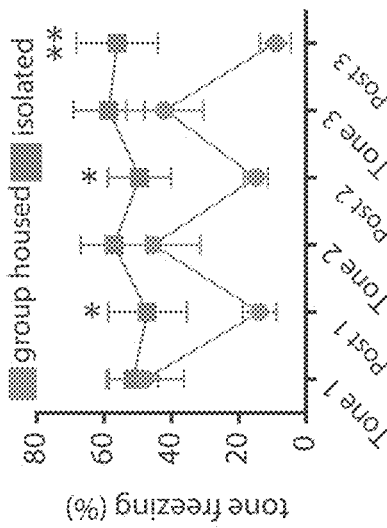
Figure 8D:
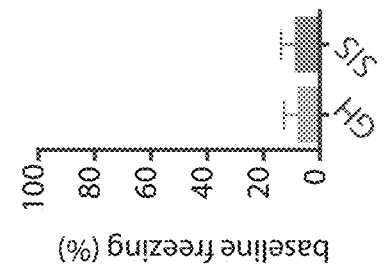
Figure 8F:
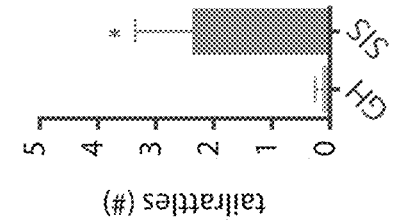

As an initial step, we broadly examined the behavioral effects produced by prolonged social isolation stress (SIS). Wildtype C57B16/N mice were subjected to two weeks of SIS or group housed (GH) with male littermates, and tested in multiple behavioral assays: aggression in the resident intruder assay (Thurmond, 1975; incorporated by reference in its entirety herein), innate freezing to an overhead looming disk (Yilmaz and Meister, 2013; incorporated by reference in its entirety herein), learned freezing to a conditioned tone (2.8 kHz) (Fanselow, 1980; incorporated by reference in its entirety herein), and reactivity to a footshock (0.7 mA) (FIGS. 1E-J and FIGS. 8A-F). Consistent with previous studies (Valzelli, 1969; Matsumoto et al., 2005; Toth et al., 2011; incorporated by reference in their entirety herein), SIS produced a robust increase in offensive aggression towards a submissive intruder, compared to non-aggressive group housed controls (FIGS. 1F-G). The magnitude of acute freezing (during the stimulus) to both the overhead looming disk and the conditioned tone was unaffected by SIS (FIG. 1H, FIG. 1I, during). However, in SIS mice, freezing persisted beyond the termination of the stimulus (FIG. 1H, FIG. 1I, post, dark gray bars labelled "SIS"), in contrast to GH controls where it terminated with stimulus offset. In addition, SIS mice showed significantly enhanced reactivity to a footshock (FIG. 1J) and increased freezing to a threatening ultrasonic stimulus (USS) (Mongeau et al., 2003; incorporated by reference in its entirety herein) (FIGS. 1K-L). SIS mice also exhibited increased tail rattling to the looming disk (FIGS. 8A-B), increased sensitivity to subthreshold acoustic startle stimuli (FIGS. 8G-H), and a decreased latency to flinch to a mild footshock (FIGS. 8I-J).

Mice were also tested for anxiety-like behavior in the open field test (OFT) and the elevated plus maze (EPM) (FIGS. 1M-Q, FIGS. 8K-L). SIS mice showed a modest but significant reduction in time spent in the center of the OFT arena, without a change in velocity (FIGS. 1N-O), but were no different from GH mice in the EPM test (FIGS. 1P-Q). However, SIS mice showed an increased propensity to jump off the EPM platform (FIGS. 8K-L).

Lastly, mice were tested in a 3-chamber social interaction test with a conspecific mouse and in a rat exposure test. SIS mice spent less time interacting with a new mouse in a social interaction assay, although their latency to initially approach the mouse was reduced (FIGS. 8M-P). In addition, SIS mice spent more time closer to a rat than farther away (FIGS. 8Q-R). Collectively, these findings demonstrate that SIS produces penetrant, persistent, and pervasive effects on a variety of behavioral responses to various stimuli (summarized in FIG. 1R). This profile appears behaviorally distinct from that typically indicative of anxiety (Blanchard et al., 2003; Bourin et al., 2007; incorporated by reference in their entirety herein), consistent with earlier studies in mice (Hilakivi et al., 1989; incorporated by reference in its entirety herein). Moreover, the observation that prolonged deprivation of social contact produces effects on subsequent social behavior, such as enhanced aggression, distinguishes SIS from other stressors including short-term social isolation (Matthews et al., 2016; incorporated by reference in its entirety herein), which does not promote aggression in mice.

The data show that, in accordance with some embodiments, chronic social isolation stress (SIS) produces widespread effects on multiple defensive behaviors, including, but not limited to, enhanced aggressiveness towards a submissive intruder, increased freezing, increased sensitivity to the looming disk, increased sensitivity to acoustic startle stimuli, decreased latenency to flinch to a mild footshock, and increased anxiety-like behavior.

Example 2

This example describes the effect of chronic social isolation stress (SIS) on Tac2 transcription.

In *Drosophila*, an unbiased screen of peptidergic neurons identified DTK (*Drosophila tachykinin*)-expressing neurons, and identified the DTK peptide, as required for social isolation-induced aggression (Asahina et al., 2014; incorporated by reference in its entirety herein). To determine whether this role might extend to mammals, we investigated the role of tachykinins in SIS. In rodents, the tachykinin gene family comprises Tac1 and Tac2 (Maggio, 1988; incorporated by reference in its entirety herein). Tac1 encodes the peptides substance P (SP), as well as neurokinin A (NkA); Tac2 encodes neurokinin B (NkB). These peptides bind with the highest affinities to the Nk1, Nk2, and Nk3 receptors, respectively (FIG. 2A) (Ebner et al., 2009; incorporated by reference in its entirety herein). Notably, Tac1 and Tac2 are expressed in a variety of brain regions that have been implicated in emotion and social behavior (FIGS. 2B-C) (Culman and Unger, 1995; incorporated by reference in its entirety herein).

Figure 2A:
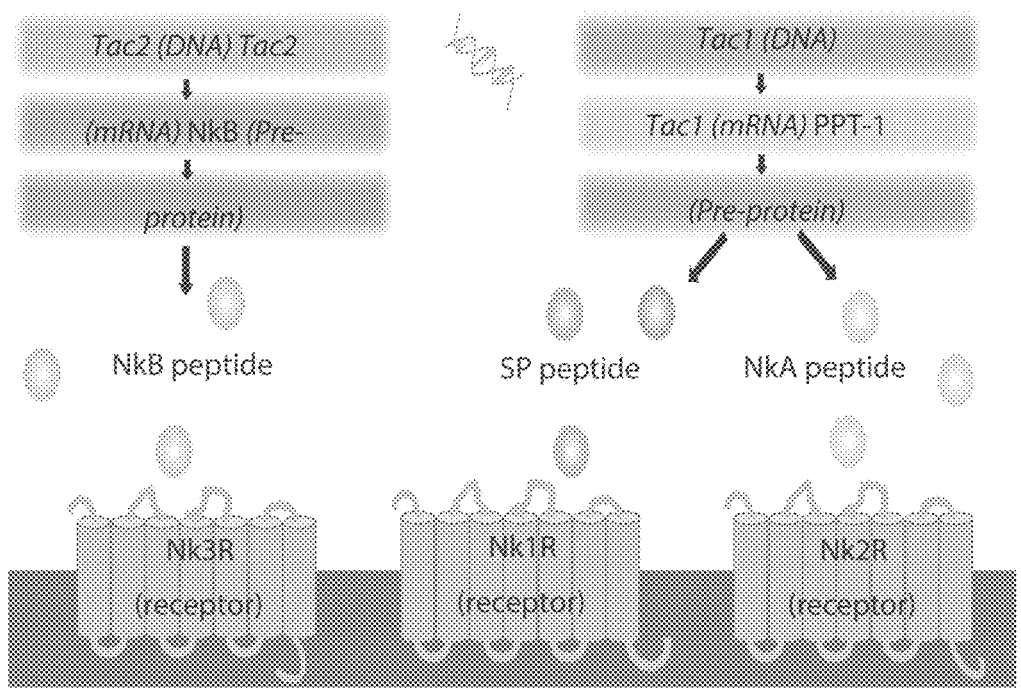
FIGS. 2A-AA show that SIS causes an increase in Tac2 expression in accordance with some embodiments.
Figure 2B:
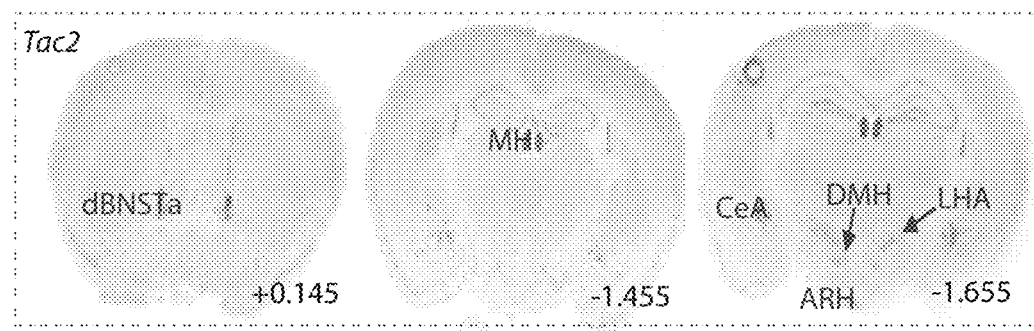
FIGS. 2B-C show Tac2 (top panels) and Tac1 (bottom panels) mRNA expression (coronal sections) revealed by in situ hybridization (ISH) (data from Mouse Brain Atlas, Allen Institute of Brain Science; Tac2, Exp. 72339556; accessible on the world wide web at mouse-.brain-map.org/experiment/show/72339556; Tac1, Exp.1038; accessible on the world wide web at mouse.brain-map.org/experiment/show/1038). Abbreviations: dBNSTa, antero-dorsal bed nucleus of the stria terminalis; MH, medial habenula; CeA, central amygdala; DMH, dorsomedial hypothalamus; ARE, arcuate nucleus; LEA, lateral hypothalamus; CP, caudate putamen; MeA, medial amygdala; VMH, ventral medial hypothalamus; ZI, zona incerta.
Figure 2C:
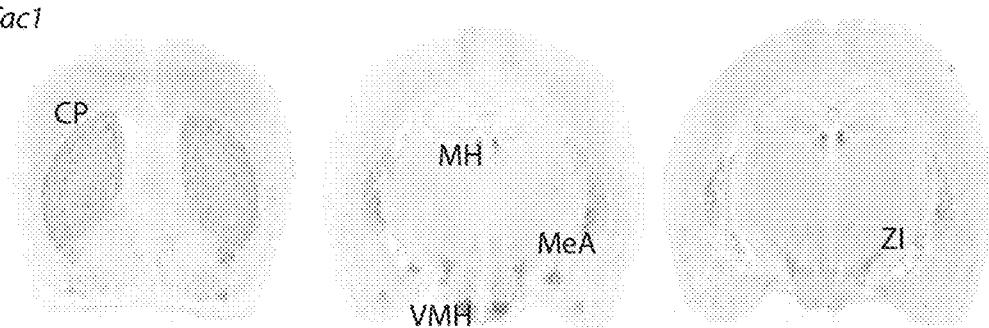
Figure 2D:
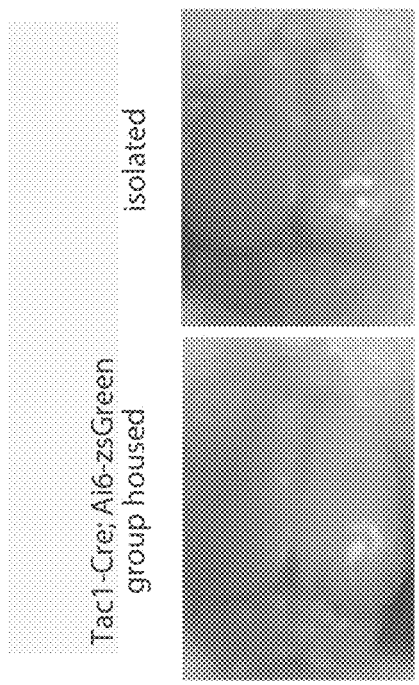
FIGS. 2D-G show expression of zsGreen in GH vs. 2 week-isolated Tac2-Cre (FIG. 2D, FIG. 2F) or Tac1-Cre (FIG. 2E, FIG. 2G) mice crossed to Ai6 (zsGreen) Cre reporter mice. Intact brains under ambient light (FIG. 2D, FIG. 2E) or coronal sections (FIG. 2F, FIG. 2G) are shown.
Figure 9L:
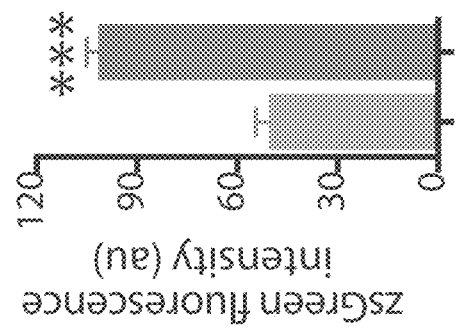
Figure 9K:
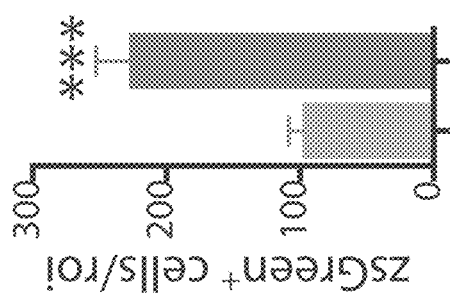
Figure 9J:
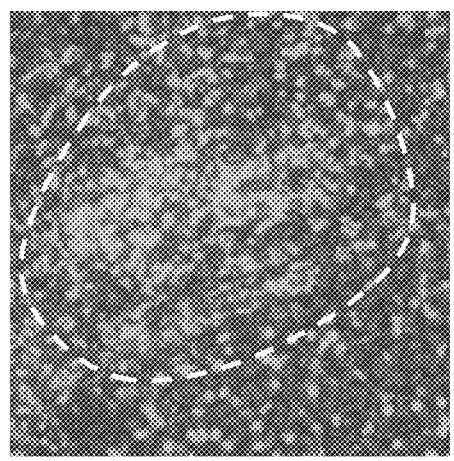
Figure 9I:
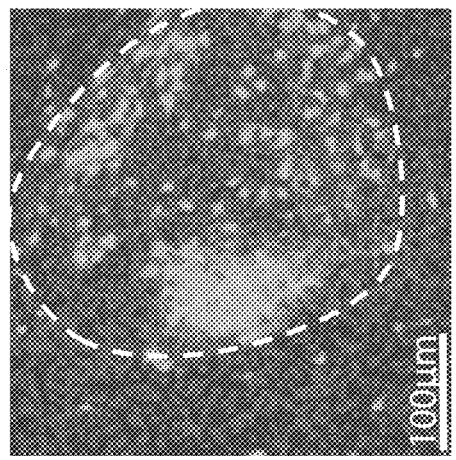
Figure 9P:
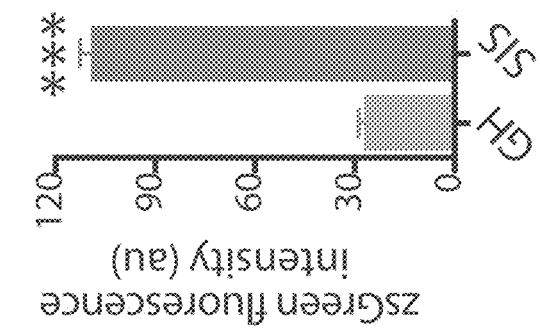
Figure 9O:
Figure 9N:
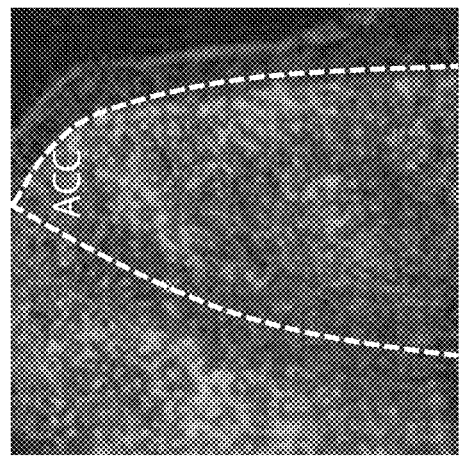
Figure 9M:
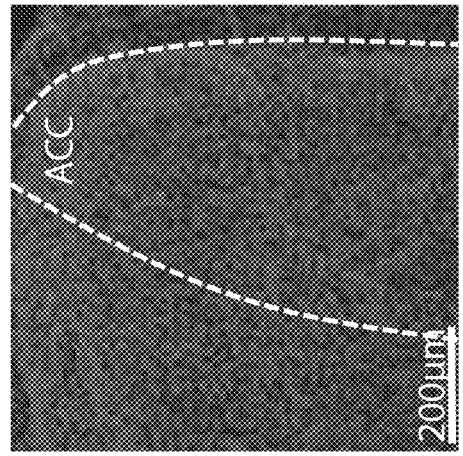
Figure 9Q:
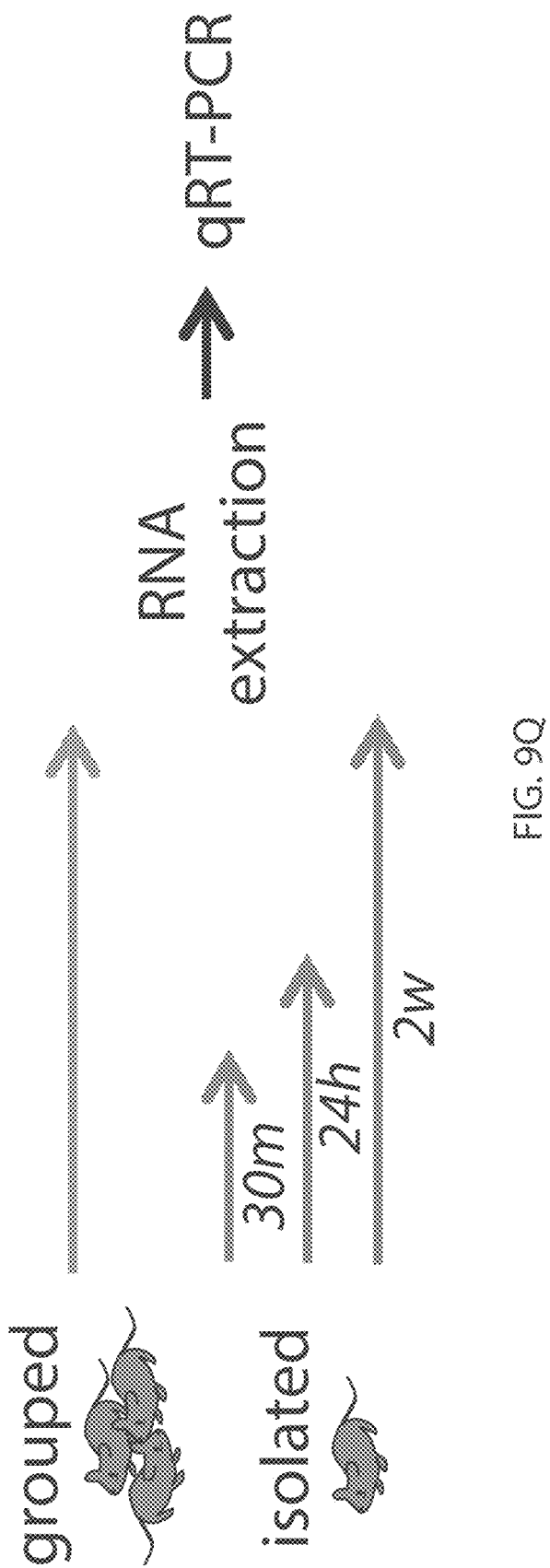
FIG. 9Q shows an experimental schematic. Mice were GH or isolated for 2 weeks, 24 hrs, or 30 minutes (n=4 mice/condition), and tissue for each indicated region was dissected and processed for qRT-PCR analyses.
Figures 9R, 9S, 9T, 9U:
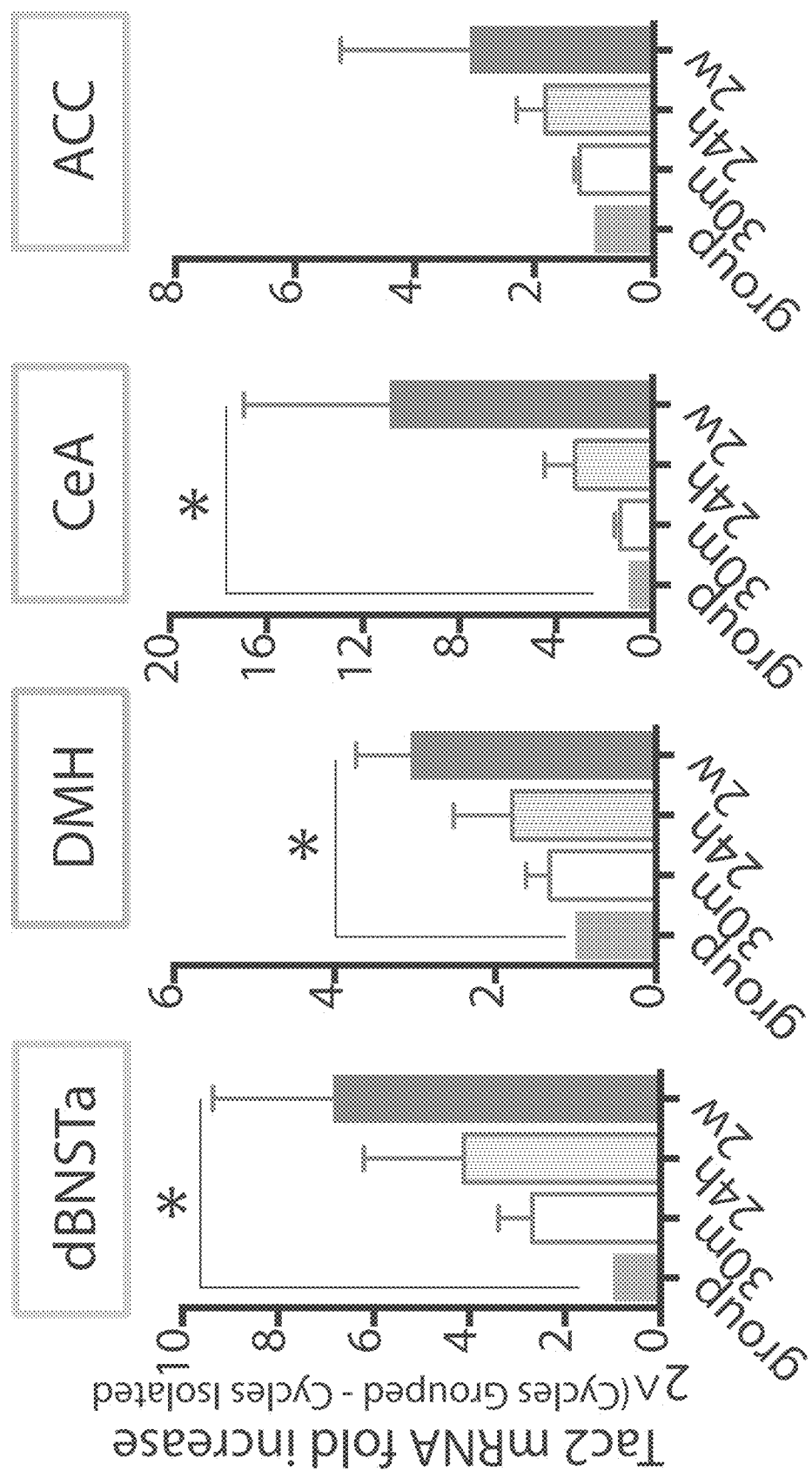
FIGS. 9R-Y show quantification of fold increases in Tac2 (R-U) or Tac1 (V-Y) mRNA that revealed significant increases in Tac2, but not Tac1, following 2 weeks of SIS. Data from the GH vs. 2 week condition are also presented in FIGS. 2H-Q and are included here for comparison purposes.
Figures 9V, 9W, 9X, 9Y:
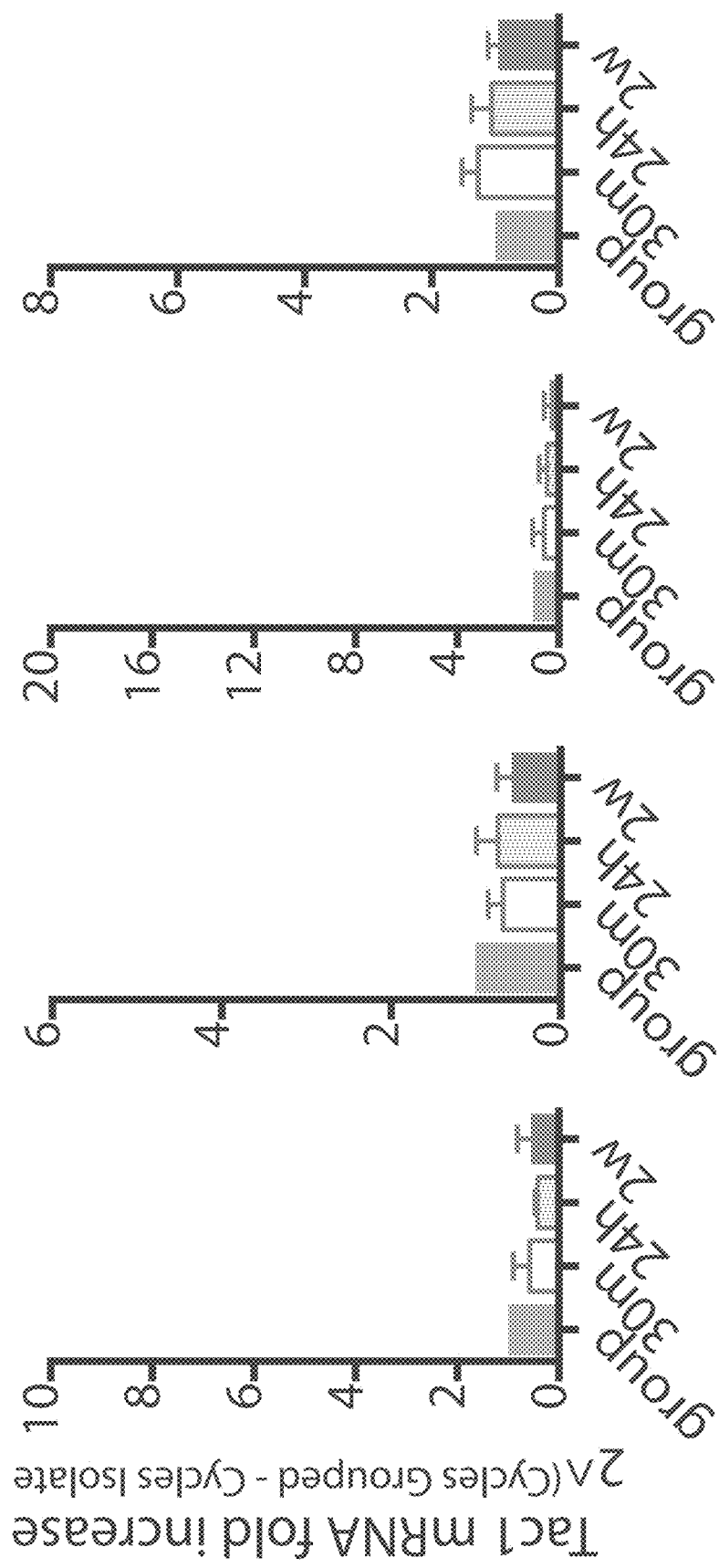
Figure 9Z:
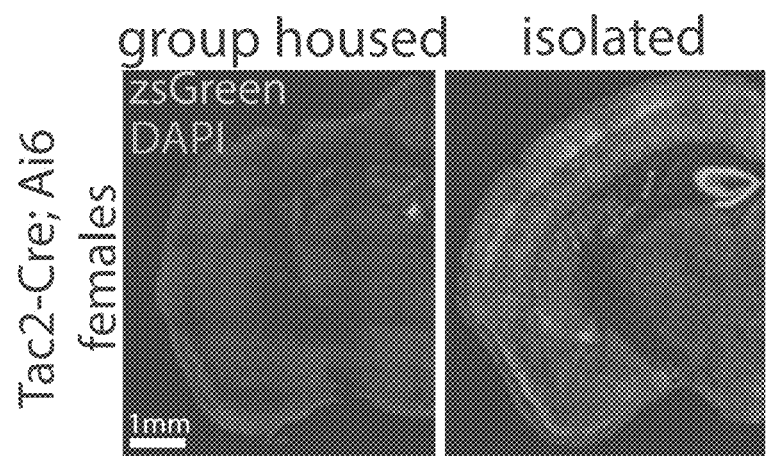
FIG. 9Z shows coronal images of Tac2-Cre; Ai6-zsGreen female mice illustrating that zsGreen expression is increased in females as well as in males (See FIGS. 2A-AA). Greater fluorescent intensity was seen in isolated females as compared to group housed females.
Figure 9A:
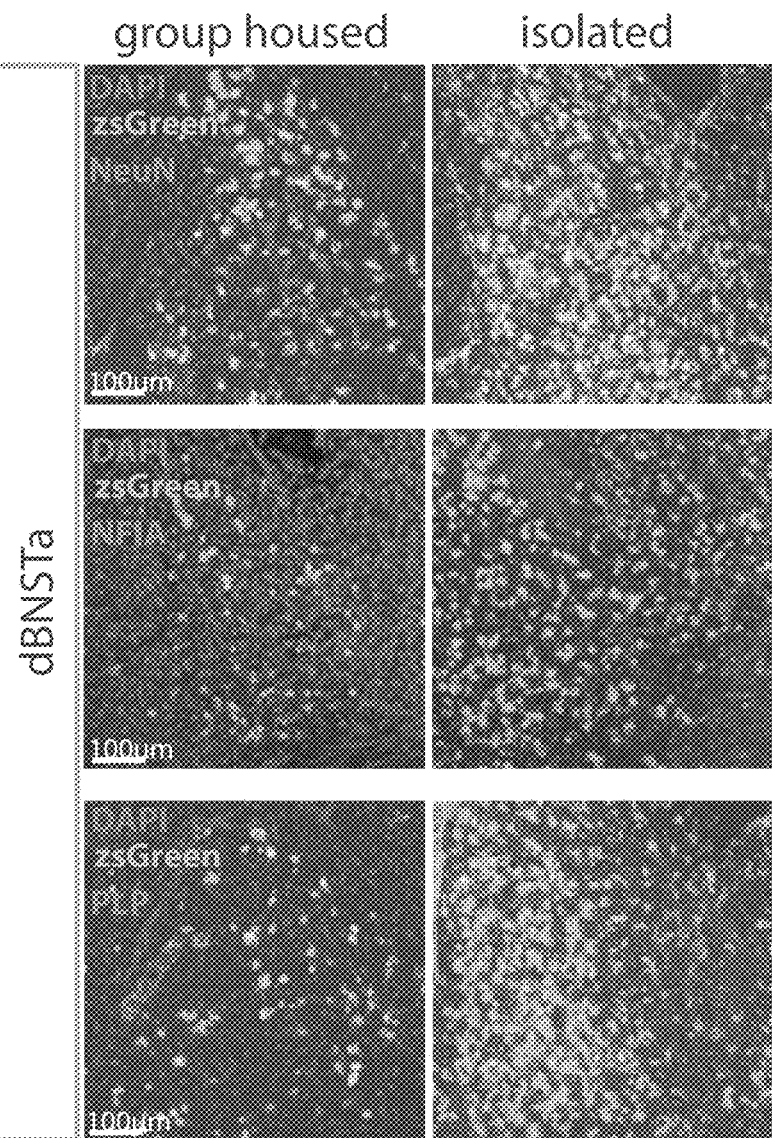
FIGS. 9A-GG show that SIS produces an increase in Tac2 expression in accordance with some embodiments.
Figure 9B:
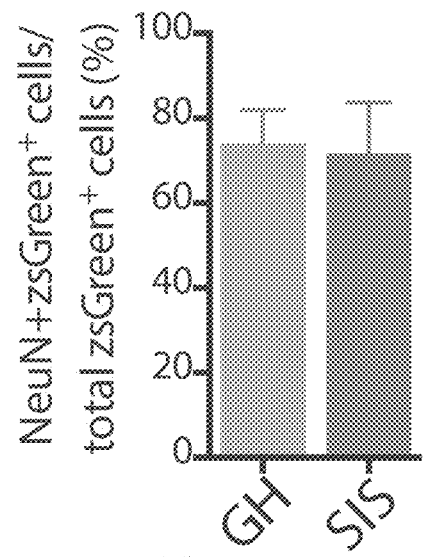
FIG. 9BB quantitates NeuN and zsGreen double staining shown in group housed (GH) and social isolation stress (SIS) mice (See FIG. 9AA, top row of panels).
Figure 9C:
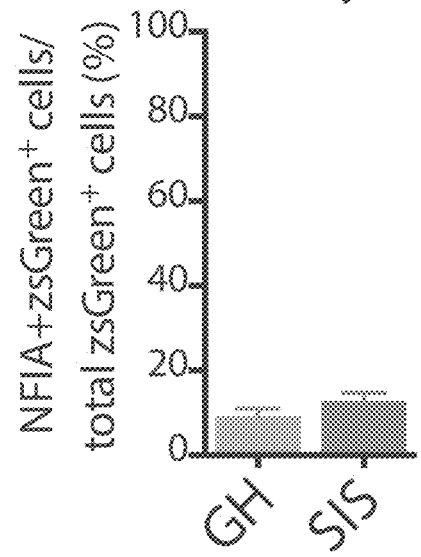
FIG. 9CC quantitates NFIA and zsGreen double staining shown in group housed (GH) and social isolation stress (SIS) mice (See FIG. 9AA, middle row of panels).
Figure 9D:
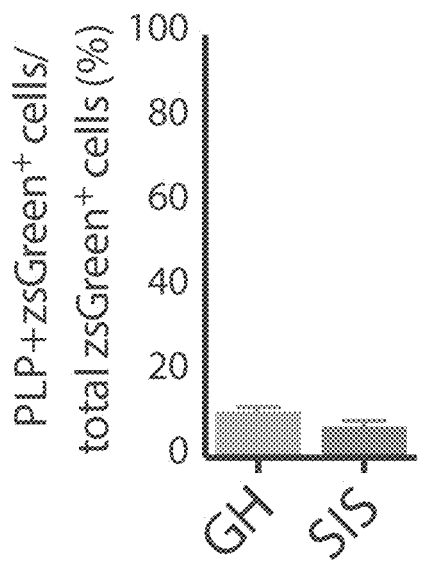
FIG. 9DD quantitates PLP and zsGreen double staining shown in group housed (GH) and social isolation stress (SIS) mice (See FIG. 9AA, bottom row of panels). The percentage of double labeled cells was similar for isolated and group housed mice for each marker analyzed, with the greatest percentage of double labeling seen with NeuN and relatively lower incidences of double labeling for NFIA and zsGreen (Tac2) and PLP and zsGreen (Tac2).

To determine whether Tac expression is affected by SIS, we crossed Tac2-IRES-Cre or Tac1-IRES-Cre knock-in mice (Tasic et al., 2016; incorporated by reference in its entirety herein) to Cre-reporter mice expressing zsGreen from the Rosa-26 locus under control of the ubiquitous CAG promoter-enhancer (line Ai6) (Madisen et al., 2010; incorporated by reference in its entirety herein). Double-heterozygous mice were socially isolated for two weeks or group housed prior to sacrifice. Strikingly, freshly dissected brains from isolated Tac2-Cre; Ai6 mice exhibited broadly enhanced zsGreen expression that could be detected by the naked eye under ambient lighting (FIG. 2D). Sectioning confirmed a widespread increase in zsGreen expression throughout the brain, in both males (FIG. 2F) and females (FIG. 9Z). Induction was apparent in the anterior dorsal bed nucleus the stria terminalis (dBNSTa), central nucleus of the amygdala (CeA), dorsomedial hypothalamus (DMH), and anterior cingulate cortex (ACC) (FIGS. 9A-P). Counterstaining with neuronal and glia markers indicated that most zsGreen expression occurred in neuronal cells (FIGS. 9AA-DD). Increased zsGreen expression was also detected in peripheral endocrine tissues, such as the pancreas, testes and submandibular gland (not shown).

Figure 2E:
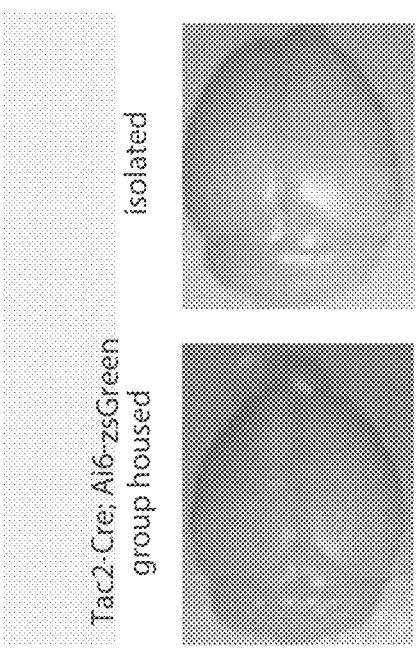
Figure 2F:
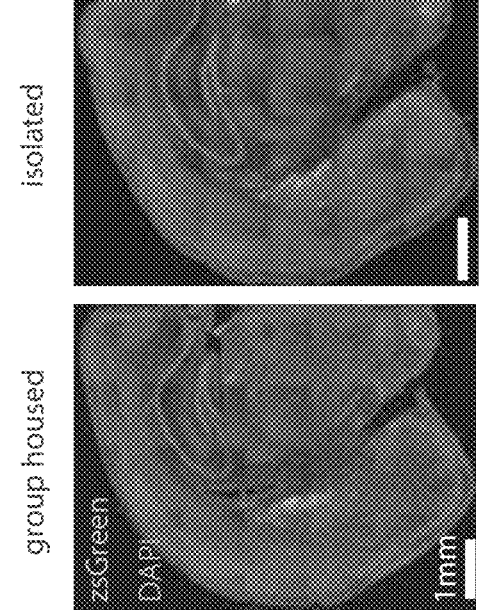
Figure 2G:
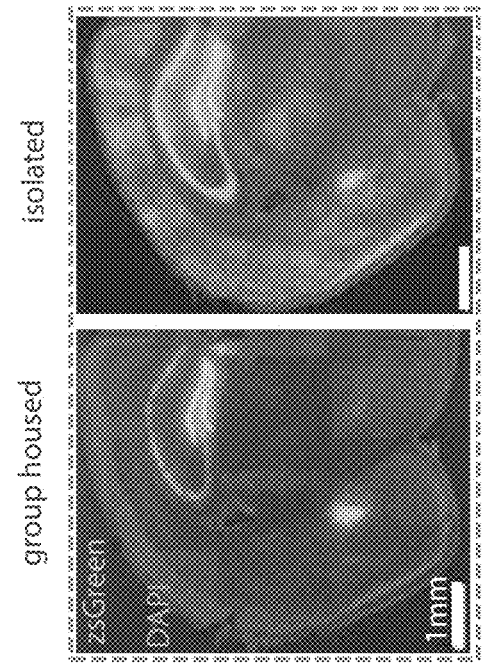

Similar results were obtained using a different Cre reporter mouse, Ai14 (Madisen et al., 2010; incorporated by reference in its entirety herein) expressing mCherry (FIG. 9EE), indicating that the induction was not a peculiarity of the Ai6 line. Notably, no such change was observed in socially isolated Tac1-Cre; Ai6 mice (FIG. 2E, FIG. 2G). Without being limited by theory, these data suggest that the broad induction of zsGreen observed in SIS mice is specific to the Tac2Cre allele, and is not a non-specific effect of SIS to increase Cre-mediated recombination at the Rosa-26 locus or a peculiarity of the zsGreen reporter.

Figure 2R:
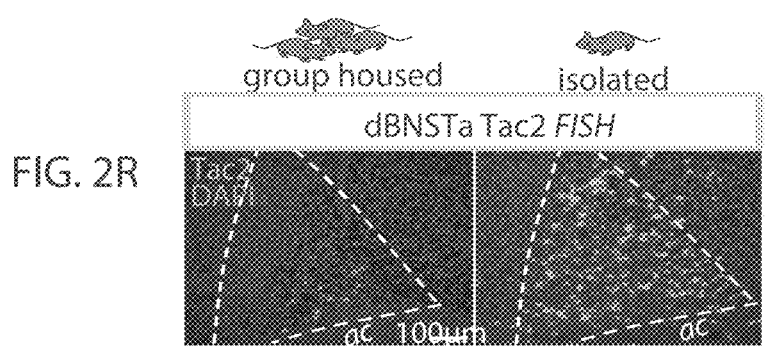
FIGS. 2R-V show Tac2 mRNA detected by FISH in GH or SIS mice in the indicated regions (n=3-4 mice/condition, 1-4 sections/region/mouse); representative sections from each area are shown, Dashed lines indicate regions of interest (ROIs) used for quantification.
Figure 2S:
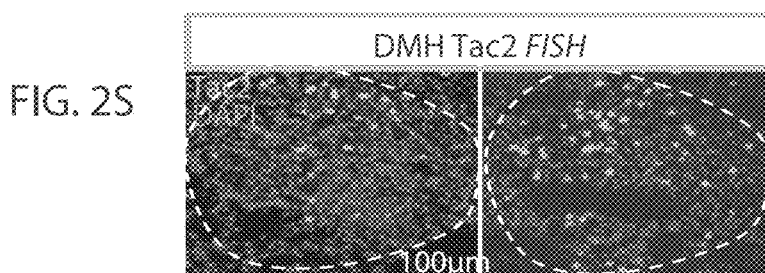
Figure 2T:
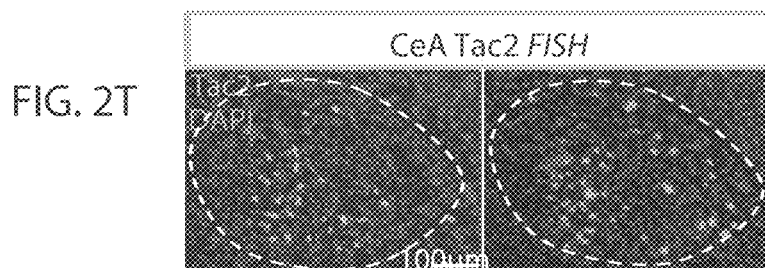
Figure 2U:
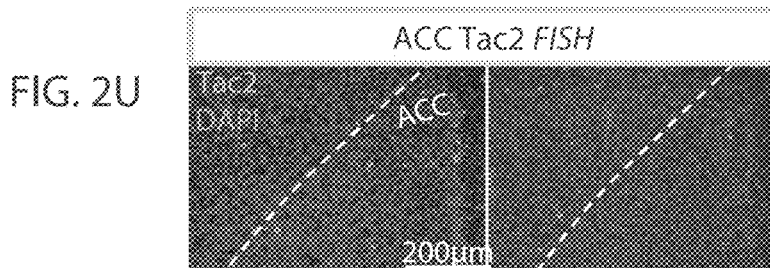
Figure 2V:
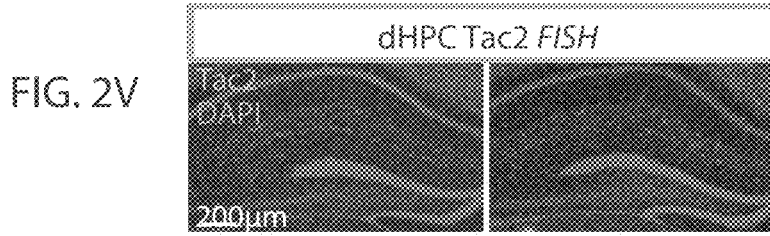
Figure 2W:
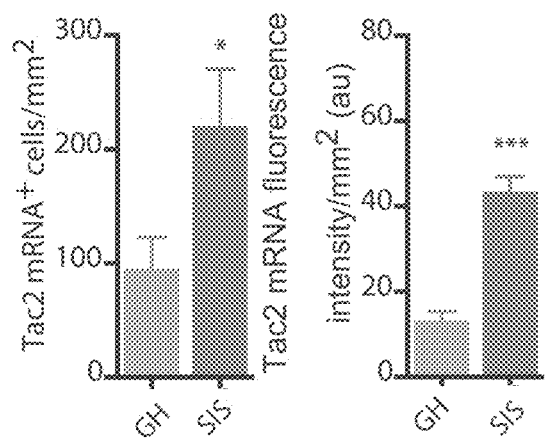
FIGS. 2W-AA show the average number of Tac2 mRNA$^+$ cells/mm$^2$ in ROIs (left) and the average fluorescence intensity/mm$^2$ (right) in the regions shown in FIGS. 2R-V, respectively. Fold-increases in Tac2 mRNA fluorescence intensity are greater than increases in cell number, indicating an increase in expression level per cell. See, also related FIGS. 9A-GG. For all panels shown in FIGS. 2R-V, the intensity of fluorescent staining was representative of the quantitations shown in FIGS. 2W-AA. Greater fluorescent intensity was seen in isolated mice as compared to group housed mice for dBNSTa, DMH, and CeA, while fluorescent intensity was comparably low for isolated and group housed mice in ACC and dHPC.
Figure 2X:
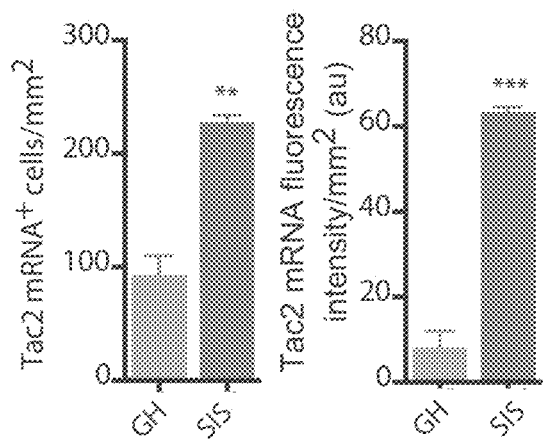
FIGS. 2H-Q show quantification of Tac2 or Tac1 mRNAs by qRT-PCR in the indicated regions, hand-dissected from the brains of GH or SIS mice (n=4 mice/condition)
Figure 2Y:
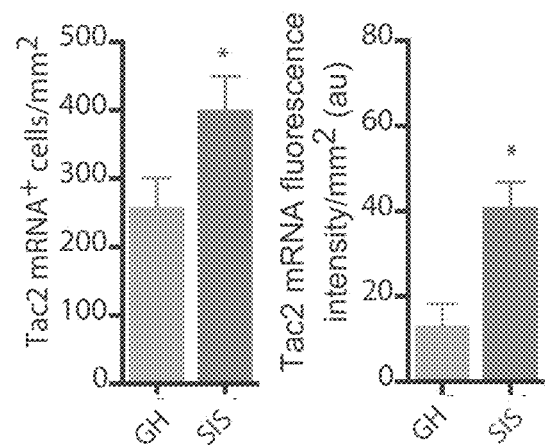
Figure 2Z:
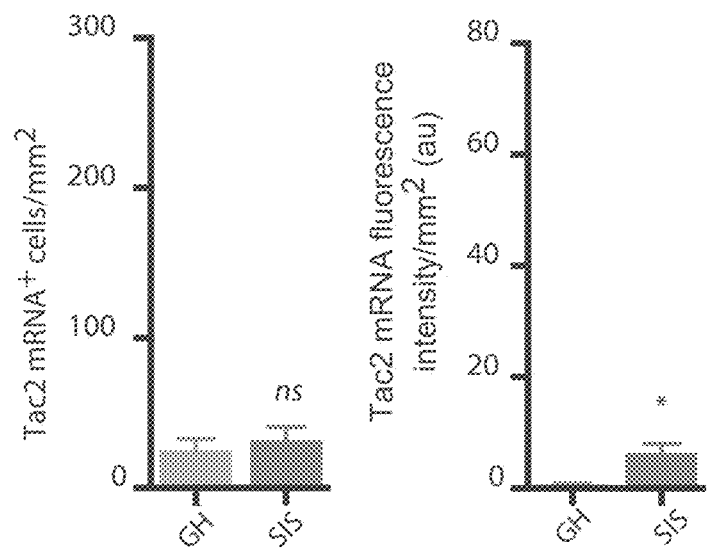
Figure 2A:
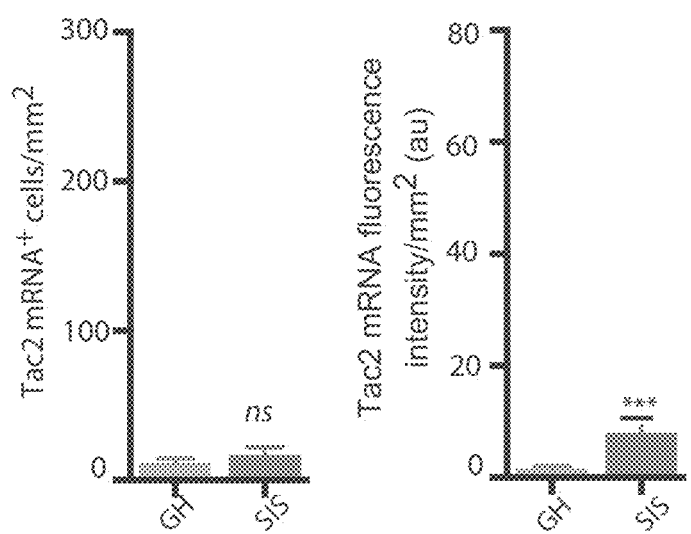

To confirm that SIS up-regulated endogenous Tac2 expression, we quantified Tac2 mRNA in selected brain regions from SIS or GH wild-type mice, using qRT-PCR. QRT-PCR analyses indicated that SIS caused a large (~3-8-fold) and statistically significant increase in Tac2 mRNA levels in the dBNSTa, DMH and CeA, with trends that did not reach significance observed in the ACC and dHPC (FIGS. 2H-L). A time-course revealed an increase in Tac2 mRNA from 30 min to 2 weeks of SIS (FIGS. 9Q-U). No increase in Tac1 mRNA was observed in these regions (FIG. 2M-Q, FIG. 9V-Y). An increase in NkB protein expression was also observed in the dBNSTa by immunostaining (FIGS. 9FF-GG). Endogenous Tac2 mRNA up-regulation was also observed in wild-type mice in dBNSTa, CeA and DMH using RNA fluorescent in situ hybridization (FISH) (FIGS. 2R-T). The fold-increase in fluorescence intensity per mm2 was much greater than the fold-increase in the number of Tac2 mRNA+ cells (FIGS. 2W-Y), suggesting a broad increase in expression per cell, rather than in the number of strongly positive cells. This likely explains why the Cre reporter mouse, which integrates and amplifies expression, yielded a larger fold-increase in the number of positive cells (FIGS. 9A-P). This difference was particularly evident in the ACC or dHPC, where the intensity of Tac2 mRNA FISH signal increased only slightly but a pronounced increase in the number of zsGreen+ cells was observed (FIGS. 2U-V, FIGS. 2Z-AA and FIGS. 9A-P). Despite these quantitative differences between methods, the data indicate that SIS up-regulates Tac2 mRNA expression in multiple brain regions.

In sum, the data show that, in accordance with some embodiments, chronic social isolation stress (SIS) causes widespread upregulation of Tac2 but not Tac1 transcription.

Example 3

This example shows the effect of acute systemic antagonism on the effects of social isolation stress (SIS).

Figure 3A:
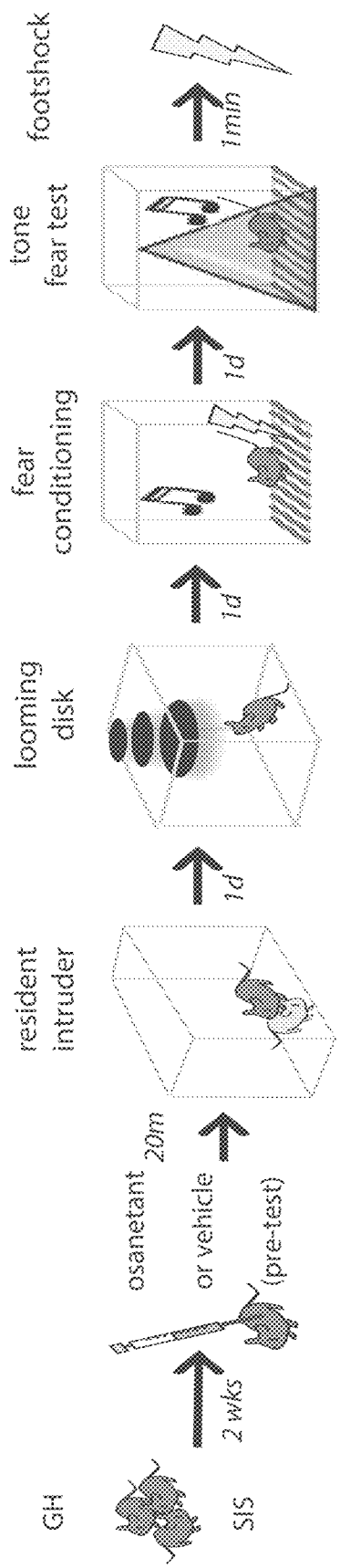
Figures 3B, 3C, 3D:
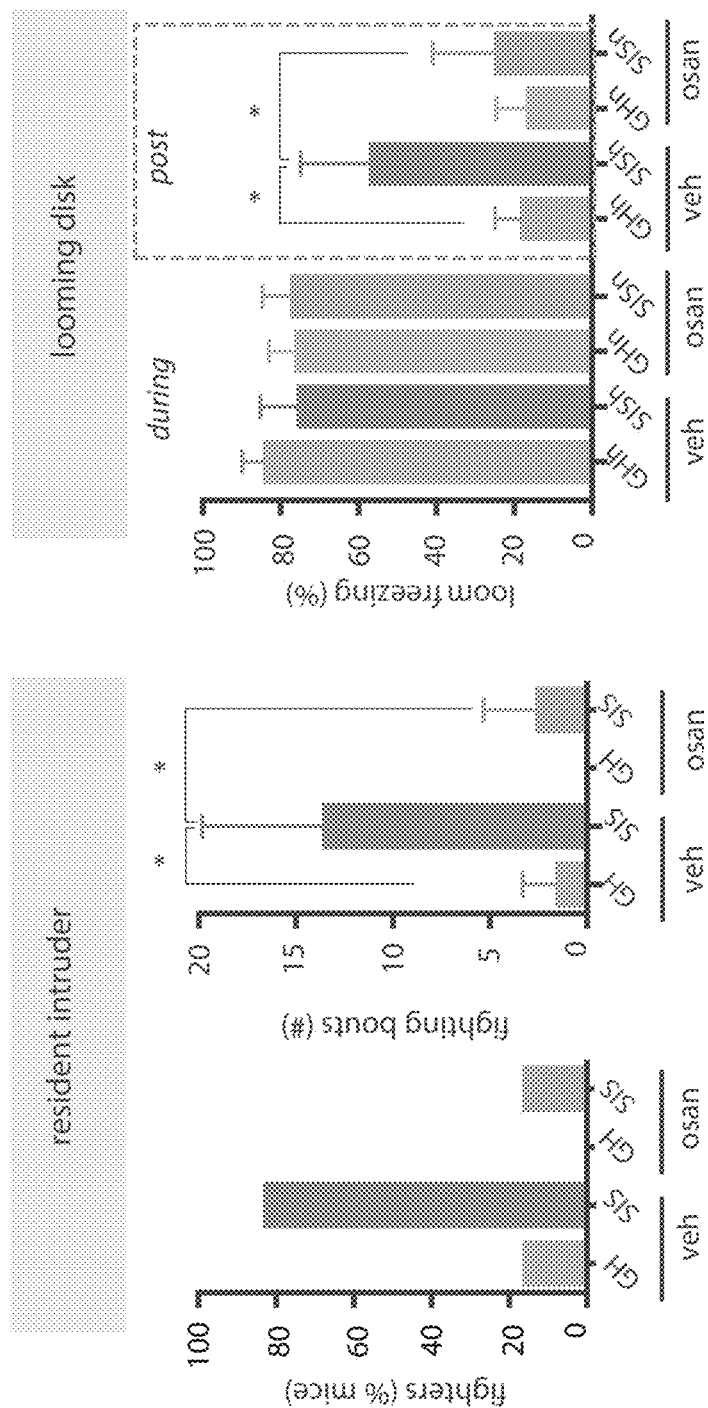
Figures 3E, 3F:
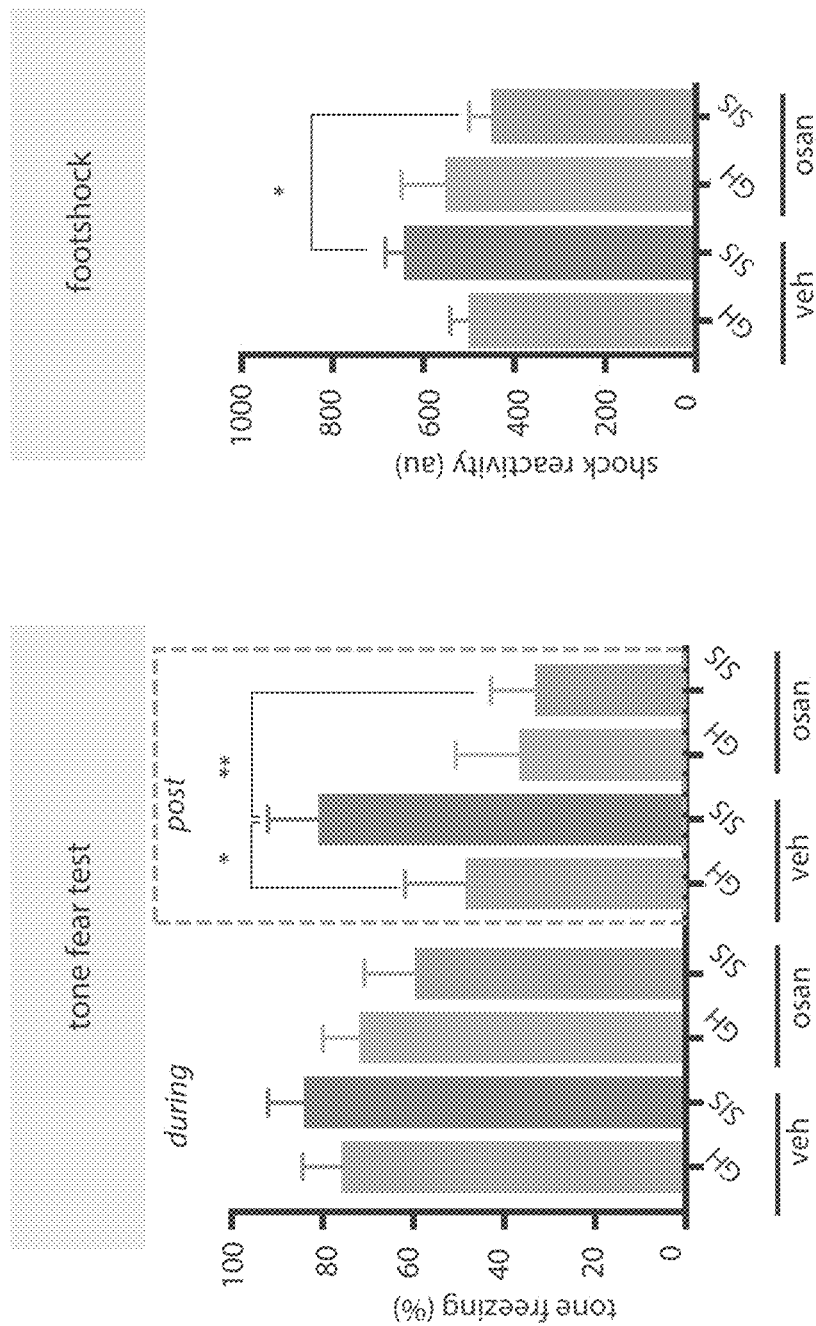
Figure 10A:
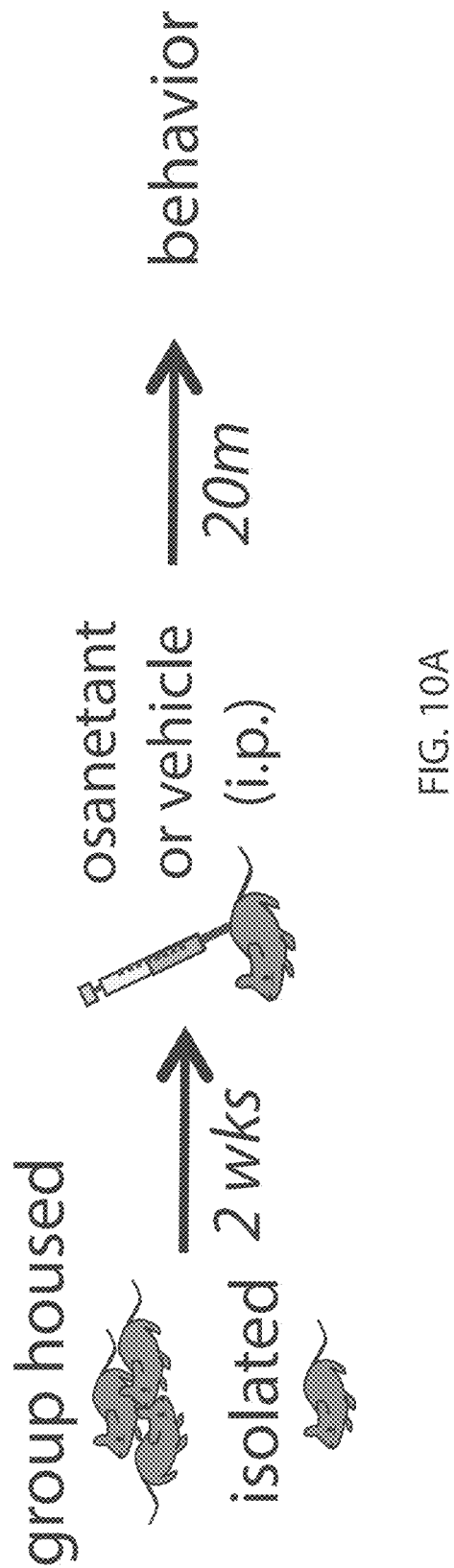
FIGS. 10A-J show the effects of systemic acute osanetant on behavior in some embodiments.
Figure 10B:
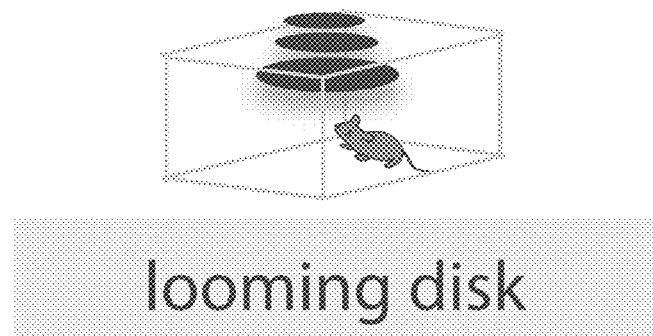
Figure 10C:
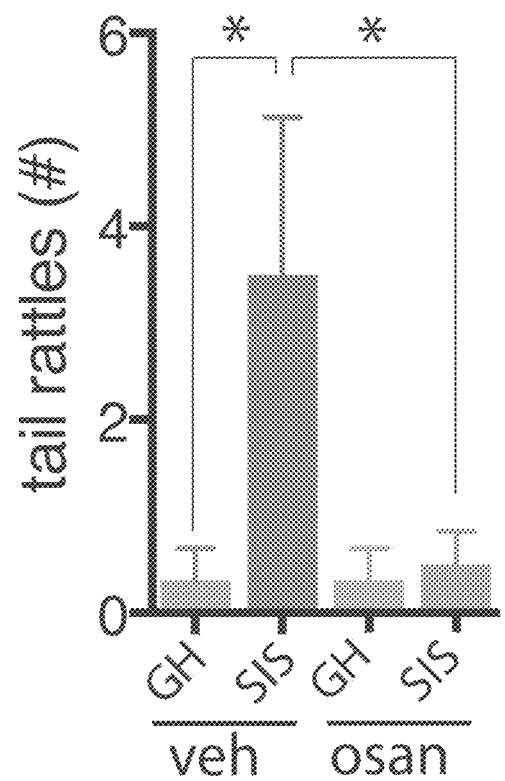
Figure 10D:
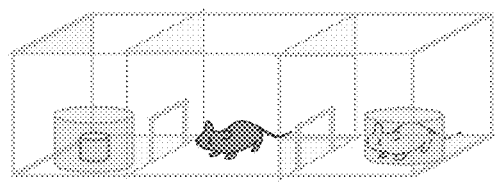
Figure 10E:
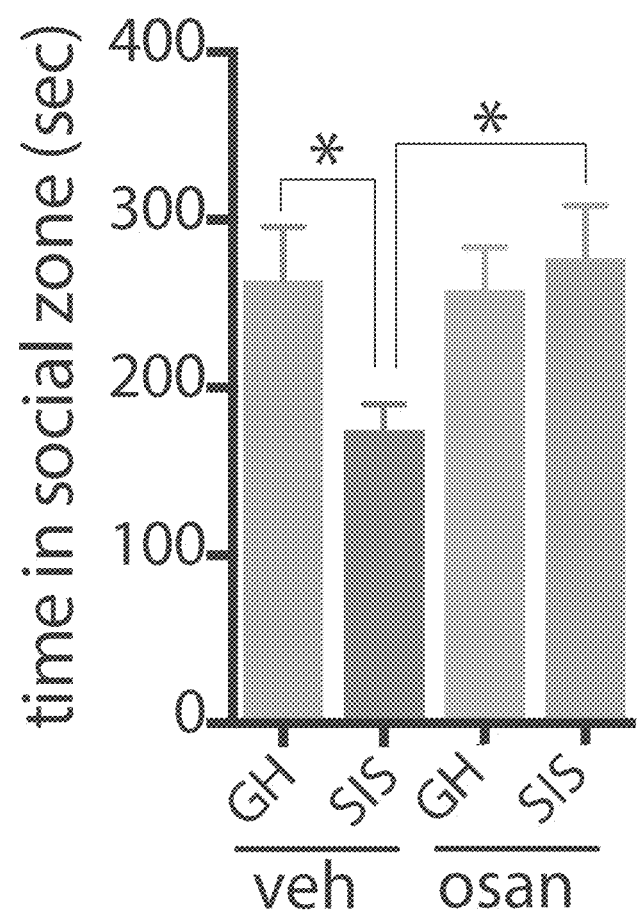
Figure 10F:
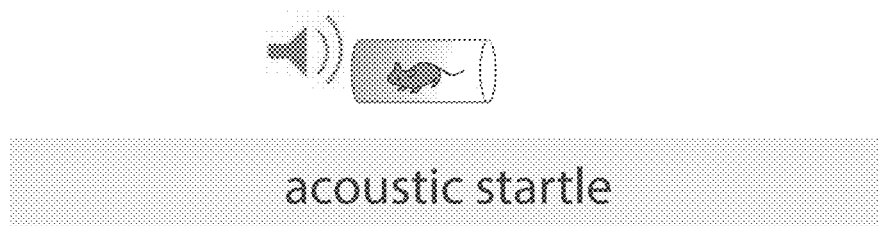
Figure 10G:
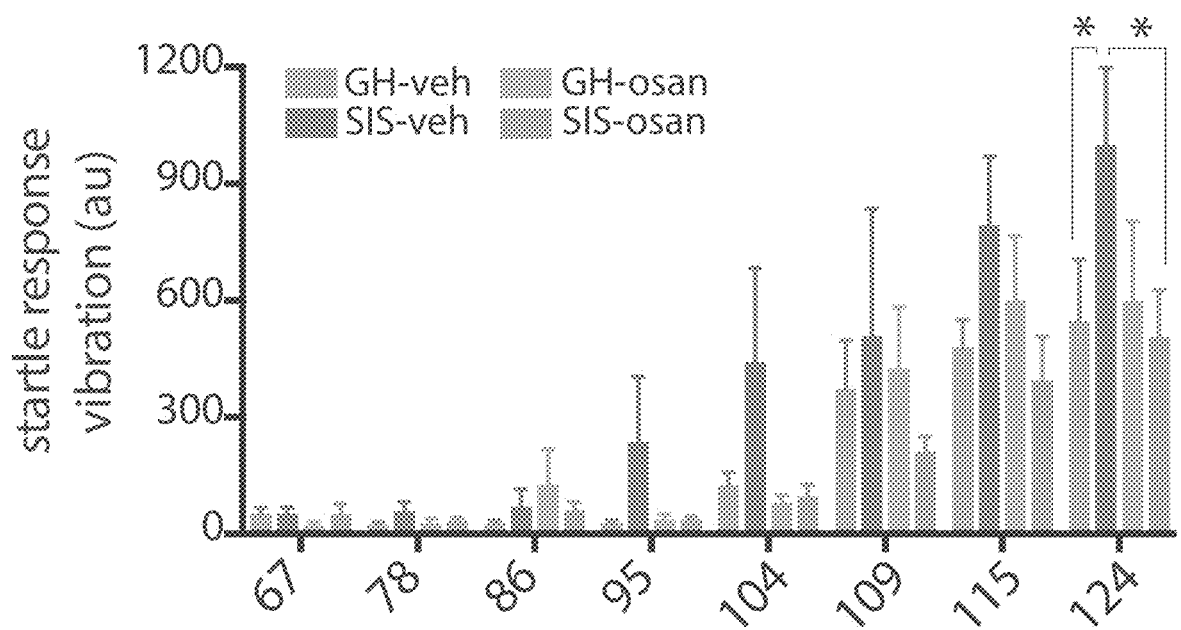
Figure 10H:
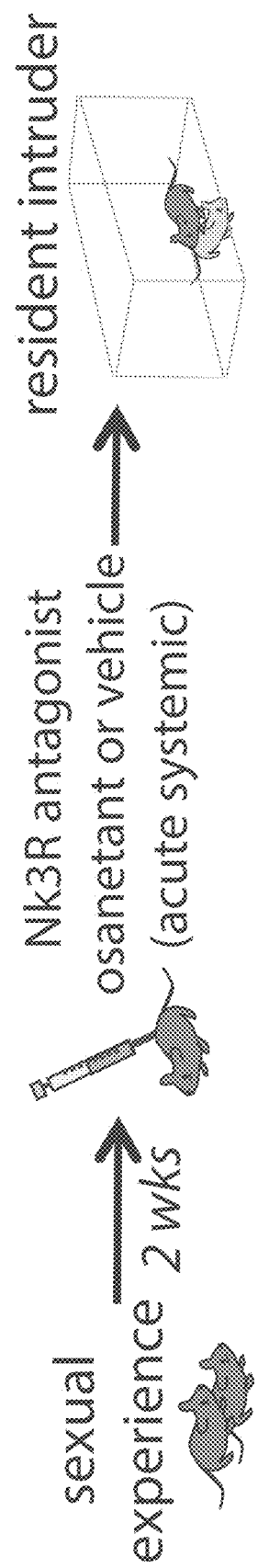
Figure 10I:
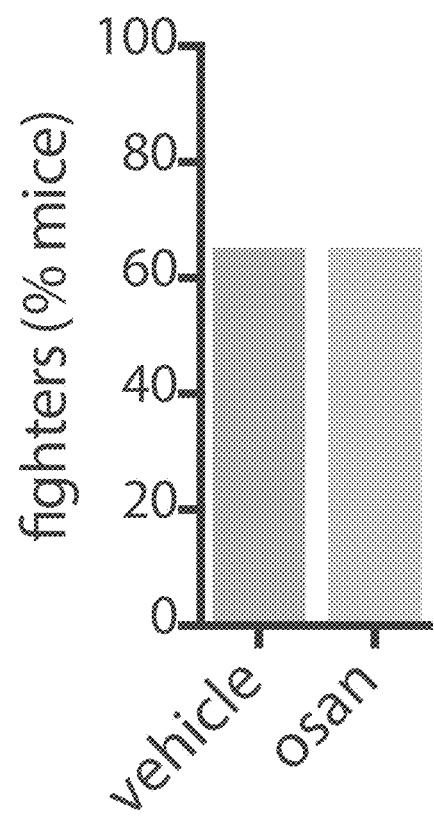
Figure 10J:
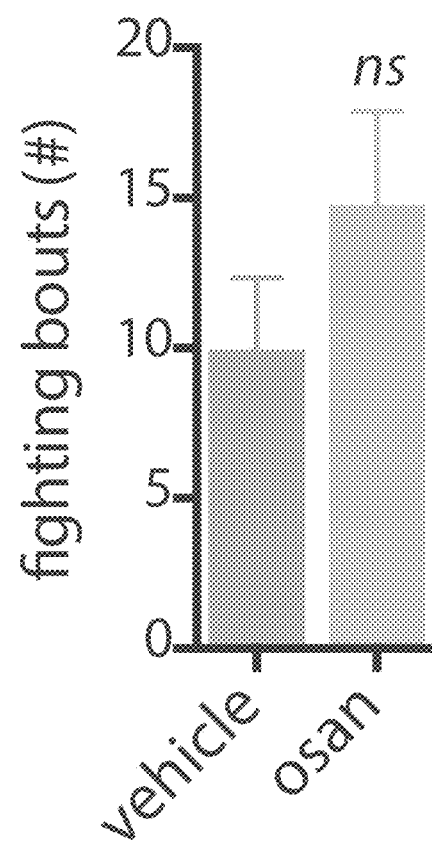

As a first step to investigate whether the induction of Tac2 expression reflects a causal role for this peptide in mediating the behavioral effects of SIS, we inhibited NkB signaling by systemic administration of osanetant (FIG. 3A) (Emonds-Alt et al., 1995; incorporated by reference in its entirety herein), a specific Nk3R antagonist that crosses the blood-brain barrier (Spooren et al., 2005; incorporated by reference in its entirety). Osanetant (5 mg/kg) administered 20 minutes prior to each behavioral assay strongly reduced SIS-enhanced aggression (FIGS. 3B-C), but had no effect on aggression promoted by sexual experience (Remedios et al., 2017; incorporated by reference in its entirety herein) (FIGS. 10H-J). Osanetant also attenuated the SIS-induced enhancement of persistent freezing to both the looming disk and the fear-conditioned tone (FIG. 3D, FIG. 3E, post). There were no significant differences between groups during the presentation of these threatening stimuli. Osanetant also blocked other SIS-induced alterations in behavior including increased shock reactivity (FIG. 3F), increased tail-rattling (FIGS. 10B-C), decreased social interaction (FIGS. 10D-E) and enhanced responding in the acoustic startle assay (FIGS. 10F-G). Thus, systemic antagonism of Nk3Rs administered prior to testing was able to block virtually all of the measured behavioral effects of chronic SIS, while leaving other, non-SIS altered behaviors (e.g. acute freezing, sexual-experience-dependent aggression) intact.

The data show that acute systemic NK3R antagonism, in accordance with some embodiments, attenuates the effects of SIS, including, but not limited to, SIS-enhanced aggression, SIS-induced enhancement of persistent freezing, increased shock reactivity, increased tail rattling, decreased social interaction, and enhanced responses in the acoustic startle assay.

Example 4

This example shows the protective effect of chronic systemic antagonism of Nk3Rs during social isolation stress (SIS).

Figure 3G:
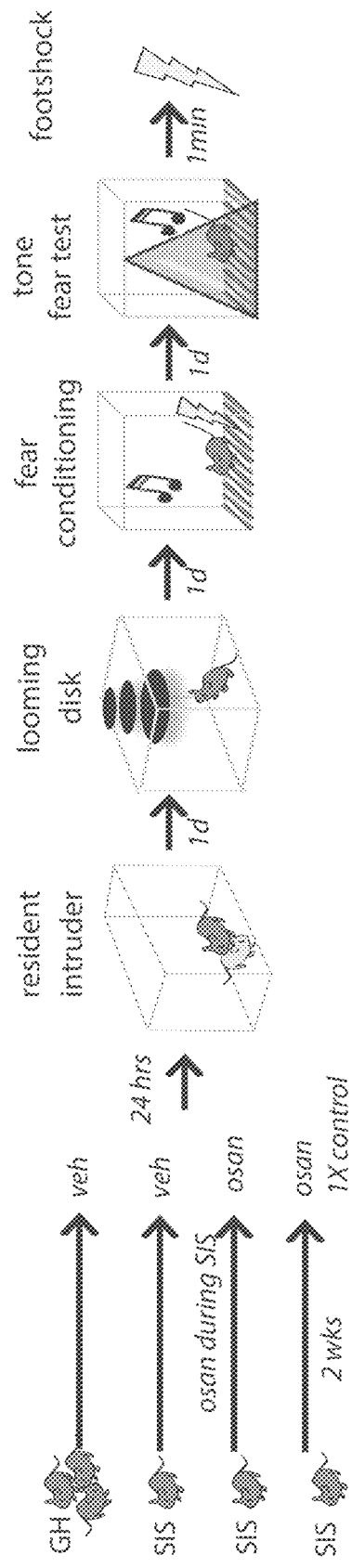

We asked whether Tac2 signaling is required during the period of social isolation to observe the changes in behavior. Mice were administered osanetant daily in their home cage during the two-week social isolation period, but were then tested off-drug. To control for carry-over of the drug from the final homecage administration into the testing period (24 hrs later), an additional group of mice was subjected to two weeks of SIS without drug, and given a single home-cage administration of osanetant 24 hours prior to testing (FIG. 3G).

Figure 3M:
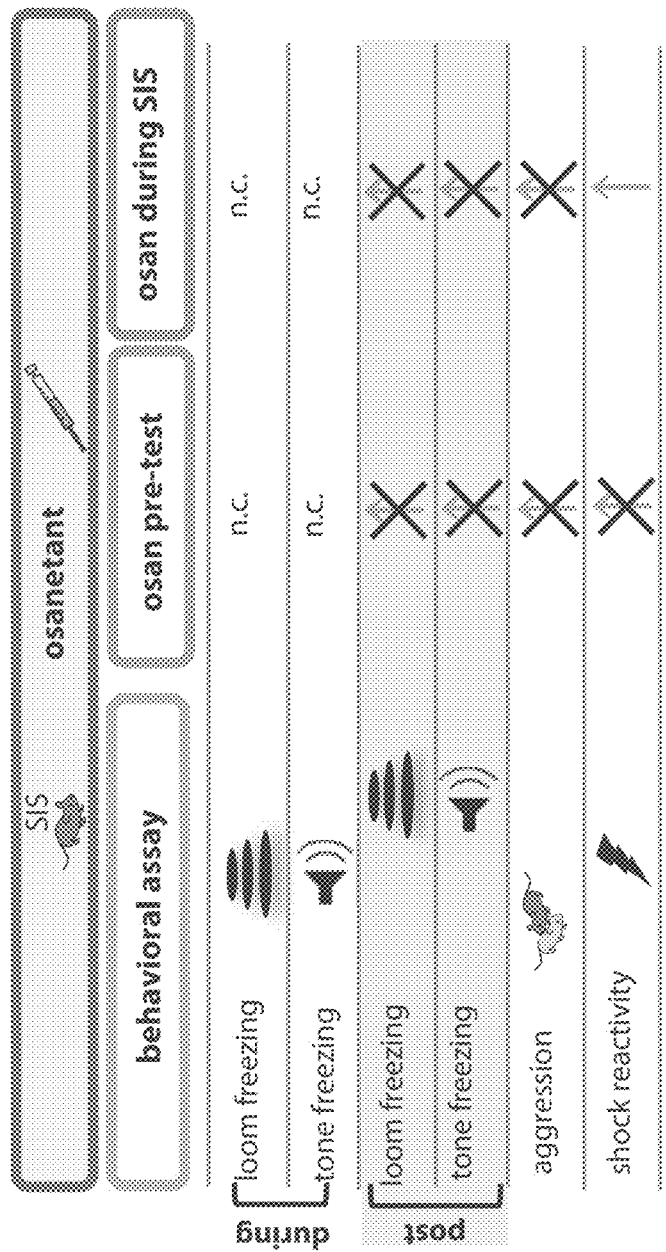

Remarkably, treatment with daily osanetant during isolation prevented SIS-enhanced aggression (FIGS. 3H-I), persistent freezing to the looming disk (FIG. 3J), and persistent freezing to the fear conditioned tone (FIG. 3K). The SIS-induced increase in shock reactivity was reduced, but not significantly (FIG. 3L, FIG. 3M). Mice that had been treated with osanetant during SIS could be returned to housing with their pre-isolation cagemates without any subsequent fighting observed, in contrast to control SIS mice which vigorously attacked their cagemates when reintroduced to the group (data not shown).

The data show that chronic systemic antagonism of Nk3Rs during SIS, in accordance with some embodiments, has a protective effect by preventing SIS-enhanced aggression and presistent freezing behaviors, for example.

Example 5

This example shows the role of Nk3Rs in dBNSTa, CeA, and DMH in mediating the effects of social isoation stress (SIS) on different behaviors.

Figure 4A:
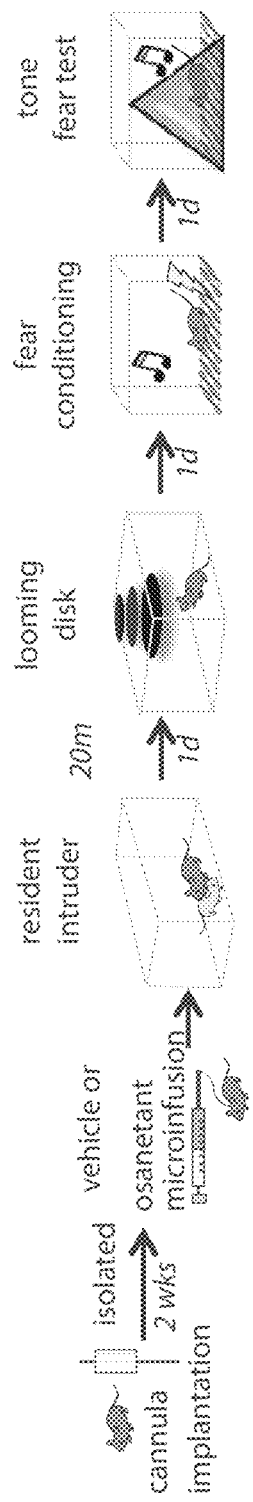
FIGS. 4A-Q, show that targeted Nk3R antagonism in dBNSTa, DMH, or CeA attenuates different effects of SIS in a dissociable manner in accordance with some embodiments.
Figure 4Q:
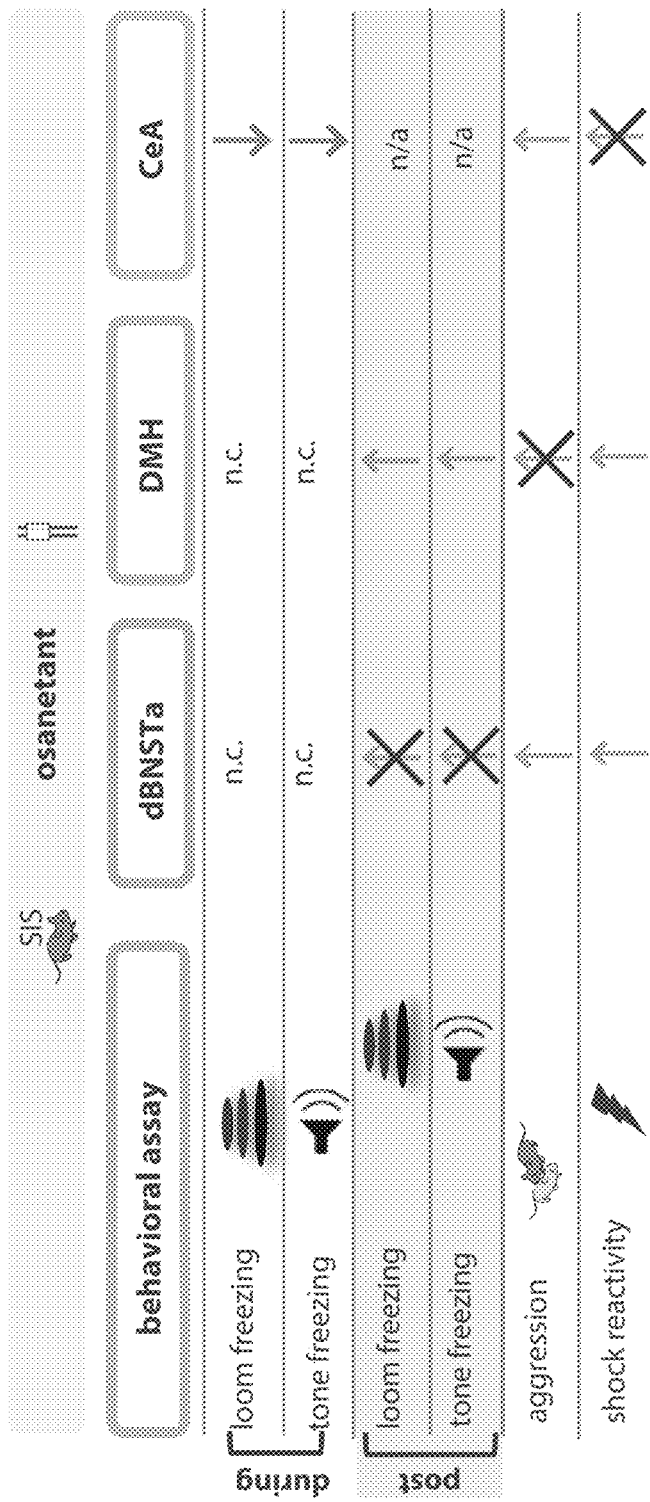

Without being limited by theory, the foregoing results suggested that Tac2/NkB signaling is required for the effect of chronic SIS to alter multiple defensive behaviors. We next asked where in the brain this signaling is required. As a first step, we pharmacologically inhibited Nk3Rs in dBNSTa, DMH, and CeA, as these regions contain cells expressing Nk3Rs (FIGS. 11A-C), and exhibited a strong induction of Tac2 expression following SIS (FIGS. 2A-AA). Cannulated mice were subjected to SIS and then received bilateral microinfusions of osanetant into the region of interest 20 minutes prior to each behavioral test (FIG. 4A). We selected four assays—the resident intruder assay, looming disk, fear conditioning, and shock reactivity—because they exhibited robust SIS-induced changes and could be performed sequentially within the same animals without affecting each other (as indicated by initial pilot experiments in which each assay was performed independently). This multiplexed approach allowed comparison of 4 different behavioral effects of SIS in animals with multiple manipulations in each of 3 different brain regions, without requiring an exponential increase in the number of implanted animals.

Figures 11A, 11B, 11C:
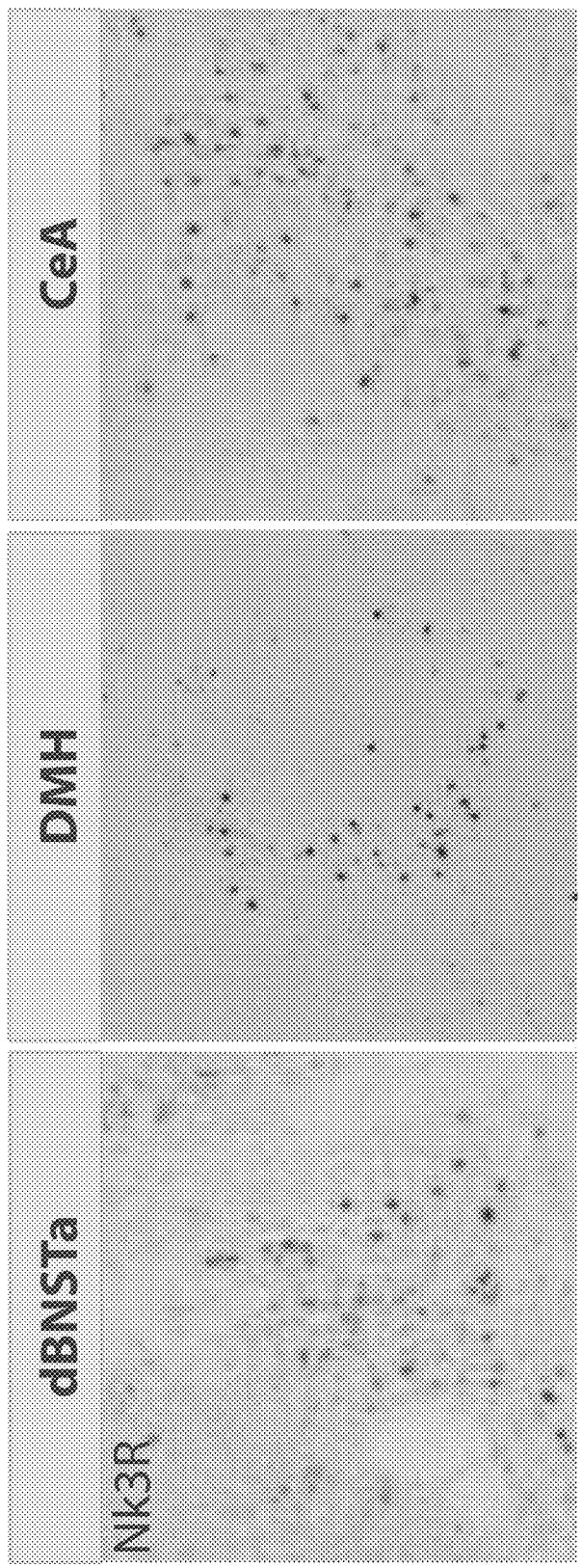
Figure 11D:
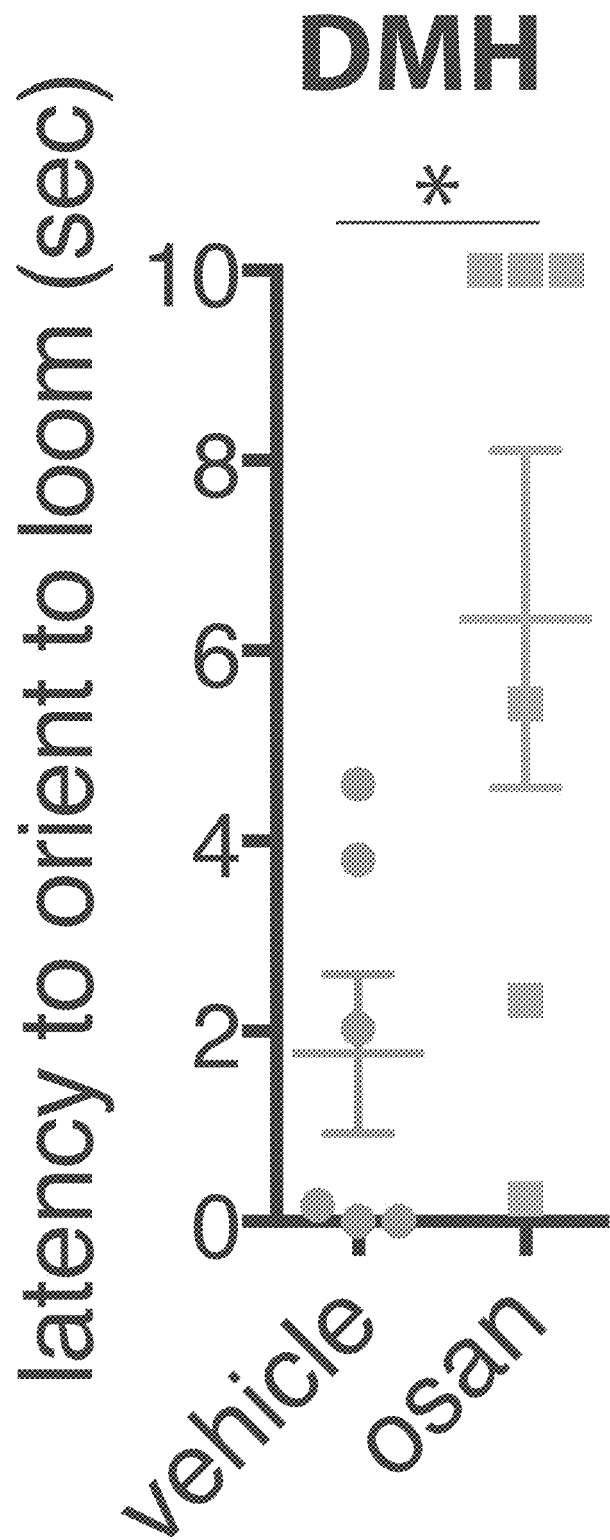
Figure 11H:
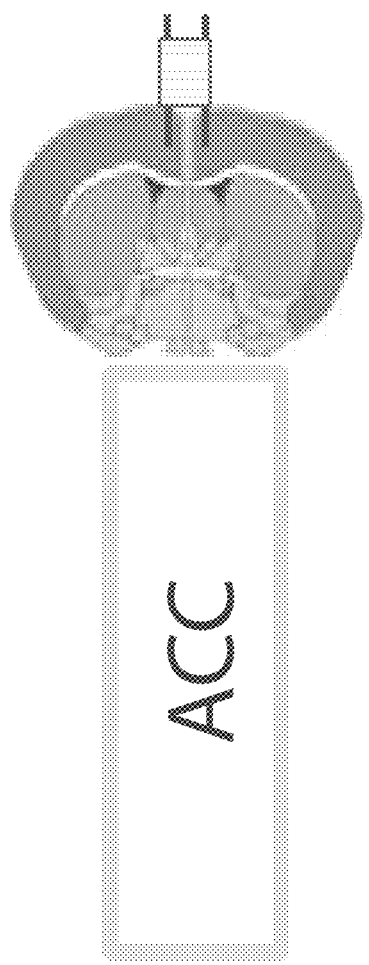
Figure 11I:
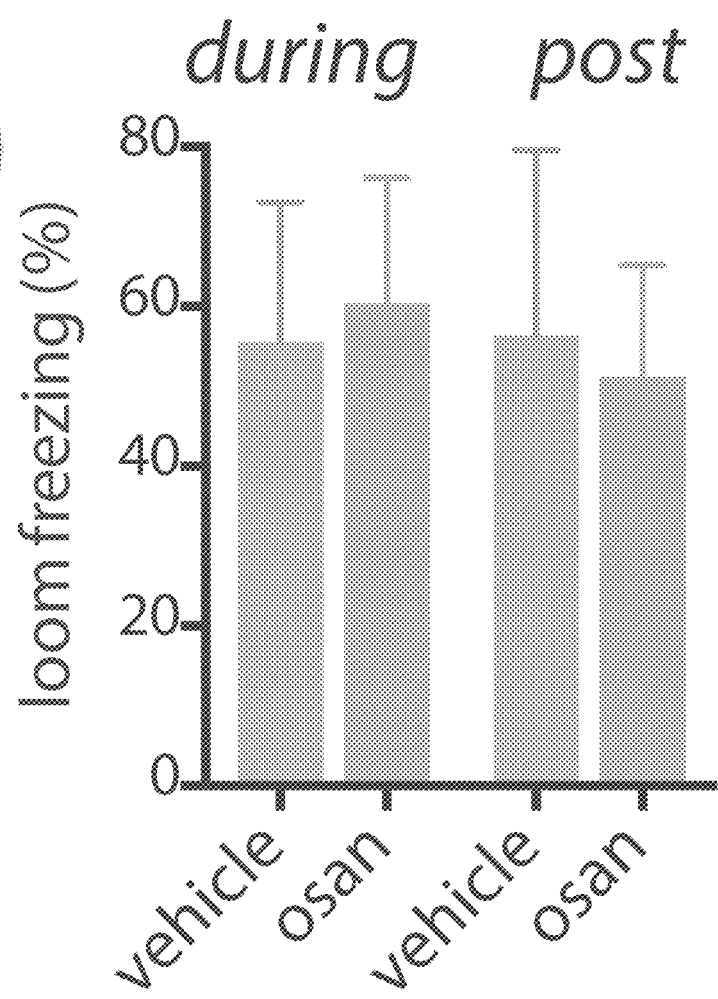
Figure 11J:
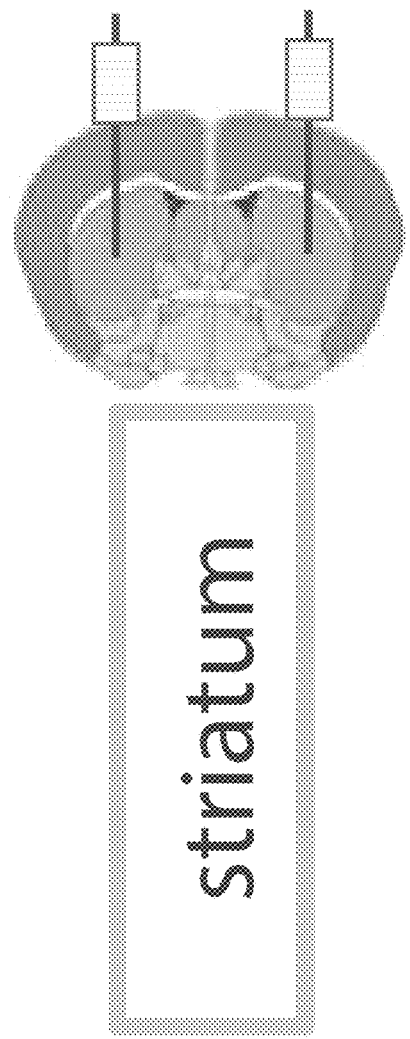
Figure 11K:
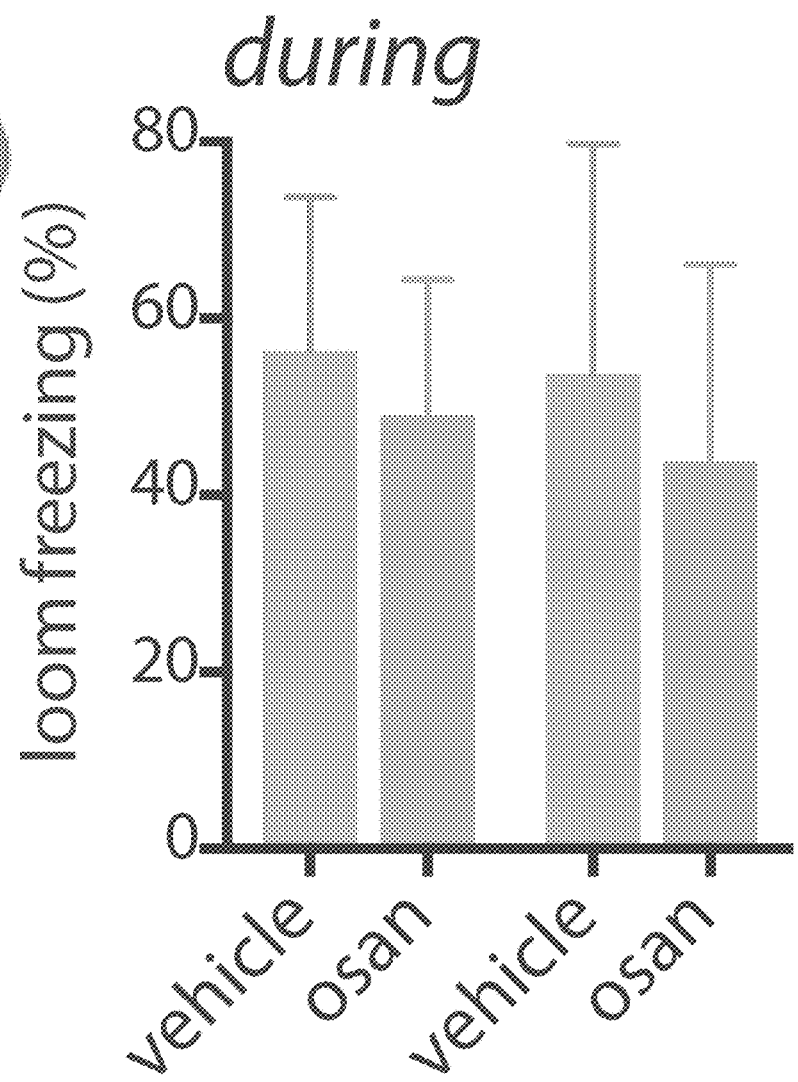
Figures 12A, 12B, 12C:
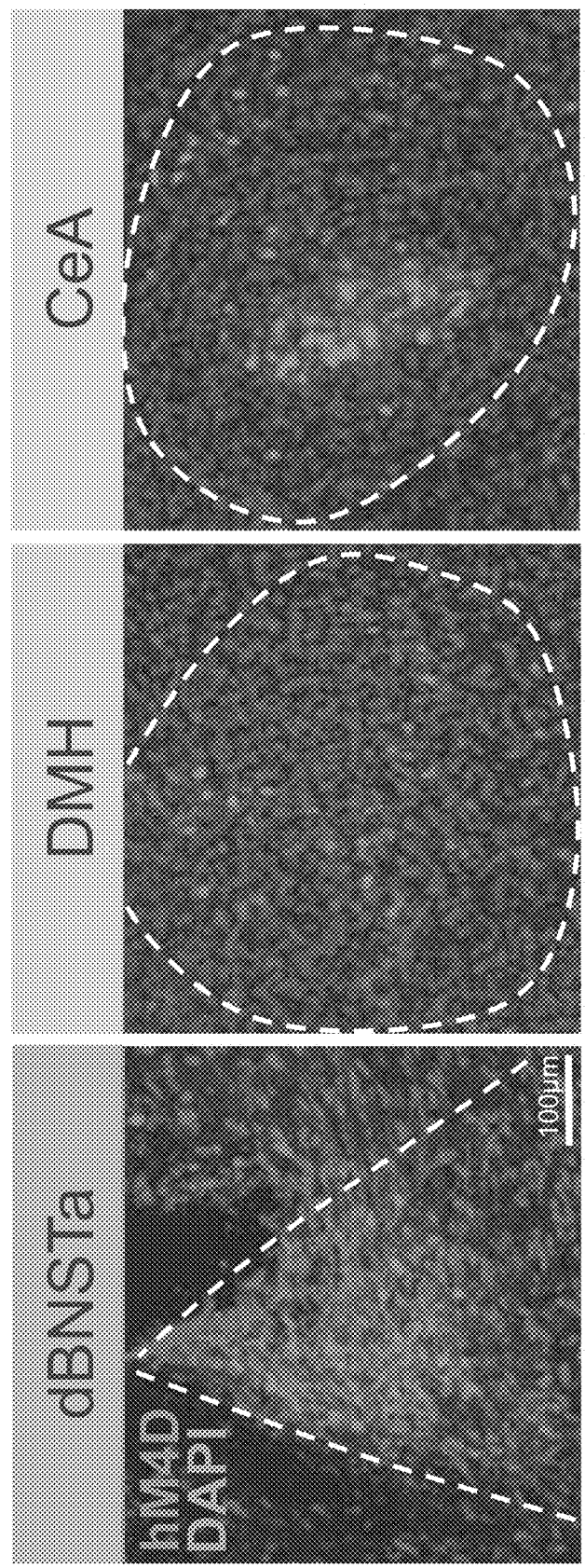
FIGS. 12A-G show that local chemogenetic silencing of Tac2+ neurons reduces the effects of SIS in some embodiments.
Figures 12D, 12E, 12F:
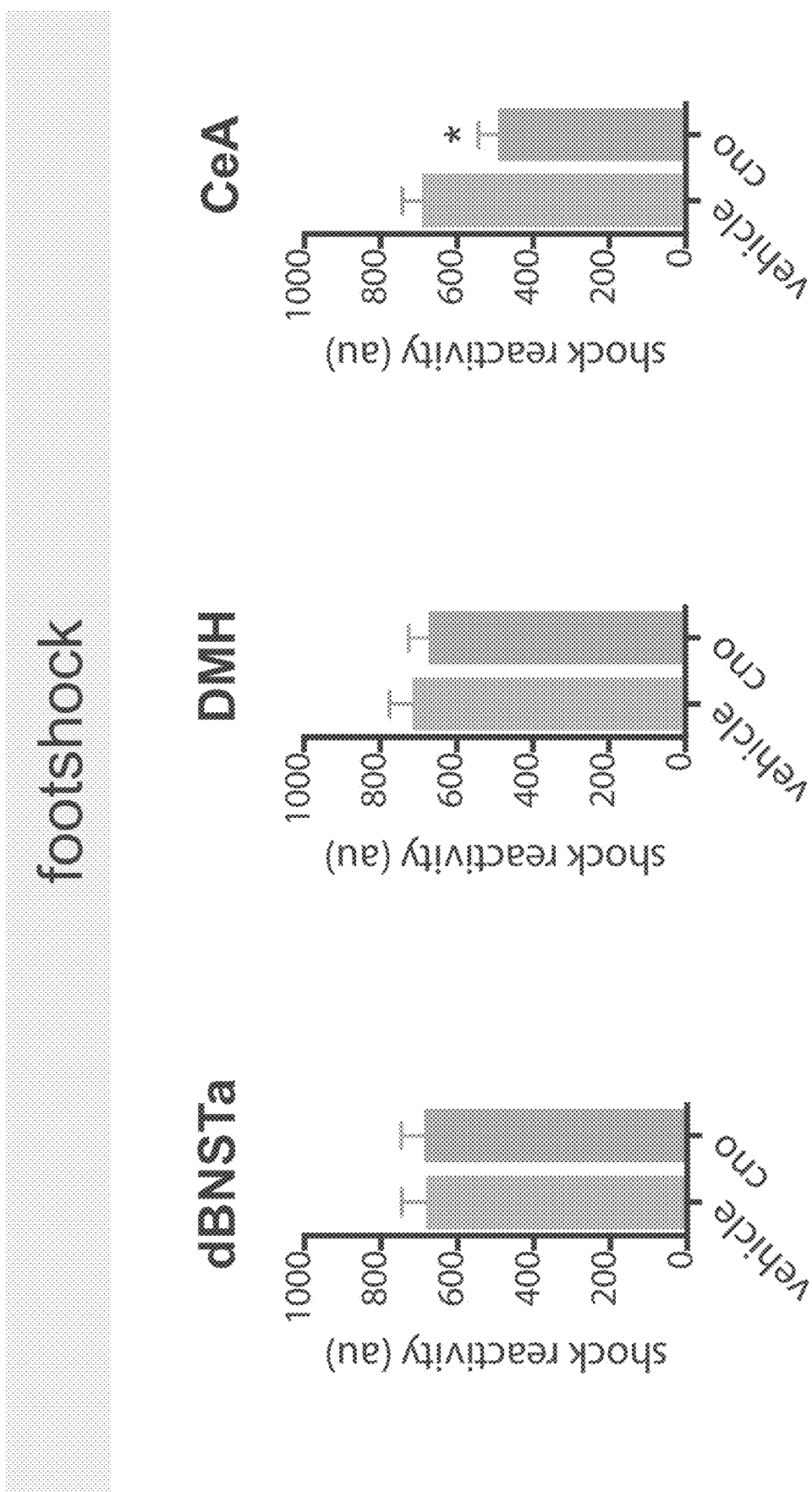
Figure 12G:
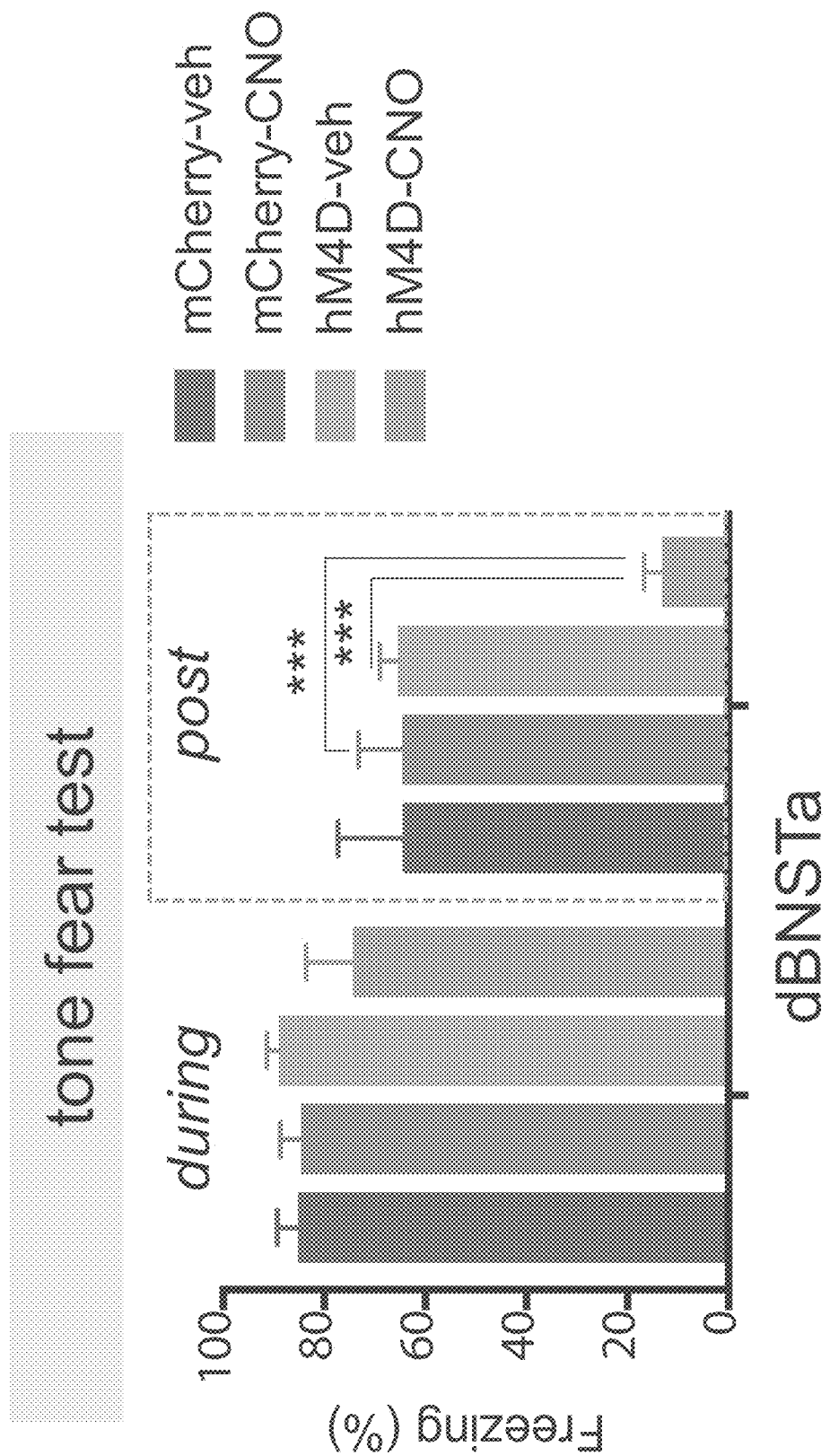

Local infusion of osanetant in dBNSTa selectively inhibited the SIS-induced persistent (but not acute) freezing to both the looming disk and the conditioned tone (FIGS. 4E-F), with no effect on aggression (FIGS. 4C-D) or shock reactivity (FIG. 11E). By contrast, osanetant microinfused into the DMH abolished SIS-induced aggression (FIG. 4H-I), but had no effect on persistent responses to the looming stimulus (FIG. 4J) or the conditioned tone (FIG. 4K), or on responses to the footshock (FIG. 11F). However, DMH-infused mice showed an increase in latency to first orient and freeze to the looming stimulus (FIG. 11D). Lastly, osanetant injection into the CeA left aggression unaffected, but reduced acute (and thereby persistent) freezing to innate and conditioned threatening stimuli, as well as reactivity to footshock (FIGS. 4L-Q, FIG. 11G). Experiments targeting osanetant to the ACC or striatum failed to yield significant effects on the SIS-induced persistent freezing to the looming disk (FIGS. 11H-K).

The data show that, in accordance with some embodiments, Nk3Rs in dBNSTa, CeA, and DMH dissociably mediate the effects of SIS on different behaviors, with the dBNSTa region selectively regulating SIS-induced persistent freezing, the DMH region selectively regulating SIS-induced aggression, and the CeA region selectively regulating acute (and thus presistent) freezing as well as reactivity to footshock, for example.

The Mouse Connectivity Atlas, Allen Institute for Brain Science identifies connectivity for projection target regions of the dBNST (Experiment #265138021); DMH (Experiment #300927483); and CeA (Experiment #241279261). Tac2 neurons of the dBNSTa have been identified as projecting to the Reticular nucleus of the thalamus (RT), Vascular organ of the lamina terminalis (OV), Supramammillary nucleus (SUM), Tuberomammillary nucleus, ventral part (TMv), Paraventricular hypothalamic nucleus, descending division (PVHd), Lateral hypothalamic area (LHA), Lateral preoptic area (LPO), Preparasubthalamic nucleus (PST), Parasubthalamic nucleus (PSTN), Subthalamic nucleus (STN), Tubueral nucleus (TU), Midbrain trigeminal nucleus (MEV), Ventral tegmental area (VTA), Midbrain reticular nucleus, retrorubral area (RR), Midbrain reticular nucleus (MRN), Periaqueductal gray (PAG), Cuneiform nucleus (CUN), Edinger-Westphal nucleus (EW), *Substantia nigra*, compact part (SNc), Pedunculopontine nucleus (PPN), Rostral linear nucleus raphe (RL), Central linear nucleus raphe (CLI), Dorsal nucleus raphe (DR), Parabrachial nucleus (PB), Barrington's nucleus (B), Supratrigeminal nucleus (SUT), External cuneate nucleus (ECU), Nucleus ambiguus (MB), Lateral reticular nucleus (LRN), Magnocellular reticular nucleus (MARN), Parvicellular reticular nucleus (PARN), Paragigantocellular reticular nucleus, lateral part (PGRN1), Parapyramidal nucleus (PPY), Nucleus raphe magnus (RM), Nucleus raphe pallidus (RPA), and Nucleus raphe obscurus (RO). Tac 2 neurons of the DMH have been identified as projecting to the Induseum griseum (IG), Hypothalamus (HY), Dorsal medial hypothalamus (DMH), Ventrolateral preoptic nucleus (VLPO), Supramammallary nucleus (SUM), Ventral tuberomammallary nucleus (TMv), Dorsal premammillary nucleus (PMd), Ventral premammillary nucleus (PMv), Posterior hypothalamic nucleus (PH), Lateral hypothalamic area (LHA), Parasubthalamic nucleus (PSTN), Tuberal nucleus (TU), Medulla (MY), and Nucleus raphe pallidus (RPA). Tac 2 neurons of the CEA have been identified as projecting to the Central amygdalar nucleus (CEA), Pallidum (PAL), Globus pallidus, internal segment (GPi), *Substantia* innominate (SI), Subparafascicular nucleus, magnocellular part (SPFm), Subparafascicular nucleus, parvicellular part (SPFp), Subparafascicular area (SPA), Peripeduncular nucleus (PP), Reticular nucleus of the thalamus (RT), Paraventricular hypothalamic nucleus, descending division (PVHd), Lateral hypothalamic area (LHA), Lateral preoptic area (LPO), Preparasubthalamic nucleus (PST), Parasubthalamic nucleus (PSTN), Subthalamic nucleus (STN), Zona incerta (ZI), Midbrain trigeminal nucleus (MEV), Ventral tegmental area (VTA), Midbrain reticular nucleus, retrorubral area (RR), Midbrain reticular nucleus (MRN), Periaqueductal gray (PAG), Edinger-Westphal nucleus (EW), Trochlear nucleus (IV), *Substantia nigra*, compact part (SNc), Pedunculopontine nucleus (PPN), Parabrachial nucleus (PB), Pontine reticular nucleus, caudal part (PRNc), Supratrigeminal nucleus (SUT), Tegmental reticular nucleus (TRN), Accessory facial motor nucleus (ACVII), Inferior salivatory nucleus (ISN), Magnocellular reticular nucleus (MARN), Parvicellular reticular nucleus (PARN), Parapyramidal nucleus (PPY), Nucleus raphe magnus (RM), Nucleus raphe pallidus (RPA), and Nucleus raphe obscurus (RO).

Example 6

This example shows the effect of region-specific chemogenetic silencing of Tac2+ neurons on behavioral responses to social isolation stress (SIS).

Figure 5A:
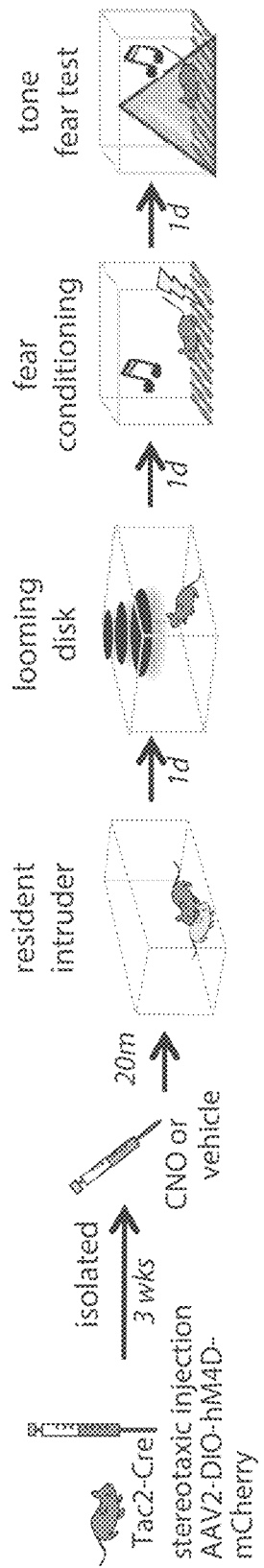
FIGS. 5A-Q show that targeted chemogenic silencing of $Tac2^+$ cells attenuates the effects of SIS in accordance with some embodiments.
Figure 5F:
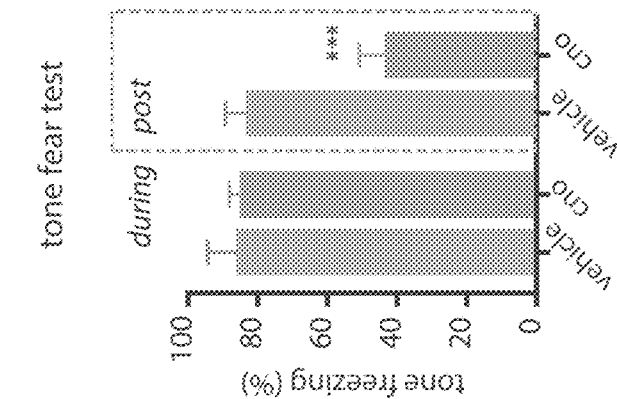
FIGS. 5E-F), aggression in DMH (FIGS. 5H-I), and acute freezing in CeA ("during"
Figure 5E:
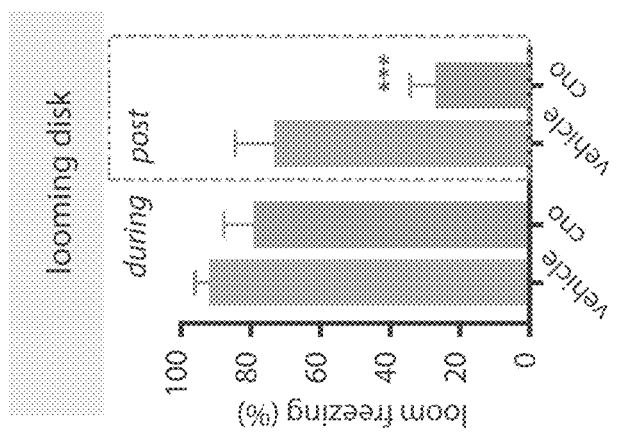
Figures 5C, 5D:
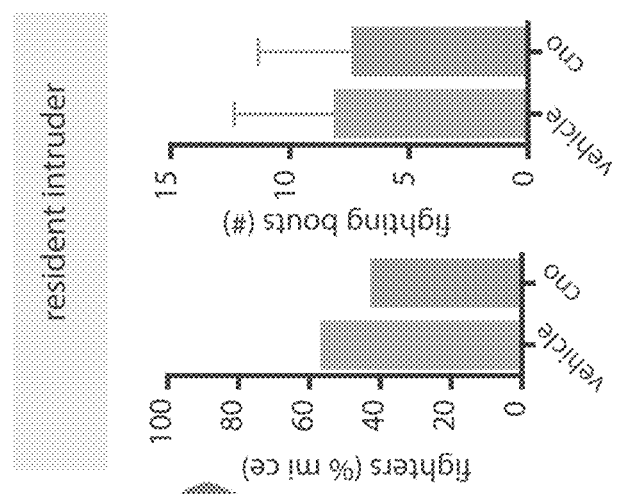
Figure 5B:
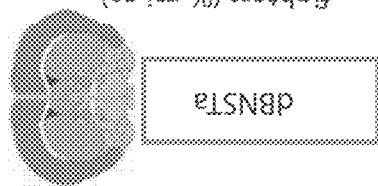
Figure 5K:
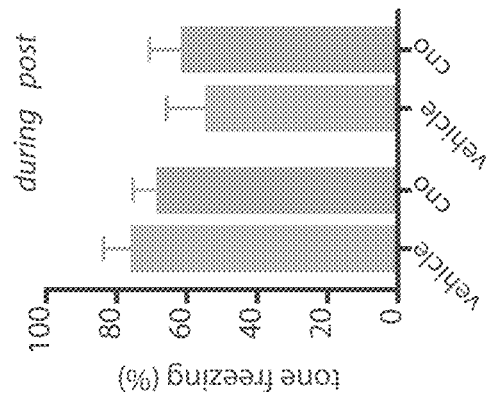
Figure 5J:
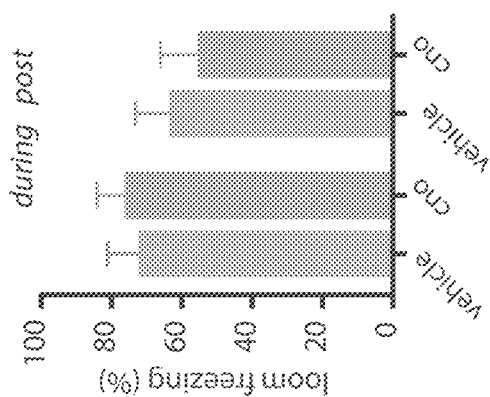
Figure 5I:
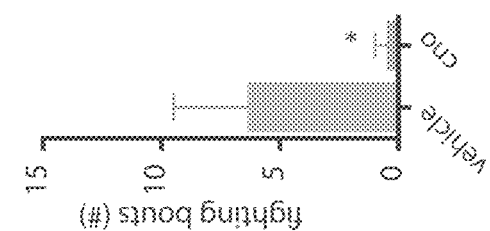
Figure 5H:
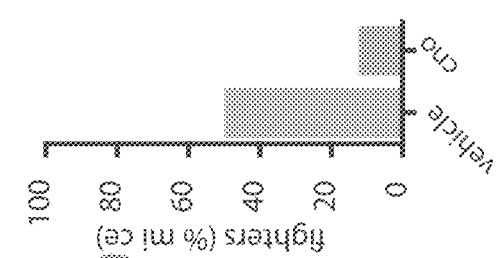
Figure 5G:
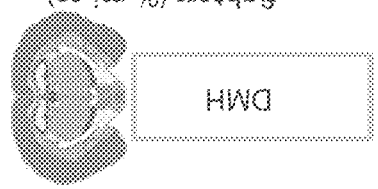
Figure 5Q:
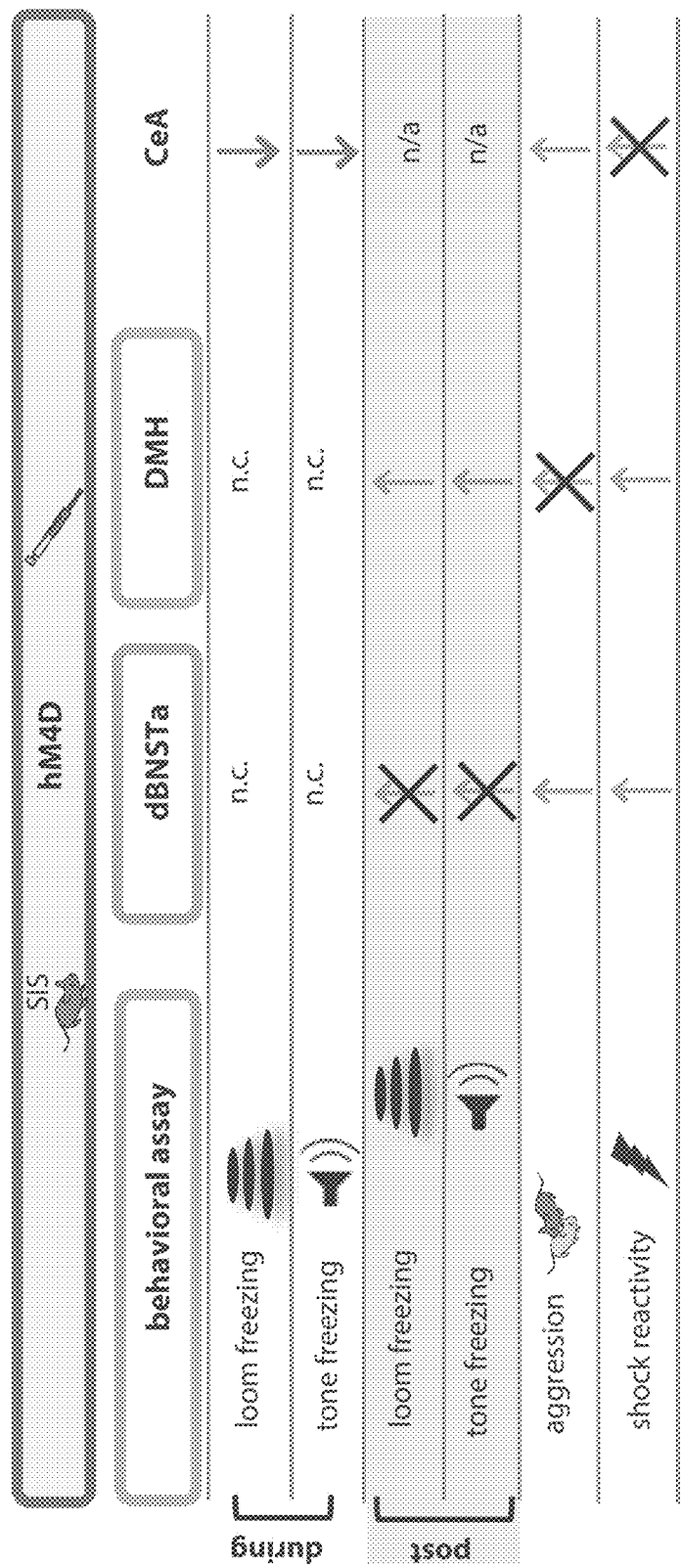

To determine whether the induction of Tac2 mRNA in dBNSTa, DMH and CeA reflected a requirement for NkB release in these structures, we first asked whether the activity of Tac2+ neurons in these regions was required for the effects of SIS. Tac2-Cre mice were bilaterally injected with a Cre-dependent AAV encoding hM4DREADD (AAV2-DIO-hM4D-mCherry) for neuronal inhibition of Tac2+ cells (Conklin et al., 2008; incorporated by reference in its entirety). Following 3 weeks to allow for adequate viral expression (FIGS. 12A-C), mice were tested for SIS-induced behavior following injection of clozapine-N-oxide (CNO) or vehicle (FIG. 5A).

Chemogenetic silencing of Tac2+ cells in dBNSTa, DMH, and CeA essentially phenocopied the effect of local osanetant infusions. In dBNSTa, persistent freezing responses were selectively attenuated (FIGS. 5B-F), in DMH, aggression was inhibited (FIGS. 5G-K), and in CeA, acute freezing and shock reactivity were suppressed (FIGS. 5L-Q, FIG. 12F). Notably, the effects of CNO were dependent on hM4DREADD expression, as we did not observe any effects of CNO in mCherry control mice (FIG. 12G) (Gomez et al., 2017; incorporated by reference in its entirety). Without being limited by theory, these results demonstrate that the activity of Tac2+ neurons plays differential roles in each of these regions for different behavioral effects of SIS.

In sum, the data show that, in accordance with some embodiments, region-specific chemogenetic silencing of Tac2$^+$ neurons in dBNSTa, DMH, and CeA blocks distinct behavioral responses to SIS.

Example 7

This example shows that Tac2 synthesis impacts distinct behavioral responses to social isolation stress (SIS).

Figure 6A:
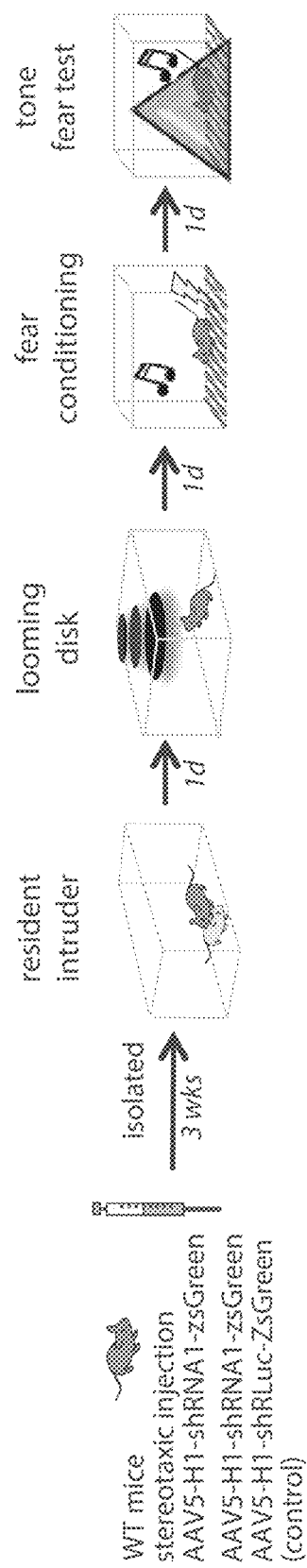
FIGS. 6A-Q show that targeted knockdown of Tac2 attenuates the effects of SIS in accordance with some embodiments.
Figure 6F:
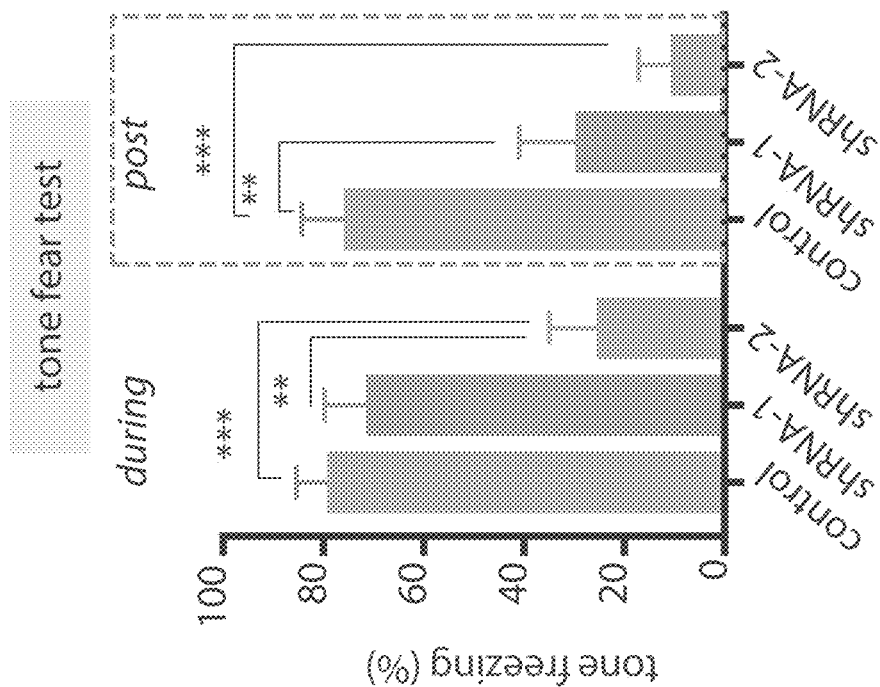
FIGS. 6E-F); aggression in DMH (FIGS. 6H-I) and freezing in CeA (FIGS. 6O-P). shRNA-2 (bars labelled "shRNA-2") yielded similar effects but additionally reduced acute freezing in dBNSTa ("during"
Figure 6E:
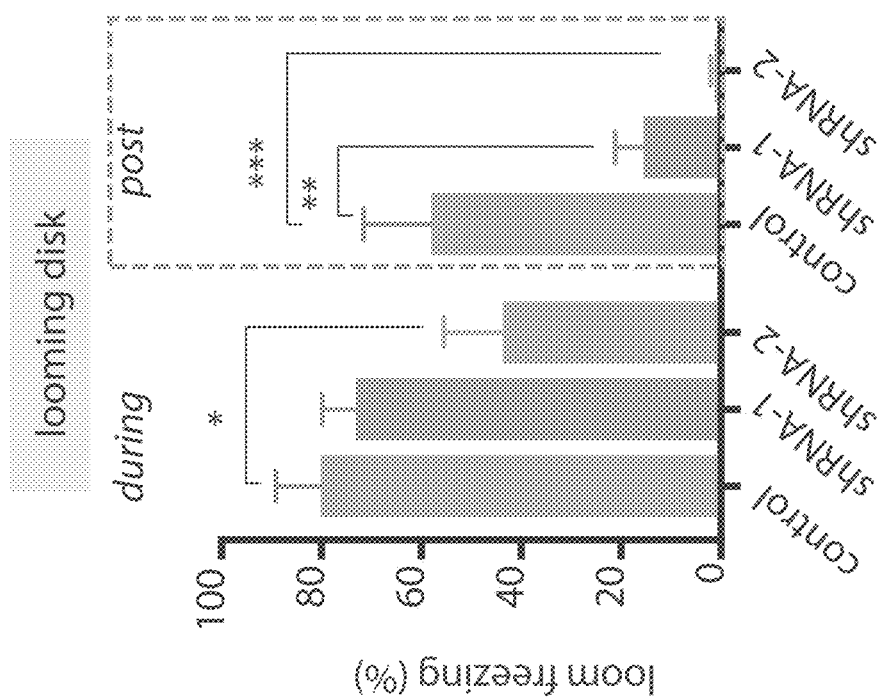
Figure 6I:
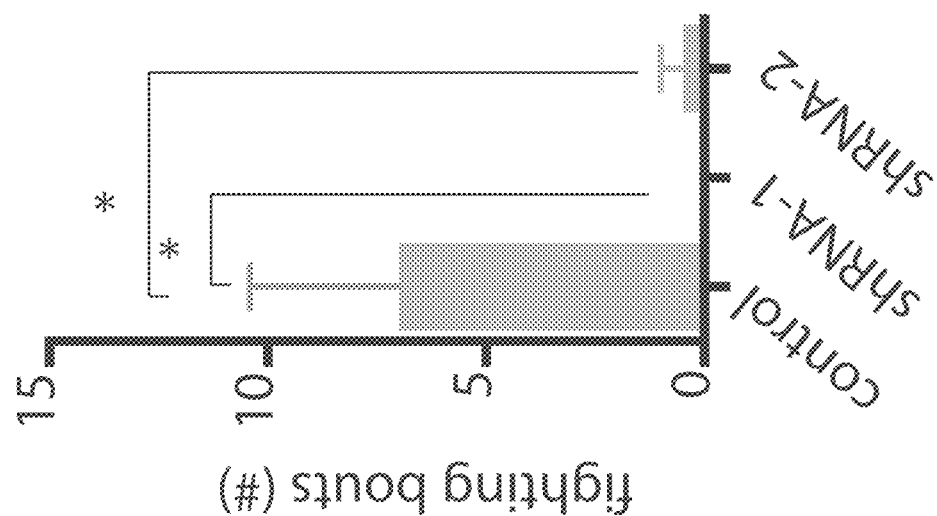
FIGS. 6B-P show the effect of shRNAs in dBNSTa (FIGS. 6B-F); DMH (FIGS. 6G-K), or CeA (FIGS. 6L-P) on indicated assays. shRNA-1 (bars labelled "shRNA-1") blocked persistent freezing in dBNSTa ("post"
Figure 6H:
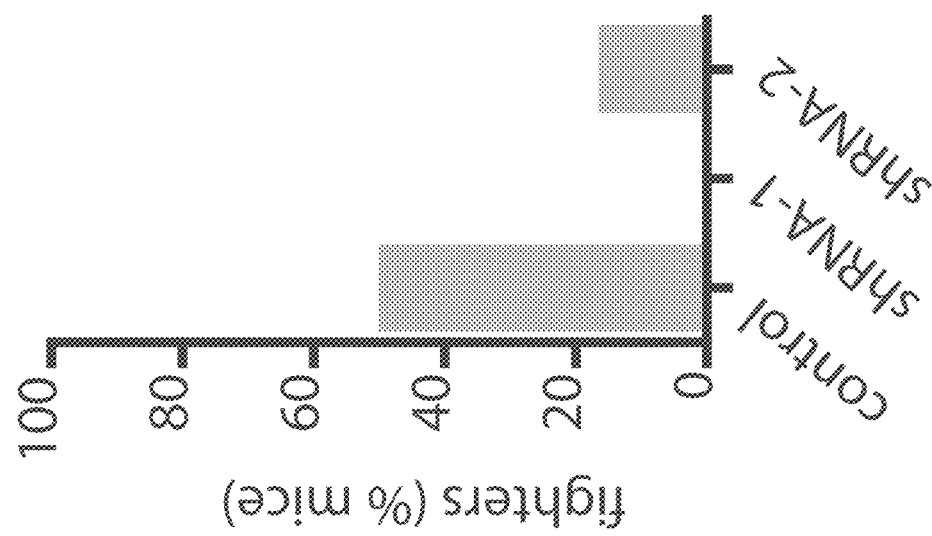
Figure 6G:
Figure 6K:
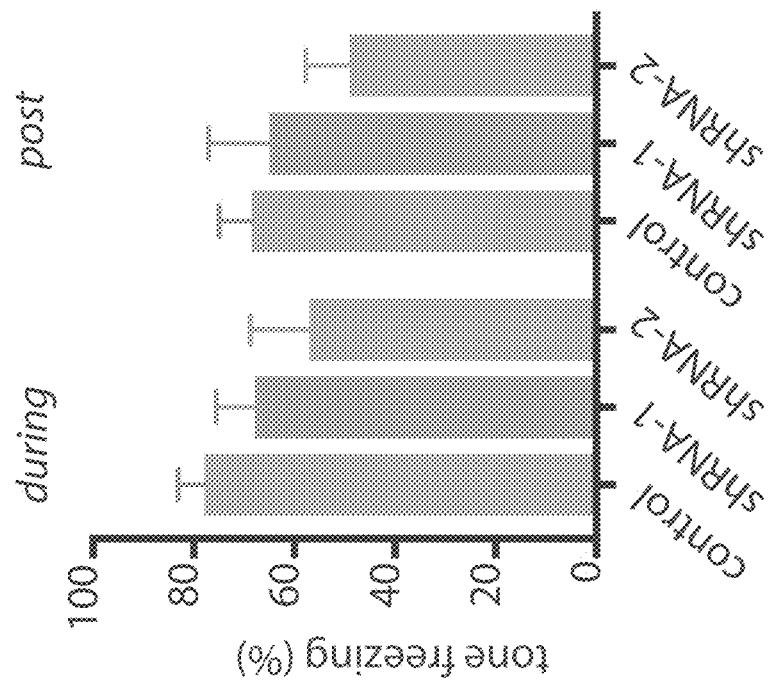
Figure 6J:
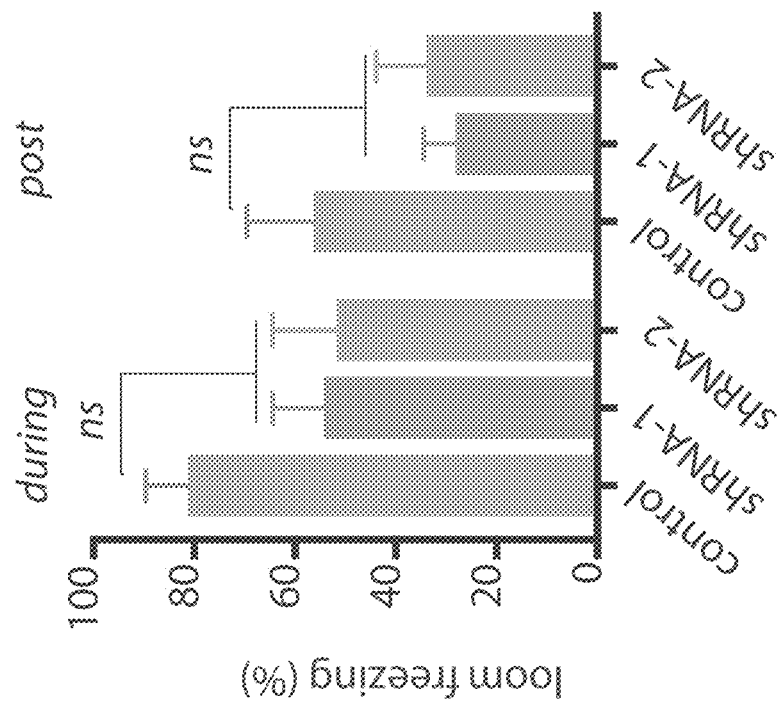
Figure 6L:
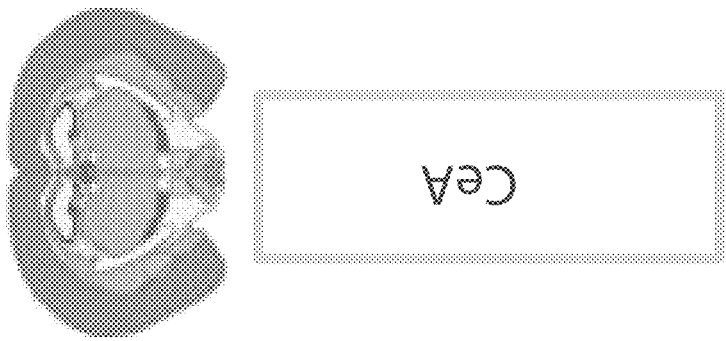

To further investigate a role for local Tac2 release in mediating different effects of SIS, we asked next whether Tac2 synthesis played a role in each of the three brain regions studied, via targeted shRNAi-mediated knockdown of Tac2. Mice were injected stereotaxically in dBNSTa, DMH, or CeA with adeno-associated viruses (AAVs) expressing small hairpin RNAs (shRNAs), together with a CMV promoter-driven zsGreen fluorescent reporter to assess cell viability (AAV5-H1-shRNA-CMV-zsGreen). Of four different shRNAs originally generated, two (shRNA-1 and shRNA-2) proved effective as determined by FISH and qRT-PCR, with shRNA-2 yielding the strongest reductions in Tac2 mRNA (FIGS. 13J-AA). Control mice were injected with an AAV encoding an shRNA targeted to the luciferase gene. Injections were histologically verified by zsGreen fluorescence. The number of zsGreen+ neurons was not significantly different between animals injected with control vs. experimental shRNAs, suggesting that the reduction in the number of Tac2 mRNA+ cells was not due to cell death (FIGS. 13D-I). Following virus injections, mice were isolated for three weeks and tested for behavior (FIG. 6A).

Figure 6M:
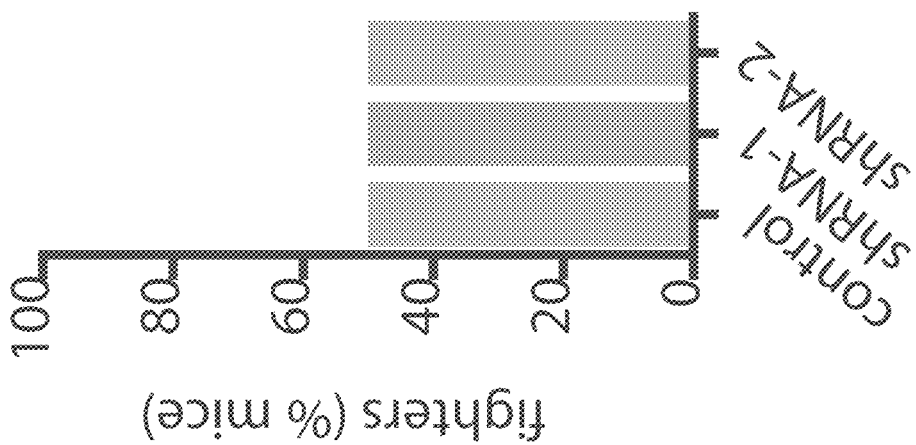
Figure 6N:
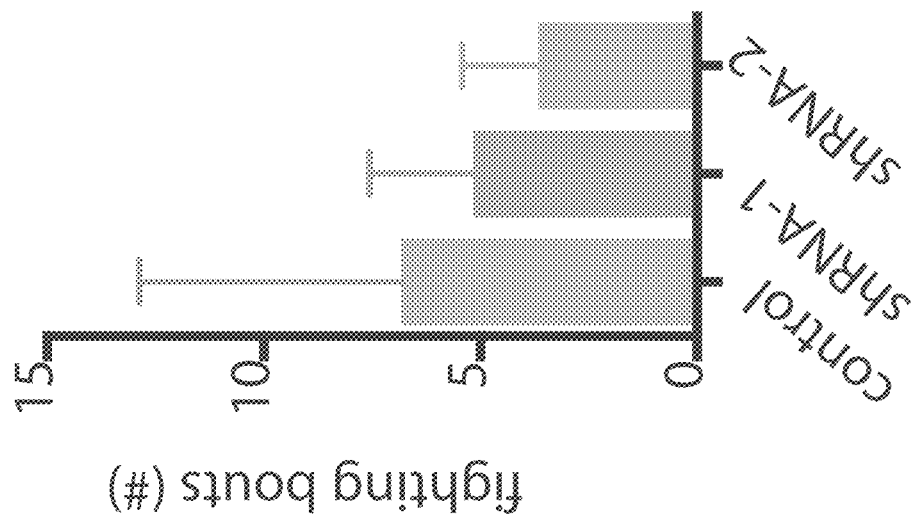
Figure 6P:
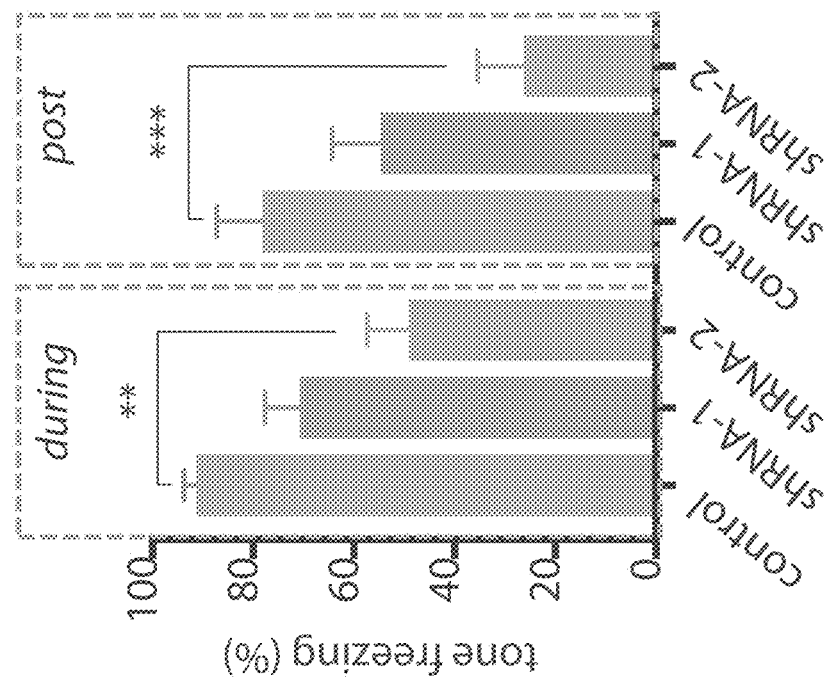
Figure 6O:
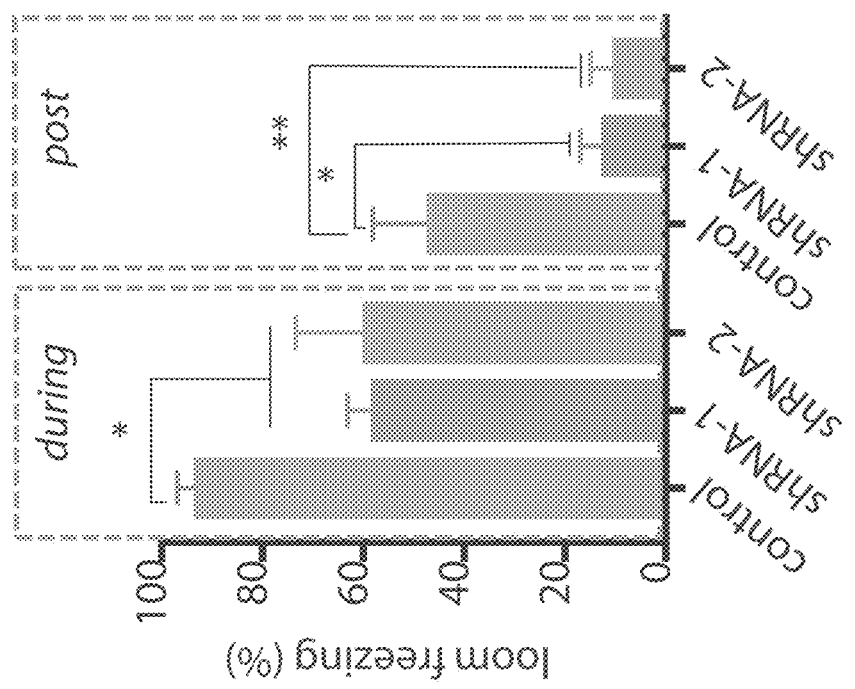
Figure 6Q:
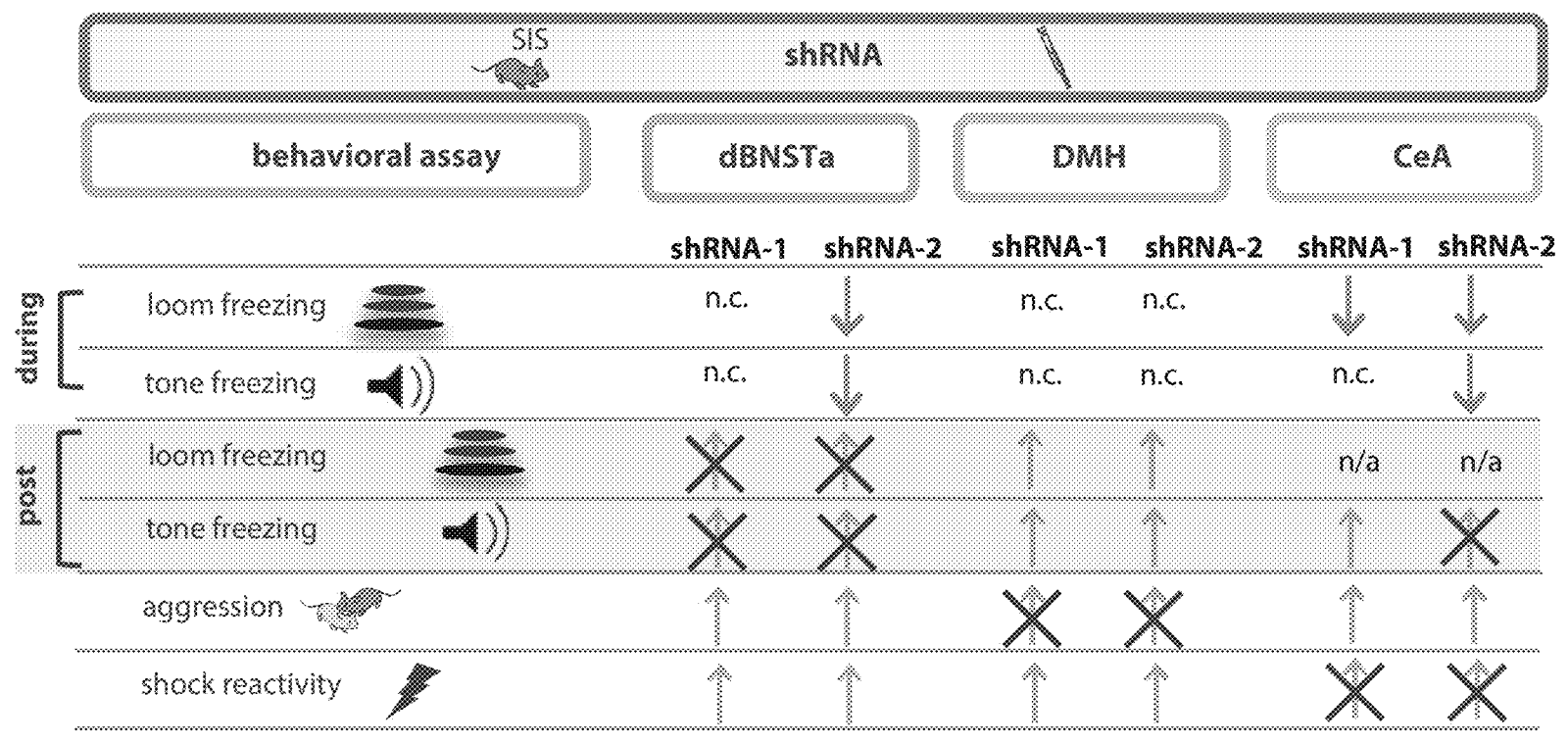

In DMH, both shRNAs strongly attenuated SIS-induced aggression, but had no significant effect on freezing (FIGS. 6G-K), similar to the effect of Tac2+ neuron silencing or local infusion of osanetant in this region (FIGS. 4G-K and FIGS. 5G-K). Conversely, in the dBNSTa, shRNA-1 strongly reduced persistent freezing to both the looming disk and the conditioned tone (FIGS. 6E-F, bars labelled "shRNA-1," post), but had no effect on SIS-induced aggression (FIGS. 6C-D) or acute freezing to the threatening stimuli (FIG. 6E, FIG. 6F, bars labelled "shRNA-1," during). Unlike Tac2+ neuron silencing and local osanetant infusion, the more effective shRNA-2 in dBNSTa significantly reduced acute freezing during presentation of both the looming disk and conditioned tone, to an extent similar to that observed in CeA (FIGS. 6E-F, O-P, during, bars labelled "shRNA-2"). In CeA, Tac2 shRNAs reduced acute freezing during stimulus presentation (FIG. 6O), and had no effect on aggression (FIGS. 6M-N). Together these data support a region-specific effect of local Tac2 synthesis in the control of different SIS-induced behaviors (FIG. 6Q).

The data show that Tac2 synthesis in dBNSTa, CeA, and DMH, in accordance with some embodiments, results in distinct behavioral responses to SIS.

Example 8

This example shows the effects of enhanced Tac2 expression and neuronal activation on Tac2+ neurons on behavior.

The foregoing findings indicate that Tac2 is up-regulated in several brain regions by SIS, and that Tac2 signaling in several of these brain regions results in the collective behavioral effects of SIS. However, because there already is Tac2 expression in these regions in group housed mice (FIGS. 2B-C, FIG. 2F), these data do not address whether Tac2 up-regulation per se mediates the behavioral effects of SIS, or whether Tac2 is simply involved in a permissive manner with respect to these behaviors. To address this question, we asked whether increasing the level and/or release of Tac2 was sufficient to mimic any of the behavioral effects of SIS, in group housed animals.

Figure 7A:
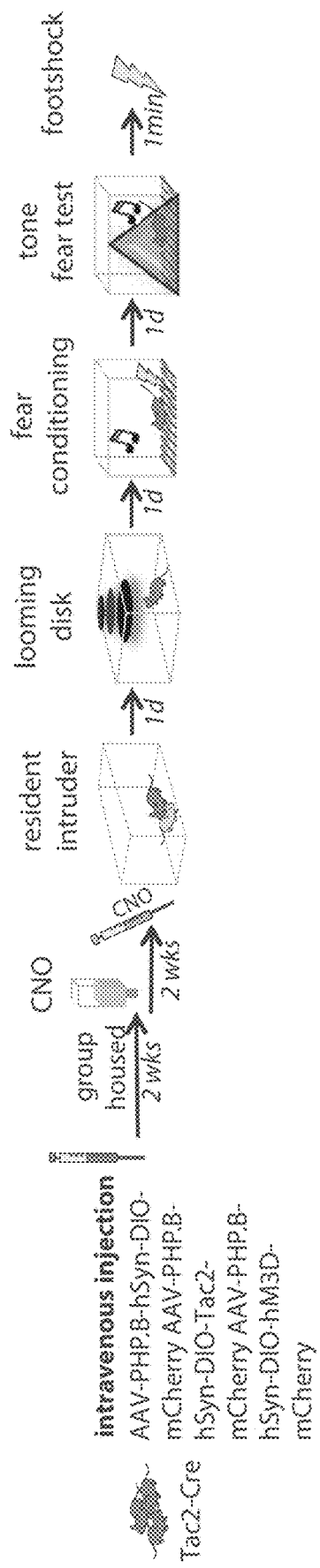
Figures 7B, 7C, 7D:
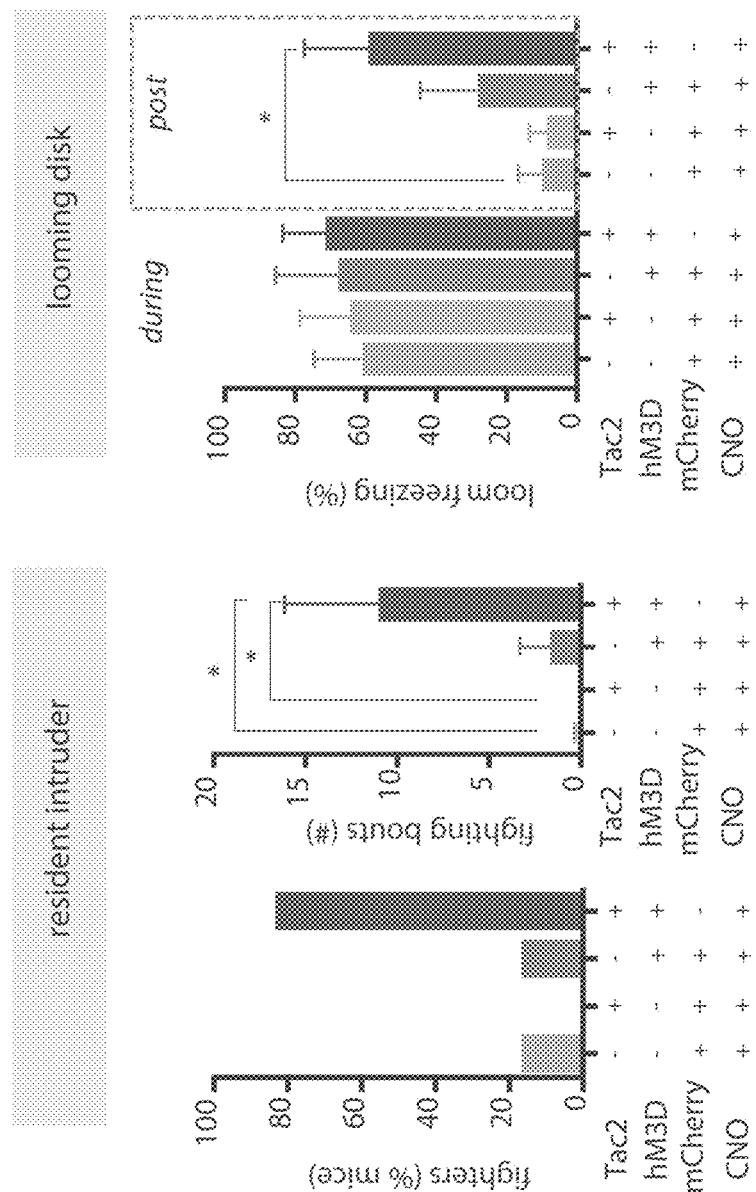
Figure 7E:
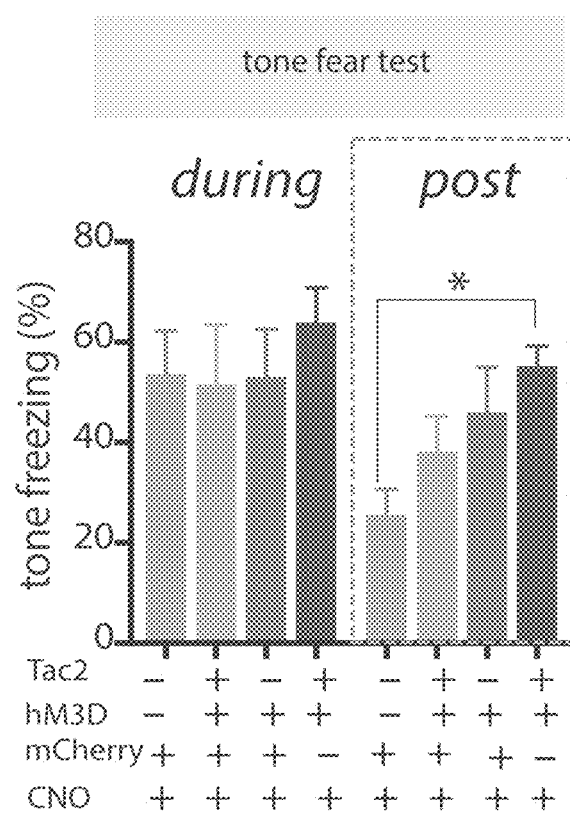
Figure 7F:
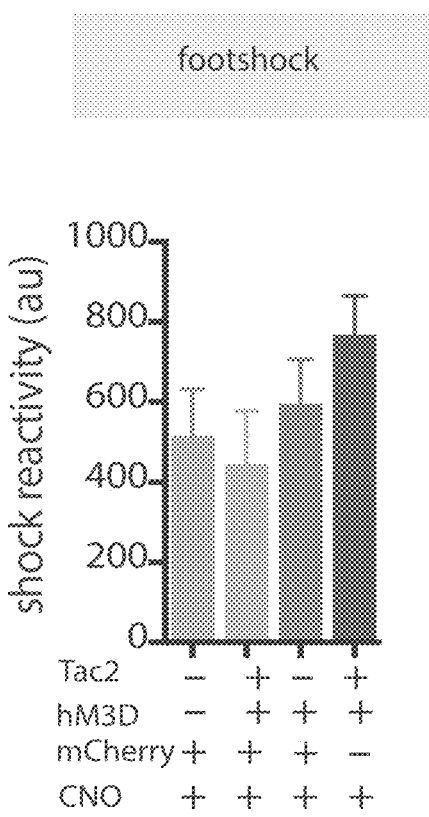
Figure 7G:
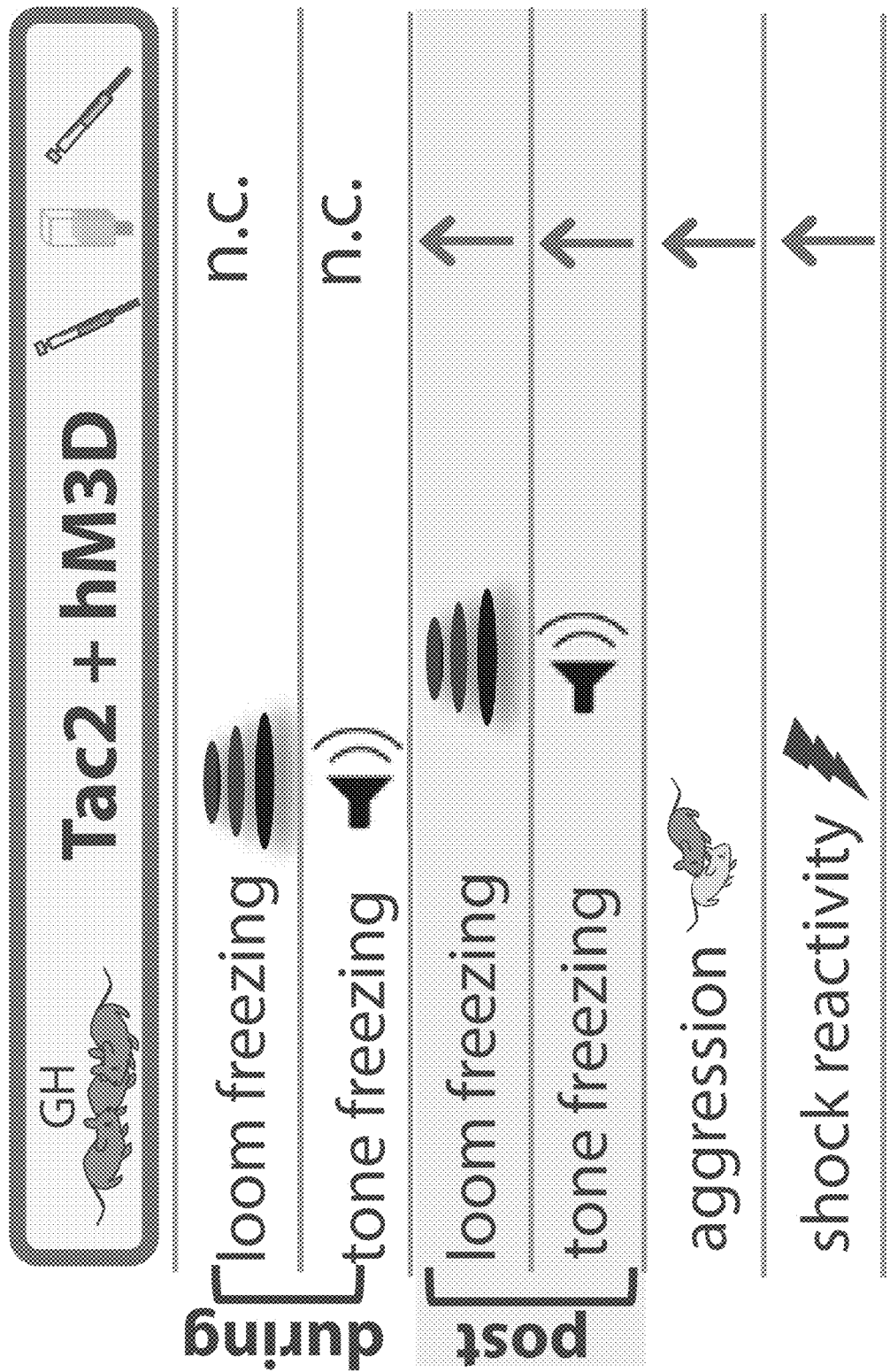

We packaged Cre-dependent vectors encoding the DREADD neuronal activator hM3D, a Tac2 cDNA or control mCherry, in AAV-PHP.B—a viral capsid that crosses the blood-brain barrier (Deverman et al., 2016; incorporated by reference in its entirety). These viruses were intravenously injected (individually or in combination) into GH Tac2-Cre mice (FIGS. 14A-T). Following three weeks to allow for viral expression, all mice (including mCherry-expressing controls) were given CNO in their drinking water for 2 weeks. Mice were then behaviorally tested following a CNO injection (FIG. 7A). This procedure was designed to achieve Tac2 over-expression and/or neuronal activation during both a two-week mock SIS period, as well as during testing.

Increasing Tac2 expression or activating Tac2+ neurons on its own was insufficient to generate significant SIS-like effects in any of our assays (FIGS. 7B-F, second and third bars from left, including "during" and "post" conditions). In contrast, concomitant over-expression of the Tac2 cDNA and activation of Tac2+ neurons using CNO/hM3DREADD recapitulated key behavioral effects of SIS in GH mice, including increased aggression and persistent freezing to threats (FIGS. 7B-E; summarized in FIG. 7G). No such effects were observed in control mice injected with mCherry-only virus and treated with CNO, indicating that the results are not due to CNO itself (Gomez et al., 2017; incorporated by reference in its entirety herein). Histological analysis confirmed expression of mCherry-tagged AAV cargo genes in the dBNSTa, CeA, and DMH (FIGS. 14A-L), as well as in several additional regions (FIGS. 14M-T).

The data show that enhancement of both Tac2 expression and neuronal activity in Tac2$^+$ neurons, in accordance with some embodiments, mimics the effects of social isolation stress (SIS) in group housed mice.

Example 9

Discussion of Examples 1-8

The conventional view of stress has been dominated by the HPA axis activation paradigm, focusing research on corticotropin releasing hormone (CRH) and related neuropeptides as substantial mediators of brain responses to psychogenic stress (Koob, 1999; Sapolsky et al., 2000; McEwen, 2007; Bruchas et al., 2009; Bruchas et al., 2010; Griebel and Holsboer, 2012; Kormos and Gaszner, 2013;

McCall et al., 2015; Chen, 2016; incorporated by reference in their entirety herein). However this view is largely based on studies using acute or intermittent chronic stressors. There is ongoing debate as to whether the effects of prolonged, continuous stress differ only quantitatively or are qualitatively different from that of acute stress (McEwen, Bowles, et al., 2015; Musazzi et al., 2017; incorporated by reference in their entirety herein). Here, we have studied the effects of continuous chronic stress produced by prolonged social isolation. The significance of this mechanism across many species is consistent with the results of a screen in Drosophila (Asahina et al., 2014; incorporated by reference in its entirety herein). Thus, without being limited by theory, it is contemplated that Tac2/NkB represents a significant mediator of chronic SIS effects on the brain, which to Applicant's knowledge has previously been overlooked.

Tac2/NkB Acts in a Distributed Manner to Control Multiple Components of the SIS Response Multiple neuropeptides have been implicated in stress (Kormos and Gaszner, 2013; incorporated by reference in its entirety herein). However, with few exceptions (Regev et al., 2011; Regev et al., 2012; incorporated by reference in their entirety herein), conventional studies of a given peptide have typically focused on a single brain region, stressor and/or behavior (e.g., the BNST and anxiety assays; reviewed in Kash et al., 2015 and incorporated by reference in its entirety herein), and have used a single type of manipulation (but see (McCall et al., 2015; incorporated by reference in its entirety herein). Conventionally, this made it difficult to determine whether and how a given neuropeptide acts in different brain regions to contribute to a stress-induced brain state (Kormos and Gaszner, 2013; Chen, 2016; incorporated by reference in their entirety herein).

The multiplexed approach described herein permitted comparison of the results of the same experimental manipulation in different brain regions, or of different types of manipulations in the same brain region, using a battery of behavioral assays. Surprisingly, in each of the regions studied, targeted loss-of-function (LOF) manipulations of Tac2/NkB peptide (via shRNAi), Tac2+ neurons (via hM4DREADD), or Nk3Rs (via osanetant), yielded qualitatively similar results. Without being limited by theory, taken together with the fact that Tac2/NkB and its receptor Nk3R are both expressed in each of these regions (Allen Institute for Brain Science; (Beaujouan et al., 2004; Duarte et al., 2006; incorporated by reference in their entirety herein), these data are suggestive of local actions of the peptide within each structure, with the possibility that the same or different cells express both the peptide and the receptor. However, our results do not rule out effects of the peptide at distal targets as well.

Together, these results reveal that Tac2/NkB acts in multiple areas to control different aspects of the SIS-induced state, in a dissociable manner. This finding is counter-intuitive to conventional understanding, because one might have expected that, to the contrary, such global control would be most efficiently exerted in a hierarchical manner, with release of the peptide from a single region modulating multiple downstream sites (e.g. FIG. 1B, FIG. 1C, Example 1). Nevertheless, without being limited by theory, such a distributed mechanism to coordinate the influences of a neuropeptide is reminiscent of that played by Pigment-Dispersing Factor (PDF) in controlling circadian circuits in Drosophila (Taghert and Nitabach, 2012; Dubowy and Sehgal, 2017; incorporated by reference in their entirety herein), or roaming vs. dwelling states in C. elegans (Flavell et al., 2013; incorporated by reference in its entirety herein), and may explain some of the diverse functions of CRF (Regev et al., 2011; McCall et al., 2015; each of which is incorporated by reference in its entirety herein).

Activation and Peptide Overexpression in Tac2+ Neurons Mimics the Effects of SIS It was surprising that combined overexpression of Tac2 and activation of Tac2+ neurons recapitulated multiple effects of SIS in GH mice. It has been set forth that a stress peptide can elicit behavioral responses, e.g., when injected into the brain (reviewed in (Koob, 1999; Kormos and Gaszner, 2013; each of which is incorporated by reference in is entirety herein). However, this case represents, to our knowledge, the first example of a neuropeptide that mimics many of the effects of a stressor in unstressed animals. For example, it has been posited that even CRF when exogenously administered to unstressed animals in low arousal conditions does not produce stress-like responses (Koob, 1999; incorporated by reference in its entirety herein). Furthermore, overexpression of CRF using genetic methods has been posited to produce different responses, depending on the mode and site of expression, leading to conflicting results (Regev et al., 2011; Flandreau et al., 2012; Regev et al., 2012; Sink et al., 2012; Kash et al., 2015; each of which is incorporated by reference in its entirety herein).

We observed that simply overexpressing Tac2 in Tac2+ neurons had no behavioral effect. When this manipulation was combined with chemogenetic activation of Tac2+ neurons, a phenotype was observed; neuronal activation on its own had little effect. Without being limited by theory, these data suggest that neuronal activity is limiting for effects of neuropeptide overexpression. These experiments were facilitated by an experimental design that affords the ability to independently manipulate the expression of Tac2, and the activity of Tac2+ neurons, in a brain-wide, non-invasive manner in adult mice (Deverman et al., 2016; Chan et al., 2017; each of which is incorporated by reference in its entirety herein), without the need to employ complex transgenic strategies (Lu et al., 2008; incorporated by reference in its entirety herein).

Figure 7H:
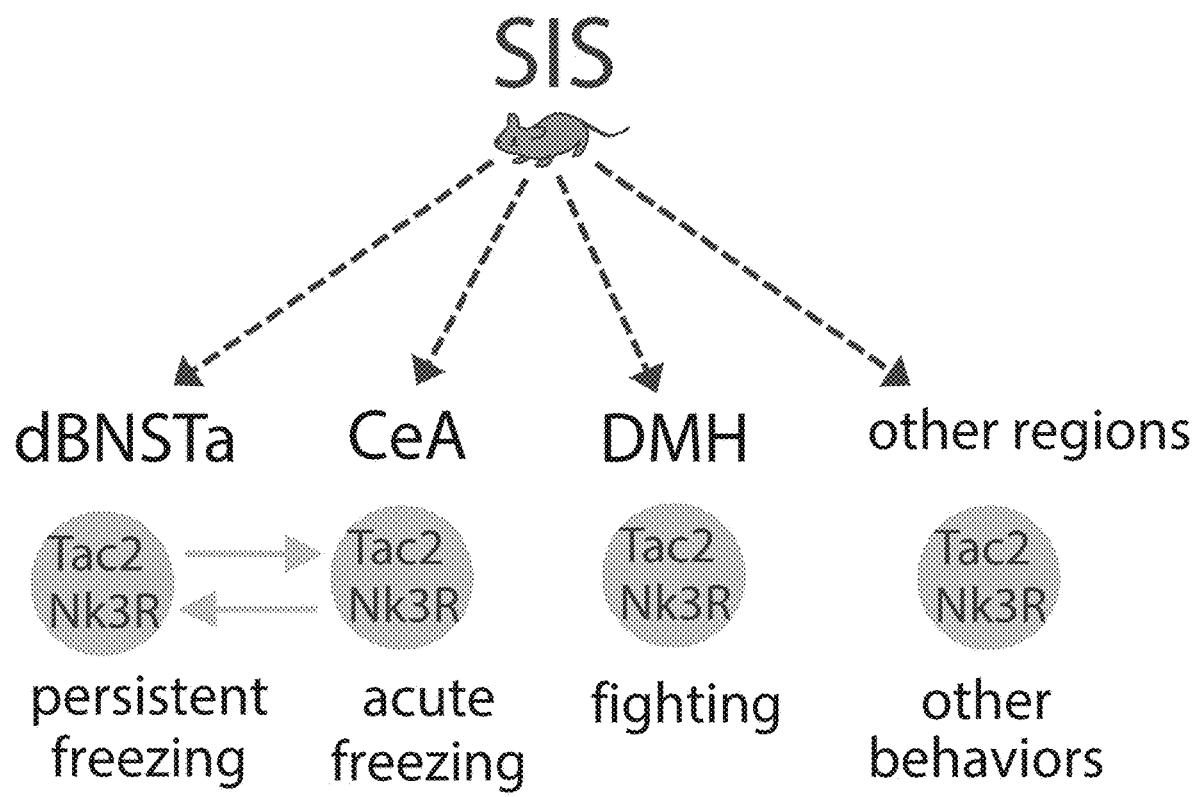
Figure 7I:
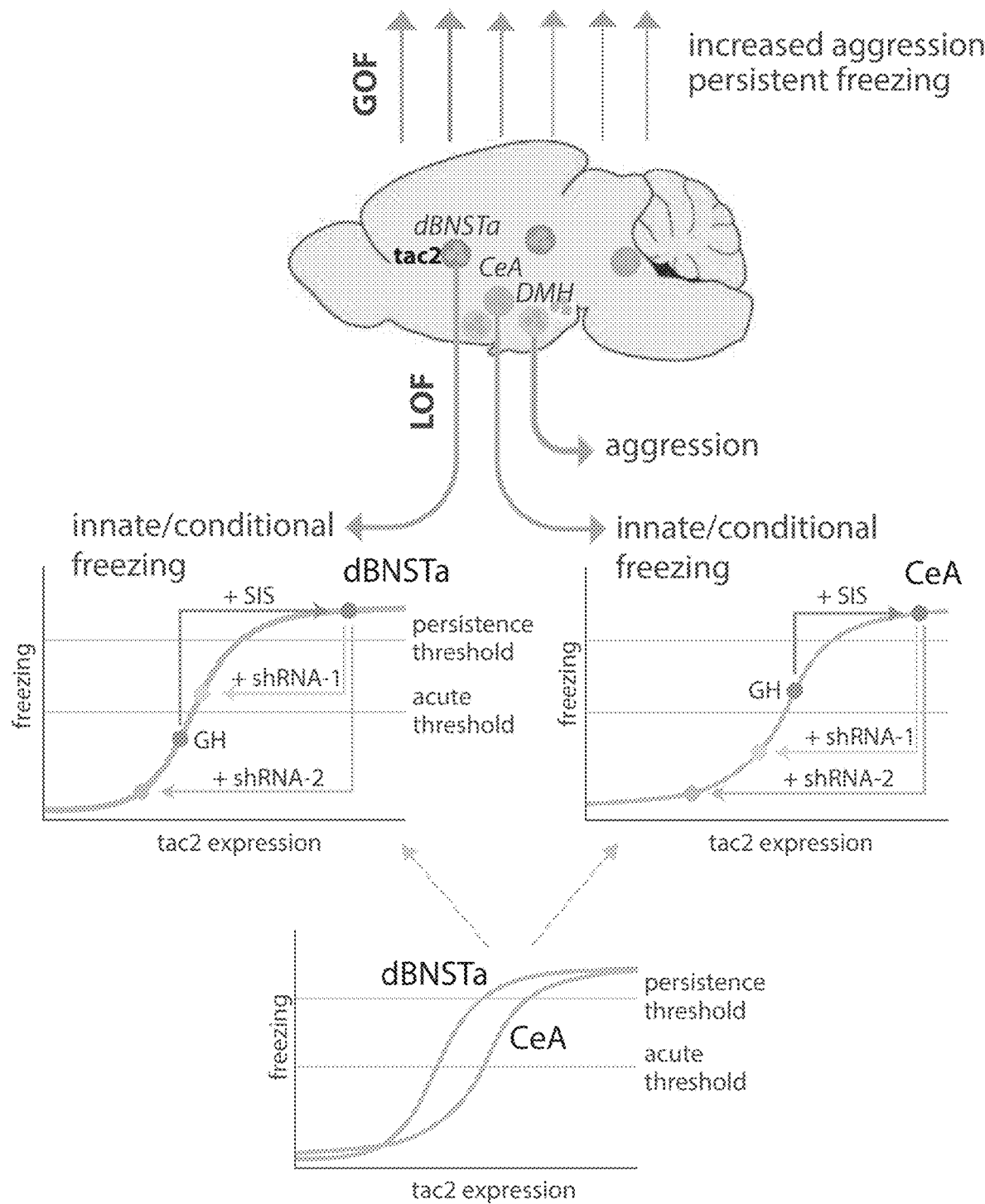

Tac2/NkB Controls Both Acute and Persistent Responses to Threats Depending on Level of the Peptide In dBNSTa, most of our LOF manipulations reduced persistent but not acute (during stimulus) freezing, while in CeA these same manipulations inhibited acute freezing. Without being limited by theory, while persistent freezing was also inhibited in CeA, there was no manipulation in this region that prevented persistent but not acute freezing, suggesting that the lack of persistence is secondary to the reduced acute response. This dissociation is consistent with the conventional view that CeA controls phasic, stimulus-locked responses to threats, while dBNSTa controls more persistent responses (Walker et al., 2009; Kash et al., 2015; incorporated by reference in its entirety). However, without being limited by theory, closer inspection of the data indicates that the functional distinction between these regions is more subtle. Specifically, in dBNSTa, the more potent shRNA-2 also reduced acute freezing during the stimulus, while the less potent shRNA-1 only reduced post-stimulus freezing. Without being limited by theory, these data suggest that the effects of Tac2/NkB signaling on acute vs. enduring responses to threats are not determined simply by the region(s) in which the neuropeptide acts, but also by the level of its expression and the "dose-response" properties or threshold sensitivity of each region to the neuropeptide (FIG. 7I, Example 8). Without being limited by theory, reciprocal connections between CeA and dBNST (Dong et al., 2001; Dong and Swanson, 2006b, a; incorporated by reference in their entirety herein) may contribute to their partially overlapping functions as well (FIG. 7H, Example 8).

We find that acute freezing responses to threats in GH animals can be converted to persistent ones simply by artificially promoting Tac2 expression and release. Preliminary data indicate that Tac2 plays a role in acute freezing in GH animals as well. Without being limited by theory, together, these data suggest that the up-regulation of Tac2 expression may convert defensive reactions to threats from transient to more enduring responses. In this way, the scalable property of neuropeptides—their concentration is a continuous variable—may be used to promote persistence, another feature of emotion states (Anderson and Adolphs, 2014; incorporated by reference in its entirety).

Identification of Tac2/NkB as a Substantial Mediator of Brain Responses to Chronic SIS In addition to CRF, a large number of other neuropeptides have been posited to play a role in stress responses, including the urocortins (UCNs 1-3), neuropeptide Y (NPY), vasopressin (AVP), pituitary adenyl cyclase-activating peptide (PACAP), neuropeptide S and others (reviewed in (Kormos and Gaszner, 2013; Kash et al., 2015; Chen, 2016; incorporated by reference in their entirety herein). Conventionally, most work on the tachykinins in stress has focused on Tac1/Substance P/NkA (Bilkei-Gorzo et al., 2002; Beaujouan et al., 2004; Ebner et al., 2004; Ebner et al., 2008; incorporated by reference in their entirety herein). Conventional pharmacological and genetic studies have yielded conflicting results regarding the direction of NkB influences on stress responses (Ebner et al., 2009; incorporated by reference in its entirety herein). Without being limited by theory, our data identify Tac2/NkB as a significant and previously unrecognized mediator of chronic SIS influences on the brain.

The role of Tac2/NkB to mediate SIS-enhanced aggression (Hatch et al., 1963; Valzelli, 1969; incorporated by reference in their entirety herein) distinguishes it from peptides involved in other forms of stress, which typically decrease rather than increase aggression (Maier, 1984; Hammack et al., 2012; each of which is incorporated by reference in its entirety herein). Without being limited by theory, the effect of Tac2/NkB on aggression is dissociable from its role in SIS-enhanced defensive behavior, and is exerted via the hypothalamus and not the amygdala, as generally assumed (Chattarji et al., 2015; incorporated by reference in its entirety herein). Without being limited by theory, the finding that tachykinins play a role in the control of social isolation-induced aggression in both flies (Asahina et al., 2014; incorporated by reference in its entirety herein) and mice is consistent with evidence supporting an evolutionary conservation of neuropeptide function in behavior across phylogeny (Bargmann, 2012; Katz and Lillvis, 2014; incorporated by reference in their entirety herein). In that context, without being limited by theory, it is possible that Tac2/NkB may play a role in the effect of solitary confinement to increase aggressiveness in humans (Arrigo and Bullock, 2008; incorporated by reference in its entirety herein).

While we uncovered a role for Tac2 in the SIS paradigm, and without being limited by theory, the role of Tac2 may be specific to SIS or extend to other stressors as well. Our SIS paradigm differs from acute and repeated intermitted stressors (footshock, restraint, forced swim) not only in its quality, but also in its extended duration and continuous nature. Without being limited by theory, the engagement of the Tac2/NkB system, therefore, could reflect any of these differences. However, it is currently difficult to directly compare acute stressors to SIS using the same continuous schedule. Nevertheless, a role for Tac2/NkB in consolidation of a conditioned fear memory in CeA, acting on a time scale of a day, has been proposed (Andero et al., 2014; incorporated by reference in its entirety herein). Therefore, without being limited by theory, Tac2 may play a broader role in responses to stressors other than SIS.

Nk3R Antagonists as Potential Treatments for Effects of Long-Term Isolation

It has been set forth that social isolation promotes poor health, clinical psychiatric symptoms and increased mortality in humans (Cacioppo and Hawkley, 2009; Umberson and Montez, 2010; Cacioppo et al., 2015; Holt-Lunstad et al., 2015; incorporated by reference in their entirety herein). Osanetant and several other Nk3R antagonists have been tested in clinical trials as therapies for schizophrenia, bipolar and panic disorder (Spooren et al., 2005; incorporated by reference in its entirety herein). Although these drugs were well tolerated, they were abandoned for lack of efficacy (Griebel and Holsboer, 2012; incorporated by reference in its entirety herein). Without being limited by theory, the profound effect of osanetant to prevent and reverse an SIS-induced global brain state in accordance with some embodiments herein suggests that Nk3R antagonists may merit re-examination as potential indications for, e.g., mood disorders caused by extended periods of social isolation in humans as well as in animals.

RERFERENCES

Each of the following references is incorporated herein by reference in its entirety:

Beaujouan, J. C., Torrens, Y., Saffroy, M., Kemel, M. L., and Glowinski, J. (2004). A 25 year adventure in the field of tachykinins. Peptides 25, 339-357.

Culman, J., and Unger, T. (1995). Central Tachykinins—Mediators of Defense Reaction and Stress Reactions. Canadian Journal of Physiology and Pharmacology 73, 885-891.

Griebel, G., and Holsboer, F. (2012). Neuropeptide receptor ligands as drugs for psychiatric diseases: the end of the beginning? Nature review Drug discovery, 1-17.

Maggio, J. E. (1988). Tachykinins. Annual review of neuroscience 11, 13-28.

Anthony, T. E., Dee, N., Bernard, A., Lerchner, W., Heintz, N., and Anderson, D. J. (2014). Control of stress-induced persistent anxiety by an extra-amygdala septohypothalamic circuit. Cell 156, 522-536.

Blanchard, D. C., Blanchard, R. J., and Griebel, G. (2005). Defensive responses to predator threat in the rat and mouse. Current protocols in neuroscience Chapter 8, Unit 8 19.

Blanchard, D. C., Griebel, G., and Blanchard, R. J. (2003). The Mouse Defense Test Battery: pharmacological and behavioral assays for anxiety and panic. European journal of pharmacology 463, 97-116.

Cai, H., Haubensak, W., Anthony, T. E., and Anderson, D. J. (2014). Central amygdala PKC-delta(+) neurons mediate the influence of multiple anorexigenic signals. Nature neuroscience 17, 1240-1248.

Cushman, J. D., Moore, M. D., Olsen, R. W., and Fanselow, M. S. (2014). The role of the delta GABA(A) receptor in ovarian cycle-linked changes in hippocampus-dependent learning and memory. Neurochemical research 39, 1140-1146.

Deneen, B., Ho, R., Lukaszewicz, A., Hochstim, C.J., Gronostajski, R. M., and Anderson, D. J. (2006). The transcription factor NFIA controls the onset of gliogenesis in the developing spinal cord. Neuron 52, 953-968.

Deverman, B. E., Pravdo, P. L., Simpson, B. P., Kumar, S. R., Chan, K. Y., Banerjee, A., Wu, W. L., Yang, B., Huber, N., Pasca, S. P., et al. (2016). Cre-dependent selection yields AAV variants for widespread gene transfer to the adult brain. Naturebiotechnology 34, 204-209.

Haubensak, W., Kunwar, P. S., Cai, H., Ciocchi, S., Wall, N. R., Ponnusamy, R., Biag, J., Dong, H. W., Deisseroth, K., Callaway, E. M., et al. (2010). Genetic dissection of an amygdala microcircuit that gates conditioned fear. Nature 468, 270-276.

Hong, W., Kennedy, A., Burgos-Artizzu, X. P., Zelikowsky, M., Navonne, S. G., Perona, P., and Anderson, D. J. (2015). Automated measurement of mouse social behaviors using depth sensing, video tracking, and machine learning. Proceedings of the National Academy of Sciences of the United States of America 112, E5351-5360.

Hong, W., Kim, D. W., and Anderson, D. J. (2014). Antagonistic control of social versus repetitive self-grooming behaviors by separable amygdala neuronal subsets. Cell 158, 1348-1361.

Hsiao, E. Y., McBride, S. W., Hsien, S., Sharon, G., Hyde, E. R., McCue, T., Codelli, J. A., Chow, J., Reisman, S. E., Petrosino, J. F., et al. (2013). Microbiota modulate behavioral and physiological abnormalities associated with neurodevelopmental disorders. Cell 155, 1451-1463.

Kim, J. J., DeCola, J. P., Landeira-Fernandez, J., and Fanselow, M. S. (1991). N-methyl-D-aspartate receptor antagonist APV blocks acquisition but not expression of fear conditioning. Behavioral neuroscience 105, 126-133.

Koch, M. (1999). The neurobiology of startle. Progress in neurobiology 59, 107-128.

Kunwar, P. S., Zelikowsky, M., Remedios, R., Cai, H., Yilmaz, M., Meister, M., and Anderson, D. J. (2015). Ventromedial hypothalamic neurons control a defensive emotion state. eLife 4.

Lee, H., Kim, D. W., Remedios, R., Anthony, T. E., Chang, A., Madisen, L., Zeng, H., and Anderson, D. J. (2014). Scalable control of mounting and attack by Esr1+ neurons in the ventromedial hypothalamus. Nature 509, 627-632.

Lein, E. S., Hawrylycz, M. J., Ao, N., Ayres, M., Bensinger, A., Bernard, A., Boe, A. F., Boguski, M. S., Brockway, K. S., Byrnes, E. J., et al. (2007). Genome-wide atlas of gene expression in the adult mouse brain. Nature 445, 168-176.

Madisen, L., Zwingman, T. A., Sunkin, S. M., Oh, S. W., Zariwala, H. A., Gu, H., Ng, L. L., Palmiter, R. D., Hawrylycz, M. J., Jones, A. R., et al. (2010). A robust and high-throughput Cre reporting and characterization system for the whole mouse brain. Nature neuroscience 13, 133-140.

Mongeau, R., Miller, G. A., Chiang, E., and Anderson, D. J. (2003). Neural correlates of competing fear behaviors evoked by an innately aversive stimulus. The Journal of neuroscience: the official journal of the Society for Neuroscience 23, 3855-3868.

Naito, Y., Yoshimura, J., Morishita, S., and Ui-Tei, K. (2009). siDirect 2.0: updated software for designing functional siRNA with reduced seed-dependent off-target effect. BMC bioinformatics 10, 392.

Shi, L., Fatemi, S. H., Sidwell, R. W., and Patterson, P. H. (2003). Maternal influenza infection causes marked behavioral and pharmacological changes in the offspring. The Journal of neuroscience: the official journal of the Society for Neuroscience 23, 297-302.

Thompson, C. L., Pathak, S. D., Jeromin, A., Ng, L. L., MacPherson, C. R., Mortrud, M. T., Cusick, A., Riley, Z. L., Sunkin, S. M., Bernard, A., et al. (2008). Genomic anatomy of the hippocampus. Neuron 60, 1010-1021.

Yilmaz, M., and Meister, M. (2013). Rapid innate defensive responses of mice to looming visual stimuli. Current biology: CB 23, 2011-2015.

Zelikowsky, M., Hersman, S., Chawla, M. K., Barnes, C. A., and Fanselow, M. S. (2014). Neuronal ensembles in amygdala, hippocampus, and prefrontal cortex track differential components of contextual fear. The Journal of neuroscience: the official journal of the Society for Neuroscience 34, 8462-8466.

With respect to the use of substantially any plural and/or singular terms herein, those having skill in the art can translate from the plural to the singular and/or from the singular to plural as is appropriate to the context and/or application. The various singular/plural permutations can be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Wherever a method of using a compound (e.g., a method comprising administering a first nucleic acid and/or a second nucleic acid) is disclosed herein, the corresponding compound for use is also expressly contemplated. For example, for the disclosure of a method of inhibiting, ameliorating, reducing the severity of, treating, reducing the likelihood of, or preventing degenerative neurological disease in a subject in need thereof comprising administering a first nucleic acid and a second nucleic acid (or a vector comprising the first and second nucleic acids), the corresponding first nucleic acid and second nucleic acid for use in inhibiting, ameliorating, reducing the severity of, treating, reducing the likelihood of, or preventing degenerative neurological disease are also contemplated.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

---

What is claimed is:

1. A method of expressing a neuropeptide in a neuron of a subject, the method comprising:

administering a first nucleic acid to the neuron in the subject, the first nucleic acid encoding the neuropeptide, wherein a first promoter is operably linked to the first nucleic acid, whereby the neuropeptide is expressed in the neuron;

administering a second nucleic acid to the neuron in the subject, the second nucleic acid encoding a conditional receptor configured to increase activity of the neuron upon application of an agonist or stimulus, wherein the first promoter or a second promoter is operably linked to the second nucleic acid, whereby the conditional receptor is expressed in the neuron; and applying the agonist or stimulus to the neuron of the subject, causing the conditional receptor to increase activity of the neuron that expresses the neuropeptide.

2. The method of claim 1, wherein the increased activity induces an action potential by the neuron.

3. The method of claim 1, wherein the neuron is a neuropeptidergic neuron.

4. The method of claim 3, wherein the neuropeptidergic neuron is a neuron of one or more of the antero-dorsal bed nucleus of the stria terminalis (dBNSTa), central nucleus of the amygdala (CeA), dorsomedial hypothalamus (DMH), and the anterior cingulate cortex (ACC).

5. The method of claim 3, wherein the neuron endogenously expresses the neuropeptide.

6. The method of claim 1, wherein the neuropeptide comprises a neurokinin.

7. The method of claim 1, wherein the neuropeptide is selected from the group consisting of neurokinin A, neurokinin B, neuropeptide K, neuropeptide gamma, and substance P.

8. The method of claim 1, wherein the first nucleic acid and the second nucleic acid are administered to the neuron in the subject in a single vector.

9. The method of claim 8, wherein the single vector is an AAV.

10. The method of claim 9, wherein the single vector comprises the first nucleic acid under the control of the first promoter, and the second nucleic acid under the control of the first promoter or second promoter.

11. The method of claim 1, wherein the first nucleic acid is administered to the neuron in the subject in a first vector, and wherein the second nucleic acid is administered to the neuron in the subject in a second vector.

12. The method of claim 11, wherein one or both of the first vector and second vector is an AAV.

13. The method of claim 1, wherein the conditional receptor comprises a hM3DREADD and the agonist comprises clozapine-N-oxide, or wherein the conditional receptor comprises an optogenetic channel and the agonist comprises electromagnetic radiation.

14. The method of claim 1, wherein the first promoter is a synapsin promoter.

15. The method of claim 1, wherein the subject is a human subject.

* * * * *